US012509495B2

(12) United States Patent
Bernett et al.

(10) Patent No.: US 12,509,495 B2
(45) Date of Patent: Dec. 30, 2025

(54) LAG-3 TARGETED HETERODIMERIC FUSION PROTEINS CONTAINING IL-15/IL-15RA Fc-FUSION PROTEINS AND LAG-3 ANTIGEN BINDING DOMAINS

(71) Applicant: Xencor, Inc., Pasadena, CA (US)

(72) Inventors: Matthew J. Bernett, Monrovia, CA (US); John Desjarlais, Pasadena, CA (US); Rumana Rashid, Temple City, CA (US); Rajat Varma, Monrovia, CA (US); Christine Bonzon, Los Angeles, CA (US)

(73) Assignee: Xencor, Inc., Pasadena, CA (US)

( * ) Notice: Subject to any disclaimer, the term of this patent is extended or adjusted under 35 U.S.C. 154(b) by 97 days.

(21) Appl. No.: 18/309,303

(22) Filed: Apr. 28, 2023

(65) Prior Publication Data

US 2023/0279071 A1 Sep. 7, 2023

Related U.S. Application Data

(63) Continuation of application No. 16/388,646, filed on Apr. 18, 2019, now abandoned.

(60) Provisional application No. 62/783,107, filed on Dec. 20, 2018, provisional application No. 62/659,624, filed on Apr. 18, 2018.

(51) Int. Cl.
*C07K 14/54* (2006.01)

(52) U.S. Cl.
CPC ...... *C07K 14/5443* (2013.01); *C07K 2317/53* (2013.01); *C07K 2317/56* (2013.01); *C07K 2317/622* (2013.01); *C07K 2317/66* (2013.01); *C07K 2319/30* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 5,595,756 | A | 1/1997 | Bally et al. |
| 5,731,168 | A | 3/1998 | Carter et al. |
| 5,821,333 | A | 10/1998 | Carter et al. |
| 6,013,480 | A | 1/2000 | Grabstein et al. |
| 6,737,056 | B1 | 5/2004 | Presta |
| 7,276,585 | B2 | 10/2007 | Lazar et al. |
| 7,355,008 | B2 | 4/2008 | Stavenhagen et al. |
| 7,632,497 | B2 | 12/2009 | Stavenhagen |
| 7,834,152 | B2 | 11/2010 | Strom et al. |
| 7,858,081 | B2 | 12/2010 | Bernard et al. |
| 7,960,512 | B2 | 6/2011 | Stavenhagen et al. |
| 8,003,774 | B2 | 8/2011 | Stavenhagen et al. |
| 8,124,084 | B2 | 2/2012 | LeFrancois et al. |
| 8,192,737 | B2 | 6/2012 | Stavenhagen et al. |
| 8,216,574 | B2 | 7/2012 | Stavenhagen |
| 8,216,805 | B2 | 7/2012 | Carter et al. |
| 8,309,690 | B2 | 11/2012 | Allan et al. |
| 8,592,562 | B2 | 11/2013 | Gunasekaran Kannan et al. |
| 8,629,245 | B2 | 1/2014 | Georgiou et al. |
| 8,679,493 | B2 | 3/2014 | Georgiou et al. |
| 8,742,074 | B2 | 6/2014 | Behrens et al. |
| 8,871,912 | B2 | 10/2014 | Davis et al. |
| 8,940,288 | B2 | 1/2015 | LeFrancois et al. |
| 8,940,289 | B2 | 1/2015 | Wong et al. |
| 8,951,517 | B2 | 2/2015 | Stavenhagen et al. |
| 9,028,815 | B2 | 5/2015 | Stavenhagen et al. |
| 9,150,663 | B2 | 10/2015 | Labrijn et al. |
| 9,308,258 | B2 | 4/2016 | Kannan et al. |
| RE45,992 | E | 5/2016 | Behrens et al. |
| 9,365,630 | B2 | 6/2016 | LeFrancois et al. |
| 9,371,368 | B2 | 6/2016 | LeFrancois et al. |
| 9,464,127 | B2 | 10/2016 | Wong et al. |
| 9,493,533 | B2 | 11/2016 | Bernard et al. |
| 9,505,848 | B2 | 11/2016 | Davis et al. |
| 9,527,926 | B2 | 12/2016 | Ho et al. |
| 9,562,109 | B2 | 2/2017 | Von Kreudenstein et al. |
| 9,683,052 | B2 | 6/2017 | Blein et al. |
| 9,683,053 | B2 | 6/2017 | Blein et al. |
| 9,763,705 | B2 | 9/2017 | Faulhaber |
| 9,763,765 | B2 | 9/2017 | Horan et al. |
| 9,931,377 | B2 | 4/2018 | Pavlakis et al. |
| 9,932,387 | B2 | 4/2018 | LeFrancois et al. |
| 9,969,790 | B2 | 5/2018 | LeFrancois et al. |
| 10,011,858 | B2 | 7/2018 | Igawa et al. |
| 10,138,303 | B2 | 11/2018 | Ho et al. |
| 10,350,270 | B2 | 7/2019 | McCauley |
| 10,550,185 | B2 | 2/2020 | Bernett et al. |
| 2003/0050236 | A1 | 3/2003 | Dawson et al. |
| 2004/0126372 | A1 | 7/2004 | Banarjee et al. |
| 2006/0257361 | A1 | 11/2006 | Watanabe et al. |
| 2006/0263857 | A1 | 11/2006 | LeFrancois et al. |

(Continued)

FOREIGN PATENT DOCUMENTS

| | | |
|---|---|---|
| AU | 2014377106 | 8/2016 |
| EP | 0927254 | 6/2005 |
| EP | 3263581 | 1/2008 |
| EP | 1801119 B1 | 6/2009 |
| EP | 1718670 | 7/2011 |
| EP | 1934353 | 10/2011 |
| EP | 2388266 | 4/2014 |
| EP | 2724728 | 4/2014 |
| EP | 2986312 | 2/2016 |
| EP | 3093295 | 11/2016 |
| EP | 3113858 | 1/2017 |
| EP | 2769984 | 8/2017 |
| EP | 3235830 | 10/2017 |

(Continued)

OTHER PUBLICATIONS

Mortier et al. (J. Biol. Chem. Jan. 20, 2006; 281 (3): 1612-9.*

(Continued)

*Primary Examiner* — Peter J Reddig
(74) *Attorney, Agent, or Firm* — Kelly A. Plummer; Christopher J. Betti; Morgan, Lewis & Bockius, LLP

(57) ABSTRACT

The present invention is directed to novel targeted heterodimeric fusion proteins comprising an IL-15/IL-15Rα Fc-fusion protein and a LAG-3 antibody fragment-Fc fusion protein.

5 Claims, 74 Drawing Sheets

Specification includes a Sequence Listing.

(56) References Cited

U.S. PATENT DOCUMENTS

| | | | |
|---|---|---|---|
| 2009/0238791 | A1 | 9/2009 | Jacques et al. |
| 2010/0068191 | A1 | 3/2010 | Danilkovich et al. |
| 2010/0267934 | A1 | 10/2010 | Van de Winkel et al. |
| 2011/0039334 | A1 | 2/2011 | Bennett et al. |
| 2011/0054151 | A1 | 3/2011 | Lazar et al. |
| 2012/0149876 | A1 | 6/2012 | Von Kreudenstein et al. |
| 2012/0177595 | A1 | 7/2012 | Wong et al. |
| 2013/0039913 | A1 | 2/2013 | Labrijn et al. |
| 2013/0131319 | A1 | 5/2013 | Igawa et al. |
| 2013/0178605 | A1 | 7/2013 | Blein et al. |
| 2014/0134128 | A1 | 5/2014 | Wong et al. |
| 2014/0187753 | A1 | 7/2014 | Blein et al. |
| 2014/0199294 | A1 | 7/2014 | Mimoto et al. |
| 2014/0288275 | A1 | 9/2014 | Moore et al. |
| 2014/0335089 | A1 | 11/2014 | Igawa et al. |
| 2014/0356381 | A1 | 12/2014 | Moore et al. |
| 2014/0363426 | A1 | 12/2014 | Moore et al. |
| 2015/0293193 | A1 | 10/2015 | Alford et al. |
| 2015/0351275 | A1 | 12/2015 | Imbimbo et al. |
| 2016/0017038 | A1 | 1/2016 | Koenig |
| 2016/0068584 | A1 | 3/2016 | Bechard et al. |
| 2016/0157951 | A1 | 6/2016 | Schoenig et al. |
| 2016/0175459 | A1 | 6/2016 | Gey et al. |
| 2016/0176969 | A1 | 6/2016 | Bernett et al. |
| 2016/0184399 | A1 | 6/2016 | Bechard et al. |
| 2016/0257749 | A1 | 9/2016 | Lifke et al. |
| 2016/0318986 | A1 | 11/2016 | Morisseau et al. |
| 2016/0333067 | A1 | 11/2016 | LeFrancois et al. |
| 2016/0347818 | A1 | 12/2016 | LeFrancois et al. |
| 2016/0355608 | A1 | 12/2016 | Bernett et al. |
| 2016/0367635 | A1 | 12/2016 | Wong et al. |
| 2017/0020963 | A1 | 1/2017 | Qu et al. |
| 2017/0056874 | A1 | 3/2017 | Bechard et al. |
| 2017/0088597 | A1 | 3/2017 | Wong et al. |
| 2017/0145078 | A1 | 5/2017 | Davis et al. |
| 2017/0151310 | A1 | 6/2017 | Felber et al. |
| 2017/0233497 | A1 | 8/2017 | Labrijn et al. |
| 2018/0094077 | A1 | 4/2018 | Blein et al. |
| 2018/0118805 | A1 | 5/2018 | Bernett et al. |
| 2018/0118828 | A1 | 5/2018 | Bernett et al. |
| 2018/0118836 | A1 | 5/2018 | Bernett et al. |
| 2018/0127500 | A1 | 5/2018 | Kehry et al. |
| 2018/0194860 | A1 | 7/2018 | Von Kreudenstein et al. |
| 2018/0200366 | A1 | 7/2018 | Wong et al. |
| 2018/0298079 | A1 | 10/2018 | LeFrancois et al. |
| 2018/0312560 | A1 | 11/2018 | Morisseau et al. |
| 2019/0016778 | A1 | 1/2019 | Bernett et al. |
| 2019/0016793 | A1 | 1/2019 | Cini et al. |
| 2019/0263877 | A1 | 8/2019 | Yeung et al. |
| 2019/0270816 | A1 | 9/2019 | Bernett et al. |
| 2019/0359684 | A1 | 11/2019 | Bernett et al. |
| 2019/0359732 | A1 | 11/2019 | Cheung et al. |
| 2019/0365861 | A1 | 12/2019 | Bernett et al. |
| 2020/0040083 | A1 | 2/2020 | Bernett et al. |
| 2020/0247862 | A1 | 8/2020 | Bernett et al. |
| 2020/0392235 | A1 | 12/2020 | Lu et al. |
| 2020/0399338 | A1 | 12/2020 | Caffaro et al. |
| 2021/0047407 | A1 | 2/2021 | Christian et al. |
| 2022/0106392 | A1 | 4/2022 | Cini et al. |
| 2023/0149509 | A1 | 5/2023 | Ungewickell et al. |
| 2023/0233649 | A1 | 7/2023 | Liu et al. |

FOREIGN PATENT DOCUMENTS

| | | | |
|---|---|---|---|
| EP | 3030575 | | 7/2018 |
| EP | 2723869 | B1 | 2/2019 |
| EP | 3265478 | B1 | 9/2019 |
| EP | 3030262 | B1 | 10/2019 |
| EP | 1899364 | B1 | 2/2020 |
| WO | WO96027011 | | 9/1996 |
| WO | WO1997041232 | | 11/1997 |
| WO | WO2001010912 | A1 | 2/2001 |
| WO | WO2005014642 | A2 | 2/2005 |
| WO | WO2005085282 | | 9/2005 |
| WO | WO2006063974 | | 6/2006 |
| WO | WO2007001677 | | 1/2007 |
| WO | WO2007046006 | | 4/2007 |
| WO | WO2007084342 | | 7/2007 |
| WO | WO2007110205 | | 10/2007 |
| WO | WO2007128563 | A1 | 11/2007 |
| WO | WO2007147901 | | 12/2007 |
| WO | WO2008143794 | | 11/2008 |
| WO | WO2009002562 | | 12/2008 |
| WO | WO2009036209 | | 3/2009 |
| WO | WO2009089004 | | 7/2009 |
| WO | WO2010017103 | | 2/2010 |
| WO | WO2011005621 | | 1/2011 |
| WO | WO2011020047 | A1 | 2/2011 |
| WO | WO2011063348 | | 5/2011 |
| WO | WO2011143545 | | 11/2011 |
| WO | WO2011131746 | | 12/2011 |
| WO | WO2012032080 | | 3/2012 |
| WO | WO2012040323 | A2 | 3/2012 |
| WO | WO2012146628 | | 11/2012 |
| WO | WO2012131555 | | 12/2012 |
| WO | WO2012175222 | | 12/2012 |
| WO | WO2013/055809 | | 4/2013 |
| WO | WO2013107791 | A1 | 7/2013 |
| WO | WO2014079000 | | 5/2014 |
| WO | WO2014/110601 | | 7/2014 |
| WO | WO2014145806 | | 9/2014 |
| WO | WO2014145907 | | 9/2014 |
| WO | WO2014170032 | | 10/2014 |
| WO | WO2014207173 | | 12/2014 |
| WO | WO2015018528 | | 2/2015 |
| WO | WO2015018529 | | 2/2015 |
| WO | WO2015103928 | | 7/2015 |
| WO | WO2015131994 | | 9/2015 |
| WO | WO2015195163 | | 12/2015 |
| WO | WO2016004060 | | 1/2016 |
| WO | WO2016018920 | A1 | 2/2016 |
| WO | WO2016086186 | | 6/2016 |
| WO | WO2016086189 | A2 | 6/2016 |
| WO | WO2016086196 | A2 | 6/2016 |
| WO | WO2016095642 | | 6/2016 |
| WO | WO2016106159 | | 6/2016 |
| WO | WO2016141387 | | 9/2016 |
| WO | WO2016142314 | | 9/2016 |
| WO | WO2016182751 | A1 | 11/2016 |
| WO | WO2017055547 | A1 | 4/2017 |
| WO | WO2018007919 | A1 | 1/2018 |
| WO | WO2018071918 | | 4/2018 |
| WO | WO2018071919 | | 4/2018 |
| WO | WO2018075989 | | 4/2018 |
| WO | WO2018091661 | | 5/2018 |
| WO | WO2019006472 | | 1/2019 |
| WO | WO2019094637 | A1 | 5/2019 |
| WO | WO2019204592 | | 10/2019 |
| WO | WO2019204646 | A1 | 10/2019 |
| WO | WO2019204665 | | 10/2019 |
| WO | WO2020077276 | | 4/2020 |
| WO | WO2020132646 | | 6/2020 |
| WO | WO2020172631 | A2 | 8/2020 |
| WO | WO2020185739 | | 9/2020 |
| WO | WO2020186176 | A1 | 9/2020 |
| WO | WO2021072298 | A1 | 4/2021 |
| WO | WO2021119429 | A1 | 6/2021 |
| WO | WO2021155042 | A1 | 8/2021 |
| WO | WO2022076462 | A1 | 4/2022 |
| WO | WO2022140701 | A1 | 6/2022 |
| WO | WO2023010031 | A1 | 2/2023 |
| WO | WO2023196905 | A1 | 10/2023 |
| WO | WO2024011179 | | 1/2024 |

OTHER PUBLICATIONS

Vincent et al. (Int. J. Cancer. Aug. 1, 2013; 133 (3): 757-65).*

U.S. Appl. No. 15/785,401, 2018-0118805, U.S. Pat. No. 10,501,543, filed Oct. 16, 2017, May 3, 2018, Dec. 10, 2019, Bernett et al.

U.S. Appl. No. 16/660,028, 2020-0040083, filed Oct. 22, 2019, Feb. 6, 2020, Bernett et al.

U.S. Appl. No. 17/692,755, 2022-0195048, filed Mar. 11, 2022, Jun. 23, 2022, Bernett et al.

(56) References Cited

OTHER PUBLICATIONS

U.S. Appl. No. 15/785,393, 2018-0118828, U.S. Pat. No. 10,550,185, filed Oct. 16, 2017, May 3, 2018, Feb. 4, 2020, Bernett et al.
U.S. Appl. No. 16/718,072, 2020-0123259, U.S. Pat. No. 11,584,794, filed Dec. 17, 2019, Apr. 23, 2020, Feb. 21, 2023, Bernett et al.
U.S. Appl. No. 18/065,462, 2023-0220081, filed Dec. 13, 2022, Jul. 13, 2023, Bernett et al.
U.S. Appl. No. 16/388,174, 2019-0365861, filed Apr. 18, 2019, Dec. 5, 2019, Bernett et al.
U.S. Appl. No. 17/209,047, 2022-0040264, filed Mar. 22, 2021, Feb. 10, 2022, Bernett et al.
U.S. Appl. No. 16/388,811, 2019-0389933, U.S. Pat. No. 11,524,991, filed Apr. 18, 2019, Dec. 26, 2019, Dec. 13, 2022, Bernett et al.
U.S. Appl. No. 17/878,903, filed Aug. 1, 2022, Bernett et al.
U.S. Appl. No. 16/600,236, 2020-0140512, U.S. Pat. No. 11,377,477, filed Oct. 11, 2019, May 7, 2020, Jul. 5, 2022, Bernett et al.
U.S. Appl. No. 16/025,963, 2019-0016778, U.S. Pat. No. 11,084,863, filed Jul. 2, 2018, Jan. 17, 2019, Aug. 10, 2021, Bernett et al.
U.S. Appl. No. 17/366,565, 2022-0073588, filed Jul. 2, 2021, Mar. 10, 2022, Bernett et al.
U.S. Appl. No. 16/184,895, 2019-0263909, U.S. Pat. No. 11,312,770, filed Nov. 8, 2018, Aug. 29, 2019, Apr. 26, 2022, Bernett et al.
U.S. Appl. No. 17/696,799, 2022-0204624, filed Mar. 16, 2022, Jun. 30, 2022, Bernett et al.
U.S. Appl. No. 16/388,646, 2019-0352362, filed Apr. 18, 2019, Nov. 21, 2019, Bernett et al.
U.S. Appl. No. 16/388,729, 2019-0359684, U.S. Pat. No. 11,505,595, filed Apr. 18, 2019, Nov. 28, 2019, Nov. 22, 2022, Bernett et al.
U.S. Appl. No. 17/965,593, filed Oct. 13, 2022, Bernett et al.
U.S. Appl. No. 16/724,118, 2020-0247862, U.S. Pat. No. 11,618,776, filed Dec. 20, 2019, Aug. 6, 2020, Apr. 4, 2023, Bernett et al.
U.S. Appl. No. 17/968,611, filed Oct. 18, 2022, Bernett et al.
U.S. Appl. No. 17/067,508, 2021-0230243, filed Oct. 9, 2020, Jul. 29, 2021, Desjarlais et al.
U.S. Appl. No. 18/296,591, filed Apr. 6, 2023, Bernett et al.
Chappel et al., "Identification of a Secondary FcY RI Binding Site within a Genetically Engineered Human IgG Antibody," J. Biol. Chem., 268(33):25124-25131 (Nov. 1993).
Chappel et al., "Identification of the FcY receptor class I binding site in human IgG through the use of recombinant IgG1/IgG2 hybrid and point-mutated antibodies," PNAS, USA, 88:9036-9040 (Oct. 1991).
Miranda-Carus et al., IL-15 and the initiation of cell contact-dependent synovial fibroblast-T lymphocyte cross-talk in rheumatoid arthritis: effect of methotrexate., 2004 J. Immunol. 13:1463-1476.
Koka et al, Cutting edge: murine dendritic cells require IL-15R alpha to prime NK cells., 2004 J. Immunol. 173:3594-3598.
Matsumoto et al., On-column refolding and characterization of soluble human interleukin-15 receptor alpha-chain produced in *Escherichia coli*., Protein Purification and Expression, 2003 64-71.
Schluns et al., Distinct cell types control lymphoid subset development by means of IL-15 and IL-15 receptor alpha expression., 2004, PNAS 101(5):5616-5621.
Wei et al., The Sushi domain of soluble IL-15 receptor alpha is essential for binding IL-15 and inhibiting inflammatory and allogenic responses in vitro and in vivo., 2001, J. Immunol. 167:277-282.
Han et al., IL-15:IL-15 receptor alpha superagonist complex: high-level co-expression in recombinant mammalian cells, purification and characterization., Cytokine. Dec. 2011;56(3):804-10.
Stone et al., Design and characterization of a protein superagonist of IL-15 fused with IL-15Rα and a high-affinity T cell receptor., Biotechnol Prog. 2012; Nov.-Dec. 28(6):1588-97.
Kermer et al., An antibody fusion protein for cancer immunotherapy mimicking IL-15 trans-presentation at the tumor site., Mol Cancer Ther. Jun. 2012;11(6):1279-88.
Kermer et al., Combining Antibody-Directed Presentation of IL-15 and 4-1BBL in a Trifunctional Fusion Protein for Cancer Immunotherapy, Mol Cancer Ther. Jan. 2014;13(1):112-21.
C. Bergamaschi et al, "Intracellular Interaction of Interleukin-15 with Its Receptor during Production Leads to Mutual Stabilization and Increased Bioactivity", 2008, Journal of Biological Chemistry, vol. 283, No. 7, pp. 4189-4199.
Genbank accession No. NM_172174, 1998.
Genbank accession No. NP_002180, Jul. 4, 2020.
S. Dubois et al, "IL-15Rα Recycles and Presents IL-15 in Trans to Neighbouring Cells", Immunity, vol. 17, 537-547, Nov. 2002.
Y Tagaya et al, "Generation of secretable and non-secretable interleukin-15 isoforms through alternate usage of signal peptides", 1997, Proc. Natl. Acad. Sci. USA, vol. 44, 14444-14449.
D Anderson et al, "Functional Characterization of the Human IL-15 Receptor α Chain and Close Linkage of IL15RA and IL2RA genes", J. Biol. Chem., vol. 270, No. 50, 29862-29869.
Mortier E et al, "Natural, Proteolytic Release of a Soluble Form of Human IL-15 Receptor α-Chain That Behaves as a Specific, High Affinity IL-15 Antagonist", J. Immunol 2004; 173: 1681-1688.
Matthew J Bernett et al: Abstract 5565: Potency-reduced IL15/IL15R[alpha] heterodimeric Fe-fusions display enhanced in vivo activity through increased exposure 11 , Cancer Research, vol. 78, No. 13(Suppl)., Apr. 18, 2018 (Apr. 18, 2018), pp. 1-2, XP055658295. abstract.
Kowalsky Stacy Jet al: "Superagonist IL-15-Armed Oncolytic Virus Elicits Potent Antitumor Immunity and Therapy That Are Enhanced with PD-1 Blockade", Molecular Therapy, Nature Publishing Group, GB, vol. 26, No. 10, Oct. 3, 2018 (Oct. 3, 2018), pp. 2476-2486, XP002794091, ISSN: 1525-0024, DOI: 10.1016/J.YMTHE.2018.07.013 abstract, figures 5 and 6.
John M Wrangle et al: "ALT-803, an IL-15 superagonist, in combination with nivolumab in patients with metastatic non-small cell lung cancer: a non randomised, open-label, phase lb trial", The Lancet Oncology, vol. 19, No. 5, Apr. 5, 2018 (Apr. 5, 2018), pp. 694-704, XP055605963, DOI: 10.1016/S1470-2045(18)30148-7 abstract, figures 2, 3 table 3.
Ha et al., Immunoglobulin Fc Heterodimer Platform Technology: From Design to Applications in Therapeutic Antibodies and Proteins., Front Immunol. 2016; 7: 394. Published online Oct. 6, 2016. doi: 10.3389/fimmu.2016.00394.
Rhode et al., Comparison of the Superagonist Complex, ALT-803, to IL15 as Cancer Immunotherapeutics in Animal Models., Cancer Immunol Res. Jan. 2016;4(1):49-60. doi: 10.1158/2326-6066.CIR-15-0093-T. Epub Oct. 28, 2015.
Steinbacher et al., An Fc-optimized NKG2D-immunoglobulin G Fusion Protein for Induction of Natural Killer Cell Reactivity Against Leukemia., Int J Cancer. Mar. 1, 2015;136(5):1073-84. doi: 10.1002/ijc.29083. Epub Jul. 28, 2014.
Prajapati et al., Functions of NKG2D in CD8 + T Cells: An Opportunity for Immunotherapy., Cell Mol Immunol. May 2018;15(5):470-479. doi: 10.1038/cmi.2017.161. Epub Feb. 5, 2018.
Wells, Additivity of mutational effects in proteins., Biochemistry 1990, 29, 37, 8509-8517.
Bork, Powers and Pitfalls in Sequence Analysis: The 70% Hurdle., Genome Res. 2000. 10: 398-400.
Skolnick et al., From Genes to Protein Structure and Function: Novel Applications of Computational Approaches in the Genomic Era., Trends Biotechnol. Jan. 2000;18(1):34-9.
Doerks et al., Protein annotation: detective work for function prediction., Trends in Genetics, 1998 vol. 14, Issue 6, p. 248-250, Jun. 1, 1998.
Tokuriki et al., Stability effects of mutations and protein evolvability., Current Opinion in Structural Biology 2009, 19: 596-604.
Fabbi et al, Dual Roles of IL-15 in Cancer Biology, Journal of Cytokine Biology, 2016, vol. 1, No. 2, pp. 1-7.
Mathios et al., Therapeutic administration of IL-15 superagonist complex ALT-803 leads to long-term survival and durable antitumor immune response in a murine glioblastoma model., International Journal of Cancer, 2016; vol. 138, pp. 187-194.
Alter et al., Targeted IL-15-based Protein Fusion Complexes as Cancer Immunotherapy Approaches., J Immunological Sci. (2018); 2(1): 15-18.
Bailey et al., New interleukin-15 superagonist (IL-15SA) significantly enhances graft-versus-tumor activity., Oncotarget. Jul. 4, 2017; 8(27): 44366-44378.

(56) References Cited

OTHER PUBLICATIONS

Charych et al., NKTR-214, an Engineered Cytokine with Biased IL2 Receptor Binding, Increased Tumor Exposure, and Marked Efficacy in Mouse Tumor Models., Clin Cancer Res; 22(3) Feb. 1, 2016.
Chen et al., A targeted IL-15 fusion protein with potent antitumor activity., (2015) Cancer Biology & Therapy, 16:9, 1415-1421, DOI: 10.1080/15384047.2015.1071739.
Ghasemi et al., Selective targeting of IL-2 to NKG2D bearing cells for improved immunotherapy., Nature Communications vol. 7, Article No. 12878 (2016).
Jochems et al., The multi-functionality of N-809, a novel fusion protein encompassing anti-PD-L1 and the IL-15 superagonist fusion complex., OncoImmunology, 2019, vol. 8, No. 2, e1532764 (15 pages).
Klein et al., Cergutuzumab amunaleukin (CEA-IL2v), a CEAtargeted IL-2 variant-based immunocytokine for combination cancer immunotherapy: Overcoming limitations of aldesleukin and conventional IL-2-based immunocytokines.,(2017) OncoImmunology, 6:3, e1277306, DOI: 10.1080/2162402X.2016.1277306.
Olsen et al., Crystal Structure of the Interleukin-15 * Interleukin-15 Receptor α Complex., The Journal of Biological Chemistry vol. 282, No. 51, pp. 37191-37204, Dec. 21, 2007.
Vallera et al., IL15 Trispecific Killer Engagers (TriKE) Make Natural Killer Cells Specific to CD33þ Targets While Also Inducing Persistence, In Vivo Expansion, and Enhanced Function., Clin Cancer Res; 22(14) Jul. 15, 2016.
Xu et al., Efficacy and Mechanism-of-Action of a Novel Superagonist Interleukin-15: Interleukin-15 Receptor α Su/Fc Fusion Complex in Syngeneic Murine Models of Multiple Myeloma., Cancer Res. May 15, 2013;73(10):3075-86.
Bernard et al., Identification of an Interleukin-15α Receptor-binding Site on Human Interleukin-15*., The Journal of Biological Chemistry; 2004; vol. 279, No. 23, pp. 24313-24322.
Robinson et al., The potential and promise of IL-15 in immuno-oncogenic therapies, Immunology Letters, vol. 190, 2017, pp. 159-168.
Schmid et al., Design and characterisation of a novel interleukin-15 receptor alpha fusion protein and analysis of interleukin-15 complexation., PLoS One. Jul. 26, 2019;14(7):e0219313.
Genbank accession No. U31628, Dec. 19, 1995.
Muller, Dafne, Targeted cancer immunotherapy, Mimicking physiological trans-presentation of IL-15., Oncoimmunology. Oct. 1, 2012; 1(7): 1213-1214.
Garcin et al. High efficiency cell-specific targeting of cytokine activity. Nat Commun 5, 3016 (2014).
Kaspar et al, The antibody-mediated targeted delivery of interleukin-15 and GM-CSF to the tumor neovasculature inhibits tumor growth and metastasis., Cancer Res. May 15, 2007;67(10):4940-8.
Conlon et al., Redistribution, hyperproliferation, activation of natural killer cells and CD8 T cells, and cytokine production during first-in-human clinical trial of recombinant human interleukin-15 in patients with cancer., J Clin Oncol. Jan. 1, 2015;33(1):74-82.
List et al., Immunocytokines: a review of molecules in clinical development for cancer therapy., Clin Pharmacol. 2013; 5(Suppl 1): 29-45.
Gillies et al., Antibody-targeted interleukin 2 stimulates T-cell killing of autologous tumor cells., PNAS Feb. 15, 1992 89 (4) 1428-1432.
Albertini et al. Phase II trial of hu14.18-IL2 for patients with metastatic melanoma., Cancer Immunol Immunother. Dec. 2012;61(12):2261-71.
Ribas et al., Phase I/II open-label study of the biologic effects of the interleukin-2 immunocytokine EMD 273063 (hu14.18-IL2) in patients with metastatic malignant melanoma., J Transl Med. Jul. 29, 2009;7:68.
Hofmann et al., Generation, selection and preclinical characterization of an Fc-optimized FLT3 antibody for the treatment of myeloid leukemia., Leukemia. Jun. 2012;26(6):1228-37.
Kellner et al., Heterodimeric bispecific antibody-derivatives against CD19 and CD16 induce effective antibody-dependent cellular cytotoxicity against B-lymphoid tumor cells., Cancer Lett. Apr. 28, 2011;303(2):128-39.
Skerra, Arne, 'Anticalins': a new class of engineered ligand-binding proteins with antibody-like properties., J Biotechnol. Jun. 2001;74(4):257-75.
Skerra, Arne, Engineered protein scaffolds for molecular recognition., J Mol Recognit. Jul.-Aug. 2000;13(4):167-87.
Horton et al. Potent in vitro and in vivo activity of an Fc-engineered anti-CD19 monoclonal antibody against lymphoma and leukemia., Cancer Res, 2008, vol. 68, 8049-8057.
Ortiz-Sánchez et al., Antibody-cytokine fusion proteins: applications in cancer therapy., Expert Opin Biol Ther. May 2008 ; 8(5): 609-632.
Zhu et al., Novel Human Interleukin-15 Agonists., J Immunol Sep. 15, 2009, 183 (6) 3598-3607.
Xia et al., In vivo effect of recombined IL-15/Fc fusion protein on EAU. Sichuan Da Xue Xue Bao Yi Xue Ban. Nov. 2008;39(6) 944-949.
Wu et al., IL-15Rα-IgG1-Fc Enhances IL-2 and IL-15 Anti-tumor Action through NK and CD8+ T Cells Proliferation and Activation., Journal of Molecular Cell Biology, vol. 2, Issue 4, Aug. 2010, pp. 217-222.
Ridgway et al., 'Knobs-into-holes' engineering of antibody CH3 domains for heavy chain heterodimerization., Protein Engineering, Design and Selection, vol. 9, Issue 7, Jul. 1996, pp. 617-621.
Carter P. Bispecific human IgG by design. J Immunol Methods. Feb. 1, 2001;248(1-2):7-15. doi: 10.1016/s0022-1759(00)00339-2. PMID: 11223065.
Atwell et al., Stable heterodimers from remodeling the domain interface of a homodimer using a phage display library 1.,Journal of Molecular Biology, vol. 270, Issue 1,1997,pp. 26-35, ISSN 0022-2836, https://doi.org/10.1006/jmbi.1997.1116.
Merchant, et al., An efficient route to human bispecific IgG, Nature Biotechnology, 1998, vol. 16, pp. 677-681.
Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.
Deshpande et al., (2013), Kinetic analysis of cytokine-mediated receptor assembly using engineered FC heterodimers. Protein Science, 22: 1100-1108. https://doi.org/10.1002/pro.2285.
Dumont et al. Monomeric Fc Fusions. BioDrugs 20, 151-160 (2006). https://doi.org/10.2165/00063030-200620030-00002.
Belladonna et al., (2013) Bioengineering heterodimeric cytokines: turning promiscuous proteins into therapeutic agents, Biotechnology and Genetic Engineering Reviews, 29:2, 149-174, DOI: 10.1080/02648725.2013.801228.
Hinrichs, Christian S., Can interleukin-15 keep its therapeutic promise? Science Translational Medicine Mar. 7, 2018:vol. 10, Issue 431, eaar7532, DOI: 10.1126/scitranslmed.aar7532.
Rubinstein et al., Converting IL-15 to a superagonist by binding to soluble IL-15R{alpha}. Proc Natl Acad Sci U S A. Jun. 13, 2006;103(24):9166-71. doi: 10.1073/pnas.0600240103. Epub Jun. 6, 2006. PMID: 16757567; PMCID: PMC1482584.
Stoklasek et al., Combined IL-15/IL-15Ralpha immunotherapy maximizes IL-15 activity in vivo. J Immunol. Nov. 1, 2006;177(9):6072-80. doi: 10.4049/jimmunol.177.9.6072. PMID: 17056533; PMCID: PMC2847275.
Landolfi NF. A chimeric IL-2/lg molecule possesses the functional activity of both proteins. J Immunol. Feb. 1, 1991;146(3):915-9. PMID: 1988502.
Zheng et al., Administration of noncytolytic IL-10/Fc in murine models of lipopolysaccharide-induced septic shock and allogeneic islet transplantation., J Immunol May 15, 1995, 154 (10) 5590-5600.
Low, et al., Oral and pulmonary delivery of FSH-Fc fusion proteins via neonatal Fc receptor-mediated transcytosis, Human Reproduction, vol. 20, Issue 7, Jul. 2005, pp. 1805-1813.
Kim et al., Targeting the IL-15 Receptor with an Antagonist IL-15 Mutant/Fcγ2a Protein Blocks Delayed-Type Hypersensitivity., J Immunol Jun. 15, 1998, 160 (12) 5742-5748.

(56) References Cited

OTHER PUBLICATIONS

Larrick et al., 2013, Inflammation, Advancing Age and Nutrition. D26 Chapter 28. Trophokines: Novel Therapy for Senescence-Related Fibrosis htto://dx rlo1.ora/10 1016/B978-0-12-397803-5. 00028-9.

Mortier et al., Soluble interleukin-15 receptor alpha (IL-15R alpha)-sushi as a selective and potent agonist of IL-15 action through IL-15R beta/gamma. Hyperagonist IL-15 x IL-15R alpha fusion proteins. J Biol Chem. Jan. 20, 2006;281(3):1612-9. doi: 10.1074/jbc.M508624200. Epub Nov. 11, 2005. PMID: 16284400.

Wu J. IL-15 Agonists: The Cancer Cure Cytokine. J Mol Genet Med. Oct. 28, 2013;7:85. doi: 10.4172/1747-0862.1000085. PMID: 24587813; PMCID: PMC3938108.

C. Spiess et al., J. Biol. 288(37):26583-93 (2013), Development of a Human IgG4 Bispecific Antibody for Dual Targeting of Interleukin-4 (IL-4) and Interleukin-13 (IL-13) Cytokines.

Hopp et al. 1988. “A Short Polypeptide Marker Sequence Useful for Recombinant Protein Identification and Purification” Nat. Biotechnol. 6, 1204-1210.

Budagian et al., IL-15/IL-15 receptor biology: a guided tour through an expanding universe., Cytokine Growth Factor Rev. Aug. 2006;17(4):259-8.

Bodnar et al., A biophysical approach to IL-2 and IL-15 receptor function: Localization, conformation and interactions., Immunology Letters 116 (2008) 117-125.

Numerof et al., Cytokines as Potential Therapeutic Targets for Inflammatory Skin Diseases., Springer-Verlag, Berlin Heidelberg 2006.

Dumont, Francis J. (2005) Interleukin-2 family cytokines: potential for therapeutic immmunoregulation, Expert Opinion on Therapeutic Patents, 15:5, 521-554.

Savio et al., IL-15: a relevant cytokine for lymphoid homeostasis and autoimmune diseases., Biotecnologia Aplicada 2006;23:87-93.

Lichtenegger et al., Targeting LAG-3 and PD-1 to Enhance T Cell Activation by Antigen-Presenting Cells., Front. Immunol. Feb. 27, 2018; 9: 385; pp. 1-12.

Guo et al., Immunobiology of the IL-15/IL-15Rα complex as an antitumor and antiviral agent., Cytokine Growth Factor Rev. Dec. 2017; 38: 10-21.

Ng et al., Heterodimeric IL15 Treatment Enhances Tumor Infiltration, Persistence, and Effector Functions of Adoptively Transferred Tumor-specific T Cells in the Absence of Lymphodepletion., Clin. Cancer Res. Jun. 2017; 23 (11): 2817-30.

Liang et al., Targeting IFNα to tumor by anti-PD-L1 creates feedforward antitumor responses to overcome checkpoint blockade resistance ., Nat. Commun. Nov. 2, 2018; 9 (1): 4586.

Chen et al., Therapeutic efficacy of an anti-PD-L1 antibody based immunocytokine in a metastatic mouse model of colorectal cancer ., Biochem. Biophys. Res. Commun. Nov. 11, 2016; 480 (2): 160-5.

Kiefer et al., Immunocytokines and bispecific antibodies: two complementary strategies for the selective activation of immune cells at the tumor site., Immunol. Rev. Mar. 2016; 270 (1): 178-92; author manuscript; pp. 1-27.

Sondel et al., Current and Potential Uses of Immunocytokines as Cancer Immunotherapy., Antibodies. 212; 1: 149-71.

Kim et al., IL-15 superagonist/IL-15RαSushi-Fc fusion complex (IL-15SA/IL-15RαSu-Fc; ALT-803) markedly enhances specific subpopulations of NK and memory CD8+ T cells, and mediates potent anti-tumor activity against murine breast and colon carcinomas., Oncotarget. Mar. 29, 2016; 7 (13): 16130-45.

Rogers et al., Molecular characterization of immunoglobulin D in mammals: immunoglobulin heavy constant delta genes in dogs, chimpanzees and four old world monkey species., Immunology. May 2006; 118 (1): 88-100.

Rowley J. et al., Inhibition of tumor growth by NK1. 1+ cells and CD8+ T cells activated by IL-15 through receptor β/common γ signaling in trans, The Journal of Immunology, 2008, V. 181, N. 12, p. 8237-8247, p. 8237.

Shen J. et al., Single variable domain-IgG fusion: a novel recombinant approach to Fc domain-containing bispecific antibodies, Journal of Biological Chemistry, 2006, V. 281, N. 16, p. 10706-10714, p. 10713.

Chen X. et al., Fusion protein linkers: property, design and functionality, Advanced drug delivery reviews, 2013, V. 65, N. 10, p. 1357-1369, the whole text, p. 1365.

Maeda Y. et al., Engineering of functional chimeric protein G-Vargula Luciferase, Analytical biochemistry, 1997, V. 249, N. 2, p. 147-152, the whole text, p. 148, p. 151.

Gasser B. et al., Antibody production with yeasts and filamentous fungi: on the road to large scale? Biotechnology letters, 2007, V. 29, N. 2, p. 201-212, p. 208.

An Z., Therapeutic monoclonal antibodies: from bench to clinic, John Wiley And Sons, 2011, 896 p., p. 350.

Burns W. R. et al., A high molecular weight melanoma-associated antigen-specific chimeric antigen receptor redirects lymphocytes to target human melanomas, Cancer research, 2010, V. 70, N. 8, p. 3027-3033, p. 3028.

Colman P. M., Effects of amino acid sequence changes on antibody-antigen interactions, Research in Immunology, 1994, V. 145, N. 1, p. 33-36, c.33.

Safdari Y. et al., Antibody humanization methods—a review and update, Biotechnology and Genetic Engineering Reviews, 2013, V. 29, N. 2, p. 175-186, p. 178, 180.

Teplyakov A. et al., Antibody modeling assessment II. Structures and models, Proteins: Structure, Function, and Bioinformatics, 2014, V. 82, N. 8, p. 1563-1582, the whole text, p. 1582).

Yu et al. Simultaneous blockade of multiple immune system inhibitory checkpoints enhances antitumor activity mediated by interleukin-15 in a murine metastatic colon carcinoma model. Clin Cancer Res. 2010;16(24):6019-6028.

Vincent et al. Tumor targeting of the IL-15 superagonist RLI by an anti-GD2 antibody strongly enhances its antitumor potency. Int J Cancer. 2013;133(3):757-765.

Vincent et al. CS14-6. Development of two IL15 immunocytokines targeting either GD2- or CD20-tumoral bearing cells. Cytokine. 2011;56 (1):102.

Xu et al. The tumor immunosuppressive microenvironment impairs the therapy of anti-HER2/neu antibody. Protein Cell. 2012;3(6):441-449.

Bessard et al. High antitumor activity of RLI, an interleukin-15 (IL-15)-IL-15 receptor alpha fusion protein, in metastatic melanoma and colorectal cancer. Mol Cancer Ther. 2009;8(9):2736-2745.

Yu et al., “Simultaneous inhibition of two regulatory T-cell subsets enhanced Interleukin-15 efficacy in a prostate tumor model.”, Proc Natl Acad Sci USA. 2012;109(16):6187-6192.

Perdreau et al. “Different dynamics of IL-15R activation following IL-15 cis- or trans-presentation.” Eur Cytokine Netw. Dec. 2010;21(4):297-307.

Desbois et al. “IL-15 Trans-Signaling with the Superagonist RLI Promotes Effector/Memory CD8+ T Cell Responses and Enhances Antitumor Activity of PD-1 Antagonists.”, J Immunol. Jul. 1, 2016;197(1):168-78. doi: 10.4049/jimmunol. 1600019. Epub May 23, 2016.

Intlekofer et al., “At the Bench: Preclinical rationale for CTLA-4 and PD-1 blockade as cancer immunotherapy”, Journal of Leukocyte Biology, vol. 94, Jul. 2013.

Melero et al.: “Evolving synergistic combinations of targeted immunotherapies to combat cancer”, Nature Reviews, Cancer, vol. 15, 2015.

Waldmann: “The biology of interleukin-2 and interleukin-15: implications for cancer therapy and vaccine design”, 2006, Nat Rev Immunol 6(8): 595-601.

Dubois et al., Preassociation of IL-15 with IL-15Rα-IgG1-Fc Enhances Its Activity on Proliferation of NK and CD8+/CD44high T Cells and Its Antitumor Action., J Immunol Feb. 15, 2008, 180 (4) 2099-2106; DOI: https://doi.org/10.4049/jimmunol.180.4.2099.

Mazzarella et al., The evolving landscape of ‘next-generation’ immune checkpoint inhibitors: A review., Eur J Cancer. Aug. 2019;117:14-31. doi: 10.1016/j.ejca.2019.04.035. Epub Jun. 21, 2019.

(56) References Cited

OTHER PUBLICATIONS

Kosobokova, E.N. at al. Fusion proteins based antibodies cytokines: production, functionality and perspectives applications of oncology, CTM, 2013, vol. 5(4): 102-111.
Bulanova et al., Soluble Interleukin (IL)-15Rα is Generated by Alternative Splicing or Proteolytic Cleavage and Forms Functional Complexes with IL-15*., Protein Structure and Folding| vol. 282, Issue 18, p. 13167-13179, May 2007.
Burkett et al., IL-15Rα expression on CD8+ T cells is dispensable for T cell memory., 4724-4729, PNAS, Apr. 15, 2003, vol. 100, No. 8.
Carson, William E. III, Braking Bad: Blockade of Inhibitory Pathways Improves Interleukin-15 Therapy., Clin Cancer Res (2010) 16 (24): 5917-5919.
Dubois et al., Natural splicing of exon 2 of human interleukin-15 receptor alpha-chain mRNA results in a shortened form with a distinct pattern of expression., J Biol Chem. Sep. 17, 1999;274(38):26978-84. doi: 10.1074/jbc.274.38.26978.
Giri et al., Identification and cloning of a novel IL-15 binding protein that is structurally related to the alpha chain of the IL-2 receptor., EMBO J. Aug. 1, 1995;14(15):3654-63. doi: 10.1002/j.1460-2075.1995.tb00035.x.
Ruchatz et al., Soluble IL-15 receptor alpha-chain administration prevents murine collagen-induced arthritis: a role for IL-15 in development of antigen-induced immunopathology., J Immunol. Jun. 1, 1998;160(11):5654-60.
Romee et al., First-in-human phase 1 clinical study of the IL-15 superagonist complex ALT-803 to treat relapse after transplantation., Blood. Jun. 7, 2018;131(23):2515-2527. doi: 10.1182/blood-2017-12-823757. Epub Feb. 20, 2018.
Ding et al., Fusion Proteins of NKG2D/NKG2DL in Cancer Immunotherapy., Int J Mol Sci. Jan. 7, 2018;19(1):177. doi: 10.3390/ijms19010177.
Auerbach et al., Angiogenesis assays: problems and pitfalls. Cancer Metastasis Rev. 2000;19(1-2):167-72. doi: 10.1023/a:1026574416001. PMID: 11191056.
Beans et al., Targeting metastasis to halt cancer's spread., PNAS, Dec. 11, 2018, 115 (50) 12539-12543, https://doi.org/10.1073/pnas.1818892115.
Gravanis et al., The changing world of cancer drug development: the regulatory bodies' perspective., Chin Clin Oncol. Jun. 2014;3(2):22. doi: 10.3978/j.issn.2304-3865.2014.05.08.
Gura, T., Systems for identifying new drugs are often faulty., Science. Nov. 7, 1997;278(5340):1041-2. doi: 10.1126/science.278.5340.1041.
Hamanishi et al., PD-1/PD-L1 blockade in cancer treatment: perspectives and issues., Int J Clin Oncol. Jun. 2016;21(3):462-73. doi: 10.1007/s10147-016-0959-z.
Heppner et al., Tumor heterogeneity: biological implications and therapeutic consequences., Cancer Metastasis Rev. 1983;2(1):5-23. doi: 10.1007/BF00046903.
Jain, R.K., Barriers to drug delivery in solid tumors., Sci Am. Jul. 1994;271(1):58-65. doi: 10.1038/scientificamerican0794-58.
Sporn, M.B., Chemoprevention of cancer., Carcinogenesis. Mar. 2000;21(3):525-30. doi: 10.1093/carcin/21.3.525.
Hait, W.N., Anticancer drug development: the grand challenges., Nat Rev Drug Discov. Apr. 2010;9(4):253-4. doi: 10.1038/nrd3144.
Nellis et al., Characterization of recombinant human IL-15 deamidation and its practical elimination through substitution of asparagine 77., Pharm Res. Mar. 2012;29(3):722-38. doi: 10.1007/s11095-011-0597-0. Epub Oct. 19, 2011.
Perez et al., Epitope mapping of 10 monoclonal antibodies against the pig analogue of human membrane cofactor protein (MCP)., Immunology. Apr. 1999;96(4):663-70. doi: 10.1046/j.1365-2567.1999.00732.x.
Tosic V. Enhancing Efficacy of Oncolytic Myxoma Virus and Adoptive T Cell Therapy Against Tumors (Doctoral dissertation, University of Illinois at Urbana-Champaign).
Fc IgG1 heavy chain constant region, partial [*Homo sapiens*]. GenBank: AEV43323.1, Jul. 15, 2016.
Cohen et al., Initial Clinical Activity and Safety of BFCR4350A, a FcRH5/CD3 T-Cell-Engaging Bispecific Antibody, in Relapsed/Refractory Multiple Myeloma., BLOOD, vol. 136, No. Supplement 1, Nov. 5, 2020 (Nov. 5, 2020), pp. 42-43, XP055951835.
Xu et al., A novel multimeric IL15/IL15Rα-Fc complex to enhance cancer immunotherapy., Oncoimmunology. Mar. 11, 2021;10(1):1893500. doi: 10.1080/2162402X.2021.1893500.
Lancman et al., Bispecifics, trispecifics, and other novel immune treatments in myeloma., Hematology Am Soc Hematol Educ Program. Dec. 4, 2020;2020(1):264-271. doi: 10.1182/hematology.2020000110.
Anonymous: "NCT05646836: A Study to Evaluate the Safety, Pharmacokinetics, and Activity of XmAb24306 in Combination With Cevostamab in Participants With Relapsed/Refractory Multiple Myeloma", ClinicalTrials.gov, Jun. 28, 2023 (Jun. 28, 2023), XP093093022, Retrieved from the Internet:URLhttps://classic.clinicaltrials.gov/ct2/show/NCT05646836.
Sakamoto et al., Contributions of Interfacial Residues of Human Interleukin15 to the Specificity and Affinity for Its Private α-Receptor., Journal of Molecular Biology, vol. 389, Issue 5, Jun. 26, 2009, pp. 880-894.
Stark and Canton, Antibodies that are specific for a single amino acid interchange in a protein epitope use structurally distinct variable regions., J Exp Med. Sep. 1, 1991; 174(3): 613-624.
Lu et al., Complex PK-PD of an engineered IL-15/IL-15Rα-Fc fusion protein in cynomolgus monkeys: QSP modeling of lymphocyte dynamics., European Journal of Pharmaceutical Sciences 186 (2023) 106450.
Mando et al., Targeting ADCC: A different approach to HER2 breast cancer in the immunotherapy era., Breast. Dec. 2021:60:15-25. doi: 10.1016/j.breast.2021.08.007. Epub Aug. 19, 2021.
Li et al., IL-15/IL-15Rα-Fc-Fusion Protein XmAb24306 Potentiates Activity of CD3 Bispecific Antibodies through Enhancing T-Cell Expansion., Mol Cancer Ther. Sep. 4, 2024;23(9):1305-1316. doi: 10.1158/1535-7163.MCT-23-0910.

* cited by examiner

Figure 2A

Human IL-15 precursor sequence (SEQ ID NO:1)

>sp|P40933
MRISKPHLRSISIQCYLCLLLNSHFLTEAGIHVFILGCFSAGLPKTEANWVNVISDLKKIEDLIQSMHIDATLYTES
DVHPSCKVTAMKCFLLELQVISLESGDASIHDTVENLIILANNSLSSNGNVTESGCKECEELEEKNIKEFLQSFVHI
VQMFINTS

Human IL-15 mature form sequence (SEQ ID NO:2)

>sp|P40933|49-162
NWVNVISDLKKIEDLIQSMHIDATLYTESDVHPSCKVTAMKCFLLELQVISLESGDASIHDTVENLIILANNSLSSN
GNVTESGCKECEELEEKNIKEFLQSFVHIVQMFINTS

Human IL-15Rα sequence (SEQ ID NO:3)

>sp|Q13261
MAPRRARGCRTLGLPALLLLLLLRPPATRGITCPPPMSVEHADIWVKSYSLYSRERYICNSGFKRKAGTSSLTECVL
NKATNVAHWTTPSLKCIRDPALVHQRPAPPSTVTTAGVTPQPESLSPSGKEPAASSPSSNNTAATTAAIVPGSQLMP
SKSPSTGTTEISSHESSHGTPSQTTAKNWELTASASHQPPGVYPQGHSDTTVAISTSTVLLCGLSAVSLLACYLKSR
QTPPLASVEMEAMEALPVTWGTSSRDEDLENCSHHL

Human IL-15Rα, extracellular domain (SEQ ID NO:5)

>sp|Q13261|31-205
ITCPPPMSVEHADIWVKSYSLYSRERYICNSGFKRKAGTSSLTECVLNKATNVAHWTTPSLKCIRDPALVHQRPAPP
STVTTAGVTPQPESLSPSGKEPAASSPSSNNTAATTAAIVPGSQLMPSKSPSTGTTEISSHESSHGTPSQTTAKNWE
LTASASHQPPGVYPQGHSDTT

Human IL-15Rα, sushi domain (SEQ ID NO:4)

>sp|Q13261|31-95
ITCPPPMSVEHADIWVKSYSLYSRERYICNSGFKRKAGTSSLTECVLNKATNVAHWTTPSLKCIR

Human IL-15Rß sequence (SEQ ID NO: 6)

>sp|P14784
MAAPALSWRLPLLILLLPLATSWASAAVNGTSQFTCFYNSRANISCVWSQDGALQDTSCQVHAWPDRRRWNQTCELL
PVSQASWACNLILGAPDSQKLTTVDIVTLRVLCREGVRWRVMAIQDFKPFENLRLMAPISLQVVHVETHRCNISWEI
SQASHYFERHLEFEARTLSPGHTWEEAPLLTLKQKQEWICLETLTPDTQYEFQVRVKPLQGEFTTWSPWSQPLAFRT
KPAALGKDTIPWLGHLLVGLSGAFGFIILVYLLINCRNTGPWLKKVLKCNTPDPSKFFSQLSSEHGGDVQKWLSSPF
PSSSFSPGGLAPEISPLEVLERDKVTQLLLQQDKVPEPASLSSNHSLTSCFTNQGYFFFHLPDALEIEACQVYFTYD
PYSEEDPDEGVAGAPTGSSPQPLQPLSGEDDAYCTFPSRDDLLLFSPSLLGGPSPPSTAPGGSGAGEERMPPSLQER
VPRDWDPQPLGPPTPGVPDLVDFQPPPELVLREAGEEVPDAGPREGVSFPWSRPPGQGEFRALNARLPLNTDAYLSL
QELQGQDPTHLV

Human IL-15Rß, extracellular domain(SEQ ID NO: 7)

>sp|P14784|27-240
AVNGTSQFTCFYNSRANISCVWSQDGALQDTSCQVHAWPDRRRWNQTCELLPVSQASWACNLILGAPDSQKLTTVDI
VTLRVLCREGVRWRVMAIQDFKPFENLRLMAPISLQVVHVETHRCNISWEISQASHYFERHLEFEARTLSPGHTWEE
APLLTLKQKQEWICLETLTPDTQYEFQVRVKPLQGEFTTWSPWSQPLAFRTKPAALGKDT

Figure 2B

Human common gamma chain sequence (SEQ ID NO: 8)

>sp|P31785
MLKPSLPFTSLLFLQLPLLGVGLNTTILTPNGNEDTTADFFLTTMPTDSLSVSTLPLPEVQCFVFNVEYMNCTWNSS
SEPQPTNLTLHYWYKNSDNDKVQKCSHYLFSEEITSGCQLQKKEIHLYQTFVVQLQDPREPRRQATQMLKLQNLVIP
WAPENLTLHKLSESQLELNWNNRFLNHCLEHLVQYRTDWDHSWTEQSVDYRHKFSLPSVDGQKRYTFRVRSRFNPLC
GSAQHWSEWSHPIHWGSNTSKENPFLFALEAVVISVGSMGLIISLLCVYFWLERTMPRIPTLKNLEDLVTEYHGNFS
AWSGVSKGLAESLQPDYSERLCLVSEIPPKGGALGEGPGASPCNQHSPYWAPPCYTLKPET

Human common gamma chain, extracellular domain(SEQ ID NO: 9)

>sp|P31785|23-262
LNTTILTPNGNEDTTADFFLTTMPTDSLSVSTLPLPEVQCFVFNVEYMNCTWNSSSEPQPTNLTLHYWYKNSDNDKV
QKCSHYLFSEEITSGCQLQKKEIHLYQTFVVQLQDPREPRRQATQMLKLQNLVIPWAPENLTLHKLSESQLELNWNN
RFLNHCLEHLVQYRTDWDHSWTEQSVDYRHKFSLPSVDGQKRYTFRVRSRFNPLCGSAQHWSEWSHPIHWGSNTSKE
NPFLFALEA

Figure 3

Human LAG-3 sequence (SEQ ID NO: 10)

>sp|P18627

MWEAQFLGLLFLQPLWVAPVKPLQPGAEVPVVWAQEGAPAQLPCSPTIPLQDLSLLRRAGVTWQHQPDSGPPAAAPG
HPLAPGPHPAAPSSWGPRPRRYTVLSVGPGGLRSGRLPLQPRVQLDERGRQRGDFSLWLRPARRADAGEYRAAVHLR
DRALSCRLRLRLGQASMTASPPGSLRASDWVILNCSFSRPDRPASVHWFRNRGQGRVPVRESPHHHLAESFLFLPQV
SPMDSGPWGCILTYRDGFNVSIMYNLTVLGLEPPTPLTVYAGAGSRVGLPCRLPAGVGTRSFLTAKWTPPGGGPDLL
VTGDNGDFTLRLEDVSQAQAGTYTCHIHLQEQQLNATVTLAIITVTPKSFGSPGSLGKLLCEVTPVSGQERFVWSSL
DTPSQRSFSGPWLEAQEAQLLSQPWQCQLYQGERLLGAAVYFTELSSPGAQRSGRAPGALPAGHLLLFLILGVLSLL
LLVTGAFGFHLWRRQWRPRRFSALEQGIHPPQAQSKIEELEQEPEPEPEPEPEPEPEPEPEQL

Human LAG-3 sequence, extracellular domain (SEQ ID NO: 11)

>sp|P18627|29-450

VPVVWAQEGAPAQLPCSPTIPLQDLSLLRRAGVTWQHQPDSGPPAAAPGHPLAPGPHPAAPSSWGPRPRRYTVLSVG
PGGLRSGRLPLQPRVQLDERGRQRGDFSLWLRPARRADAGEYRAAVHLRDRALSCRLRLRLGQASMTASPPGSLRAS
DWVILNCSFSRPDRPASVHWFRNRGQGRVPVRESPHHHLAESFLFLPQVSPMDSGPWGCILTYRDGFNVSIMYNLTV
LGLEPPTPLTVYAGAGSRVGLPCRLPAGVGTRSFLTAKWTPPGGGPDLLVTGDNGDFTLRLEDVSQAQAGTYTCHIH
LQEQQLNATVTLAIITVTPKSFGSPGSLGKLLCEVTPVSGQERFVWSSLDTPSQRSFSGPWLEAQEAQLLSQPWQCQ
LYQGERLLGAAVYFTELSSPGAQRSGRAPGALPAGHL

Macaca fascicularis LAG-3 sequence (predicted) (SEQ ID NO: 12)

>gi|544467815|ref|XP_005570011.1

MWEAQFLGLLFLQPLWVAPVKPPQPGAEISVVWAQEGAPAQLPCSPTIPLQDLSLLRRAGVTWQHQPDSGPPAXAPG
HPPVPGHRPAAPYSWGPRPRRYTVLSVGPGGLRSGRLPLQPRVQLDERGRQRGDFSLWLRPARRADAGEYRATVHLR
DRALSCRLRLRVGQASMTASPPGSLRTSDWVILNCSFSRPDRPASVHWFRSRGQGRVPVQGSPHHHLAESFLFLPHV
GPMDSGLWGCILTYRDGFNVSIMYNLTVLGLEPATPLTVYAGAGSRVELPCRLPPAVGTQSFLTAKWAPPGGGPDLL
VAGDNGDFTLRLEDVSQAQAGTYICHIRLQGQQLNATVTLAIITVTPKSFGSPGSLGKLLCEVTPASGQEHFVWSPL
NTPSQRSFSGPWLEAQEAQLLSQPWQCQLHQGERLLGAAVYFTELSSPGAQRSGRAPGALRAGHLPLFLILGVLFLL
LLVTGAFGFHLWRRQWRPRRFSALEQGIHPPQAQSKIEELEQEPELEPEPELERELGPEPEPGPEPEPEQL

Macaca fascicularis LAG-3 sequence, extracellular domain (predicted) (SEQ ID NO: 13)

>gi|544467815|ref|XP_005570011.1|29-450

ISVVWAQEGAPAQLPCSPTIPLQDLSLLRRAGVTWQHQPDSGPPAXAPGHPPVPGHRPAAPYSWGPRPRRYTVLSVG
PGGLRSGRLPLQPRVQLDERGRQRGDFSLWLRPARRADAGEYRATVHLRDRALSCRLRLRVGQASMTASPPGSLRTS
DWVILNCSFSRPDRPASVHWFRSRGQGRVPVQGSPHHHLAESFLFLPHVGPMDSGLWGCILTYRDGFNVSIMYNLTV
LGLEPATPLTVYAGAGSRVELPCRLPPAVGTQSFLTAKWAPPGGGPDLLVAGDNGDFTLRLEDVSQAQAGTYICHIR
LQGQQLNATVTLAIITVTPKSFGSPGSLGKLLCEVTPASGQEHFVWSPLNTPSQRSFSGPWLEAQEAQLLSQPWQCQ
LHQGERLLGAAVYFTELSSPGAQRSGRAPGALRAGHL

Figure 4A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| | |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 4B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 4C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 4D

| **Monomer 1** | **Monomer 2** |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

Figure 4E

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| K247Q/R355Q/N384S/K392N/V397M/Q419E/K447_ | P217R/P228R/N276K |
| K247Q/R355Q/N384S/K392N/V397M/Q419E/K447_ | N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| K247Q/R355Q/Q419E/K447_ | P217R/P228R/N276K |
| K247Q/R355Q/Q419E/K447_ | N276K |
| I199T/N203D/K274Q/R355Q/N384S/K392N/V397M/Q419E/K447_ | |
| N208D/Q295E/N384D/Q418E/N421D | |
| N208D/Q295E/Q418E/N421D | |
| Q196K/I199T/P217R/P228R/N276K | |
| Q196K/I199T/N276K | |
| K274Q/R355Q/N384S/K392N/V397M/Q419E/K447_ | |
| Q295E/N384D/Q418E/N421D | |
| Q295E/Q418E/N421D | |
| P217R/P228R/N276K | |
| N276K | |
| E269Q/E272Q/E283Q/E357Q | |
| E269Q/E272Q/E283Q | |
| E269Q/E272Q | |
| E269Q/E283Q | |
| E272Q/E283Q | |
| E269Q | |

Figure 5

| **Variant constant region** | **Substitutions** |
|---|---|
| pI_ISO(-) | I199T/N203D/K274Q/R355Q/N384S/K392N/V397M/Q419E/K447_ |
| pI_ISO(-)-Fc only | K274Q/R355Q/N384S/K392N/V397M/Q419E/K447_ |
| pI_(-)_isosteric A | N208D/Q295E/N384D/Q418E/N421D |
| pI_(-)_isosteric A-Fc only | Q295E/N384D/Q418E/N421D |
| pI_(-)_isosteric_B | N208D/Q295E/Q418E/N421D |
| pI_(-)_isosteric_B-Fc only | Q295E/Q418E/N421D |
| pI_ISO(+RR) | Q196K/I199T/P217R/P228R/N276K |
| pI_ISO(+RR)-Fc only | P217R/P228R/N276K |
| pI_ISO(+) | Q196K/I199T/N276K |
| pI_ISO(+)-Fc only | N276K |
| pI_(+)_isosteric_A | E269Q/E272Q/E283Q/E357Q |
| pI_(+)_isosteric_B | E269Q/E272Q/E283Q |
| pI_(+)_isosteric_E269Q/E272Q | E269Q/E272Q |
| pI_(+)_isosteric_E269Q/E283Q | E269Q/E283Q |
| pI_(+)_isosteric_E272Q/E283Q | E272Q/E283Q |
| pI_(+)_isosteric_E269Q | E269Q |

Figure 6

Ablation Variants

G236R
S239G
S239K
S239Q
S239R
V266D
S267K
S267R
H268K
E269R
299R
299K
K322A
A327G
A327L
A327N
A327Q
L328E
P329K
A330L
A330S/P331S
I332K
I332R
V266D/A327Q
V266D/P329K
S267R/A327Q
S267R/P329K
G236R/L328R
E233P/L234V/L235A/G236_/S239K
E233P/L234V/L235A/G236_/S267K
E233P/L234V/L235A/G236_/S239K/A327G
E233P/L234V/L235A/G236_/S267K/A327G
E233P/L234V/L235A/G236_
S239K/S267K
267K/P329K

Figure 7A

| **scIL-15/Rα-Fc monomer (-)** | **scFv-Fc monomer (+)** |
|---|---|
| C220S | C220S |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7B

| **scFv-Fc monomer (-)** | **IL-15Rα(sushi)-Fc monomer (+)** |
|---|---|
| C220S | C220S |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7C

| **scIL-15/Rα-Fc monomer (-)** | **Heavy Chain (+)** |
|---|---|
| C220S | |
| Heterodimer skew variants L368D/K370S | Heterodimer skew variants S364K/E357Q |
| Isosteric pI substitutions Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7D

| **Heavy Chain (-)** | **IL-15Rα(sushi)-Fc monomer (+)** |
|---|---|
| | C220S |
| Heterodimer skew variants L368D/K370S | Heterodimer skew variants S364K/E357Q |
| Isosteric pI substitutions N208D/Q295E/N384D/Q418E/N421D | |
| FcKO E233P/L234V/L235A/G236_/S267K | FcKO E233P/L234V/L235A/G236_/S267K |
| ±M428L/N434S | ±M428L/N434S |

Figure 7E

| **Heavy Chain-IL-15Rα(sushi) (-)** | **Heavy Chain (+)** |
|---|---|
| Heterodimer skew variants L368D/K370S | Heterodimer skew variants S364K/E357Q |
| Isosteric pI substitutions<br>N208D/Q295E/N384D/Q418E/N421D | Isosteric pI subsitutions<br>Q196K/I199T/P217R/P228R/N276K |
| FcKO<br>E233P/L234V/L235A/G236_/S267K | FcKO<br>E233P/L234V/L235A/G236_/S267K |
| ±M428L/N434S | ±M428L/N434S |

Figure 7F

| **Heavy Chain (-)** | **Heavy Chain-IL-15Rα(sushi) (+)** |
|---|---|
| Heterodimer skew variants L368D/K370S | Heterodimer skew variants S364K/E357Q |
| Isosteric pI substitutions<br>N208D/Q295E/N384D/Q418E/N421D | Isosteric pI subsitutions<br>Q196K/I199T/P217R/P228R/N276K |
| FcKO<br>E233P/L234V/L235A/G236_/S267K | FcKO<br>E233P/L234V/L235A/G236_/S267K |
| ±M428L/N434S | ±M428L/N434S |

Figure 8

| **Name** | **Sequence** | **SEQ ID NO:** |
|---|---|---|
| $(GGGGS)_1$ or GGGGS | GGGGS | SEQ ID NO: 14 |
| $(GGGGS)_2$ | GGGGSGGGGS | SEQ ID NO: 15 |
| $(GGGGS)_3$ | GGGGSGGGGSGGGGS | SEQ ID NO: 16 |
| $(GGGGS)_4$ | GGGGSGGGGSGGGGSGGGGS | SEQ ID NO: 17 |
| $(GGGGS)_5$ | GGGGSGGGGSGGGGSGGGGSGGGGS | SEQ ID NO: 18 |
| $(GGGGS)_6$ | GGGGSGGGGSGGGGSGGGGSGGGGSGGGGS | SEQ ID NO: 19 |
| $(GGGGS)_7$ | GGGGSGGGGSGGGGSGGGGSGGGGSGGGGSGGGGS | SEQ ID NO: 20 |
| 30AA-linker | DPALVHQRPAPPGGGGSGGGGSGGGGSGGG | SEQ ID NO: 21 |
| $(GKPGS)_1$ or GKPGS | GKPGS | SEQ ID NO: 22 |
| $(GKPGS)_5$ | GKPGSGKPGSGKPGSGKPGSGKPGS | SEQ ID NO: 23 |
| $(GKPGS)_6$ | GKPGSGKPGSGKPGSGKPGSGKPGSGKPGS | SEQ ID NO: 24 |
| $(GGGES)_1$ or GGGES | GGGES | SEQ ID NO: 25 |

<u>Additional useful domain linkers</u>

| | |
|---|---|
| KTHTCPPCP ("half hinge") | SEQ ID NO: 26 |
| EPKSSDKTHTCPPCP ("full hinge C220S variant") | SEQ ID NO: 27 |
| GGGGSGGGGSKTHTCPPCP ("flex half hinge") | SEQ ID NO: 28 |
| GKPGSGKPGSKTHTCPPCP ("charged half hinge1") | SEQ ID NO: 29 |
| GKPGSKTHTCPPCP ("charged half hinge2") | SEQ ID NO: 30 |

Figure 9A

Positive Charged scFv Linkers

| Name | Sequence | Length | Charge | SEQ ID NO: |
|---|---|---|---|---|
| Gly-Ser 15 | GGGGSGGGGSGGGGS | 15 | 0 | SEQ ID NO: 31 |
| Whitlow linker | GSTSGSGKPGSGEGSTKG | 18 | +1 | SEQ ID NO: 32 |
| 6paxA_1 (+A) | IRPRAIGGSKPRVA | 14 | +4 | SEQ ID NO: 33 |
| +B | GKGGSGKGGSGKGGS | 15 | +3 | SEQ ID NO: 34 |
| +C | GGKGSGGKGSGGKGS | 15 | +3 | SEQ ID NO: 35 |
| +D | GGGKSGGGKSGGGKS | 15 | +3 | SEQ ID NO: 36 |
| +E | GKGKSGKGKSGKGKS | 15 | +6 | SEQ ID NO: 37 |
| +F | GGGKSGGKGSGKGGS | 15 | +3 | SEQ ID NO: 38 |
| +G | GKPGSGKPGSGKPGS | 15 | +3 | SEQ ID NO: 39 |
| +H | GKPGSGKPGSGKPGSGKPGS | 20 | +4 | SEQ ID NO: 40 |
| +I | GKGKSGKGKSGKGKSGKGKS | 20 | +8 | SEQ ID NO: 41 |

Figure 9B

Negative Charged scFv Linkers

| Name | Sequence | Length | Charge | SEQ ID NO: |
|---|---|---|---|---|
| Gly-Ser 20 | GGGGSGGGGSGGGGSGGGGS | 20 | 0 | SEQ ID NO: 42 |
| 3hsc_2 (-A) | STAGDTHLGGEDFD | 14 | -4 | SEQ ID NO: 43 |
| -B | GEGGSGEGGSGEGGS | 15 | -3 | SEQ ID NO: 44 |
| -C | GGEGSGGEGSGGEGS | 15 | -3 | SEQ ID NO: 45 |
| -D | GGGESGGGESGGGES | 15 | -3 | SEQ ID NO: 46 |
| -E | GEGESGEGESGEGES | 15 | -6 | SEQ ID NO: 47 |
| -F | GGGESGGEGSGEGGS | 15 | -3 | SEQ ID NO: 48 |
| -G | GEGESGEGESGEGESGEGES | 20 | -8 | SEQ ID NO: 49 |

Figure 9C

Additional scFv Linkers

| | |
|---|---|
| GGGGSGGGGSGGGGS | SEQ ID NO: 50 |
| GGGGSGGGGSGGGGSGGGGS | SEQ ID NO: 51 |
| GSTSGSGKPGSGEGSTKG | SEQ ID NO: 52 |
| PRGASKSGSASQTGSAPGS | SEQ ID NO: 53 |
| GTAAAGAGAAGGAAAGAAG | SEQ ID NO: 54 |
| GTSGSSGSGSGGSGSGGGG | SEQ ID NO: 55 |
| GKPGSGKPGSGKPGSGKPGS | SEQ ID NO: 56 |

Figure 10

IL-15/Rα x anti-LAG-3 Backbone 1

>Chain 1 (SEQ ID NO: 57)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSNT
KVDKKVEPKSCDKTHTCPPCPAPPVAGPSVFLFPPKPKDTLMISRTPEVTCVVVDVKHEDPEVKFNWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWESNGQPENNYKTTPP
VLDSDGSFFLYSKLTVDKSRWQQGNVFSCSVMHEALHNHYTQKSLSLSPGK

>Chain 2 (SEQ ID NO: 58)
/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTV
LHQDWLNGKEYKCKVSNKALPAPIEKTISKAKGQPREPQVYTLPPSREEMTKNQVSLTCDVSGFYPSDIAVEWESDGQPENNYKTTPPVLDSD
GSFFLYSKLTVDKSRWEQGDVFSCSVMHEALHNHYTQKSLSLSPGK

IL-15/Rα x anti-LAG-3 Backbone 2

>Chain 1 (SEQ ID NO: 59)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSDT
KVDKKVEPKSCDKTHTCPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVEWESDGQPENNYKTTPP
VLDSDGSFFLYSKLTVDKSRWEQGDVFSCSVMHEALHNHYTQKSLSLSPGK

>Chain 2 (SEQ ID NO: 60)
/EPKSSDKTHTCPPCPAPPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNGQPENNYKTTPPVLDSD
GSFFLYSKLTVDKSRWQQGNVFSCSVMHEALHNHYTQKSLSLSPGK

IL-15/Rα x anti-LAG-3 Backbone 3

>Chain 1 (SEQ ID NO: 61)
/ASTKGPSVFPLAPSSKSTSGGTAALGCLVKDYFPEPVTVSWNSGALTSGVHTFPAVLQSSGLYSLSSVVTVPSSSLGTQTYICNVNHKPSDT
KVDKKVEPKSCDKTHTCPPCPAPPVAGPSVFLFPPKPKDTLMISRTPEVTCVVVDVKHEDPEVKFNWYVDGVEVHNAKTKPREEEYNSTYRVV
SVLTVLHQDWLNGKEYKCKVSNKALPAPIEKTISKAKGQPREPQVYTLPPSREEMTKNQVSLTCDVSGFYPSDIAVEWESDGQPENNYKTTPP
VLDSDGSFFLYSKLTVDKSRWEQGDVFSCSVMHEALHNHYTQKSLSLSPGK

>Chain 2 (SEQ ID NO: 62)
/ASTKGPSVFPLAPSSKSTSGGTAALGCLVKDYFPEPVTVSWNSGALTSGVHTFPAVLQSSGLYSLSSVVTVPSSSLGTKTYTCNVNHKPSNT
KVDKKVERKSCDKTHTCPRCPAPPVAGPSVFLFPPKPKDTLMISRTPEVTCVVVDVKHEDPEVKFKWYVDGVEVHNAKTKPREEQYNSTYRVV
SVLTVLHQDWLNGKEYKCKVSNKALPAPIEKTISKAKGQPREPQVYTLPPSREQMTKNQVKLTCLVKGFYPSDIAVEWESNGQPENNYKTTPP
VLDSDGSFFLYSKLTVDKSRWQQGNVFSCSVMHEALHNHYTQKSLSLSPGK

Figure 11

Constant Light Chain – Kappa (SEQ ID NO: 63)
/RTVAAPSVFIFPPSDEQLKSGTASVVCLLNNFYPREAKVQWKVDNALQSGNSQESVTEQDSKDSTYSLSSTLTLSKADYEKHKVYACEVTHQ
GLSSPVTKSFNRGEC

Constant Light Chain – Lambda (SEQ ID NO: 64)
/GQPKAAPSVTLFPPSSEELQANKATLVCLISDFYPGAVTVAWKADSSPVKAGVETTTPSKQSNNKYAASSYLSLTP
EQWKSHRSYSCQVTHEGSTVEKTVAPTECS

Figure 12

>7G8[LAG-3]_H0L0 Variable Heavy (SEQ ID NO: 65-68)
EVKLEESGGGLVQPGGSMKLSCAASGFTFSDAWMDWVRQSPEKGLEWVAEIRTKANNHATYYAESVKGRFTISRDDS
KSSVYLQMNSLRAEDTGIYYCTRLANWDWYFDVWGAGTTVTVSS

>7G8[LAG-3]_H0L0 Variable Light (SEQ ID NO: 69-72)
DTVLTQSPASLAVSLGQRATISCKASQSVDYDGDSYMNWYQQKPGQPPKLLIYAASNLESGIPARLSGSGSGTDFTL
NIHPVEEEDAATYYCQQSNEDPFTFGSGTKLEVK

>7G8[LAG-3]_H3L1 Variable Heavy (SEQ ID NO: 73-76)
EVQLVESGGGLVQPGGSLRLSCAASGFTFSDAWMDWVRQAPGKGLEWVAEIRTKANNHATYYAESVKGRFTISRDDS
KSSVYLQMNSLRAEDTAVYYCTRLANWDWYFDVWGQGTTVTVSS

>7G8[LAG-3]_H3L1 Variable Light (SEQ ID NO: 77-80)
DTVLTQSPSSLSASVGDRVTITCRASQSVDYDGDSYMNWYQQKPGKPPKLLIYAASNLESGIPARLSGSGSGTDFTL
TISSLQPEDFATYYCQQSNEDPFTFGSGTKLEIK

7G8[LAG-3]_H3.30_L1.34 Variable Heavy (SEQ ID NO: 81-84)
EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS

7G8[LAG-3]_H3.30_L1.34 Variable Light (SEQ ID NO: 85-88)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK

>2A11[LAG-3]_H0L0 Variable Heavy (SEQ ID NO: 89-92)
EVQLQQSGAELVRSGASVKLSCTASGFNIKDYYMHWVKQRPEQGLEWIGWIDPENGDTEYAPKFQGKATMTADTSSN
TAYLQLSSLTSEDTAVYYCYARGVRQALDYWGQGTSVTVSS

>2A11[LAG-3]_H0L0 Variable Light (SEQ ID NO: 93-96)
DIQMTQTTSSLSASLGDRVTISCRASQDIGNYLNWFQQKPDGTVKLLIYYTSRLHSGVPSRFSGSGSGTDYSLTISN
LEQEDIATYFCQQGNTLPYTFGGGTKLEIK

>2A11[LAG-3]_H1L2 Variable Heavy (SEQ ID NO: 97-100)
EVQLVQSGAEVKKPGATVKISCKASGFNIKDYYMHWVQQAPGKGLEWMGWIDPENGDTEYAPKFQGRVTITADTSTN
TAYMELSSLRSEDTAVYYCYARGVRQALDYWGQGTLVTVSS

>2A11[LAG-3]_H1L2 Variable Light (SEQ ID NO: 101-104)
DIQMTQSPAFLSVTPGEKVTITCQASQDIGNYLNWFQQKPDQTVKLLIYYTSRLHSGVPSRFSGSGSGTDYTFTISS
LEAEDAATYFCQQGNTLPYTFGGGTKVEIK

2A11[LAG-3]_H1.144_L2.142 Variable Heavy (SEQ ID NO: 105-108)
EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS

2A11[LAG-3]_H1.144_L2.142 Variable Light (SEQ ID NO: 109-112)
DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK

Figure 13A

>BMS-986016[LAG-3] Variable Heavy (SEQ ID NO: 113-116)
QVQLQQWGAGLLKPSETLSLTCAVYGGSFSDYYWNWIRQPPGKGLEWIGEINHRGSTNSNPSLKSRVTLSLDTSKNQ
FSLKLRSVTAADTAVYYCAFGYSDYEYNWFDPWGQGTLVTVSS

>BMS-986016[LAG-3] Variable Light (SEQ ID NO: 117-120)
EIVLTQSPATLSLSPGERATLSCRASQSISSYLAWYQQKPGQAPRLLIYDASNRATGIPARFSGSGSGTDFTLTISS
LEPEDFAVYYCQQRSNWPLTFGQGTNLEIK

>IMP731[LAG-3] Variable Heavy (SEQ ID NO: 121-124)
QVQLKESGPGLVAPSQSLSITCTVSGFSLTAYGVNWVRQPPGKGLEWLGMIWDDGSTDYNSALKSRLSISKDNSKSQ
VFLKMNSLQTDDTARYYCAREGDVAFDYWGQGTTLTVSS

>IMP731[LAG-3] Variable Light (SEQ ID NO: 125-128)
DIVMTQSPSSLAVSVGQKVTMSCKSSQSLLNGSNQKNYLAWYQQKPGQSPKLLVYFASTRDSGVPDRFIGSGSGTDF
TLTISSVQAEDLADYFCLQHFGTPPTFGGGTKLEIKR

>13E2[LAG-3] Variable Heavy (SEQ ID NO: 129-132)
QVTLKESGPGILQPSQTLSLTCSFSGFSLSTSGMGLGWIRQPSGKGLEWLTHIWWDDIKRYNPDLRSRLTISKDTSS
SQIFLKIASVDTADTATYYCARIVEGSYSSSYFDVWGAGTTVTVSS

>13E2[LAG-3] Variable Light (SEQ ID NO: 133-136)
DIVMTQPHKFMSTSVEDRVTITCKASQDVIFDVAWYQQKPGQSPKLLIYSASSRVSGVPDRFTGSGSGTDFTFTISS
VQAEDLAVYYCQQHYSTPYTFGGGTTLEIK

>34F4[LAG-3] Variable Heavy (SEQ ID NO: 137-140)
QVTLKESGPGILQPSQTLSLTCSFSGFSLNTSGMGVGWIRQPSGKGLEWLTHIWWDDVKRYNPALKSRLTISKDTSS
SQVFLKIASVDTADTATYYCARIEGDTYYDYYFDYWGQGVTLTVSS

>34F4[LAG-3] Variable Light (SEQ ID NO: 141-144)
DIVMTQSHKLMSTSVGDGLSITCKASQDVSIAVVWYQQKPGQSPKLLIYSASFRYTGVPDRFTGSGSGTDFTFTISS
VQAEDLAVYYCQQHYSIPWTFGGGTKLEIK

>IMP761[LAG-3] Variable Heavy (SEQ ID NO: 145-148)
QITLKESGPTLVKPTQTLTLTCTFSGFSLSTSGMGLGWIRQPPGKTLEWLTHIWWDDIKRYNPDLRSRLSITKDTSK
NQVVLTMTNMDPLDTGTYYCARIVEGSYSSSYFDVWGQGTLVTVSS

>IMP761[LAG-3] Variable Light (SEQ ID NO: 149-152)
DIVMTQTPSSLSASVGDRVTITCKASQDVIFDVAWYQQRPGQAPKLLIYSASSRVSGVPSRFSGSGSGTDFTLTISS
LQPEDFATYYCQQHYSTPYTFGQGTRLDIK

>H5L7[LAG-3] Variable Heavy (SEQ ID NO: 153-156)
QVQLQESGPGLVKPSETLSLTCTVSGFSLTAYGVNWIRQPPGKGLEWIGMIWDDGSTDYDSALKSRVTISVDTSKNQ
FSLKLSSVTAADTAVYYCAREGDVAFDYWGQGTLVTVSS

>H5L7[LAG-3] Variable Light (SEQ ID NO: 157-160)
DIQMTQSPSSLSASVGDRVTITCKSSQSLLNPSNQKNYLAWYQQKPGKAPKLLVYFASTRDSGVPSRFSGSGSGTDF
TLTISSLQPEDFATYYCLQHFGTPPTFGQGTKLEIKR

>hu22D2[LAG-3] Variable Heavy (SEQ ID NO: 161-164)
QMQLVQSGPEVKKPGTSVKVSCKASGYTFTDYNVDWVRQARGQRLEWIGDINPNNGGTIYAQKFQERVTITVDKSTS
TAYMELSSLRSEDTAVYYCARNYRWFGAMDHWGQGTTVTVSS

Figure 13B

>hu22D2[LAG-3] Variable Light (SEQ ID NO: 165-168)
DIVMTQTPLSLSVTPGQPASISCKASQSLDYEGDSDMNWYLQKPGQPPQLLIYGASNLESGVPDRFSGSGSGTDFTL
KISRVEAEDVGVYYCQQSTEDPRTFGGGTKVEIK

>H4sH15482P[LAG-3] Variable Heavy (SEQ ID NO: 169-172)
QVQLVESGGGVVQPGRSLRLSCVASGFTFSSYGMHWVRQAPGKGLEWVAIIWYDGSNKYYADSVKGRFTISRDNSKN
TQYLQMNSLRAEDTAVYYCASVATSGDFDYYGMDVWGQGTTVTVSS

>H4sH15482P[LAG-3] Variable Light (SEQ ID NO: 173-176)
EIVLTQSPATLSLSPGERTTLSCRASQRISTYLAWYQQKPGQAPRLLIYDASKRATGIPARFSGSGSGTGFTLTISS
LEPEDFAVYYCQQRSNWPLTFGGGTKVEIK

>L35D4[LAG-3] Variable Heavy (SEQ ID NO: 177-180)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L35D4[LAG-3] Variable Light (SEQ ID NO: 181-184)
QSVLTQPPSASGSPGQSVTISCTGTSSDVGGYNYVSWYQQYPGKAPRLMIFEVTERASGVPDRFSGSKSGNTASLTV
SGLQTEDEAVYFCSSYSGSNNPGAMFGGGTKLTVL

>L35G6[LAG-3] Variable Heavy (SEQ ID NO: 185-188)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L35G6[LAG-3] Variable Light (SEQ ID NO: 189-192)
QAGLTQPASVSGSPGQSITISCTGSSSDVGGYSYVSWYQKHPGKAPKLMIYDVTNRPSGVSNRFSGSKSGNTASLTI
SGLQAEDEADYYCSTYTRSNTLVFGPGTKVTVL

>L33H11[LAG-3] Variable Heavy (SEQ ID NO: 193-196)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L33H11[LAG-3] Variable Light (SEQ ID NO: 197-200)
LPVLTQPASVSGSPGQSITISCTGTSSDVGGYNYVSWYQQHPGKAPKLMIYDVTNRPSGVSNRFSGSKSGNTASLTI
SGLQAEDEADYYCSSYTSSNTLLFGGGTQLTVL

>L32A9[LAG-3] Variable Heavy (SEQ ID NO: 201-204)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L32A9[LAG-3] Variable Light (SEQ ID NO: 205-208)
QSVVTQPPSVSAAPGQKVTISCSGSSSNIGNNYVSWYQQLPGTAPKLLIYDNNKRHSGIPDRFSGSTSDTSATLGIT
RLQTGDEADYYCGTWDSSLSAYVFGTGTKVTVL

>L32D10[LAG-3] Variable Heavy (SEQ ID NO: 209-212)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L32D10[LAG-3] Variable Light (SEQ ID NO: 213-216)
QSVLTQPPSASGSPGQSVTISCTGTSSDVGGYDYVSWYQQHQGKAPKLMIYDVSNRPSGVSNRFSGSKSGNTASLTI
SGLQAEDEADYYCSSYTSSTTLVFGGGTKLTVL

Figure 13C

>L32A4[LAG-3] Variable Heavy (SEQ ID NO: 217-220)
QVQLVQSGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L32A4[LAG-3] Variable Light (SEQ ID NO: 221-224)
QSVLTQPASVSGSPGQSITISCTGTSSDIGAYNFVSWYQQHPGKAPKLMIYGVSNRPSGVSSRFSGSKSGSTASLTI
SGLQAEDEADYYCSSYTTSGSAVFGTGTKLTVL

>L3A1[LAG-3] Variable Heavy (SEQ ID NO: 225-228)
EVQLLESGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L3A1[LAG-3] Variable Light (SEQ ID NO: 229-232)
QSVLTQPASVSGSPGQSITISCTGTSSDIGAYNFVSWYQQHPGKAPKLMIYGVSNRPSGVSSRFSGSKSGSTASLTI
TGLQAEDEADYYCSSYTTSGSAVFGTGTKLTVL

>L3A10[LAG-3] Variable Heavy (SEQ ID NO: 233-236)
EVQLLESGGGVVQPGRSLRVSCAASGFTFSNHAMHWVRQAPGKGLEWVAVISYDGSKKFYSDSVRGRFTISRDNSKN
TLYLQMNSLRPEDTAVYYCAKGAHGYTSGWHDYWGQGTLVTVSS

>L3A10[LAG-3] Variable Light (SEQ ID NO: 237-240)
DVVMTQSPSSLSASVGDRVSITCRASQNIGRYLNWYQQKPGKAPKLLVSAASSLQGGVPSRFSGSGSGTDFTLTISR
LQPEDFATYFCQQTYSSPQCTFGQGTKVDIK

>L3C5[LAG-3] Variable Heavy (SEQ ID NO: 241-244)
QVQLVQSGSELKKPGASVKVSCKASGYTFTNYYMHWVRQAPGQGLEWMGIINPSGGATNYAQKFQGRVTMTRDTSTS
TVYMELSSLRSEDTAVYYCARDSGYDLGYGMDVWGQGTLVTVSS

>L3C5[LAG-3] Variable Light (SEQ ID NO: 245-248)
QSVLTQPASVSGSPGQSITISCTGTSSDVGGYNYVSWYQQHPGKAPKLMIYDVSNRPSGASNRFSGSKSGNTASLTI
SGLQAEDEADYYCSSYTNRNTLLFGGGTKLTVL

>L3E3[LAG-3] Variable Heavy (SEQ ID NO: 249-252)
EVQLLESGAEVKKPGASVKVSCKASGYTFTSYYMHWVRQAPGQGLEWMGIINPSAGSTSYAQKFQGRVTMTRDTSTS
TVYMELSSLRSEDTAVYYCARELMATGGFDYWGQGTLVTVSS

>L3E3[LAG-3] Variable Light (SEQ ID NO: 253-256)
QSVLTQPASASGSPGQSITISCTGTSSDVGGYNYVSWYQQHPGKAPKLMIYDVSNRPSGVSNRFSGSKSGNTASLTI
SGLQAEDEANYYCSSYTSSSTNVFGTGTKVTVL

Figure 15

IL-15Rα(sushi-D96) (SEQ ID NO: 257)
ITCPPPMSVEHADIWVKSYSLYSRERYICNSGFKRKAGTSSLTECVLNKATNVAHWTTPSLKCIRD

IL-15Rα(sushi-D96/P97) (SEQ ID NO: 258)
ITCPPPMSVEHADIWVKSYSLYSRERYICNSGFKRKAGTSSLTECVLNKATNVAHWTTPSLKCIRDP

IL-15Rα(sushi-D96/P97/A98) (SEQ ID NO: 259)
ITCPPPMSVEHADIWVKSYSLYSRERYICNSGFKRKAGTSSLTECVLNKATNVAHWTTPSLKCIRDPA

Figure 16

IL-15 (E87C) (SEQ ID NO: 260)
NWVNVISDLKKIEDLIQSMHIDATLYTESDVHPSCKVTAMKCFLLELQVISLESGDASIHDTVENLIILANNSLSSN
GNVTESGCKCCEELEEKNIKEFLQSFVHIVQMFINTS

IL-15 (V49C) (SEQ ID NO: 261)
NWVNVISDLKKIEDLIQSMHIDATLYTESDVHPSCKVTAMKCFLLELQCISLESGDASIHDTVENLIILANNSLSSN
GNVTESGCKECEELEEKNIKEFLQSFVHIVQMFINTS

IL-15 (L52C) (SEQ ID NO: 262)
NWVNVISDLKKIEDLIQSMHIDATLYTESDVHPSCKVTAMKCFLLELQVISCESGDASIHDTVENLIILANNSLSSN
GNVTESGCKECEELEEKNIKEFLQSFVHIVQMFINTS

IL-15 (E89C) (SEQ ID NO: 263)
NWVNVISDLKKIEDLIQSMHIDATLYTESDVHPSCKVTAMKCFLLELQVISLESGDASIHDTVENLIILANNSLSSN
GNVTESGCKECCELEEKNIKEFLQSFVHIVQMFINTS

IL-15 (Q48C) (SEQ ID NO: 264)
NWVNVISDLKKIEDLIQSMHIDATLYTESDVHPSCKVTAMKCFLLELCVISLESGDASIHDTVENLIILANNSLSSN
GNVTESGCKECEELEEKNIKEFLQSFVHIVQMFINTS

IL-15 (E53C) (SEQ ID NO: 265)
NWVNVISDLKKIEDLIQSMHIDATLYTESDVHPSCKVTAMKCFLLELQVISLCSGDASIHDTVENLIILANNSLSSN
GNVTESGCKECEELEEKNIKEFLQSFVHIVQMFINTS

IL-15 (C42S) (SEQ ID NO: 266)
NWVNVISDLKKIEDLIQSMHIDATLYTESDVHPSCKVTAMKSFLLELQVISLESGDASIHDTVENLIILANNSLSSN
GNVTESGCKECEELEEKNIKEFLQSFVHIVQMFINTS

IL-15 (L45C) (SEQ ID NO: 267)
NWVNVISDLKKIEDLIQSMHIDATLYTESDVHPSCKVTAMKCFLCELQVISLESGDASIHDTVENLIILANNSLSSN
GNVTESGCKECEELEEKNIKEFLQSFVHIVQMFINTS

Figure 17

IL-15Rα(sushi-D96/C97) (SEQ ID NO: 268)
ITCPPPMSVEHADIWVKSYSLYSRERYICNSGFKRKAGTSSLTECVLNKATNVAHWTTPSLKCIRDC

IL-15Rα(sushi-D96/P97/C98) (SEQ ID NO: 269)
ITCPPPMSVEHADIWVKSYSLYSRERYICNSGFKRKAGTSSLTECVLNKATNVAHWTTPSLKCIRDPC

IL-15Rα(sushi-D96/C97/A98) (SEQ ID NO: 270)
ITCPPPMSVEHADIWVKSYSLYSRERYICNSGFKRKAGTSSLTECVLNKATNVAHWTTPSLKCIRDCA

IL-15Rα(sushi-S40C) (SEQ ID NO: 271)
ITCPPPMSVEHADIWVKSYSLYSRERYICNSGFKRKAGTCSLTECVLNKATNVAHWTTPSLKCIR

IL-15Rα(sushi-K34C) (SEQ ID NO: 272)
ITCPPPMSVEHADIWVKSYSLYSRERYICNSGFCRKAGTSSLTECVLNKATNVAHWTTPSLKCIR

IL-15Rα(sushi-G38C) (SEQ ID NO: 273)
ITCPPPMSVEHADIWVKSYSLYSRERYICNSGFKRKACTSSLTECVLNKATNVAHWTTPSLKCIR

IL-15Rα(sushi-L42C) (SEQ ID NO: 274)
ITCPPPMSVEHADIWVKSYSLYSRERYICNSGFKRKAGTSSCTECVLNKATNVAHWTTPSLKCIR

IL-15Rα(sushi-A37C) (SEQ ID NO: 275)
ITCPPPMSVEHADIWVKSYSLYSRERYICNSGFKRKCGTSSLTECVLNKATNVAHWTTPSLKCIR

Figure 19A

N1D (SEQ ID NO: 276)
DWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

N4D (SEQ ID NO: 277)
NWVDVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D8N (SEQ ID NO: 278)
NWVNVISNLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D30N (SEQ ID NO: 279)
NWVNVISDLKKIEDLIQSMHIDATLYTESNVHPSCKVTAMKCFLLELQVISLESGDASIHDTVENLIILANNSLSSNGNVTESGCKECEELEE
KNIKEFLQSFVHIVQMFINTS

D61N (SEQ ID NO: 280)
NWVNVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

E64Q (SEQ ID NO: 281)
NWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

N65D (SEQ ID NO: 282)
NWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

Q108E (SEQ ID NO: 283)
NWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVEMFINTS

N1D/D61N (SEQ ID NO: 284)
DWVNVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

N1D/E64Q (SEQ ID NO: 285)
DWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

N4D/D61N (SEQ ID NO: 286)
NWVDVISDLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

N4D/E64Q (SEQ ID NO: 287)
NWVDVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

D8N/D61N (SEQ ID NO: 288)
NWVNVISNLKKIEDLIQSMHIDATLYTESDVHPSCKVTAMKCFLLELQVISLESGDASIHNTVENLIILANNSLSSNGNVTESGCKECEELEE
KNIKEFLQSFVHIVQMFINTS

Figure 19B

D8N/E64Q (SEQ ID NO: 289)
NWVNVISNLKKIEDLIQSMHIDATLYTESDVHPSCKVTAMKCFLLELQVISLESGDASIHDTVQNLIILANNSLSSNGNVTESGCKECEELEE
KNIKEFLQSFVHIVQMFINTS

D61N/E64Q (SEQ ID NO: 290)
NWVNVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVQMFINTS

E64Q/Q108E (SEQ ID NO: 291)
NWVNVISDLKKIEDLIQSMHIDATLYTESDVHPSCKVTAMKCFLLELQVISLESGDASIHDTVQNLIILANNSLSSNGNVTESGCKECEELEE
KNIKEFLQSFVHIVEMFINTS

N1D/N4D/D8N (SEQ ID NO: 292)
DWVDVISNLKKIEDLIQSMHIDATLYTESDVHPSCKVTAMKCFLLELQVISLESGDASIHDTVENLIILANNSLSSNGNVTESGCKECEELEE
KNIKEFLQSFVHIVQMFINTS

D61N/E64Q/N65D (SEQ ID NO: 293)
NWVNVISDLKKIEDLIQSMHIDATLYTESDVHPSCKVTAMKCFLLELQVISLESGDASIHNTVQDLIILANNSLSSNGNVTESGCKECEELEE
KNIKEFLQSFVHIVQMFINTS

N1D/D61N/E64Q/Q108E (SEQ ID NO: 294)
DWVNVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVEMFINTS

N4D/D61N/E64Q/Q108E (SEQ ID NO: 295)
NWVDVISDLKKIEDLIQSMHIDATLYTESDVHPSCKVTAMKCFLLELQVISLESGDASIHNTVQNLIILANNSLSSNGNVTESGCKECEELEE
KNIKEFLQSFVHIVEMFINTS

N1D/N65D (SEQ ID NO: 296)
DWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

N1D/Q108E (SEQ ID NO: 297)
DWVNVISDLKKIEDLIQSMHIDATLYTESDVHPSCKVTAMKCFLLELQVISLESGDASIHDTVENLIILANNSLSSNGNVTESGCKECEELEE
KNIKEFLQSFVHIVEMFINTS

N4D/N65D (SEQ ID NO: 298)
NWVDVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

D30N/N65D (SEQ ID NO: 299)
NWVNVISDLKKIEDLIQSMHIDATLYTESNVHPSCKVTAMKCFLLELQVISLESGDASIHDTVEDLIILANNSLSSNGNVTESGCKECEELEE
KNIKEFLQSFVHIVQMFINTS

D30N/Q108E (SEQ ID NO: 300)
NWVNVISDLKKIEDLIQSMHIDATLYTESNVHPSCKVTAMKCFLLELQVISLESGDASIHDTVENLIILANNSLSSNGNVTESGCKECEELEE
KNIKEFLQSFVHIVEMFINTS

N65D/Q108E (SEQ ID NO: 301)
NWVNVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVEMFINTS

Figure 19C

E64Q/N65D (SEQ ID NO: 302)
NWVNVISDLKKIEDLIQSMHIDATLYTESDVHPSCKVTAMKCFLLELQVISLESGDASIHDTVQDLIILANNSLSSNGNVTESGCKECEELEE
KNIKEFLQSFVHIVQMFINTS

N1D/N4D/N65D (SEQ ID NO: 303)
DWVDVISDLKKIEDLIQSMHIDATLYTESDVHPSCKVTAMKCFLLELQVISLESGDASIHDTVEDLIILANNSLSSNGNVTESGCKECEELEE
KNIKEFLQSFVHIVQMFINTS

D30N/E64Q/N65D (SEQ ID NO: 304)
NWVNVISDLKKIEDLIQSMHIDATLYTESNVHPSCKVTAMKCFLLELQVISLESGDASIHDTVQDLIILANNSLSSNGNVTESGCKECEELEE
KNIKEFLQSFVHIVQMFINTS

N4D/D61N/N65D (SEQ ID NO: 305)
NWVDVISDLKKIEDLIQSMHIDATLYTESDVHPSCKVTAMKCFLLELQVISLESGDASIHNTVEDLIILANNSLSSNGNVTESGCKECEELEE
KNIKEFLQSFVHIVQMFINTS

Figure 20

| XENP | Variant | EC50 pM (NK cells) | Fold reduced (NK cells) | EC50 pM (CD8 T cells) | Fold reduced (CD8 T cells) |
|---|---|---|---|---|---|
| 20818 | WT | 200.6 | | 637.1 | |
| 21478 | single-chain | 848.5 | 4.2 | 4982.0 | 7.8 |
| 22815 | N1D | 281.3 | 1.4 | 1051.0 | 1.6 |
| 22816 | N4D | 321.9 | 1.6 | 1190.0 | 1.9 |
| 22817 | D8N | very weak | very weak | very weak | very weak |
| 22818 | D30N | 376.3 | 1.9 | 1366.0 | 2.1 |
| 22819 | D61N | 5934.0 | 29.6 | 161937.0 | >100 |
| 22820 | E64Q | 877.0 | 4.4 | 2858.0 | 4.5 |
| 22821 | N65D | 2883.0 | 14.4 | 6928.0 | 10.9 |
| 22822 | Q108E | 9777.0 | 48.7 | very weak | >100 |
| 22823 | N1D/D61N | 918.0 | 4.6 | 4225.0 | 6.6 |
| 22824 | N1D/E64Q | 1091.0 | 5.4 | 4228.0 | 6.6 |
| 22825 | N4D/D61N | 309.0 | 1.5 | 1070.0 | 1.7 |
| 22826 | N4D/E64Q | very weak | very weak | very weak | very weak |
| 22827 | D8N/D61N | ND | ND | ND | ND |
| 22828 | D8N/E64Q | 597.7 | 3.0 | 1658.0 | 2.6 |
| 22829 | D61N/E64Q | 458.2 | 2.3 | 2115.0 | 3.3 |
| 22830 | E64Q/Q108E | 436.6 | 2.2 | 1815.0 | 2.8 |
| 22831 | N1D/N4D/D8N | very weak | very weak | very weak | very weak |
| 22832 | D61N/E64Q/N65D | ND | ND | ND | ND |
| 22833 | N1D/D61N/E64Q/Q108E | ND | ND | ND | ND |
| 22834 | N4D/D61N/E64Q/Q108E | very weak | very weak | very weak | very weak |

scIL-15/Rα x scFv scFv x ncIL-15/Rα scFv x dsIL-15/Rα scIL-15/Rα x Fab

Example: XENP27972 and XENP27973

Fab x ncIL-15/Rα

Fab x dsIL-15/Rα mAb-scIL-15/Rα mAb-ncIL-15/Rα mAb-dsIL-15/Rα central-IL-15/Rα central-scIL-15/Rα

Figure 22A

>XENP027972 human IL15Ra(sushi) (GGGGS)5-human IL15(N4D/N65D;single-Chain )-7G8[LAG-3] H3.30 L1.34 IgG1 Fc(216) IgG1 pI(- ) Isosteric A C220S/PVA /S267K/L368D/K370S-IgG1 PVA /S267K/S364K/E357Q

*Chain 1 human_IL15Ra(sushi)_(GGGGS)5-human_IL15(N4D/N65D;single-Chain )_Fc(216)_IgG1_pI(-)_Isosteric_A_C220S/PVA_/S267K/L368D/K370S scIL-15/Ra-Fc Chain* (SEQ ID NO: 306-309)
ITCPPPMSVEHADIWVKSYSLYSRERYICNSGFKRKAGTSSLTECVLNKATNVAHWTTPSLKCIR/GGGGSGGGGSG
GGGSGGGGSGGGGS/NWVDVISDLKKIEDLIQSMHIDATLYTESDVHPSCKVTAMKCFLLELQVISLESGDASIHDT
VEDLIILANNSLSSNGNVTESGCKECEELEEKNIKEFLQSFVHIVQMFINTS/EPKSSDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTT
PPVLDSDGSFFLYSKLTVDKSRWEQGDVFSCSVMHEALHNHYTQKSLSLSPGK

*Chain 2 7G8[LAG-3]_H3.30_L1.34_Fab_IgG1_PVA_/S267K/S364K/E357Q Fab-Fc Heavy Chain* (SEQ ID NO: 310-314)
EVQLVESGGGLVQPGGSLRLSCAASGFTFDDAWMSWVRQAPGKGLEWVAEISTKANNHATYYAESVKGRFTISRDDS
KSSVYLQMNSLRAEDTAVYYCTRLATWDWYFDVWGQGTTVTVSS/ASTKGPSVFPLAPSSKSTSGGTAALGCLVKDY
FPEPVTVSWNSGALTSGVHTFPAVLQSSGLYSLSSVVTVPSSSLGTQTYICNVNHKPSNTKVDKKVEPKSCDKTHTC
PPCPAPPVAGPSVFLFPPKPKDTLMISRTPEVTCVVVDVKHEDPEVKFNWYVDGVEVHNAKTKPREEQYNSTYRVVS
VLTVLHQDWLNGKEYKCKVSNKALPAPIEKTISKAKGQPREPQVYTLPPSREQMTKNQVKLTCLVKGFYPSDIAVEW
ESNGQPENNYKTTPPVLDSDGSFFLYSKLTVDKSRWQQGNVFSCSVMHEALHNHYTQKSLSLSPGK

*Chain 3 7G8[LAG-3]_H3.30_L1.34_Fab Light Chain* (SEQ ID NO: 315-319)
DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

Figure 22B

>XENP027973 human IL15Ra(sushi) (GGGGS)5-human IL15(N4D/N65D;single-Chain )-2A11[LAG-3] H1.144 L2.142 IgG1 Fc(216) IgG1 pI(- ) Isosteric A C220S/PVA /S267K/L368D/K370S-IgG1 PVA /S267K/S364K/E357Q

*Chain 1 human_IL15Ra(sushi)_(GGGGS)5-human_IL15(N4D/N65D;single-Chain )_Fc(216)_IgG1_pI(-)_Isosteric_A_C220S/PVA_/S267K/L368D/K370S scIL-15/Ra-Fc Chain* (SEQ ID NO: 320)
ITCPPPMSVEHADIWVKSYSLYSRERYICNSGFKRKAGTSSLTECVLNKATNVAHWTTPSLKCIR/GGGGSGGGGSG
GGGSGGGGSGGGGS/NWVDVISDLKKIEDLIQSMHIDATLYTESDVHPSCKVTAMKCFLLELQVISLESGDASIHDT
VEDLIILANNSLSSNGNVTESGCKECEELEEKNIKEFLQSFVHIVQMFINTS/EPKSSDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTT
PPVLDSDGSFFLYSKLTVDKSRWEQGDVFSCSVMHEALHNHYTQKSLSLSPGK

*Chain 2 2A11[LAG-3]_H1.144_L2.142_Fab_IgG1_PVA_/S267K/S364K/E357Q Fab-Fc Heavy Chain* (SEQ ID NO: 321)

EVQLVQSGAEVKKPGATVKISCKASGFNIKDYFMHWVQQAPGKGLEWMGWIDPELGDTEYAPKFQGRVTITADTSTN
TAYMELSSLRSEDTAVYYCYARGVYQALDYWGQGTLVTVSS/ASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPPC
PAPPVAGPSVFLFPPKPKDTLMISRTPEVTCVVVDVKHEDPEVKFNWYVDGVEVHNAKTKPREEQYNSTYRVVSVLT
VLHQDWLNGKEYKCKVSNKALPAPIEKTISKAKGQPREPQVYTLPPSREQMTKNQVKLTCLVKGFYPSDIAVEWESN
GQPENNYKTTPPVLDSDGSFFLYSKLTVDKSRWQQGNVFSCSVMHEALHNHYTQKSLSLSPGK

*Chain 3 2A11[LAG-3]_H1.144_L2.142_Fab Light Chain* (SEQ ID NO: 322)

DIQMTQSPAFLSVTPGEKVTITCQASQDIGNYLNWFQQKPGQTVKLLIYFTSYLHSGVPSRFSGSGSGTDYTFTISS
LEAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 23

*XENP016432 Nivolumab_H0L0_IgG1_PVA_/S267K Heavy Chain* (SEQ ID NO: 323)

QVQLVESGGGVVQPGRSLRLDCKASGITFSNSGMHWVRQAPGKGLEWVAVIWYDGSKRYYADSVKGRFTISRDNSKN
TLFLQMNSLRAEDTAVYYCATNDDYWGQGTLVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPPV
AGPSVFLFPPKPKDTLMISRTPEVTCVVVDVKHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK

*XENP016432 Nivolumab_H0L0_IgG1_PVA_/S267K Light Chain* (SEQ ID NO: 324)

EIVLTQSPATLSLSPGERATLSCRASQSVSSYLAWYQQKPGQAPRLLIYDASNRATGIPARFSGSGSGTDFTLTISS
LEPEDFAVYYCQQSSNWPRTFGQGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 29A

>XENP027977 human_IL15Ra(sushi)_(GGGGS)5-human_IL15(N4D/N65D;single-Chain )-7G8[LAG-3]_H3.30_L1.34_IgG1_Fc(216)_IgG1_pI(-)_Isosteric_A_C220S/PVA_/S267K/L368D/K370S/M428L/N434S-IgG1_PVA_/S267K/S364K/E357Q/M428L/N434S

*Chain 1 human_IL15Ra(sushi)_(GGGGS)5-human_IL15(N4D/N65D;single-Chain )_Fc(216)_IgG1_pI(-)_Isosteric_A_C220S/PVA_/S267K/L368D/K370S/M428L/N434S scIL-15/Ra-Fc Chain* (SEQ ID NO: 325)
ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVDVISDLKKIEDLIQSMHIDATLYTESDVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEALHSHYTQKSLSLSPGK

*Chain 2 7G8[LAG-3]_H3.30_L1.34_Fab_IgG1_PVA_/S267K/S364K/E357Q/M428L/N434S Fab-Fc Heavy Chain* (SEQ ID NO: 326)
EVQLVESGGGLVQPGGSLRLSCAASGFTFDDAWMSWVRQAPGKGLEWVAEISTKANNHATYYAESVKGRFTISRDDSKSSVYLQMNSLRAEDTAVYYCTRLATWDWYFDVWGQGTTVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK

*Chain 3 7G8[LAG-3]_H3.30_L1.34_Fab Light Chain* (SEQ ID NO: 327)
DIVLTQSPSSLSASVGDRVTITCRASQSVDYDGDSYMNWYQQKPGKPPKLLIYAASELESGIPARFSGSGSGTDFTLTISSLQPEDFATYYCQQSNEDPFTFGSGTKLEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 29B

>XENP027978 human_IL15Ra(sushi)_(GGGGS)5-human_IL15(N4D/N65D;single-Chain )-2A11[LAG-3]_H1.144_L2.142_IgG1_Fc(216)_IgG1_pI(-)_Isosteric_A_C220S/PVA_/S267K/L368D/K370S/M428L/N434S-IgG1_PVA_/S267K/S364K/E357Q/M428L/N434S

*Chain 1 human_IL15Ra(sushi)_(GGGGS)5-human_IL15(N4D/N65D;single-Chain )_Fc(216)_IgG1_pI(-)_Isosteric_A_C220S/PVA_/S267K/L368D/K370S/M428L/N434S scIL-15/Ra-Fc Chain* (SEQ ID NO: 328)

ITCPPPMSVEHADIWVKSYSLYSRERYICNSGFKRKAGTSSLTECVLNKATNVAHWTTPSLKCIR/GGGGSGGGGSG
GGGSGGGGSGGGGS/NWVDVISDLKKIEDLIQSMHIDATLYTESDVHPSCKVTAMKCFLLELQVISLESGDASIHDT
VEDLIILANNSLSSNGNVTESGCKECEELEEKNIKEFLQSFVHIVQMFINTS/EPKSSDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKE
YKCKVSNKALPAPIEKTISKAKGQPREPQVYTLPPSREEMTKNQVSLTCDVSGFYPSDIAVEWESDGQPENNYKTTP
PVLDSDGSFFLYSKLTVDKSRWEQGDVFSCSVLHEALHSHYTQKSLSLSPGK

*Chain 2 2A11[LAG-3]_H1.144_L2.142_Fab_IgG1_PVA_/S267K/S364K/E357Q/M428L/N434S Fab-Fc Heavy Chain* (SEQ ID NO: 329)

EVQLVQSGAEVKKPGATVKISCKASGFNIKDYFMHWVQQAPGKGLEWMGWIDPELGDTEYAPKFQGRVTITAD
TSTNTAYMELSSLRSEDTAVYYCYARGVYQALDYWGQGTLVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPPVAGPSVFLFPPKPKDTLMISRTPEVTCVVVDVKHEDPEVKFNWYVDGVEVHNAKTKPREEQYNSTYR
VVSVLTVLHQDWLNGKEYKCKVSNKALPAPIEKTISKAKGQPREPQVYTLPPSREQMTKNQVKLTCLVKGFYPSDIA
VEWESNGQPENNYKTTPPVLDSDGSFFLYSKLTVDKSRWQQGNVFSCSVLHEALHSHYTQKSLSLSPGK

*Chain 3 2A11[LAG-3]_H1.144_L2.142_Fab Light Chain* (SEQ ID NO: 330)

DIQMTQSPAFLSVTPGEKVTITCQASQDIGNYLNWFQQKPGQTVKLLIYFTSYLHSGVPSRFSGSGSGTDYTFTISSL
EAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 32
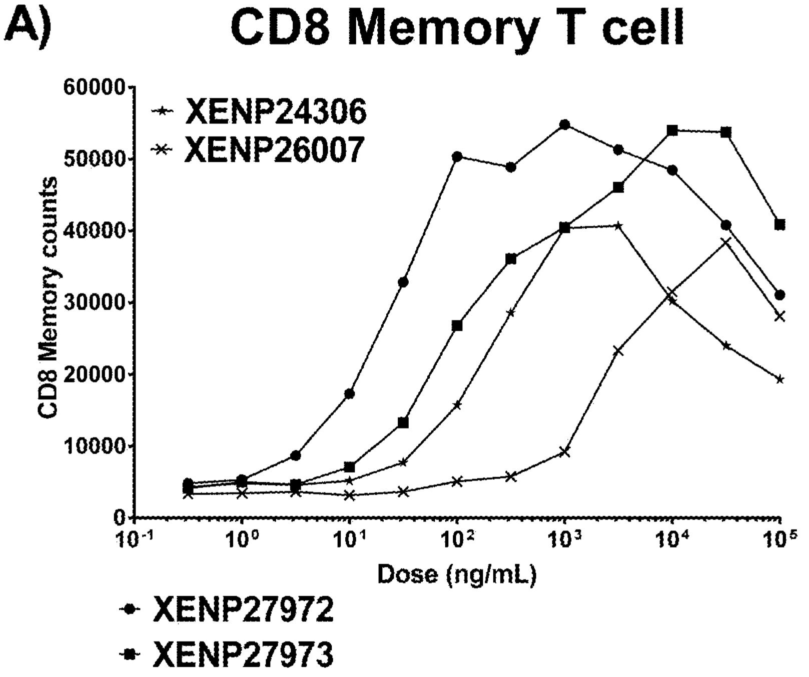
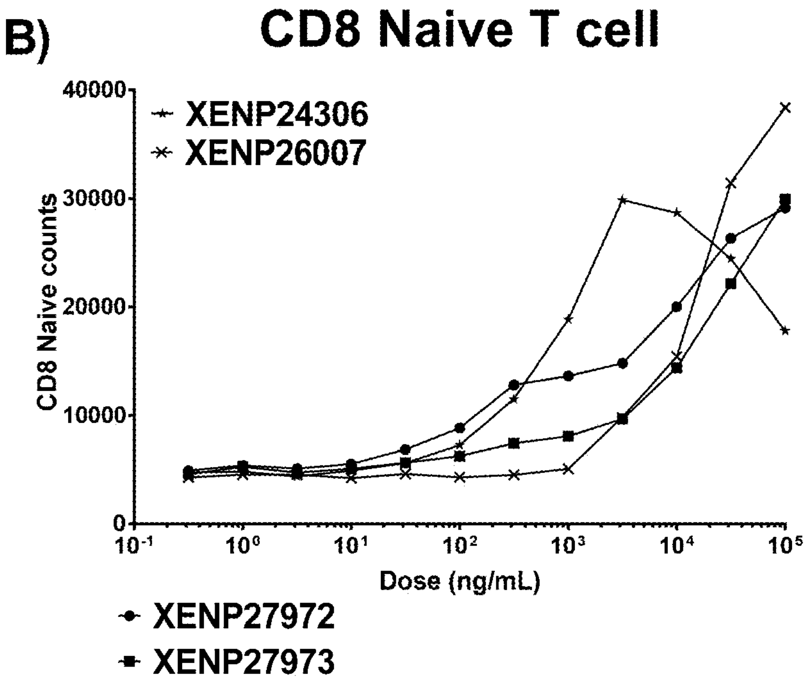

Figure 34
A)
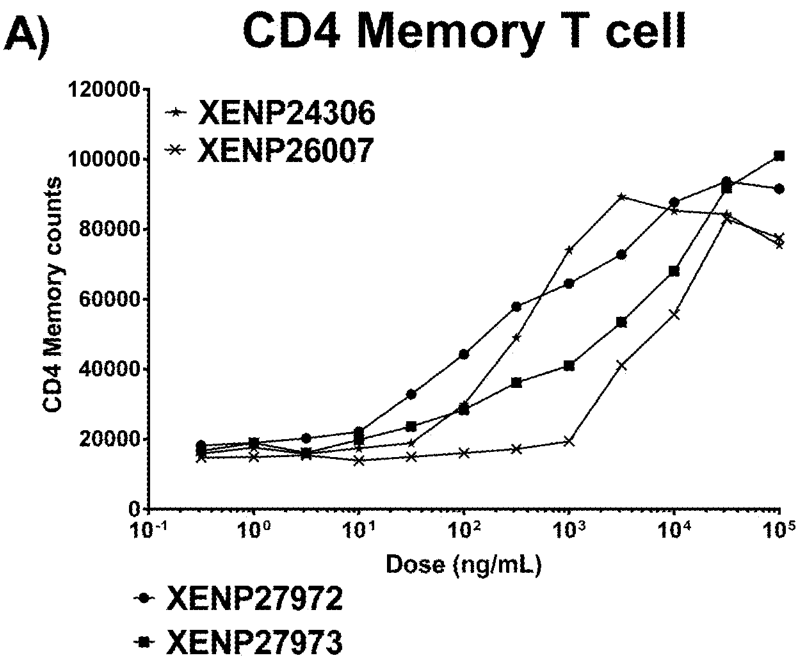
B)
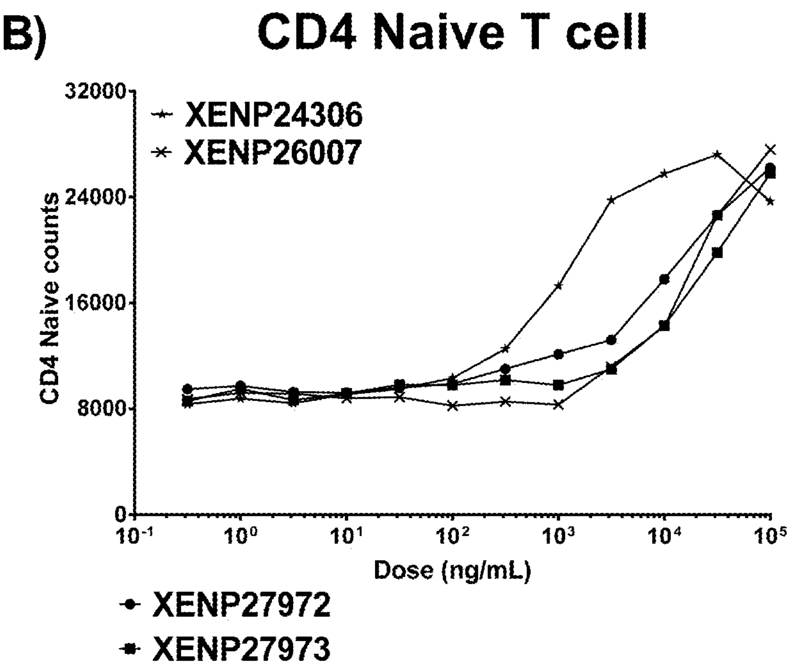

Figure 35
A)
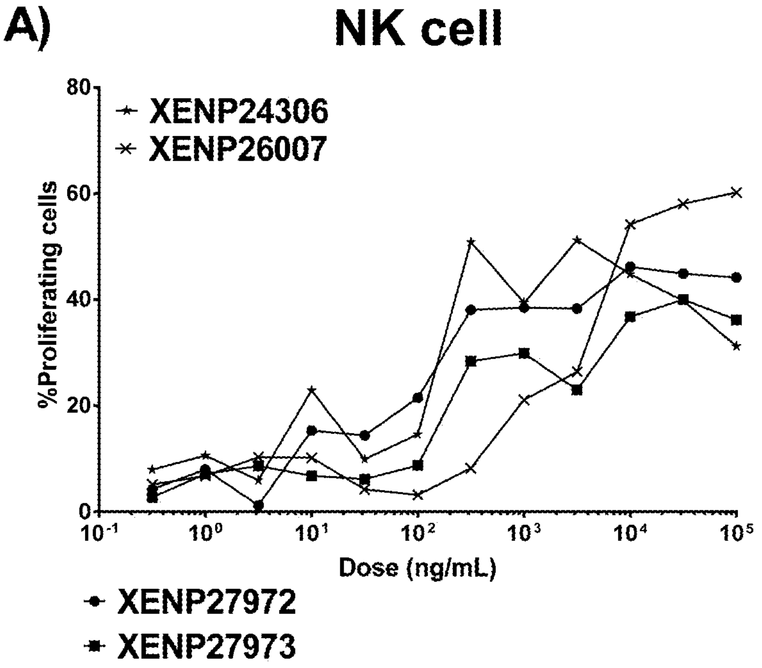
B)
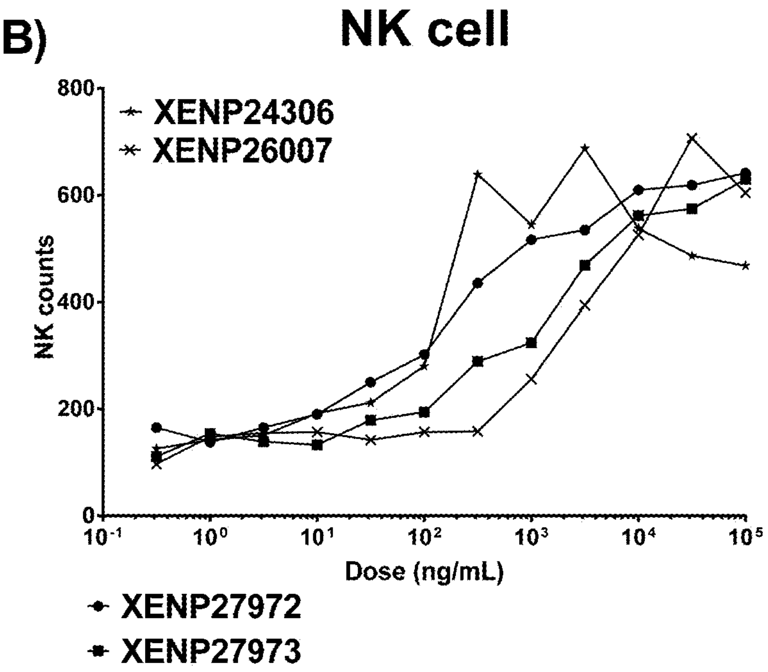

Figure 39

>XENP22853 human_IL15_(GGGGS)1-human_IL15Ra(Sushi)_(GGGGS)1_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S

XENP22853 Chain 1 - human_IL15_(GGGGS)1-Fc(216)_IgG1_pI(-)_Isosteric_A_C220S/PVA_/S267K/L368D/K370S/M428L/N434S (SEQ ID NO: 331)
NWVNVISDLKKIEDLIQSMHIDATLYTESDVHPSCKVTAMKCFLLELQVISLESGDASIHDTVENLII
LANNSLSSNGNVTESGCKECEELEEKNIKEFLQSFVHIVQMFINTS/GGGGS/EPKSSDKTHTCPPCP
APPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTC
DVSGFYPSDIAVEWESDGQPENNYKTTPPVLDSDGSFFLYSKLTVDKSRWEQGDVFSCSVLHEALHSH
YTQKSLSLSPGK

XENP22853 Chain 2 - human_IL15Ra(Sushi)_(GGGGS)1-Fc(216)_IgG1_C220S/PVA_/S267K/S364K/E357Q/M428L/N434S (SEQ ID NO: 332)
ITCPPPMSVEHADIWVKSYSLYSRERYICNSGFKRKAGTSSLTECVLNKATNVAHWTTPSLKCIR/GG
GGS/EPKSSDKTHTCPPCPAPPVAGPSVFLFPPKPKDTLMISRTPEVTCVVVDVKHEDPEVKFNWYVD
GVEVHNAKTKPREEQYNSTYRVVSVLTVLHQDWLNGKEYKCKVSNKALPAPIEKTISKAKGQPREPQV
YTLPPSREQMTKNQVKLTCLVKGFYPSDIAVEWESNGQPENNYKTTPPVLDSDGSFFLYSKLTVDKSR
WQQGNVFSCSVLHEALHSHYTQKSLSLSPGK

Figure 40

>XENP24113 human_IL15_N4D/N65D_(GGGGS)1-human_IL15Ra(Sushi)_(GGGGS)1_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S

XENP24113 Chain 1 - human_IL15_N4D/N65D_(GGGGS)1-Fc(216)_IgG1_pI(-)_Isosteric_A_C220S/PVA_/S267K/L368D/K370S/M428L/N434S (SEQ ID NO: 333)

NWVDVISDLKKIEDLIQSMHIDATLYTESDVHPSCKVTAMKCFLLELQVISLESGDASIHDTVEDLII
LANNSLSSNGNVTESGCKECEELEEKNIKEFLQSFVHIVQMFINTS/GGGGS/EPKSSDKTHTCPPCP
APPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTC
DVSGFYPSDIAVEWESDGQPENNYKTTPPVLDSDGSFFLYSKLTVDKSRWEQGDVFSCSVLHEALHSH
YTQKSLSLSPGK

XENP24113 Chain 2 - human_IL15Ra(Sushi)_(GGGGS)1-Fc(216)_IgG1_C220S/PVA_/S267K/S364K/E357Q/M428L/N434S (SEQ ID NO: 334)

ITCPPPMSVEHADIWVKSYSLYSRERYICNSGFKRKAGTSSLTECVLNKATNVAHWTTPSLKCIR/GG
GGS/EPKSSDKTHTCPPCPAPPVAGPSVFLFPPKPKDTLMISRTPEVTCVVVDVKHEDPEVKFNWYVD
GVEVHNAKTKPREEQYNSTYRVVSVLTVLHQDWLNGKEYKCKVSNKALPAPIEKTISKAKGQPREPQV
YTLPPSREQMTKNQVKLTCLVKGFYPSDIAVEWESNGQPENNYKTTPPVLDSDGSFFLYSKLTVDKSR
WQQGNVFSCSVLHEALHSHYTQKSLSLSPGK

Figure 41

>XENP24294 human_IL15Ra(sushi)_(GGGGS)5-human_IL15_N4D/N65D_(single-Chain)-empty-Fc_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S

XENP24294 Chain 1 - human_IL15Ra(sushi)_(GGGGS)5-human_IL15_N4D/N65D_(single-Chain)-Fc(216)_IgG1_pI(-)_Isosteric_A_C220S/PVA_/S267K/L368D/K370S/M428L/N434S (SEQ ID NO: 335)
ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVDVISDLKKIEDLIQSMHIDATLYTESDVHPSCKVTAMKCFL
LELQVISLESGDASIHDTVEDLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVLHEALHSHYTQKSLSLSPGK

XENP24294 Chain 2 - empty-Fc(216)_IgG1_C220S/PVA_/S267K/S364K/E357Q/M428L/N434S (SEQ ID NO: 336)
EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVLHEALHSHYTQKSLSLSPGK

Figure 42

>XENP24306 human_IL15_D30N/E64Q/N65D_(GGGGS)1-human_IL15Ra(Sushi)_(GGGGS)1_Fc(216)_IgG1_pI(-)_Isosteric_A_C220S/PVA_/S267K/L368D/K370S/M428L/N434S-Fc(216)_IgG1_C220S/PVA_/S267K/S364K/E357Q/M428L/N434S

XENP24306 Chain 1 - human_IL15_D30N/E64Q/N65D_(GGGGS)1-Fc(216)_IgG1_pI(-)_Isosteric_A_C220S/PVA_/S267K/L368D/K370S/M428L/N434S (SEQ ID NO: 337)

NWVNVISDLKKIEDLIQSMHIDATLYTESNVHPSCKVTAMKCFLLELQVISLESGDASIHDTVQDLII
LANNSLSSNGNVTESGCKECEELEEKNIKEFLQSFVHIVQMFINTS/GGGGS/EPKSSDKTHTCPPCP
APPVAGPSVFLFPPKPKDTLMISRTPEVTCVVVDVKHEDPEVKFNWYVDGVEVHNAKTKPREEEYNST
YRVVSVLTVLHQDWLNGKEYKCKVSNKALPAPIEKTISKAKGQPREPQVYTLPPSREEMTKNQVSLTC
DVSGFYPSDIAVEWESDGQPENNYKTTPPVLDSDGSFFLYSKLTVDKSRWEQGDVFSCSVLHEALHSH
YTQKSLSLSPGK

XENP24306 Chain 2 - human_IL15Ra(Sushi)_(GGGGS)1-Fc(216)_IgG1_C220S/PVA_/S267K/S364K/E357Q/M428L/N434S (SEQ ID NO: 338)

ITCPPPMSVEHADIWVKSYSLYSRERYICNSGFKRKAGTSSLTECVLNKATNVAHWTTPSLKCIR/GG
GGS/EPKSSDKTHTCPPCPAPPVAGPSVFLFPPKPKDTLMISRTPEVTCVVVDVKHEDPEVKFNWYVD
GVEVHNAKTKPREEQYNSTYRVVSVLTVLHQDWLNGKEYKCKVSNKALPAPIEKTISKAKGQPREPQV
YTLPPSREQMTKNQVKLTCLVKGFYPSDIAVEWESNGQPENNYKTTPPVLDSDGSFFLYSKLTVDKSR
WQQGNVFSCSVLHEALHSHYTQKSLSLSPGK

Figure 44A

>XENP21993 human_IL15Ra(sushi)_(GGGGS)5-human_IL15(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

Chain 1 - human_IL15Ra(sushi)_(GGGGS)5-human_IL15(single-chain)_Fc(216)_IgG1_pI(-)_Isosteric_A_C220S/PVA_/S267K/L368D/K370S (SEQ ID NO: 339)

ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVNVISDLKKIEDLIQSMHIDATLYTESDVHPSCKVTAMKCFL
LELQVISLESGDASIHDTVENLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVMHEALHNHYTQKSLSLSPGK

Chain 2 - empty_Fc(216)_IgG1_C220S/PVA_/S267K/S364K/E357Q (SEQ ID NO: 340)

EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVMHEALHNHYTQKSLSLSPGK

>XENP24050 human_IL15Ra(sushi)_(GGGGS)5-human_IL15_N4D/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

Chain 1 - human_IL15Ra(sushi)_(GGGGS)5-human_IL15_N4D/N65D_(single-chain)_Fc(216)_IgG1_pI(-)_Isosteric_A_C220S/PVA_/S267K/L368D/K370S (SEQ ID NO: 341)

ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVDVISDLKKIEDLIQSMHIDATLYTESDVHPSCKVTAMKCFL
LELQVISLESGDASIHDTVEDLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVMHEALHNHYTQKSLSLSPGK

Chain 2 - empty_Fc(216)_IgG1_C220S/PVA_/S267K/S364K/E357Q (SEQ ID NO: 342)

EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVMHEALHNHYTQKSLSLSPGK

Figure 44B

>XENP29281 human_IL15Ra(sushi)_(GGGGS)5-human_IL15_D30N_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

Chain 1 - human_IL15Ra(sushi)_(GGGGS)5-human_IL15_D30N_(single-chain)_Fc(216)_IgG1_pI(-)_Isosteric_A_C220S/PVA_/S267K/L368D/K370S (SEQ ID NO: 343)
ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVNVISDLKKIEDLIQSMHIDATLYTESNVHPSCKVTAMKCFL
LELQVISLESGDASIHDTVENLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVMHEALHNHYTQKSLSLSPGK

Chain 2 - empty_Fc(216)_IgG1_C220S/PVA_/S267K/S364K/E357Q (SEQ ID NO: 344)
EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVMHEALHNHYTQKSLSLSPGK

>XENP29285 human_IL15Ra(sushi)_(GGGGS)5-human_IL15_D30N/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

Chain 1 - human_IL15Ra(sushi)_(GGGGS)5-human_IL15_D30N/N65D_(single-chain)_Fc(216)_IgG1_pI(-)_Isosteric_A_C220S/PVA_/S267K/L368D/K370S (SEQ ID NO: 345)
ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVNVISDLKKIEDLIQSMHIDATLYTESNVHPSCKVTAMKCFL
LELQVISLESGDASIHDTVEDLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVMHEALHNHYTQKSLSLSPGK

Chain 2 - empty_Fc(216)_IgG1_C220S/PVA_/S267K/S364K/E357Q (SEQ ID NO: 346)
EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVMHEALHNHYTQKSLSLSPGK

Figure 44C

>XENP29286 human_IL15Ra(sushi)_(GGGGS)5-human_IL15_D30N/E64Q/N65D_(single-chain)-empty-Fc_Fc(216)_IgG1_pI(-)_Isosteric_A_C220S/PVA_/S267K/L368D/K370S-Fc(216)_IgG1_C220S/PVA_/S267K/S364K/E357Q

Chain 1 - human_IL15Ra(sushi)_(GGGGS)5-human_IL15_D30N/E64Q/N65D_(single-chain)_Fc(216)_IgG1_pI(-)_Isosteric_A_C220S/PVA_/S267K/L368D/K370S (SEQ ID NO: 347)

ITCPPPMSVEHADIWVKSYSLYSRERYICNSGFKRKAGTSSLTECVLNKATNVAHWTTPSLKCIR/GG
GGSGGGGSGGGGSGGGGSGGGGS/NWVNVISDLKKIEDLIQSMHIDATLYTESNVHPSCKVTAMKCFL
LELQVISLESGDASIHDTVQDLIILANNSLSSNGNVTESGCKECEELEEKNIKEFLQSFVHIVQMFIN
TS/EPKSSDKTHTCPPCPAPPVAGPSVFLFPPKPKDTLMISRTPEVTCVVVDVKHEDPEVKFNWYVDG
VEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRW
EQGDVFSCSVMHEALHNHYTQKSLSLSPGK

Chain 2 - empty_Fc(216)_IgG1_C220S/PVA_/S267K/S364K/E357Q (SEQ ID NO: 348)

EPKSSDKTHTCPPCPAPPVAGPSVFLFPPKPKDTLMISRTPEVTCVVVDVKHEDPEVKFNWYVDGVEV
HNAKTKPREEQYNSTYRVVSVLTVLHQDWLNGKEYKCKVSNKALPAPIEKTISKAKGQPREPQVYTLP
PSREQMTKNQVKLTCLVKGFYPSDIAVEWESNGQPENNYKTTPPVLDSDGSFFLYSKLTVDKSRWQQG
NVFSCSVMHEALHNHYTQKSLSLSPGK

Figure 46A

>XENP029486 human_IL15Ra(sushi)_(GGGGS)5-human_IL15(D30N/N65D;single-Chain )-7G8[LAG-3]_H3.30_L1.34_IgG1_Fc(216)_IgG1_pI(-)_Isosteric_A_C220S/PVA_/S267K/L368D/K370S-IgG1_PVA_/S267K/S364K/E357Q

*Chain 1 human_IL15Ra(sushi)_(GGGGS)5-human_IL15(D30N/N65D;single-Chain )_Fc(216)_IgG1_pI(-)_Isosteric_A_C220S/PVA_/S267K/L368D/K370S scIL-15/Ra-Fc Chain* (SEQ ID NO: 349)
ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK

*Chain 2 7G8[LAG-3]_H3.30_L1.34_Fab_IgG1_PVA_/S267K/S364K/E357Q Fab-Fc Heavy Chain* (SEQ ID NO: 350)
EVQLVESGGGLVQPGGSLRLSCAASGFTFDDAWMSWVRQAPGKGLEWVAEISTKANNHATYYAESVKGRFTISRDDSKSSVYLQMNSLRAEDTAVYYCTRLATWDWYFDVWGQGTTVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK

*Chain 3 7G8[LAG-3]_H3.30_L1.34_Fab Light Chain* (SEQ ID NO: 351)
DIVLTQSPSSLSASVGDRVTITCRASQSVDYDGDSYMNWYQQKPGKPPKLLIYAASELESGIPARFSGSGSGTDFTLTISSLQPEDFATYYCQQSNEDPFTFGSGTKLEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 46B

>XENP029487 human_IL15Ra(sushi)_(GGGGS)5-human_IL15(D30N/N65D;single-Chain )-2A11[LAG-3]_H1.144_L2.142_IgG1_Fc(216)_IgG1_pI(-)_Isosteric_A_C220S/PVA_/S267K/L368D/K370S-IgG1_PVA_/S267K/S364K/E357Q

*Chain 1 human_IL15Ra(sushi)_(GGGGS)5-human_IL15(D30N/N65D;single-Chain )_Fc(216)_IgG1_pI(-)_Isosteric_A_C220S/PVA_/S267K/L368D/K370S scIL-15/Ra-Fc Chain* (SEQ ID NO: 352)

ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK

*Chain 2 2A11[LAG-3]_H1.144_L2.142_Fab_IgG1_PVA_/S267K/S364K/E357Q Fab-Fc Heavy Chain* (SEQ ID NO: 353)

EVQLVQSGAEVKKPGATVKISCKASGFNIKDYFMHWVQQAPGKGLEWMGWIDPELGDTEYAPKFQGRVTITADTSTNTAYMELSSLRSEDTAVYYCYARGVYQALDYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK

*Chain 3 2A11[LAG-3]_H1.144_L2.142_Fab Light Chain* (SEQ ID NO: 354)

DIQMTQSPAFLSVTPGEKVTITCQASQDIGNYLNWFQQKPGQTVKLLIYFTSYLHSGVPSRFSGSGSGTDYTFTISSLEAEDAATYFCQQGNTLPYTFGGGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 47A

> XENC1000 human_IL15Ra(sushi)_(GGGGS)5-human_IL15(D30N/E64Q/N65D;single-Chain )-7G8[LAG-3]_H3.30_L1.34_IgG1_Fc(216)_IgG1_pI(-)_Isosteric_A_C220S/PVA_/S267K/L368D/K370S-IgG1_PVA_/S267K/S364K/E357Q

*Chain 1 human_IL15Ra(sushi)_(GGGGS)5-human_IL15(D30N/E64Q/N65D;single-Chain )_Fc(216)_IgG1_pI(-)_Isosteric_A_C220S/PVA_/S267K/L368D/K370S scIL-15/Ra-Fc Chain* (SEQ ID NO: 355)

ITCPPPMSVEHADIWVKSYSLYSRERYICNSGFKRKAGTSSLTECVLNKATNVAHWTTPSLKCIR/GGGGSGGGGSG
GGGSGGGGSGGGGS/NWVNVISDLKKIEDLIQSMHIDATLYTESNVHPSCKVTAMKCFLLELQVISLESGDASIHDT
VQDLIILANNSLSSNGNVTESGCKECEELEEKNIKEFLQSFVHIVQMFINTS/EPKSSDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTT
PPVLDSDGSFFLYSKLTVDKSRWEQGDVFSCSVMHEALHNHYTQKSLSLSPGK

*Chain 2 7G8[LAG-3]_H3.30_L1.34_Fab_IgG1_PVA_/S267K/S364K/E357Q Fab-Fc Heavy Chain* (SEQ ID NO: 356)

EVQLVESGGGLVQPGGSLRLSCAASGFTFDDAWMSWVRQAPGKGLEWVAEISTKANNHATYYAESVKGRFTIS
RDDSKSSVYLQMNSLRAEDTAVYYCTRLATWDWYFDVWGQGTTVTVSS/ASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKKVEPKSC
DKTHTCPPCPAPPVAGPSVFLFPPKPKDTLMISRTPEVTCVVVDVKHEDPEVKFNWYVDGVEVHNAKTKPREEQY
NSTYRVVSVLTVLHQDWLNGKEYKCKVSNKALPAPIEKTISKAKGQPREPQVYTLPPSREQMTKNQVKLTCLVKGF
YPSDIAVEWESNGQPENNYKTTPPVLDSDGSFFLYSKLTVDKSRWQQGNVFSCSVMHEALHNHYTQKSLSLSPGK

*Chain 3 7G8[LAG-3]_H3.30_L1.34_Fab Light Chain* (SEQ ID NO: 357)

DIVLTQSPSSLSASVGDRVTITCRASQSVDYDGDSYMNWYQQKPGKPPKLLIYAASELESGIPARFSGSGSGTDFTL
TISSLQPEDFATYYCQQSNEDPFTFGSGTKLEIK/RTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

Figure 47B

> XENC1001 human_IL15Ra(sushi)_(GGGGS)5-human_IL15(D30N/E64Q/N65D;single-Chain )-2A11[LAG-3]_H1.144_L2.142_IgG1_Fc(216)_IgG1_pI(-)_Isosteric_A_C220S/PVA_/S267K/L368D/K370S-IgG1_PVA_/S267K/S364K/E357Q

*Chain 1 human_IL15Ra(sushi)_(GGGGS)5-human_IL15(D30N/E64Q/N65D;single-Chain )_Fc(216)_IgG1_pI(-)_Isosteric_A_C220S/PVA_/S267K/L368D/K370S scIL-15/Ra-Fc Chain* (SEQ ID NO: 358)

ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVQDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK

*Chain 2 2A11[LAG-3]_H1.144_L2.142_Fab_IgG1_PVA_/S267K/S364K/E357Q Fab-Fc Heavy Chain* (SEQ ID NO: 359)

EVQLVQSGAEVKKPGATVKISCKASGFNIKDYFMHWVQQAPGKGLEWMGWIDPELGDTEYAPKFQGRVTITADTSTNTAYMELSSLRSEDTAVYYCYARGVYQALDYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK

*Chain 3 2A11[LAG-3]_H1.144_L2.142_Fab Light Chain* (SEQ ID NO: 360)

DIQMTQSPAFLSVTPGEKVTITCQASQDIGNYLNWFQQKPGQTVKLLIYFTSYLHSGVPSRFSGSGSGTDYTFTISSLEAEDAATYFCQQGNTLPYTFGGGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 48A

> XENC1002 human_IL15Ra(sushi)_(GGGGS)5-human_IL15(D30N/N65D;single-Chain )-7G8[LAG-3]_H3.30_L1.34_IgG1_Fc(216)_IgG1_pI(- )_Isosteric_A_C220S/PVA_/S267K/L368D/K370S/M428L/N434S- IgG1_PVA_/S267K/S364K/E357Q/M428L/N434S

*Chain 1 human_IL15Ra(sushi)_(GGGGS)5-human_IL15(D30N/N65D;single-Chain* (SEQ ID NO: 361) *)_Fc(216)_IgG1_pI(-)_Isosteric_A_C220S/PVA_/S267K/L368D/K370S/M428L/N434S scIL-15/Ra-Fc Chain*

ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEALHSHYTQKSLSLSPGK

*Chain 2 7G8[LAG-3]_H3.30_L1.34_Fab_IgG1_PVA_/S267K/S364K/E357Q/M428L/N434S Fab-Fc Heavy Chain* (SEQ ID NO: 362)

EVQLVESGGGLVQPGGSLRLSCAASGFTFDDAWMSWVRQAPGKGLEWVAEISTKANNHATYYAESVKGRFTISRDDSKSSVYLQMNSLRAEDTAVYYCTRLATWDWYFDVWGQGTTVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK

*Chain 3 7G8[LAG-3]_H3.30_L1.34_Fab Light Chain* (SEQ ID NO: 363)

DIVLTQSPSSLSASVGDRVTITCRASQSVDYDGDSYMNWYQQKPGKPPKLLIYAASELESGIPARFSGSGSGTDFTLTISSLQPEDFATYYCQQSNEDPFTFGSGTKLEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 48B

> XENC1003 human_IL15Ra(sushi)_(GGGGS)5-human_IL15(D30N/N65D;single-Chain )-2A11[LAG-3]_H1.144_L2.142_IgG1_Fc(216)_IgG1_pI(-)_Isosteric_A_C220S/PVA_/S267K/L368D/K370S/M428L/N434S-IgG1_PVA_/S267K/S364K/E357Q/M428L/N434S

*Chain 1 human_IL15Ra(sushi)_(GGGGS)5-human_IL15(D30N/N65D;single-Chain )_Fc(216)_IgG1_pI(-)_Isosteric_A_C220S/PVA_/S267K/L368D/K370S/M428L/N434S scIL-15/Ra-Fc Chain* (SEQ ID NO: 364)

ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVEDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEALHSHYTQKSLSLSPGK

*Chain 2 2A11[LAG-3]_H1.144_L2.142_Fab_IgG1_PVA_/S267K/S364K/E357Q/M428L/N434S Fab-Fc Heavy Chain* (SEQ ID NO: 365)

EVQLVQSGAEVKKPGATVKISCKASGFNIKDYFMHWVQQAPGKGLEWMGWIDPELGDTEYAPKFQGRVTITADTSTNTAYMELSSLRSEDTAVYYCYARGVYQALDYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK

*Chain 3 2A11[LAG-3]_H1.144_L2.142_Fab Light Chain* (SEQ ID NO: 366)

DIQMTQSPAFLSVTPGEKVTITCQASQDIGNYLNWFQQKPGQTVKLLIYFTSYLHSGVPSRFSGSGSGTDYTFTISSLEAEDAATYFCQQGNTLPYTFGGGTKVEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 48C

> XENC1004 human_IL15Ra(sushi)_(GGGGS)5-human_IL15(D30N/E64Q/N65D;single-Chain )-7G8[LAG-3]_H3.30_L1.34_IgG1_Fc(216)_IgG1_pI(-)_Isosteric_A_C220S/PVA_/S267K/L368D/K370S/M428L/N434S-IgG1_PVA_/S267K/S364K/E357Q/M428L/N434S

*Chain 1 human_IL15Ra(sushi)_(GGGGS)5-human_IL15(D30N/E64Q/N65D;single-Chain )_Fc(216)_IgG1_pI(-)_Isosteric_A_C220S/PVA_/S267K/L368D/K370S/M428L/N434S scIL-15/Ra-Fc Chain* (SEQ ID NO: 367)
ITCPPPMSVEHADIWVKSYSLYSRERYICNSGFKRKAGTSSLTECVLNKATNVAHWTTPSLKCIR/GGGGSGGGGSGGGGSGGGGSGGGGS/NWVNVISDLKKIEDLIQSMHIDATLYTESNVHPSCKVTAMKCFLLELQVISLESGDASIHDTVQDLIILANNSLSSNGNVTESGCKECEELEEKNIKEFLQSFVHIVQMFINTS/EPKSSDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVLHEALHSHYTQKSLSLSPGK

*Chain 2 7G8[LAG-3]_H3.30_L1.34_Fab_IgG1_PVA_/S267K/S364K/E357Q/M428L/N434S Fab-Fc Heavy Chain* (SEQ ID NO: 368)
EVQLVESGGGLVQPGGSLRLSCAASGFTFDDAWMSWVRQAPGKGLEWVAEISTKANNHATYYAESVKGRFTISRDDSKSSVYLQMNSLRAEDTAVYYCTRLATWDWYFDVWGQGTTVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVLHEALHSHYTQKSLSLSPGK

*Chain 3 7G8[LAG-3]_H3.30_L1.34_Fab Light Chain* (SEQ ID NO: 369)
DIVLTQSPSSLSASVGDRVTITCRASQSVDYDGDSYMNWYQQKPGKPPKLLIYAASELESGIPARFSGSGSGTDFTLTISSLQPEDFATYYCQQSNEDPFTFGSGTKLEIK/RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Figure 48D

> XENC1005 human_IL15Ra(sushi)_(GGGGS)5-human_IL15(D30N/E64Q/N65D;single-Chain )-2A11[LAG-3]_H1.144_L2.142_IgG1_Fc(216)_IgG1_pI(-)_Isosteric_A_C220S/PVA_/S267K/L368D/K370S/M428L/N434S-IgG1_PVA_/S267K/S364K/E357Q/M428L/N434S

*Chain 1 human_IL15Ra(sushi)_(GGGGS)5-human_IL15(D30N/E64Q/N65D;single-Chain )_Fc(216)_IgG1_pI(-)_Isosteric_A_C220S/PVA_/S267K/L368D/K370S/M428L/N434S scIL-15/Ra-Fc Chain* (SEQ ID NO: 370)

ITCPPPMSVEHADIWVKSYSLYSRERYICNSGFKRKAGTSSLTECVLNKATNVAHWTTPSLKCIR/GGGGSGGGGSG
GGGSGGGGSGGGGS/NWVNVISDLKKIEDLIQSMHIDATLYTESNVHPSCKVTAMKCFLLELQVISLESGDASIHDT
VQDLIILANNSLSSNGNVTESGCKECEELEEKNIKEFLQSFVHIVQMFINTS/EPKSSDKTHTCPPCPAPPVAGPSVFL
FPPKPKDTLMISRTPEVTCVVVDVKHEDPEVKFNWYVDGVEVHNAKTKPREEEYNSTYRVVSVLTVLHQDWLNGK
EYKCKVSNKALPAPIEKTISKAKGQPREPQVYTLPPSREEMTKNQVSLTCDVSGFYPSDIAVEWESDGQPENNYKTT
PPVLDSDGSFFLYSKLTVDKSRWEQGDVFSCSVLHEALHSHYTQKSLSLSPGK

*Chain 2 2A11[LAG-3]_H1.144_L2.142_Fab_IgG1_PVA_/S267K/S364K/E357Q/M428L/N434S Fab-Fc Heavy Chain* (SEQ ID NO: 371)
EVQLVQSGAEVKKPGATVKISCKASGFNIKDYFMHWVQQAPGKGLEWMGWIDPELGDTEYAPKFQGRVTITAD
TSTNTAYMELSSLRSEDTAVYYCYARGVYQALDYWGQGTLVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPPVAGPSVFLFPPKPKDTLMISRTPEVTCVVVDVKHEDPEVKFNWYVDGVEVHNAKTKPREEQYNSTYR
VVSVLTVLHQDWLNGKEYKCKVSNKALPAPIEKTISKAKGQPREPQVYTLPPSREQMTKNQVKLTCLVKGFYPSDIA
VEWESNGQPENNYKTTPPVLDSDGSFFLYSKLTVDKSRWQQGNVFSCSVLHEALHSHYTQKSLSLSPGK

*Chain 3 2A11[LAG-3]_H1.144_L2.142_Fab Light Chain* (SEQ ID NO: 372)
DIQMTQSPAFLSVTPGEKVTITCQASQDIGNYLNWFQQKPGQTVKLLIYFTSYLHSGVPSRFSGSGSGTDYTFTISSL
EAEDAATYFCQQGNTLPYTFGGGTKVEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Figure 49A

>XENP26007 human_IL15Ra(sushi)_(GGGGS)5-human_IL15(N4D/N65D;single-Chain)-Numax_IgG1_Fc(216)_IgG1_pI(-)_Isosteric_A_C220S/PVA_/S267K/L368D/K370S-IgG1_PVA_/S267K/S364K/E357Q

Chain 1 - human_IL15Ra(sushi)_(GGGGS)5-human_IL15(N4D/N65D;single-Chain)_Fc(216)_IgG1_pI(-)_Isosteric_A_C220S/PVA_/S267K/L368D/K370S scIL-15/Rα-Fc Chain (SEQ ID NO: 373)

*ITCPPPMSVEHADIWVKSYSLYSRERYICNSGFKRKAGTSSLTECVLNKATNVAHWTTPSLKCIR/*GGGGSGGGG
SGGGGSGGGGSGGGGS/NWVDVISDLKKIEDLIQSMHIDATLYTESDVHPSCKVTAMKCFLLELQVISLESGDAS
IHDTVEDLIILANNSLSSNGNVTESGCKECEELEEKNIKEFLQSFVHIVQMFINTS/EPKSSDKTHTCPPCPAPP
VAGPSVFLFPPKPKDTLMISRTPEVTCVVVDVKHEDPEVKFNWYVDGVEVHNAKTKPREEEYNSTYRVVSVLTVL
HQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 - Numax_IgG1_PVA_/S267K/S364K/E357Q Heavy Chain (SEQ ID NO: 374)

QVTLRESGPALVKPTQTLTLTCTFSGFSLSTAGMSVGWIRQPPGKALEWLADIWWDDKKHYNPSLKDRLTISKDT
SKNQVVLKVTNMDPADTATYYCARDMIFNFYFDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCD
KTHTCPPCPAPPVAGPSVFLFPPKPKDTLMISRTPEVTCVVVDVKHEDPEVKFNWYVDGVEVHNAKTKPREEQYN
STYRVVSVLTVLHQDWLNGKEYKCKVSNKALPAPIEKTISKAKGQPREPQVYTLPPSREQMTKNQVKLTCLVKGF
YPSDIAVEWESNGQPENNYKTTPPVLDSDGSFFLYSKLTVDKSRWQQGNVFSCSVMHEALHNHYTQKSLSLSPGK

Chain 3 - Numax Light Chain (SEQ ID NO: 375)

DIQMTQSPSTLSASVGDRVTITCSASSRVGYMHWYQQKPGKAPKLLIYDTSKLASGVPSRFSGSGSGTEFTLTIS
SLQPDDFATYYCFQGSGYPFTFGGGTKVEIK/RTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

>XENP29481 human_IL15Ra(sushi)_(GGGGS)5-human_IL15(D30N/N65D;single-chain)-Numax_IgG1_Fc(216)_IgG1_pI(-)_Isosteric_A_C220S/PVA_/S267K/L368D/K370S-IgG1_PVA_/S267K/S364K/E357Q

Chain 1 - human_IL15Ra(sushi)_(GGGGS)5-human_IL15(D30N/N65D;single-chain)_Fc(216)_IgG1_pI(-)_Isosteric_A_C220S/PVA_/S267K/L368D/K370S (SEQ ID NO: 376)

ITCPPPMSVEHADIWVKSYSLYSRERYICNSGFKRKAGTSSLTECVLNKATNVAHWTTPSLKCIR/GGGGSGGGG
SGGGGSGGGGSGGGGS/NWVNVISDLKKIEDLIQSMHIDATLYTESNVHPSCKVTAMKCFLLELQVISLESGDAS
IHDTVEDLIILANNSLSSNGNVTESGCKECEELEEKNIKEFLQSFVHIVQMFINTS/EPKSSDKTHTCPPCPAPP
VAGPSVFLFPPKPKDTLMISRTPEVTCVVVDVKHEDPEVKFNWYVDGVEVHNAKTKPREEEYNSTYRVVSVLTVL
HQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 - Numax_IgG1_PVA_/S267K/S364K/E357Q (SEQ ID NO: 377)

QVTLRESGPALVKPTQTLTLTCTFSGFSLSTAGMSVGWIRQPPGKALEWLADIWWDDKKHYNPSLKDRLTISKDT
SKNQVVLKVTNMDPADTATYYCARDMIFNFYFDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCD
KTHTCPPCPAPPVAGPSVFLFPPKPKDTLMISRTPEVTCVVVDVKHEDPEVKFNWYVDGVEVHNAKTKPREEQYN
STYRVVSVLTVLHQDWLNGKEYKCKVSNKALPAPIEKTISKAKGQPREPQVYTLPPSREQMTKNQVKLTCLVKGF
YPSDIAVEWESNGQPENNYKTTPPVLDSDGSFFLYSKLTVDKSRWQQGNVFSCSVMHEALHNHYTQKSLSLSPGK

Figure 49B

Chain 3 - Numax LC (SEQ ID NO: 378)
DIQMTQSPSTLSASVGDRVTITCSASSRVGYMHWYQQKPGKAPKLLIYDTSKLASGVPSRFSGSGSGTEFTLTIS
SLQPDDFATYYCFQGSGYPFTFGGGTKVEIK/RTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

>XENP30432 human_IL15Ra(sushi)_(GGGGS)5-human_IL15(D30N/E64Q/N65D;single-chain)-Numax_IgG1_Fc(216)_IgG1_pI(-)_Isosteric_A_C220S/PVA_/S267K/L368D/K370S-IgG1_PVA_/S267K/S364K/E357Q

Chain 1 - human_IL15Ra(sushi)_(GGGGS)5-human_IL15(D30N/E64Q/N65D;single-chain)_Fc(216)_IgG1_pI(-)_Isosteric_A_C220S/PVA_/S267K/L368D/K370S (SEQ ID NO: 379)
ITCPPPMSVEHADIWVKSYSLYSRERYICNSGFKRKAGTSSLTECVLNKATNVAHWTTPSLKCIR/GGGGSGGGG
SGGGGSGGGGSGGGGS/NWVNVISDLKKIEDLIQSMHIDATLYTESNVHPSCKVTAMKCFLLELQVISLESGDAS
IHDTVQDLIILANNSLSSNGNVTESGCKECEELEEKNIKEFLQSFVHIVQMFINTS/EPKSSDKTHTCPPCPAPP
VAGPSVFLFPPKPKDTLMISRTPEVTCVVVDVKHEDPEVKFNWYVDGVEVHNAKTKPREEEYNSTYRVVSVLTVL
HQDWLNGKEYKCKVSNKALPAPIEKTISKAKGQPREPQVYTLPPSREEMTKNQVSLTCDVSGFYPSDIAVEWESD
GQPENNYKTTPPVLDSDGSFFLYSKLTVDKSRWEQGDVFSCSVMHEALHNHYTQKSLSLSPGK

Chain 2 - Numax_VH_IgG1_IgG1_PVA_/S267K/S364K/E357Q (SEQ ID NO: 380)
QVTLRESGPALVKPTQTLTLTCTFSGFSLSTAGMSVGWIRQPPGKALEWLADIWWDDKKHYNPSLKDRLTISKDT
SKNQVVLKVTNMDPADTATYYCARDMIFNFYFDVWGQGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCD
KTHTCPPCPAPPVAGPSVFLFPPKPKDTLMISRTPEVTCVVVDVKHEDPEVKFNWYVDGVEVHNAKTKPREEQYN
STYRVVSVLTVLHQDWLNGKEYKCKVSNKALPAPIEKTISKAKGQPREPQVYTLPPSREQMTKNQVKLTCLVKGF
YPSDIAVEWESNGQPENNYKTTPPVLDSDGSFFLYSKLTVDKSRWQQGNVFSCSVMHEALHNHYTQKSLSLSPGK

Chain 3 - Numax LC (SEQ ID NO: 381)
DIQMTQSPSTLSASVGDRVTITCSASSRVGYMHWYQQKPGKAPKLLIYDTSKLASGVPSRFSGSGSGTEFTLTIS
SLQPDDFATYYCFQGSGYPFTFGGGTKVEIK/RTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

LAG-3 TARGETED HETERODIMERIC FUSION PROTEINS CONTAINING IL-15/IL-15RA Fc-FUSION PROTEINS AND LAG-3 ANTIGEN BINDING DOMAINS

CROSS-REFERENCE TO RELATED APPLICATIONS

This application is a continuation of U.S. patent application Ser. No. 16/388,646, filed Apr. 18, 2019 (now abandoned), which claims priority to U.S. Provisional Patent Application Nos. 62/659,624 filed Apr. 18, 2018 and 62/783,107, filed Dec. 20, 2018, which are expressly incorporated herein by reference in their entirety, with particular reference to the figures, legends, and claims therein.

SEQUENCE LISTING

The instant application contains a Sequence Listing which has been submitted electronically in XML, file format and is hereby incorporated by reference in its entirety. Said XML, copy, created on Apr. 28, 2023, is named 067461-5222-US01_Sequence_Listing.xml and is 526,657 bytes in size.

BACKGROUND OF THE INVENTION

Two very promising approaches in cancer immunotherapy include cytokine-based treatments and blockade of immune checkpoint proteins such as PD-1.

Cytokines such as IL-2 and IL-15 function in aiding the proliferation and differentiation of B cells, T cells, and NK cells. Both cytokines exert their cell signaling function through binding to a trimeric complex consisting of two shared receptors, the common gamma chain (γc; CD132) and IL-2 receptor beta-chain (IL-2Rβ; CD122), as well as an alpha chain receptor unique to each cytokine: IL-2 receptor alpha (IL-2Rα; CD25) or IL-15 receptor alpha (IL-15Rα; CD215). Both cytokines are considered as potentially valuable therapeutics in oncology, and IL-2 has been approved for use in patients with metastatic renal-cell carcinoma and malignant melanoma. Currently, there are no approved uses of recombinant IL-15, although several clinical trials are ongoing. However, as potential drugs, both cytokines suffer from a very fast clearance, with half-lives measured in minutes. IL-2 immunotherapy has been associated with systemic toxicity when administered in high doses to overcome fast clearance. Such systemic toxicity has also been reported with IL-15 immunotherapy in recent clinical trials (Guo et al., J Immunol, 2015, 195(5):2353-64).

Immune checkpoint proteins such as PD-1 are up-regulated following T cell activation to preclude autoimmunity by exhausting activated T cells upon binding to immune checkpoint ligands such as PD-L1. However, immune checkpoint proteins are also up-regulated in tumor-infiltrating lymphocytes (TILs), and immune checkpoint ligands are overexpressed on tumor cells, contributing to immune escape by tumor cells. De-repression of TILs by blockade of immune checkpoint interactions by drugs such as Opdivo® (nivolumab) and Keytruda® (pembrolizumab) have proven highly effective in treatment of cancer. Despite the promise of checkpoint blockade therapies such as nivolumab and pembrolizumab, many patients still fail to achieve sufficient response to checkpoint blockade alone.

Therefore, there remains an unmet need in oncology treatment for therapeutic strategies with cytokines that do not require high doses and are targeted to tumors to avoid systemic toxicity. Further, there is a need to identify additional therapeutic modalities to stack with checkpoint blockade that could increase patient response rate.

To address these needs and caveats, provided herein are novel LAG-3-targeted IL-15 heterodimeric fusion proteins with enhanced half-life and more selective targeted of TILs to improve safety profile, and which synergistically combine with checkpoint blockade antibodies (FIG. 1).

BRIEF SUMMARY OF THE INVENTION

In one aspect, the present invention provides a targeted IL-15/IL-15Rα heterodimeric protein comprising: (a) a first monomer comprising, from N- to C-terminal: i) an IL-15 sushi domain; ii) a first domain linker; iii) a variant IL-15 domain; iv) a second domain linker; v) a first variant Fc domain comprising CH2-CH3; and (b) a second monomer comprising, from N- to C-terminal: i) a scFv domain; ii) a third domain linker; iii) a second variant Fc domain comprising CH2-CH3; wherein the scFv domain comprises a first variable heavy domain, an scFv linker and a first variable light domain, wherein the scFv domain binds human LAG-3.

In other aspects of the present invention, provided herein is a targeted IL-15/IL-15Rα heterodimeric protein comprising: (a) a first monomer comprising, from N- to C-terminal: i) an IL-15 sushi domain; ii) a first domain linker; iii) a first variant Fc domain comprising CH2-CH3; (b) a second monomer comprising, from N- to C-terminal: i) a scFv domain; ii) a third domain linker; iii) a second variant Fc domain comprising CH2-CH3; wherein the scFv domain comprises a first variable heavy domain, an scFv linker and a first variable light domain; and (c) a third monomer comprising a variant IL-15 domain; wherein the scFv domain binds human LAG-3.

In one aspect, provided are "scIL-15/Rα X Fab" format heterodimeric proteins. Such "scIL-15/Rα X Fab" format heterodimeric proteins include: a) a first monomer comprising, from N- to C-terminal: i) an IL-15Rα(sushi) domain; ii) a first domain linker; iii) an IL-15 variant; iv) a second domain linker; v) a first variant Fc domain comprising CH2-CH3; b) a second monomer comprising, from N- to C-terminal, VH-CH1-hinge-CH2-CH3, wherein CH2-CH3 is a second variant Fc domain; and c) a third monomer comprising a VL-CL. The VH and VL are a variable heavy domain and a variable light domain, respectively, that form a human LAG-3 antigen binding domain. In some embodiments, the second domain linker is an antibody hinge.

In certain embodiments of the "scIL-15/Rα X Fab" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment of the "scIL-15/Rα X Fab" format heterodimeric protein, the "scIL-15/Rα X Fab" format heterodimeric protein includes: a) a first monomer comprising, from N- to C-terminal: i) an IL-15Rα (sushi) domain; ii) a first domain linker; iii) an IL-15 variant; iv) a hinge; v) a first variant Fc domain comprising CH2-CH3; b) a second monomer comprising, from N- to C-terminal, VH-CH1-hinge-CH2-CH3, wherein the CH2-CH3 is a second variant Fc domain; and c) a third monomer comprising a VL-CL. The VH and VL are a variable heavy domain and a variable light domain, respectively, that form a human LAG-3 antigen binding domain. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pl variants Q295E/N384D/Q418E/N421D, wherein numbering is according to EU numbering. In some embodiments, the hinge of the first monomer comprises amino acid substitution C220S, wherein numbering is according to EU numbering. In an exemplary embodiment, the first and second variant Fc domains each further comprise half-life extension variants M428L/N434S.

In some embodiments of the "scIL-15/Rα X Fab" format heterodimeric protein, the IL-15 variant of the heterodimeric protein provided herein comprises an amino acid substitution(s) selected from the group consisting of N1D, N4D, D8N, D30N, D61N, E64Q, N65D, Q108E, N4D/N65D, D30N/N65D, and D30N/E64Q/N65D. In an exemplary embodiment, the IL-15 variant comprises amino acid substitutions N4D/N65D, D30N/N65D, or D30N/E64Q/N65D In an exemplary embodiment, the "scIL-15/Rα X Fab" format heterodimeric protein is XENP27972, XENP27973, XENP27977, XENP27978, XENP029486, XENP029487, XENC1000, XENC1001, XENC1002, XENC1003, XENC1004 or XENC1005.

In certain embodiment, the VH and VL of the scIL-15/Rα X Fab" format heterodimeric proteins provided herein are the variable heavy domain and variable domain of any of the LAG-3 antigen binding domains in FIGS. 12 and 13. In an exemplary embodiment, the LAG-3 antigen binding domain is 2A11_H1.144_L2.142 and 7G8_H3.30_L1.34.

In one aspect, provided herein is a heterodimeric protein having the "scIL-15/Rα X scFv" format. In one embodiment, the heterodimeric protein includes: a) a first monomer comprising, from N- to C-terminal: i) an IL-15Rα(sushi) domain; ii) a first domain linker; iii) an IL-15 variant; iv) a second domain linker; and v) a first variant Fc domain comprising CH2-CH3; and b) a second monomer comprising, from N- to C-terminal: i) a scFv domain; ii) a third domain linker; and iii) a second variant Fc domain comprising CH2-CH3. In some embodiments, the scFv domain comprises a variable heavy domain (VH), an scFv linker and a variable light domain (VL), and the scFv domain binds human LAG-3. In some embodiments of the "scIL-15/Rα X scFv" format heterodimeric protein, the second domain linker and the third domain linker are each an antibody hinge.

In certain embodiments, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In some embodiments of the "scIL-15/Rα X scFv" format, the heterodimeric protein includes: a) a first monomer comprising, from N- to C-terminal: i) an IL-15Rα (sushi) domain; ii) a first domain linker; iii) an IL-15 variant; iv) a hinge; and v) a first variant Fc domain comprising CH2-CH3; and b) a second monomer comprising, from N- to C-terminal: i) a scFv domain; ii) a hinge; and iii) a second variant Fc domain comprising CH2-CH3. In some embodiments, the scFv domain comprises a variable heavy domain (VH), an scFv linker and a variable light domain (VL), and the scFv domain binds human LAG-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pl variants Q295E/N384D/Q418E/N421D, and the numbering is according to EU numbering. In certain embodiments, the first and second hinges each comprise amino acid substitution C220S, wherein numbering is according to EU numbering. In one embodiment, the first and second variant Fc domains each further comprise half-life extension variants M428L/N434S.

In another aspect, provided herein are "scFv X ncIL-15/Rα" format heterodimeric proteins. Such heterodimeric proteins include: a) a first monomer comprising, from N- to C-terminal: i) a scFv domain; ii) a first domain linker; and iii) a first variant Fc domain comprising CH2-CH3; b) a second monomer comprising, from N- to C-terminal: i) an IL-15Rα(sushi) domain; ii) a second domain linker; and iii) a second variant Fc domain comprising CH2-CH3; and c) a third monomer comprising an IL-15 variant. The scFv domain comprises a variable heavy domain (VH), an scFv linker and a variable light domain (VL), and the scFv domain binds human LAG-3. In one embodiment, the first domain linker and the second domain linker are each an antibody hinge.

In some embodiments of the "scFv X ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "scFv X nclL-15/Ra" format heterodimeric protein includes: a) a first monomer comprising, from N- to C-terminal: i) a scFv domain; ii) a hinge; and iii) a first variant Fc domain comprising CH2-CH3; b) a second monomer comprising, from N- to C-terminal: i) an IL-15Rα (sushi) domain; ii) a hinge; and iii) a second variant Fc domain comprising CH2-CH3; and c) a third monomer comprising an IL-15 variant. Further, the scFv domain comprises a variable heavy domain (VH), an scFv linker and a variable light domain (VL), and the scFv domain binds human LAG-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pl variants Q295E/N384D/Q418E/N421D, and wherein numbering is according to EU numbering. In certain embodiments, the first and second hinges each comprise amino acid substitution C220S, wherein numbering is according to EU numbering. In one embodiment, the first and second variant Fc domains each further comprise half-life extension variants M428L/N434S.

In another aspect, provided herein are "scFv x dsIL-15/Rα" format heterodimeric proteins. The "scFv x dsIL-15/Rα" format heterodimeric protein includes: a) a first monomer comprising, from N- to C-terminal: i) a variant IL-15Rα (sushi) domain comprising an amino acid substituted for a cysteine residue; ii) a first domain linker; and iii) a first variant Fc domain comprising CH2-CH3; b) a second monomer comprising, from N- to C-terminal: i) a scFv domain; ii) a second domain linker; iii) a second variant Fc domain comprising CH2-CH3; an c) a third monomer comprising an IL-15 variant comprising an amino acid substituted for a cysteine residue. The scFv domain comprises a variable heavy domain (VH), an scFv linker and a variable light domain (VL), wherein the cysteine residue of the variant IL-15Rα(sushi) domain and the cysteine residue of the IL-15 variant form a disulfide bond and the scFv domain binds human LAG-3. In certain embodiments, the first domain linker and the second domain linker are each an antibody hinge.

In some embodiments of the "scFv x dsIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "scFv x dsIL-15/Ra" format heterodimeric protein includes: a) a first monomer comprising, from N- to C-terminal: i) a variant IL-15Rα (sushi) domain comprising an amino acid substituted for a cysteine residue; ii) a hinge; and iii) a first variant Fc domain comprising CH2-CH3; b) a second monomer comprising, from N- to C-terminal: i) a scFv domain; ii) a hinge; iii) a second variant Fc domain comprising CH2-CH3; an c) a third monomer comprising an IL-15 variant comprising an amino acid substituted for a cysteine residue. The scFv domain comprises a variable heavy domain (VH), an scFv linker and a variable light domain (VL), wherein the cysteine residue of the variant IL-15Rα (sushi) domain and the cysteine residue of the IL-15 variant form a disulfide bond and the scFv domain binds human LAG-3. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, the first variant Fc domain comprises pl variants Q295E/N384D/Q418E/N421D, wherein numbering is according to EU numbering. In certain embodiments, the hinges of the first and second monomers each comprise amino acid substitution C220S, wherein numbering is according to EU numbering. In some embodiments, the first and second variant Fc domains each comprise half-life extension variants M428L/N434S.

In one aspect, provided herein are "Fab X ncIL-15/Rα" format heterodimeric proteins. Such heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal: i) an IL-15Rα(sushi) domain; ii) a first domain linker; iii) a first variant Fc domain comprising CH2-CH3; c) a third monomer comprising a light chain comprising VL-CL; and d) a fourth monomer comprising an IL-15 variant. The VH and VL are a variable heavy domain and a variable light domain, respectively, that form a human LAG-3 antigen binding domain. In some embodiments, the first domain linker is an antibody hinge.

In some embodiments of the "Fab X ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In exemplary embodiments, the "Fab X ncIL-15/Ra" format heterodimeric protein includes: a) a first monomer comprising, from N- to C-terminal, VH-CH1-hinge-CH2-CH3, wherein the CH2-CH3 is a first variant Fc domain; b) a second monomer comprising, from N- to C-terminal: i) an IL-15Rα (sushi) domain; ii) a hinge; iii) a first variant Fc domain comprising CH2-CH3; c) a third monomer comprising a light chain comprising VL-CL; and d) a fourth monomer comprising an IL-15 variant. The VH and VL are a variable heavy domain and a variable light domain, respectively, that form a human LAG-3 antigen binding domain. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the hinge-first variant Fc domain of the first monomer comprises pl variants N208D/Q295E/N384D/Q418E/N421D, wherein numbering is according to EU numbering. In some embodiments, the hinge of the second monomer comprises amino acid substitution C220S, wherein numbering is according to EU numbering. In certain embodiments, the first and second variant Fc domains each further comprise half-life extension variants M428L/N434S.

In another aspect, provided herein are "Fab X dsIL-15/Rα" format heterodimeric proteins. Such "Fab X dsIL-15/Rα" format heterodimeric proteins include: a) a first monomer comprising, from N- to C-terminal, VH-CH1-hinge-CH2-CH3, wherein CH2-CH3 is a first variant Fc domain; b) a second monomer comprising, from N- to C-terminal: i) a variant IL-15Rα(sushi) domain comprising an amino acid substituted for a cysteine residue; ii) a first domain linker; and iii) a first variant Fc domain comprising CH2-CH3; c) a third monomer comprising, from N- to C-terminal, VL-CL; and d) a fourth monomer comprising an IL-15 variant comprising an amino acid substituted for a cysteine residue. Further, the cysteine residue of the variant IL-15Rα(sushi) domain and the cysteine residue of the IL-15 variant form a disulfide bond, and the VH and VL are a variable heavy domain and a variable light domain, respectively, that form a human LAG-3 antigen binding domain. In some embodiments, the first domain linker is an antibody hinge.

In some embodiments of the "Fab X dsIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the "Fab X dsIL-15/Ra" format heterodimeric protein includes: a) a first monomer comprising, from N- to C-terminal, VH-CH1-hinge-CH2-CH3, wherein CH2-CH3 is a first variant Fc domain; b) a second monomer comprising, from N- to C-terminal: i) a variant IL-15Rα (sushi) domain comprising an amino acid substituted for a cysteine residue; ii) a hinge; and iii) a first variant Fc domain comprising CH2-CH3; c) a third monomer comprising, from N- to C-terminal, VL-CL; and d) a fourth monomer comprising an IL-15 variant comprising an amino acid substituted for a cysteine residue. Further, the cysteine residue of the variant IL-15Rα (sushi) domain and the cysteine residue of the IL-15 variant form a disulfide bond, and the VH and VL are a variable heavy domain and a variable light domain, respectively, that form a human LAG-3 antigen binding domain. In such embodiments, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the hinge-first variant Fc domain of the first monomer comprises pl variants N208D/Q295E/N384D/Q418E/N421D, wherein numbering is according to EU numbering. In certain embodiments, the hinge of the second monomer comprises amino acid substitution C220S, wherein numbering is according to EU numbering. In some embodiments, the first and second variant Fc domains each further comprise half-life extension variants M428L/N434S.

In one aspect, provided herein are "mAb-scIL-15/Rα" format heterodimeric proteins. The "mAb-scIL-15/Rα" format heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-IL-15Rα(sushi) domain-domain linker-IL-15 variant, wherein the CH2-CH3 is a second variant Fc domain; and c) a third monomer and fourth monomer that each comprises, from N- to C-terminal, VL-CL. Further, the VH of the first monomer and the VL of the third monomer form a first human LAG-3 binding domain, and the VH of the second monomer and the VL of the fourth monomer form a second human LAG-3 binding domain.

In some embodiments of the "mAb-scIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In some embodiments of the "mAb-scIL-15/Rα" format heterodimeric protein, the first variant Fc domain comprises skew variants L368D/K370S and the second variant Fc domain comprises skew variants S364K/E357Q, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In some embodiments of the "mAb-scIL-15/Rα" format heterodimeric protein, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In such embodiments, a) the hinge-first variant Fc domain of the first monomer further comprises pI substitutions Q196K/I199T/P271R/P228R/N276K and the hinge-second variant Fc domain of the second monomer further comprises pI variants N208D/Q295E/N384D/Q418D/N421D; b) the hinge-first variant Fc domain of the first monomer further comprises pI substitutions Q196K/I199T/P271R/P228R/N276K; or c) the hinge-second variant Fc domain of the second monomer further comprises pI variants N208D/Q295E/N384D/Q418D/N421D, wherein numbering is according to EU numbering.

In some embodiments of the "mAb-scIL-15/Rα" format heterodimeric protein, the first and second variant Fc domains each further comprise half-life extension variants M428L/N434S.

In another aspect, provided herein are "mAb-ncIL-15/Rα" format heterodimeric proteins. Such heterodimeric protein include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-IL-15Rα(sushi) domain, wherein the CH2-CH3 is a second variant Fc domain; c) a third monomer comprising an IL-15 variant; and d) a fourth and fifth monomer that each comprises, from N- to C-terminal, VL-CL. The VH of the first monomer and the VL of the fourth monomer form a first human LAG-3 binding domain, and the VH of the second monomer and the VL of the fifth monomer form a second human LAG-3 binding domain.

In some embodiments of the "mAb-ncIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment of the "mAb-ncIL-15/Rα" format heterodimeric protein, the first variant Fc domain comprises skew variants L368D/K370S and the second variant Fc domain comprises skew variants S364K/E357Q, and the first and second variant Fc domains each comprise FcKO variants E233P/L234V/L235A/G236del/S267K, wherein numbering is according to EU numbering. In some embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In another exemplary embodiment of the "mAb-ncIL-15/Rα" format heterodimeric protein, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pI substitutions Q196K/I199T/P271R/P228R/N276K and the hinge-second variant Fc domain of the second monomer further comprises pI variants N208D/Q295E/N384D/Q418D/N421D; b) the hinge-first variant Fc domain of the first monomer further comprises pI substitutions Q196K/I199T/P271R/P228R/N276K; or c) the hinge-second variant Fc domain of the second monomer comprises pI variants N208D/Q295E/N384D/Q418D/N421D, wherein numbering is according to EU numbering.

In certain embodiments, the first and second variant Fc domains each further comprise half-life extension variants M428L/N434S.

In another aspect, provided herein are "mAb-dsIL-15/Rα" heterodimeric proteins. Such "mAb-dsIL-15/Rα" heterodimeric proteins include: a) a first monomer comprising, from N- to C-terminal, VH-CH1-hinge-CH2-CH3, wherein the CH2-CH3 is a first variant Fc domain; b) a second monomer comprising, from N- to C-terminal, VH-CH1-hinge-CH2-CH3-domain linker-variant IL-15Rα(sushi) domain, wherein the variant IL-15Rα(sushi) domain an amino acid substituted for a cysteine residue and wherein the CH2-CH3 is a second variant Fc domain; c) a third monomer comprising an IL-15 variant comprising an amino acid substituted for a cysteine residue; and d) a fourth and fifth monomer that each comprises, from N- to C-terminal, VL-CL. The cysteine residue of the variant IL-15Rα(sushi) domain and the cysteine residue of the IL-15 variant form a disulfide bond, the VH of the first monomer and the VL of the fourth monomer form a first human LAG-3 binding domain, and the VH of the second monomer and the VL of the fifth monomer form a second human LAG-3 binding domain.

In some embodiments, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment of the "mAb-dsIL-15/Rα" heterodimeric proteins, the first variant Fc domain comprises skew variants L368D/K370S and the second variant Fc domain comprises skew variants S364K/E357Q, and the first and second variant Fc domains each comprise FcKO variants E233P/L234V/L235A/G236del/S267K, wherein numbering is according to EU numbering. In some embodiments, a) the hinge-first variant Fc domain of the first monomer further comprises pI substitutions N208D/Q295E/N384D/Q418D/N421D and the hinge-second variant Fc domain of the second monomer further comprises pI variants Q196K/I199T/P271R/P228R/N276K; b) the hinge-first variant Fc domain of the first monomer further comprises pI substitutions N208D/Q295E/N384D/Q418D/N421D; or c) the hinge-second variant Fc domain of the second monomer further comprises pI variants Q196K/I199T/P271R/P228R/N276K, wherein numbering is according to EU numbering.

In another exemplary embodiment of the "mAb-dsIL-15/Rα" heterodimeric proteins, the first variant Fc domain comprises skew variants S364K/E357Q and the second variant Fc domain comprises skew variants L368D/K370S, and the first and second variant Fc domains each comprise FcKO variants E233P/L234V/L235A/G236del/S267K, wherein numbering is according to EU numbering. In certain embodiments, a) the hinge-first variant Fc domain of the first monomer further comprises pl substitutions Q196K/1199T/P271R/P228R/N276K and the hinge-second variant Fc domain of the second monomer further comprises pl variants N208D/Q295E/N384D/Q418D/N421D; b) the hinge-first variant Fc domain of the first monomer further comprises pl substitutions Q196K/1199T/P271R/P228R/N276K; or c) the hinge-second variant Fc domain of the second monomer further comprises pl variants N208D/Q295E/N384D/Q418D/N421D, wherein numbering is according to EU numbering. In certain embodiments, the first and second variant Fc domains each further comprise half-life extension variants M428L /N434S.

In one aspect, provided herein are "central-IL-15/Rα" format heterodimeric proteins. Such "central-IL-15/Rα" format heterodimeric proteins include: a) a first monomer comprising, from N- to C-terminal, a VH-CH1-domain linker-IL-15 variant-hinge-CH2-CH3, wherein the CH2-CH3 is a first variant Fc domain; b) a second monomer comprising, from N- to C-terminal, a VH-CH1-domain linker-IL-15Rα(sushi) domain-hinge-CH2-CH3, wherein the CH2-CH3 is a second variant Fc domain; and c) a third and fourth monomer that each comprises, from N- to C-terminal, VL-CL. The VH of the first monomer and the VL of the third monomer form a first human LAG-3 binding domain, and the VH of the second monomer and the VL of the fourth monomer form a second human LAG-3 binding domain.

In some embodiments of the "central-IL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the first variant Fc domain comprises skew variants L368D/K370S and the second variant Fc domain comprise the skew variant pair S364K/E357Q, the first and second variant Fc domains each comprise FcKO variants E233P/L234V/L235A/G236del/S267K, and the first variant Fc domain comprises pI substitutions Q295E/N384D/Q418D/N421D, wherein numbering is according to EU numbering.

In an exemplary embodiment of the "central-IL-15/Rα" format heterodimeric protein, the first variant Fc domain comprises skew variants S364K/E357Q and the second variant Fc domain comprise the skew variant pair L368D/K370S, the first and second variant Fc domains each comprise FcKO variants E233P/L234V/L235A/G236del/S267K, and the second variant Fc domain of the second monomer comprises pl substitutions Q295E/N384D/Q418D/N421D, wherein numbering is according to EU numbering. In some embodiments of the "central-IL-15/Rα" format heterodimeric protein, the hinge of the first and second monomers each comprise amino acid substitution C220S, wherein numbering is according to EU numbering. In certain embodiments, the first and second variant Fc domains each further comprise half-life extension variants M428L/N434S.

In another aspect, provided herein are "central-scIL-15/Rα" format heterodimeric proteins. Such "central-scIL-15/Rα" format heterodimeric proteins include: a) a first monomer comprising, from N- to C-terminal, VH-CH1-domain linker-IL-15Rα(sushi) domain-domain linker-IL-15 variant-hinge-CH2-CH3, wherein the CH2-CH3 is a first variant Fc domain; b) a second monomer comprising, from N- to C-terminal, a VH-CH1-hinge-CH2-CH3, wherein the CH2-CH3 is a second variant Fc domain; and c) a third and fourth monomer that each comprises, from N- to C-terminal, VL-CL. The VH of the first monomer and the VL of the third monomer form a first human LAG-3 binding domain, and the VH of the second monomer and the VL of the fourth monomer form a second human LAG-3 binding domain.

In some embodiments of the "central-scIL-15/Rα" format heterodimeric protein, the first variant Fc domain the second variant Fc domain comprises one of the following skew variant sets: S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering. In an exemplary embodiment, the skew variant set is S364K/E357Q:L368D/K370S.

In an exemplary embodiment, the first variant Fc domain comprises skew variants L368D/K370S and the second variant Fc domain comprises skew variants S364K/E357Q, the first and second variant Fc domains each comprise FcKO variants E233P/L234V/L235A/G236del/S267K, and the first variant Fc domain comprises pl variants Q295E/N384D/Q418E/N421D, wherein numbering is according to EU numbering. In some embodiments, the hinge of the first monomer comprises amino acid substitution C220S, wherein numbering is according to EU numbering. In certain embodiments, the first and second variant Fc domains each further comprise half-life extension variants M428L/N434S.

In certain embodiment, the VH and VL of any of the heterodimeric proteins provided herein are the variable heavy domain and variable domain of any of the LAG-3 antigen binding domains in FIGS. 12 and 13. In an exemplary embodiment, the LAG-3 antigen binding domain is 2A11_H1.144_L2.142 and 7G8_H3.30_L1.34.

In some embodiments, the IL-15 variant of the heterodimeric protein provided herein comprises an amino acid substitution(s) selected from the group consisting of N1D, N4D, D8N, D30N, D61N, E64Q, N65D, Q108E, N4D/N65D, D30N/N65D, and D30N/E64Q/N65D. In an exemplary embodiment, the IL-15 variant comprises amino acid substitutions N4D/N65D, D30N/N65D, or D30N/E64Q/N65D In one aspect, provided herein is a pharmaceutical composition that includes any of the heterodimeric proteins disclosed herein and a pharmaceutically acceptable carrier.

In another aspect, provided herein is a method of treating a patient in need thereof comprising administering to the patient any one of the heterodimeric proteins or pharmaceutical compositions disclosed herein. In some embodiments, the method further comprising administering an antibody, where the antibody is an anti-PD-1 antibody, an anti-PD-L1 antibody, an anti-CTLA-4 antibody, an anti-TIM-3 antibody or ananti-TIGIT antibody.

In another aspect, provided herein are nucleic acid compositions that include one or more nucleic acids encoding any of the heterodimeric proteins disclosed herein, expression vectors that include the nucleic acids, expression vector compositions that include the expression vectors, and host cells that include the nucleic acids, or expression vectors, or expression vector compositions. Also provided herein are methods of making subject heterodimeric proteins by culturing host cells under suitable conditions and recovering the heterodimeric proteins.

BRIEF DESCRIPTION OF THE DRAWINGS

FIGS. 2A-2B depict the sequences for IL-15 and its receptors.

FIG. 3 depicts the sequences for LAG-3, including both human and cyno (predicted), to facilitate the development of antigen binding domains that bind to both for ease of clinical development.

FIGS. 4A-4E depict useful pairs of Fc heterodimerization variant sets (including skew and pI variants). There are variants for which there are no corresponding "monomer 2" variants; these are pI variants which can be used alone on either monomer.

FIG. 5 depicts a list of isosteric variant antibody constant regions and their respective substitutions. pI_(−) indicates lower pI variants, while pI_(+) indicates higher pI variants. These can be optionally and independently combined with other heterodimerization variants of the inventions (and other variant types as well, as outlined herein.)

FIG. 6 depicts useful ablation variants that ablate FcγR binding (sometimes referred to as "knock outs" or "KO" variants). Generally, ablation variants are found on both monomers, although in some cases they may be on only one monomer.

FIGS. 7A-7F show particularly useful embodiments of "non-cytokine"/"non-Fv" components of the LAG-3-targeting IL-15/Rα-Fc fusion proteins of the invention.

FIG. 8 depicts a number of exemplary variable length linkers for use in IL-15/Rα-Fc fusion proteins. In some embodiments, these linkers find use linking the C-terminus of IL-15 and/or IL-15Rα(sushi) to the N-terminus of the Fc region. In some embodiments, these linkers find use fusing IL-15 to the IL-15Rα(sushi).

FIGS. 9A-9C depict a number of charged scFv linkers that find use in increasing or decreasing the pI of heterodimeric antibodies that utilize one or more scFv as a component. The (+H) positive linker finds particular use herein. A single prior art scFv linker with single charge is referenced as "Whitlow", from Whitlow et al., Protein Engineering 6(8): 989-995 (1993). It should be noted that this linker was used for reducing aggregation and enhancing proteolytic stability in scFvs.

FIG. 10 show the sequences of several useful LAG-3-targeting IL-15/Rα-Fc fusion format backbones based on human IgG1, without the cytokine sequences (e.g., the 11-15 and/or IL-15Rα(sushi)) or VH, and further excluding light chain backbones which are depicted in FIG. 11. Backbone 1 is based on human IgG1 (356E/358M allotype), and includes the S364K/E357Q:L368D/K370S skew variants, C220S and the Q295E/N384D/Q418E/N421D pI variants on the chain with L368D/K370S skew variants and the E233P/L234V/L235A/G236del/S267K ablation variants on both chains. Backbone 2 is based on human IgG1 (356E/358M allotype), and includes the S364K/E357Q:L368D/K370S skew variants, the N208D/Q295E/N384D/Q418E/N421D pI variants on the chain with L368D/K370S skew variants, C220S in the chain with S364K/E357Q variants, and the E233P/L234V/L235A/G236del/S267K ablation variants on both chains. Backbone 3 is based on human IgG1 (356E/358M allotype), and includes the S364K/E357Q:L368D/K370S skew variants, the N208D/Q295E/N384D/Q418E/N421D pI variants on the chains with L368D/K370S skew variants, the Q196K/I199T/P217R/P228R/N276K pI variants on the chains with S364K/E357Q variants, and the E233P/L234V/L235A/G236del/S267K ablation variants on both chains. Such backbone sequences can be included, for example, in the "scIL-15/Rα X Fab" format heterodimeric proteins described herein). In some embodiments, the "scIL-15/Rα X Fab" format heterodimeric protein includes: a) a first monomer that includes, from N- to C-terminus, an IL-15Rα(sushi) domain-(domain linker)-IL-15 variant- (hinge)-CH2-CH3, where hinge-CH2-CH3 has the amino acid sequence of "Chain 2" of any of the backbone sequences in FIG. 10 (SEQ ID NO: 58, 60 and 62); b) a second monomer that includes, from N- to C-terminus, a VH-CH1-hinge-CH2-CH3, where VH is a variable heavy domain and CH1-hinge-CH2-CH3 has the amino acid sequence of Chain 1 of any one of the backbone sequences in FIG. 10 (SEQ ID NO: 57, 59 and 61), and c) a light chain that includes from, N- to C-terminus, VL-VC, where VL is a variable light domain and VC has the sequence of "Constant Light Chain-Kappa" or "Constant Light Chain-Lambda "in FIG. 11 (SEQ ID NO: 63-64). In an exemplary embodiment, the IL-15 variant includes amino acid substitutions N4D/N65D, D30N/N65D, or D30N/E64Q/N65D. In exemplary embodiments, the VH and VL are the variable heavy domain and variable light domain, respectively, of any of the LAG-3 ABDs provided in FIGS. 12 and 13A-C.

Figure 1:
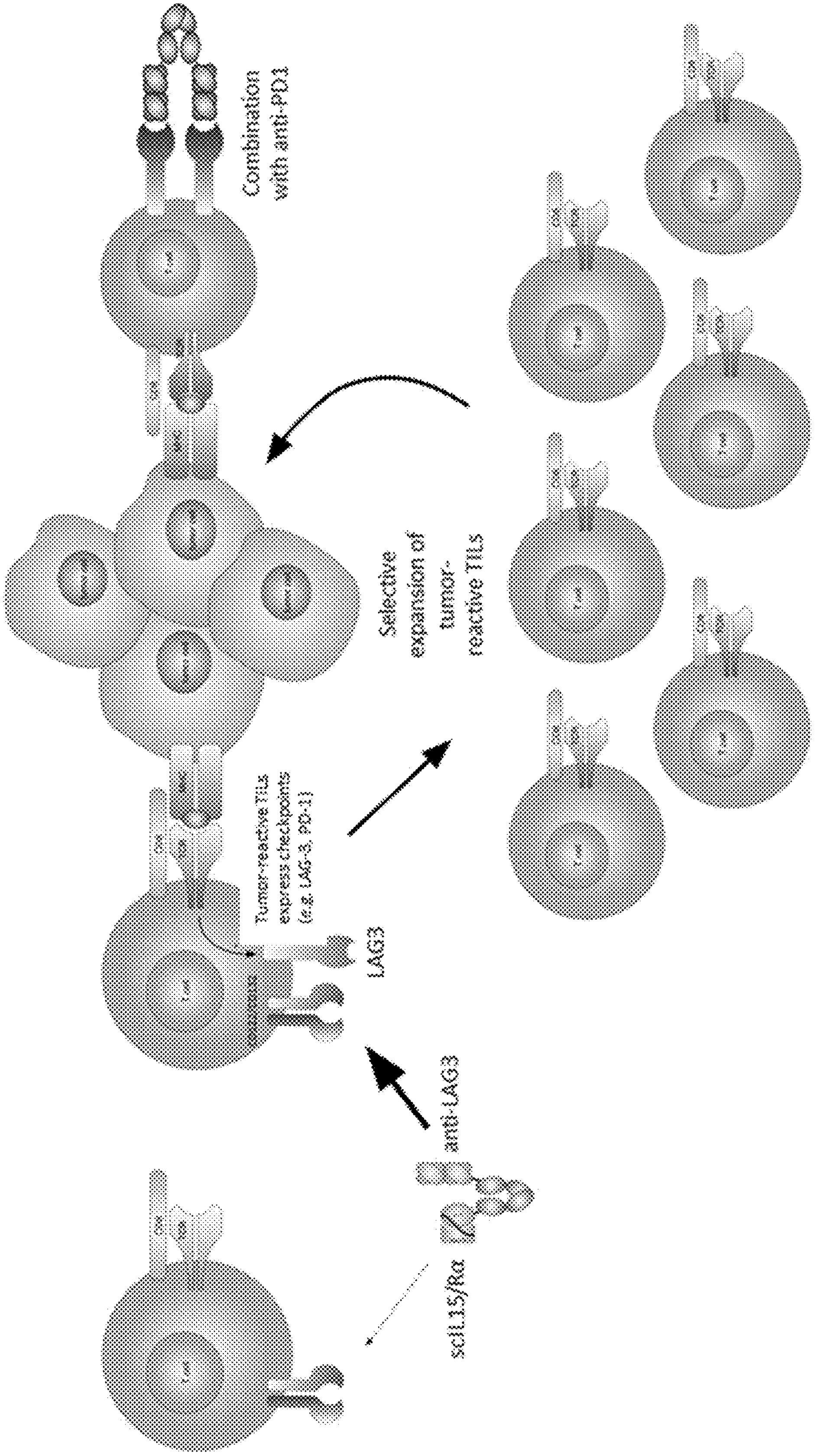
FIG. 1 depicts selectivity of LAG-3-targeted IL-15/Rα-Fc fusion proteins for tumor-reactive tumor-infiltrating lymphocytes expressing PD-1, and its combination with PD-1 blockade antibody.

In certain embodiments, these sequences can be of the 356D/358L allotype. In other embodiments, these sequences can include either the N297A or N297S substitutions. In some other embodiments, these sequences can include the M428L/N434S Xtend mutations. In yet other embodiments, these sequences can instead be based on human IgG4, and include a S228P (EU numbering, this is S241P in Kabat) variant on both chains that ablates Fab arm exchange as is known in the art. In yet further embodiments, these sequences can instead be based on human IgG2. Further, these sequences may instead utilize the other skew variants, pI variants, and ablation variants depicted in the Figures.

As will be appreciated by those in the art and outlined below, these sequences can be used with any IL-15 and IL-15Rα(sushi) pairs outlined herein, including but not limited to scIL-15/Rα, ncIL-15/Rα, and dsIL-15Rα, as schematically depicted in FIG. 21. Further as will be appreciated by those in the art and outlined below, any IL-15 and/or IL-15Rα(sushi) variants can be incorporated in these backbones. Furthermore as will be appreciated by those in the art and outlined below, these sequences can be used with any VH and VL pairs outlined herein, including either a scFv or a Fab.

Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 11 depicts the "non-Fv" backbone of light chains (i.e. constant light chain) which find use in LAG-3-targeting IL-15/Rα-Fc fusion proteins of the invention.

FIG. 12 depicts the variable region sequences for a select number of anti-LAG-3 antibody binding domains. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIGS. 13A-13C depict the variable regions of additional LAG-3 ABDs which may find use in the LAG-3-targeting IL-15/Rα-Fc fusion proteins of the invention. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

Figure 14:
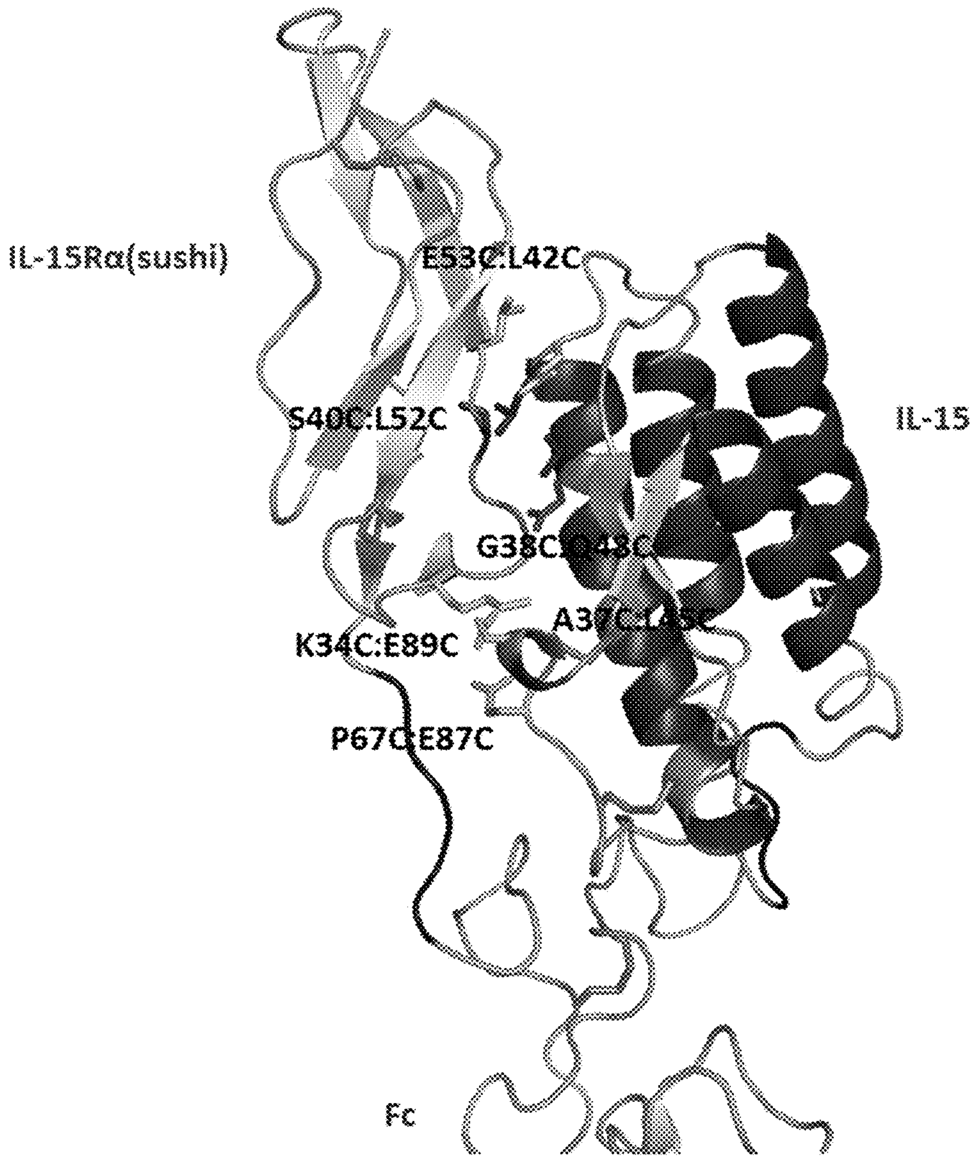

FIG. 14 depicts a structural model of the IL-15/Rα heterodimer showing locations of engineered disulfide bond pairs.

FIG. 15 depicts sequences for illustrative IL-15Rα(sushi) variants engineered with additional residues at the C-terminus to serve as a scaffold for engineering cysteine residues.

FIG. 16 depicts sequences for illustrative IL-15 variants engineered with cysteines in order to form covalent disulfide bonds with IL-15Rα(sushi) variants engineered with cysteines.

FIG. 17 depicts sequences for illustrative IL-15Rα(sushi) variants engineered with cysteines in order to form covalent disulfide bonds with IL-15 variants engineered with cysteines.

Figure 18:
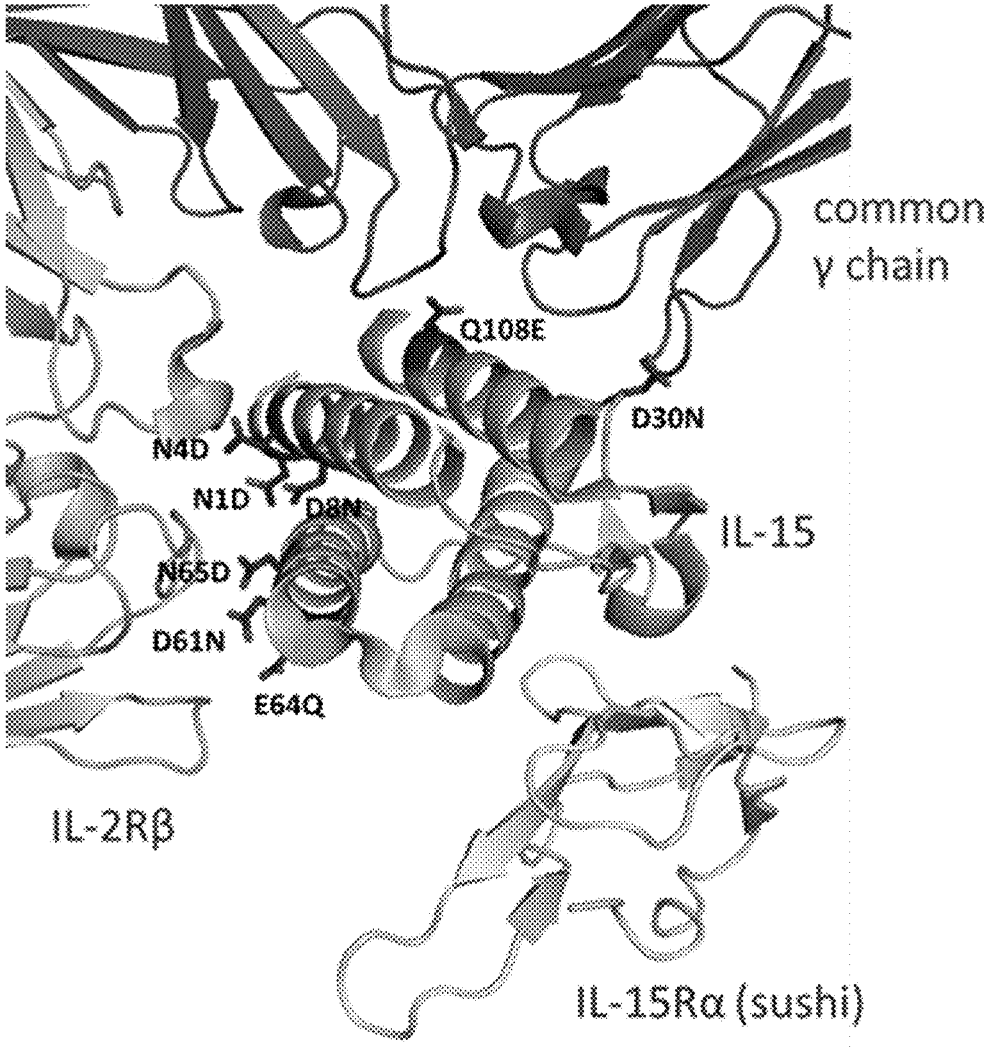

FIG. 18 depicts the structure of IL-15 complexed with IL-15Rα, IL-2Rβ, and common gamma chain. Locations of substitutions designed to reduce potency are shown.

FIGS. 19A-19C depict sequences for illustrative IL-15 variants engineered for reduced potency. Included within each of these variant IL-15 sequences are sequences that are 90, 95, 98 and 99% identical (as defined herein) to the recited sequences, and/or contain from 1, 2, 3, 4, 5, 6, 7, 8, 9 or 10 additional amino acid substitutions. In a non-limiting example, the recited sequences may contain additional amino acid modifications such as those contributing to formation of covalent disulfide bonds as shown in FIG. 14, FIG. 16, and FIG. 17.

FIG. 20 depicts EC50 for induction of NK and $CD8^+$ T cells proliferation by variant IL-15/Rα-Fc fusion proteins, and fold reduction in EC50 relative to XENP20818, the wild type. These fusion proteins do not contain a LAG-3 ABD.

FIGS. 21A-FIG. 21K depict several formats for the LAG-3-targeting IL-15/Rα-Fc fusion proteins of the present invention. The "scIL-15/Rα x scFv" format (FIG. 21A) comprises IL-15Rα(sushi) fused to IL-15 by a variable length linker (termed "scIL-15/Rα") which is then fused to the N-terminus of a heterodimeric Fc-region, with an scFv fused to the other side of the heterodimeric Fc. The "scFv x ncIL-15/Rα" format (FIG. 21B) comprises an scFv fused to the N-terminus of a heterodimeric Fc-region, with IL-15Rα (sushi) fused to the other side of the heterodimeric Fc, while IL-15 is transfected separately so that a non-covalent IL-15/Rα complex is formed. The "scFv x dsIL-15/Rα" format (FIG. 21C) is the same as the "scFv x ncIL-15/Rα" format, but wherein IL-15Rα(sushi) and IL-15 are covalently linked as a result of engineered cysteines. The "scIL-15/Rα x Fab" format (FIG. 21D) comprises IL-15Rα(sushi) fused to IL-15 by a variable length linker (termed "scIL-15/Rα") which is then fused to the N-terminus of a heterodimeric Fc-region, with a variable heavy chain (VH) fused to the other side of the heterodimeric Fc, while a corresponding light chain is transfected separately so as to form a Fab with the VH. The "ncIL-15/Rα x Fab" format (FIG. 21E) comprises a VH fused to the N-terminus of a heterodimeric Fc-region, with IL-15Rα(sushi) fused to the other side of the heterodimeric Fc, while a corresponding light chain is transfected separately so as to form a Fab with the VH, and while IL-15 is transfected separately so that a non-covalent IL-15/Rα complex is formed. The "dsIL-15/Rα x Fab" format (FIG. 21F) is the same as the "ncIL-15/Rα X Fab" format, but wherein IL-15Rα(sushi) and IL-15 are covalently linked as a result of engineered cysteines. The "mAb-scIL-15/Rα" format (FIG. 21G) comprises VH fused to the N-terminus of a first and a second heterodimeric Fc, with IL-15 is fused to IL-15Rα(sushi) which is then further fused to the C-terminus of one of the heterodimeric Fc-region, while corresponding light chains are transfected separately so as to form a Fabs with the VHs. The "mAb-ncIL-15/Rα" format (FIG. 21H) comprises VH fused to the N-terminus of a first and a second heterodimeric Fc, with IL-15Rα(sushi) fused to the C-terminus of one of the heterodimeric Fc-region, while corresponding light chains are transfected separately so as to form a Fabs with the VHs, and while and while IL-15 is transfected separately so that a non-covalent IL-15/Rα complex is formed. The "mAb-dsIL-15/Rα" format (FIG. 21I) is the same as the "mAb-ncIL-15/Rα" format, but wherein IL-15Rα(sushi) and IL-15 are covalently linked as a result of engineered cysteines. The "central-IL-15/Rα" format (FIG. 21J) comprises a VH recombinantly fused to the N-terminus of IL-15 which is then further fused to one side of a heterodimeric Fc and a VH recombinantly fused to the N-terminus of IL-15Rα(sushi) which is then further fused to the other side of the heterodimeric Fc, while corresponding light chains are transfected separately so as to form a Fabs with the VHs. The "central-scIL-15/Rα" format (FIG. 21K) comprises a VH fused to the N-terminus of IL-15Rα(sushi) which is fused to IL-15 which is then further fused to one side of a heterodimeric Fc and a VH fused to the other side of the heterodimeric Fc, while corresponding light chains are transfected separately so as to form a Fabs with the VHs.

FIGS. 22A-22B depict sequences of XENP27972 and XENP27973, illustrative LAG-3-targeting IL-15/Rα-Fc fusion protein of the "scIL-15/Rα x Fab" format. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, variable regions, and constant/Fc regions.

FIG. 23 depict the sequences for XENP16432, a bivalent anti-PD-1 mAb with an ablation variant (E233P/L234V/L235A/G236del/S267K, "IgG1_PVA_/S267k"). The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems.

Figure 24A:
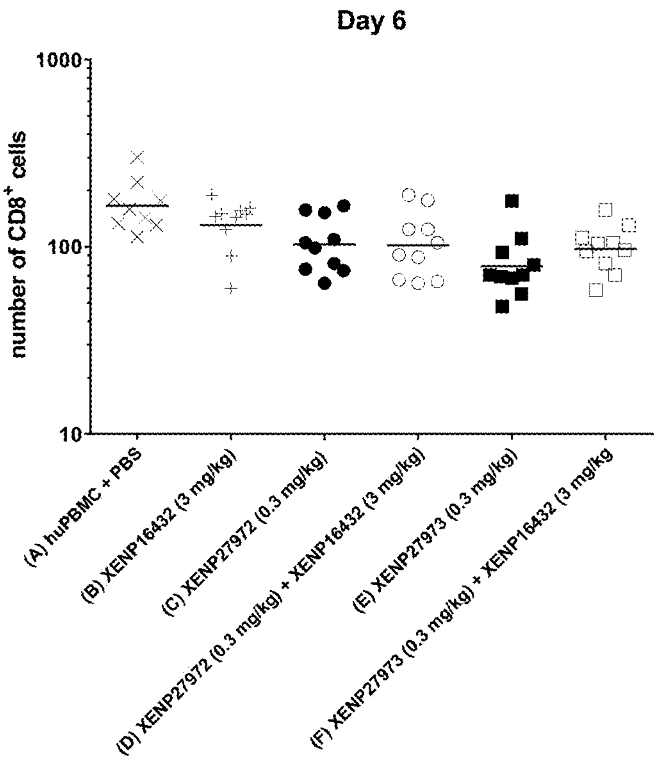
Figure 24B:
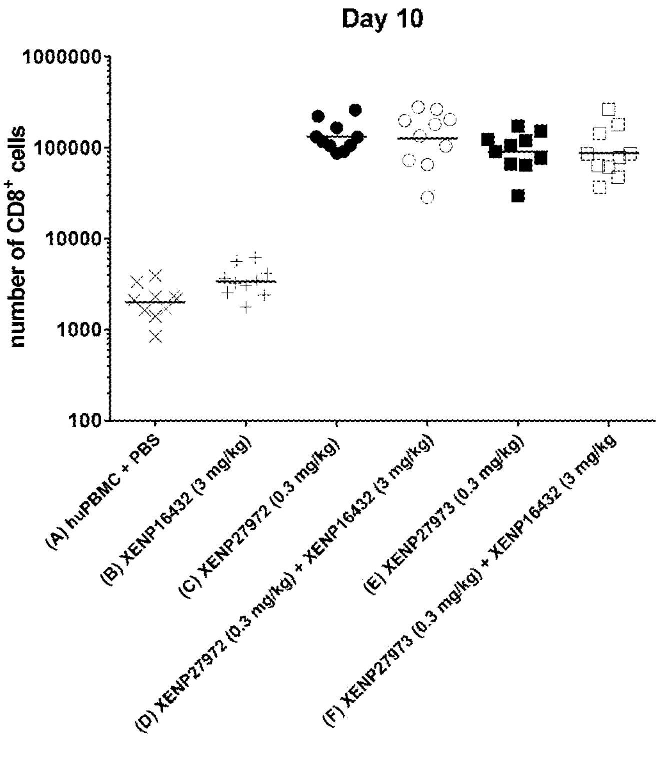

FIGS. 24A-24B depict $CD8^+$ T cell counts in whole blood of PBMC-engrafted NSG mice on Days A) 6 and B) 10 after first dose of the indicated test articles.

Figure 25A:
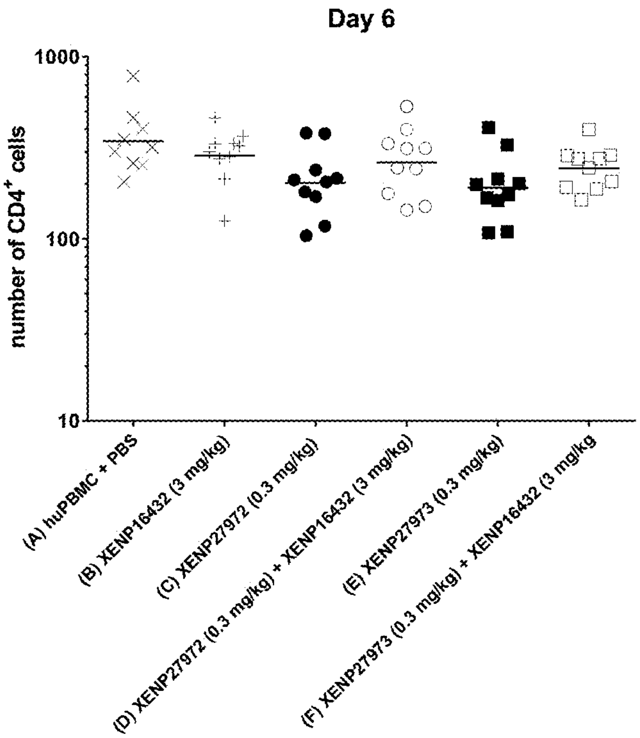
Figure 25B:
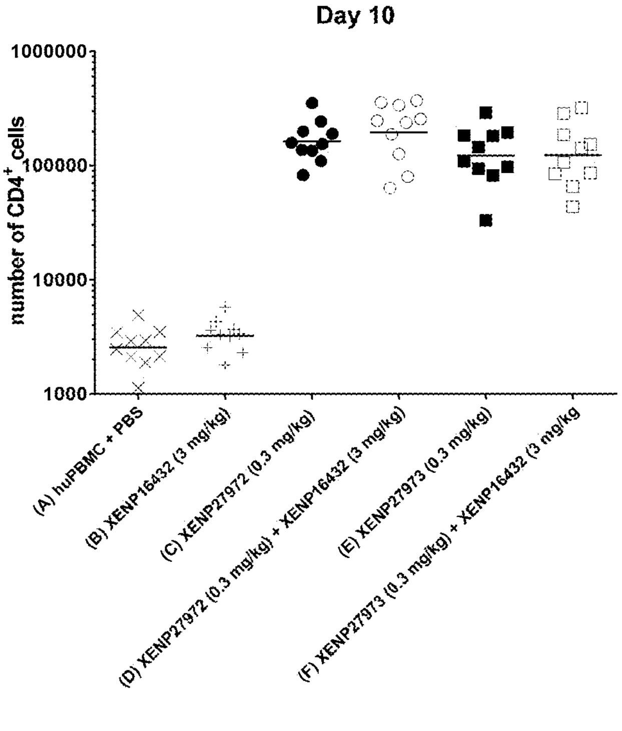

FIGS. 25A-25B depict $CD4^+$ T cell counts in whole blood of PBMC-engrafted NSG mice on Days A) 6 and B) 10 after first dose of the indicated test articles.

Figure 26A:
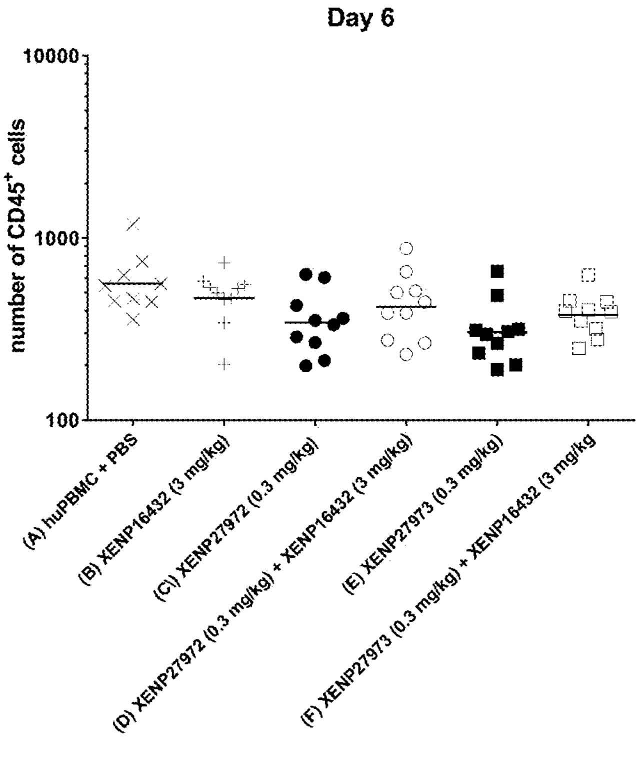
Figure 26B:
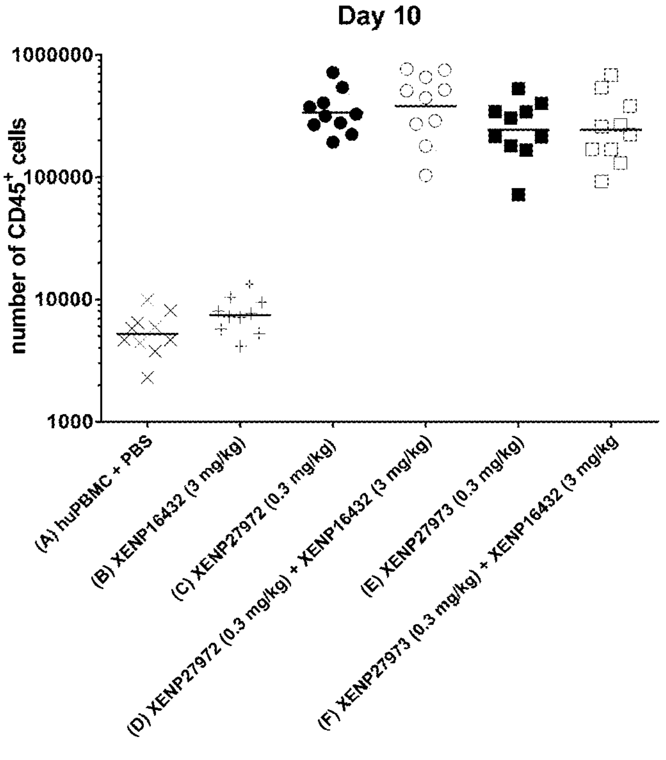

FIGS. 26A-26B depict $CD45^+$ T cell counts in whole blood of PBMC-engrafted NSG mice on Days A) 6 and B) 10 after first dose of the indicated test articles.

Figure 27A:
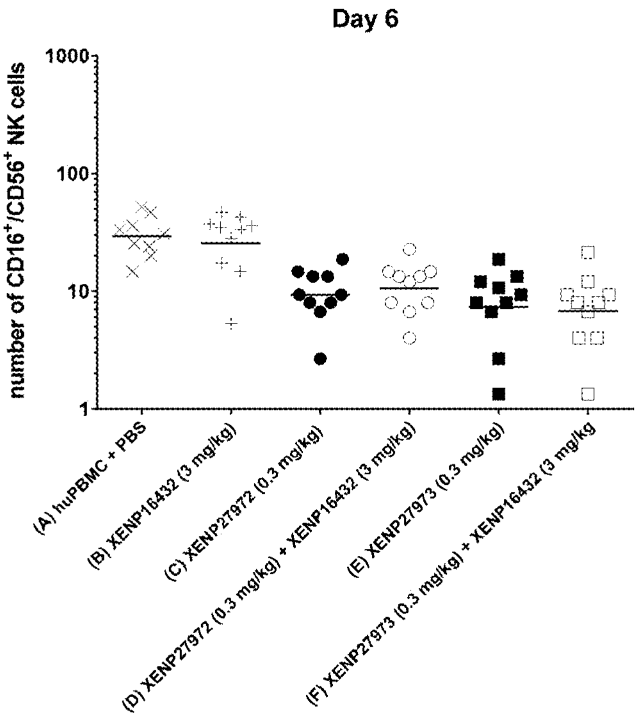
Figure 27B:
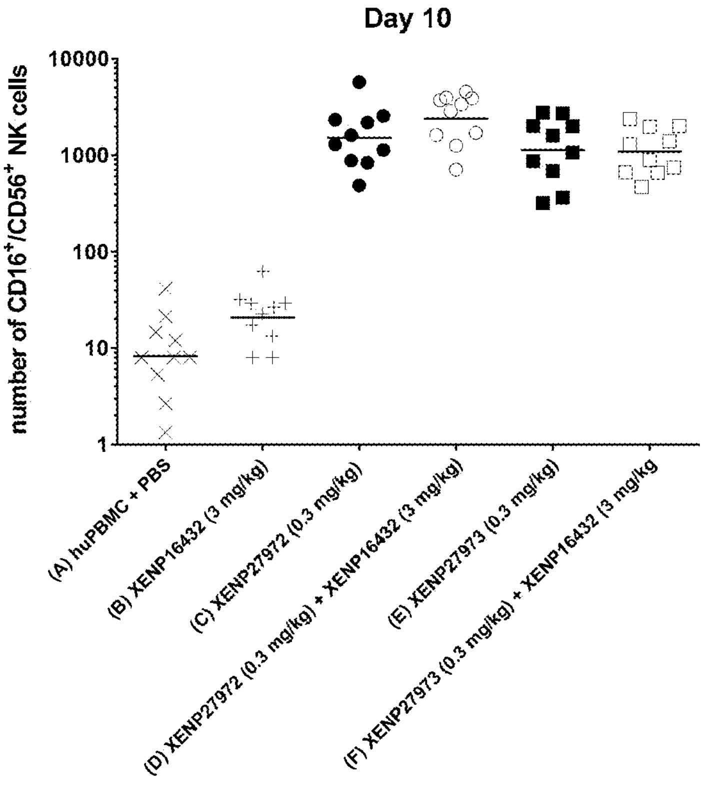

FIGS. 27A-27B depict $CD16^+CD56^+$ NK cell counts in whole blood of PBMC-engrafted NSG mice on Days A) 6 and B) 10 after first dose of the indicated test articles.

Figure 28:
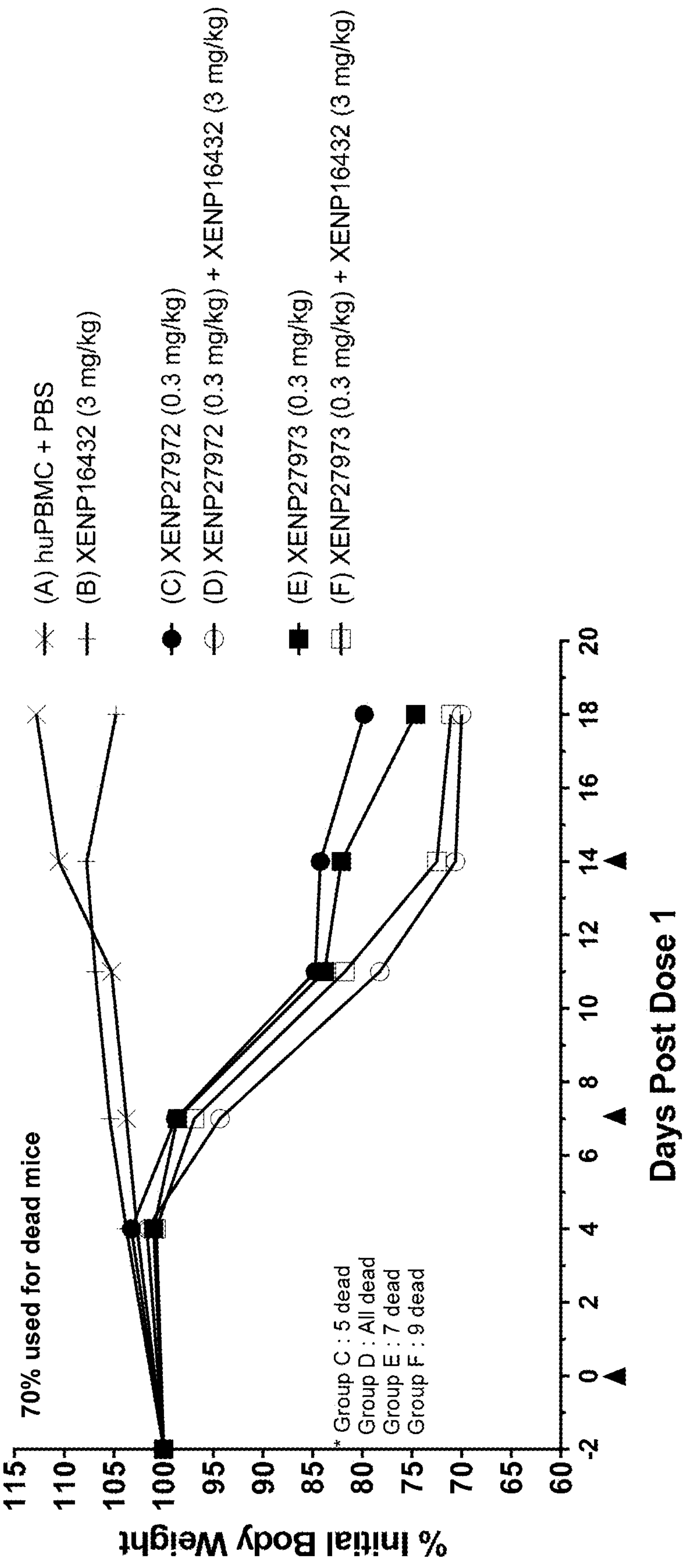

FIG. 28 depicts the change in body weight (as percentage of initial body weight) of PBMC-engrafted NSG mice after dosing with the indicated test articles.

FIGS. 29A-29B depict the sequences of XENP27977 and 27978 that include M428L/N434S variants in both Fc domains.

Figure 30:
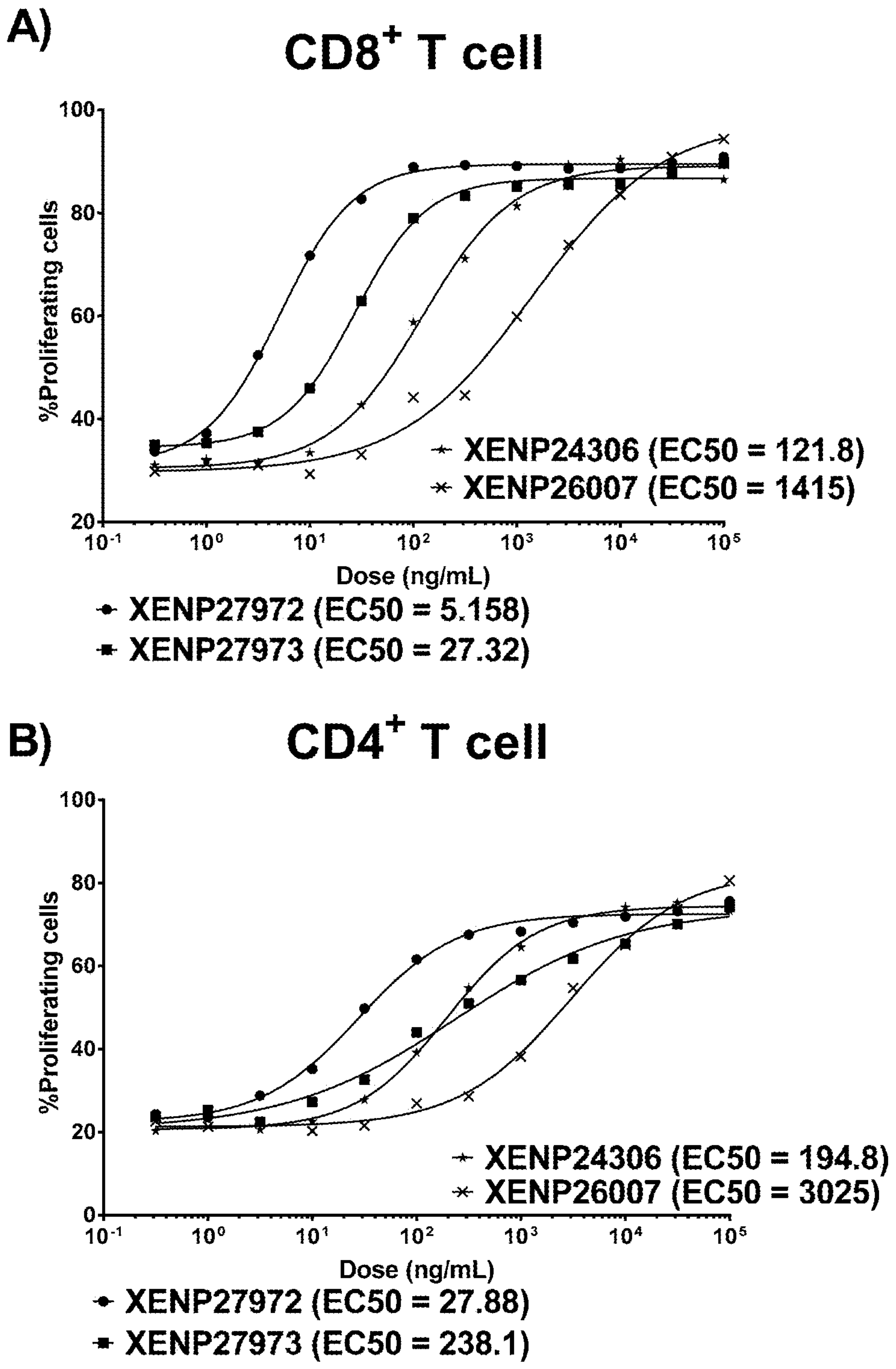

FIG. 30 depicts induction of A) $CD8^+$ T cells and B) $CD4^+$ T cells proliferation by LAG-3-targeted IL-15/Rα-Fc fusions (and controls) as indicated by percentage proliferating cells (determined based on CFSE dilution). The data show that LAG-3-targeted IL-15/Rα-Fc fusions are more potent in inducing proliferation of $CD8^+$ T cells in comparison to untargeted IL-15(D30N/E64Q/N65D)/Rα-Fc fusion (as well as control RSV-targeted IL-15/Rα-Fc fusion).

Figure 31:
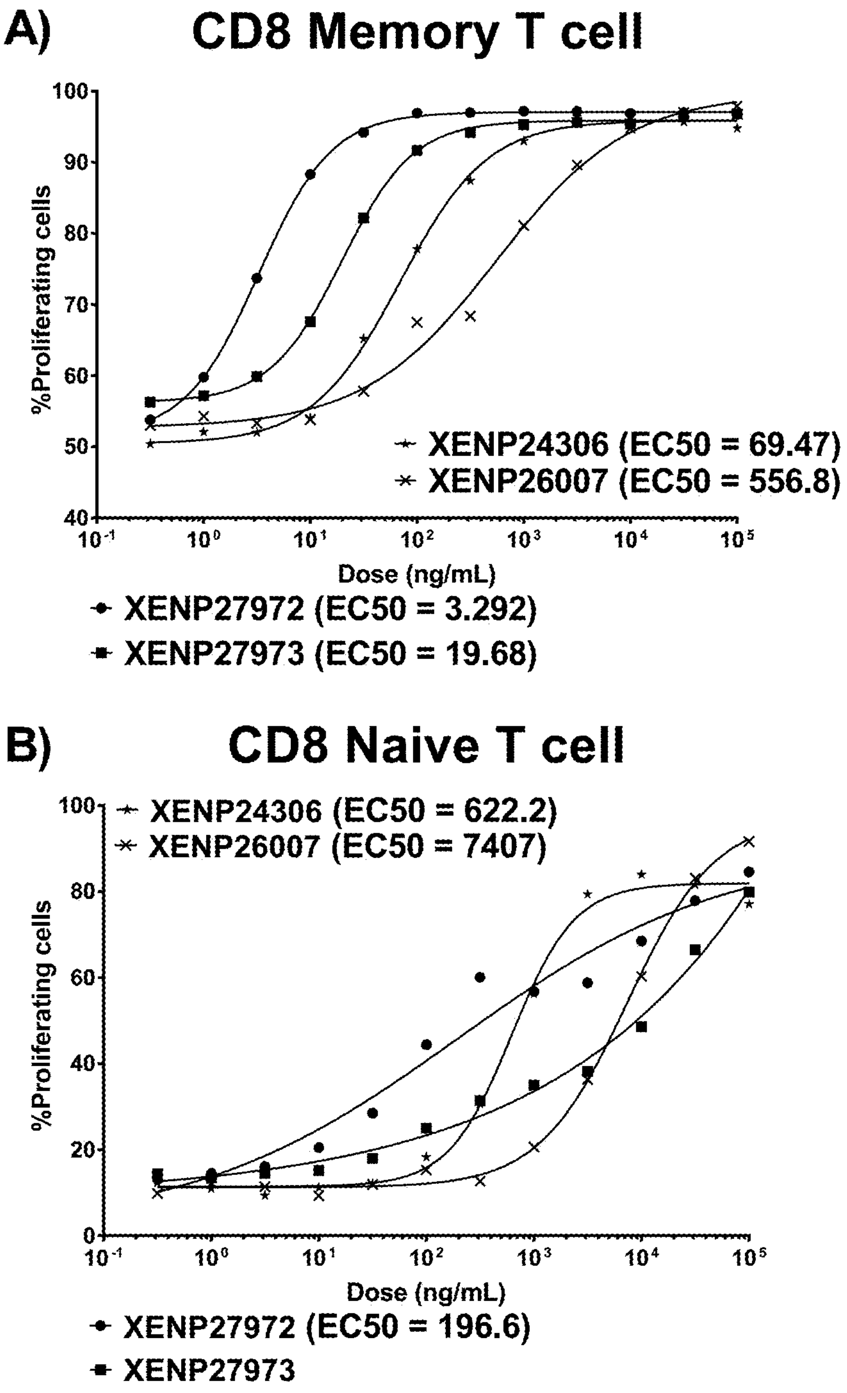

FIG. 31 depicts induction of A) CD8 memory T cell and B) CD8 naive T cell proliferation by LAG-3-targeted IL-15/Rα-Fc fusions (and controls) as indicated by percentage proliferating cells (determined based on CFSE dilution). The data show that LAG-3-targeted IL-15/Rα-Fc fusions are much more potent in inducing proliferation of CD8 memory T cells in comparison to untargeted IL-15(D30N/E64Q/N65D)/Rα-Fc fusion (as well as control RSV-targeted IL-15/Rα-Fc fusion).

FIG. 32 depicts induction of A) CD8 memory T cell and B) CD8 naive T cell proliferation by LAG-3-targeted IL-15/Rα-Fc fusions (and controls) as indicated by cell counts. The data show that LAG-3-targeted IL-15/Rα-Fc fusions are much more potent in expanding CD8 memory T cells in comparison to untargeted IL-15(D30N/E64Q/N65D)/Rα-Fc fusion (as well as control RSV-targeted IL-15/Rα-Fc fusion).

Figure 33:
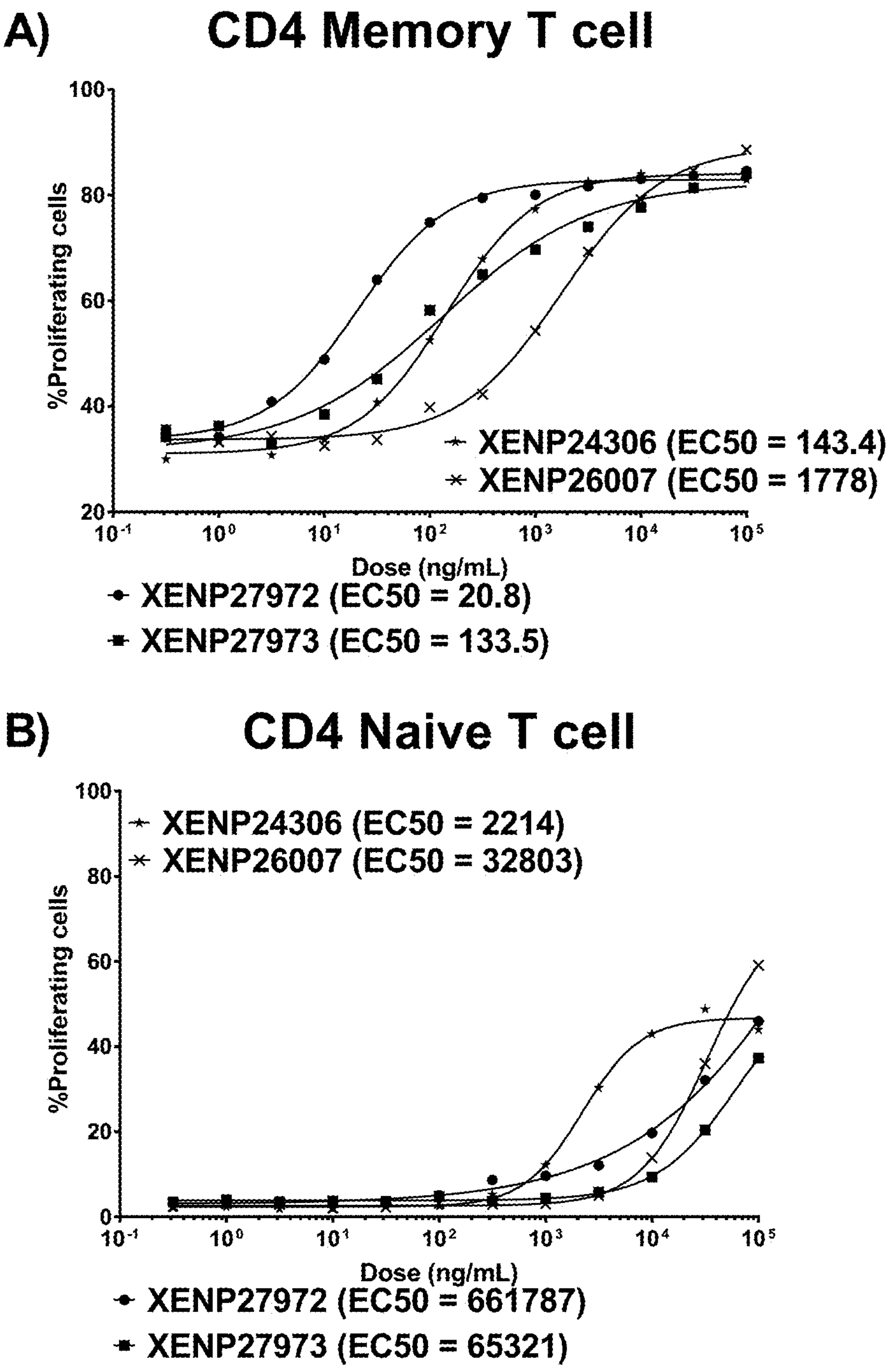

FIG. 33 depicts induction of A) CD4 memory T cell and B) CD4 naive T cell proliferation by LAG-3-targeted IL-15/Rα-Fc fusions (and controls) as indicated by percentage proliferating cells (determined based on CFSE dilution). The data show that LAG-3-targeted IL-15/Rα-Fc fusions are more potent in expanding CD4 memory T cells in comparison to untargeted IL-15(D30N/E64Q/N65D)/Rα-Fc fusion (as well as control RSV-targeted IL-15/Rα-Fc fusion).

FIG. 34 depicts induction of A) CD4 memory T cell and B) CD4 naive T cell proliferation by LAG-3-targeted IL-15/Rα-Fc fusions (and controls) as indicated by cell counts.

FIG. 35 depicts induction of NK cells proliferation by LAG-3-targeted IL-15/Rα-Fc fusions (and controls) as indicated A) percentage proliferating cells (determined based on CFSE dilution) and B) by cell counts.

Figure 36:
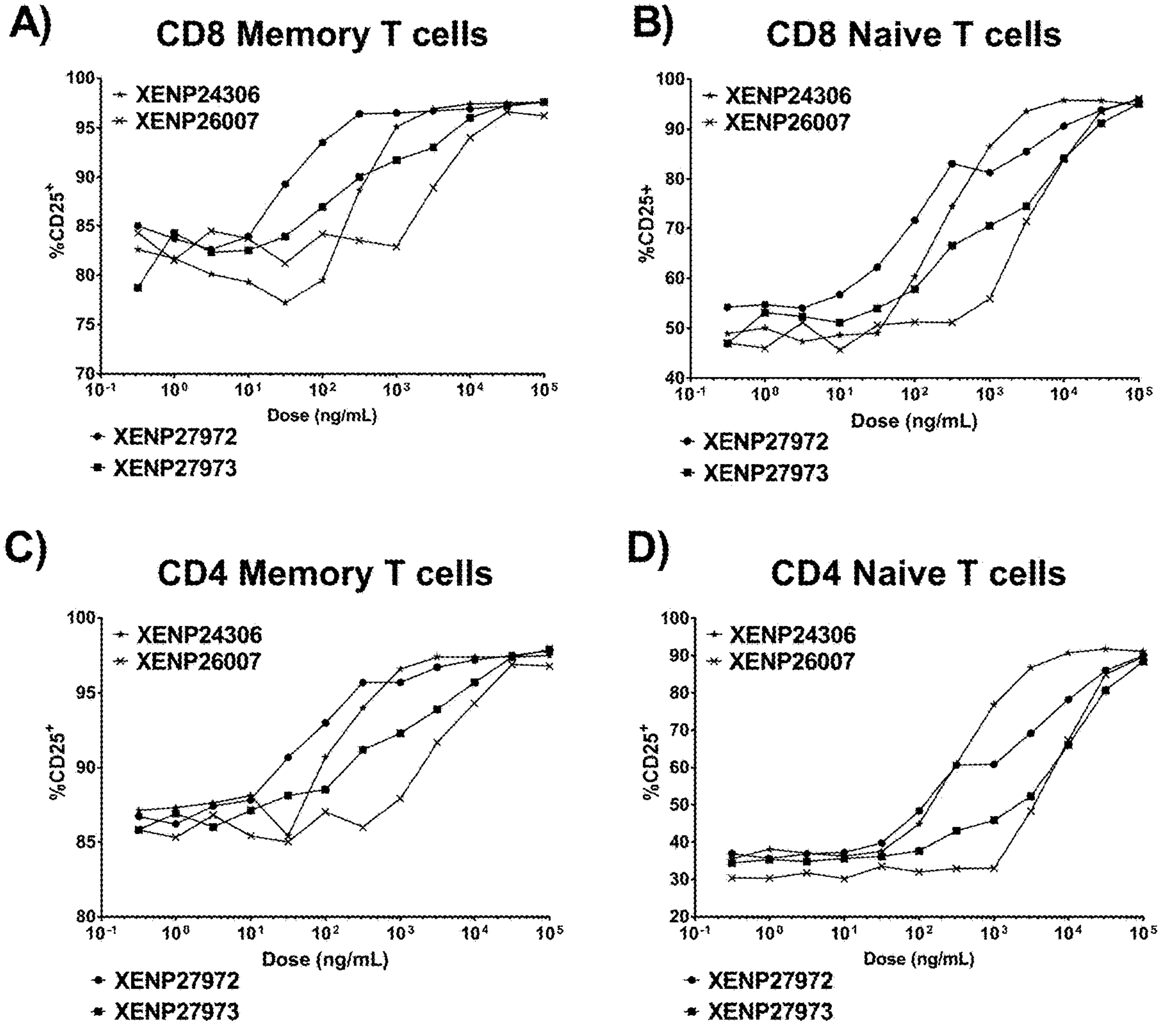

FIG. 36 depicts activation of $CD8^+$ T cells as indicated by A) percentage CD8 memory T cells expressing CD25, B) percentage CD8 naive T cells expressing CD25, C) percentage CD4 memory T cells expressing CD25, and D) percentage CD4 naive T cells expressing CD25 following incubation with LAG-3-targeted IL-15/Rα-Fc fusions (and controls). The data show that LAG-3-targeted IL-15/Rα-Fc fusions, in particular XENP27972, appear to upregulate CD25 in both CD8 and CD4 memory T cells in comparison to untargeted IL-15(D30N/E64Q/N65D)/Rα-Fc fusion (as well as control RSV-targeted IL-15/Rα-Fc fusion).

Figure 37:
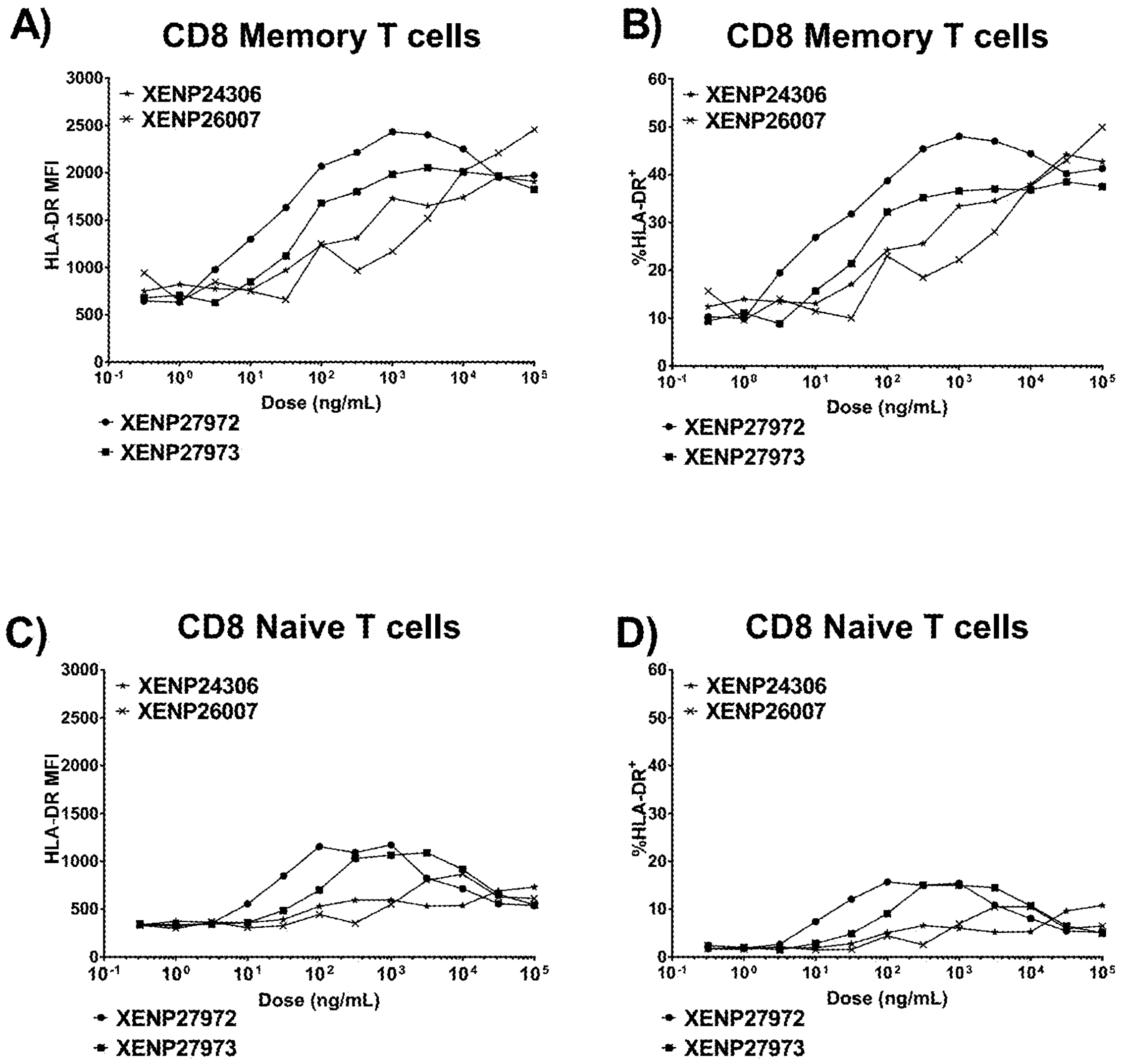

FIG. 37 depicts activation of $CD8^+$ T cells as indicated by A) HLA-DR MFI on CD8 memory T cells, B) percentage CD8 memory T cells expressing HLA-DR, C) HLA-DR MFI on CD8 naive T cells, and D) percentage CD8 naive T cells expressing HLA-DR following incubation with LAG-3-targeted IL-15/Rα-Fc fusions (and controls). The data show that LAG-3-targeted IL-15/Rα-Fc fusions appear to upregulate HLA-DR in CD8 memory T cells more potently in comparison to untargeted IL-15(D30N/E64Q/N65D)/Rα-Fc fusion (as well as control RSV-targeted IL-15/Rα-Fc fusion).

Figure 38:
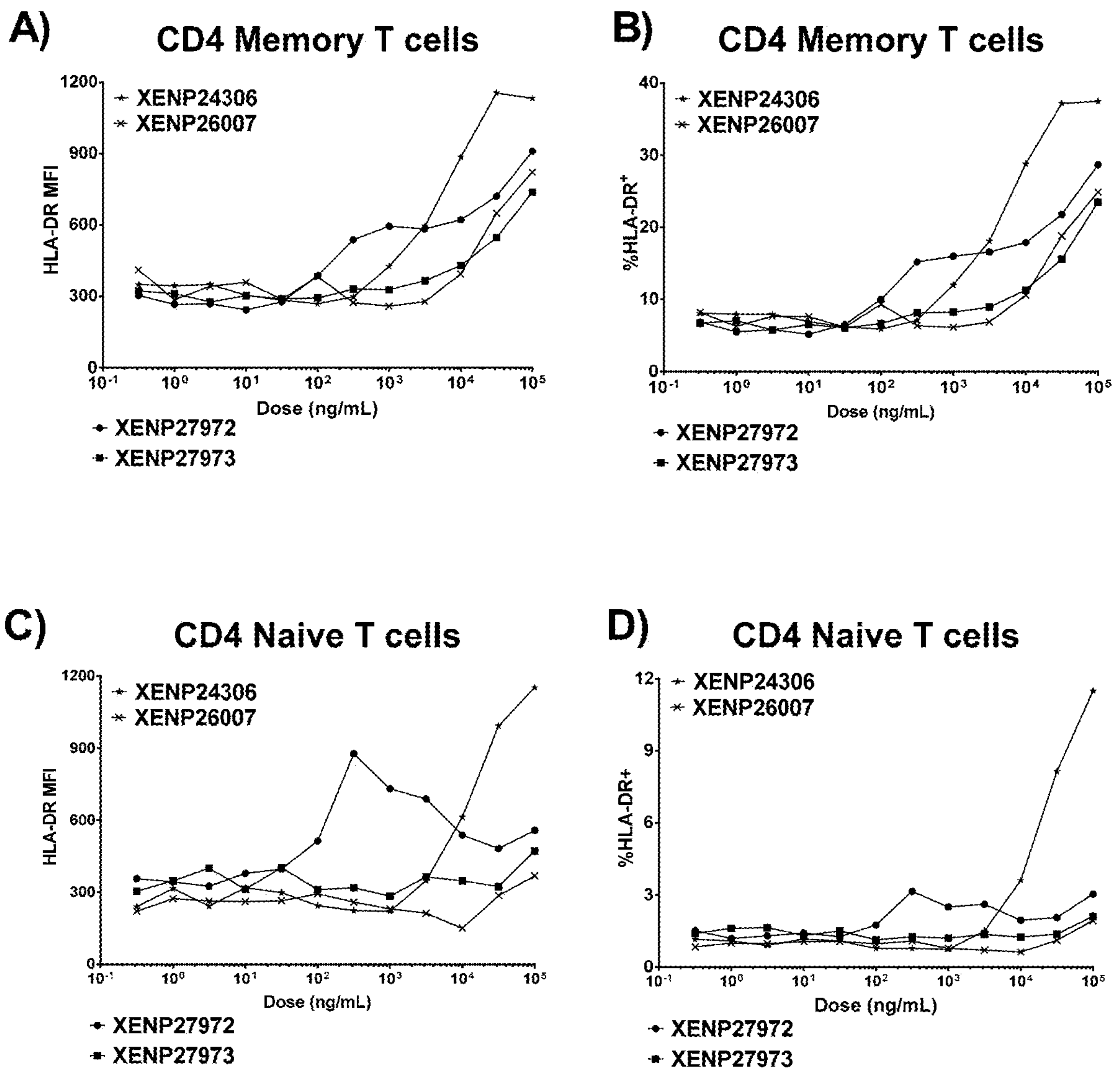

FIG. 38 depicts activation of $CD4^+$ T cells as indicated by A) HLA-DR MFI on CD4 memory T cells, B) percentage CD4 memory T cells expressing HLA-DR, C) HLA-DR MFI on CD4 naive T cells, and D) percentage CD4 naive T cells expressing HLA-DR following incubation with LAG-3-targeted IL-15/Rα-Fc fusions (and controls).

FIG. 39 depicts the sequences of XENP22853, an IL-15/Rα-heteroFc fusion comprising a wild-type IL-15 and Xtend Fc (M428L/N434S) variant. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 40 depicts the sequences of XENP24113, an IL-15/Rα-heteroFc fusion comprising an IL-15(N4D/N65D) variant and Xtend Fc (M428L/N434S) variant. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 41 depicts the sequences of XENP24294, an scIL-15/Rα-Fc fusion comprising an IL-15(N4D/N65D) variant and Xtend Fc (M428L/N434S) substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

FIG. 42 depicts the sequences of XENP24306, an IL-15/Rα-heteroFc fusion comprising an IL-15(D30N/E64Q/N65D) variant and Xtend Fc (M428L/N434S) substitution. IL-15 and IL-15Rα(sushi) are underlined, linkers are double underlined (although as will be appreciated by those in the art, the linkers can be replaced by other linkers, some of which are depicted in the Figures, and slashes (/) indicate the border(s) between IL-15, IL-15Rα, linkers, and constant/Fc regions.

Figure 43:
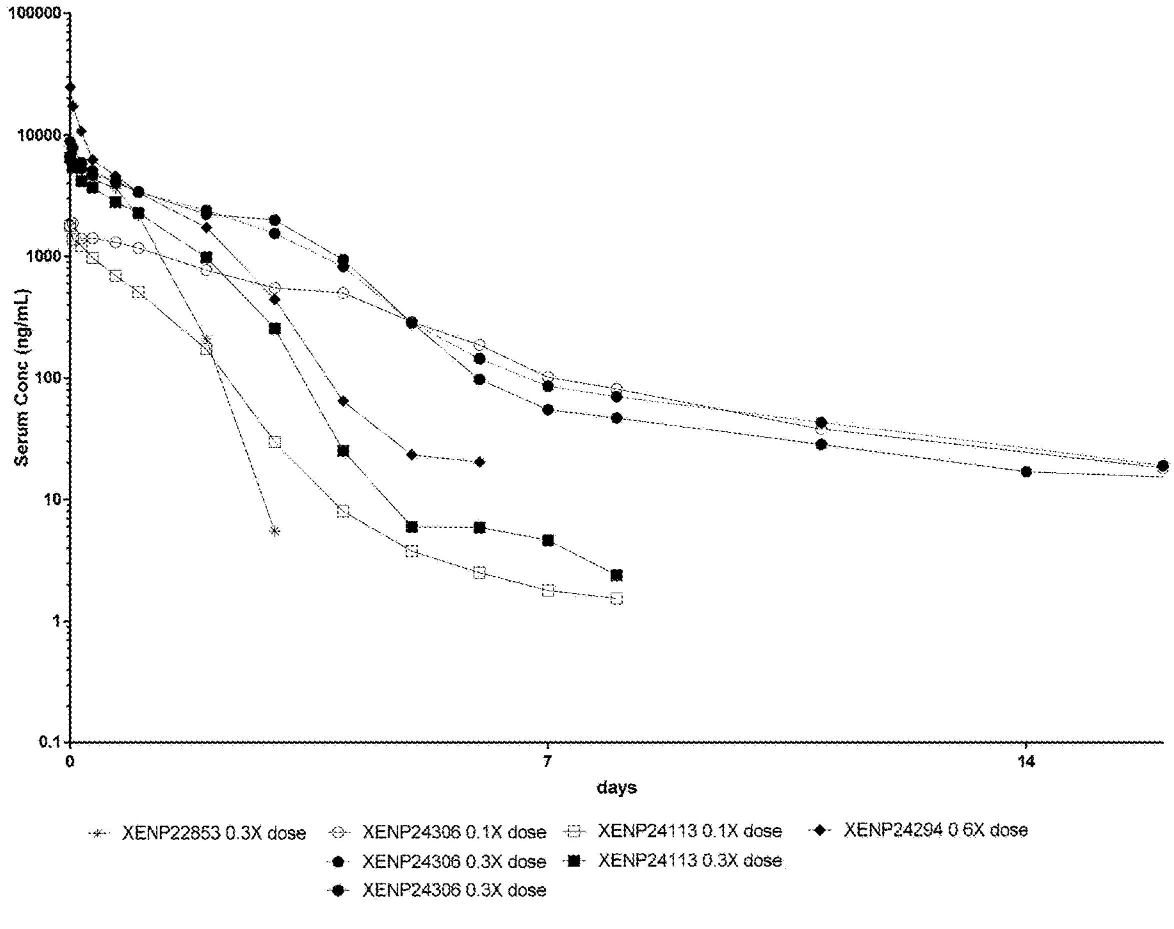
Figure 45A:
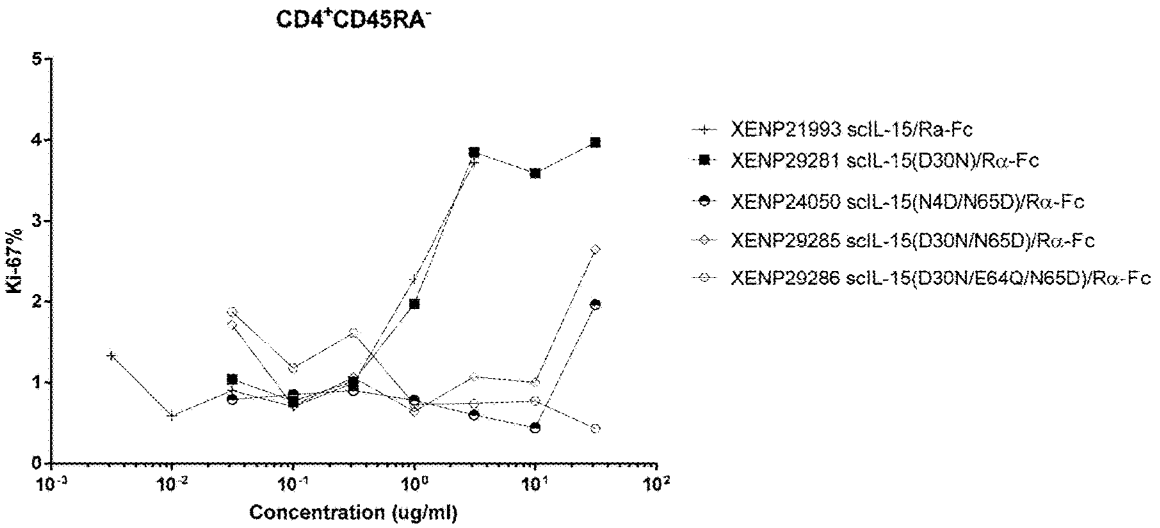
Figure 45B:
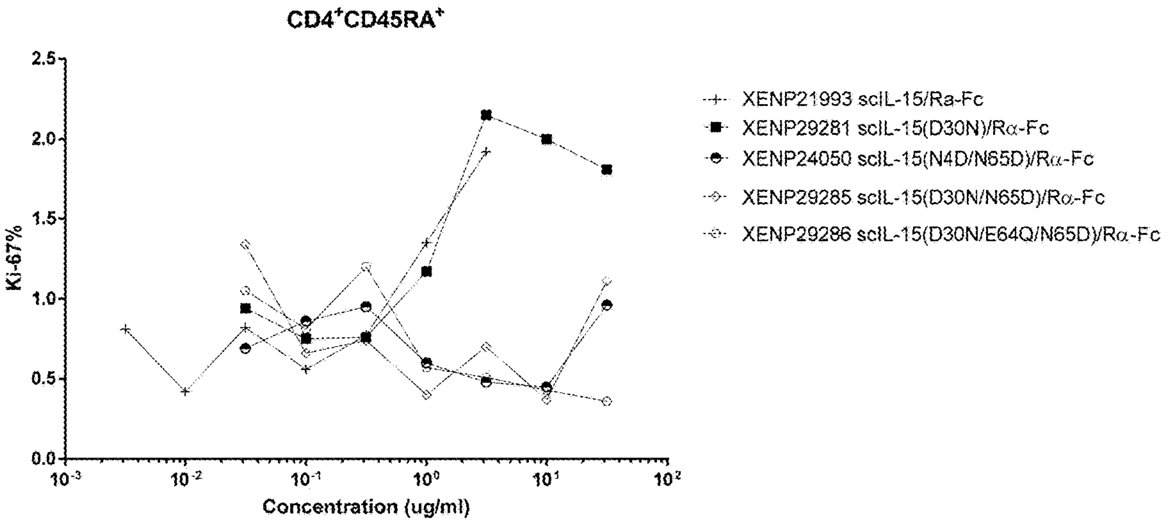
Figure 45C:
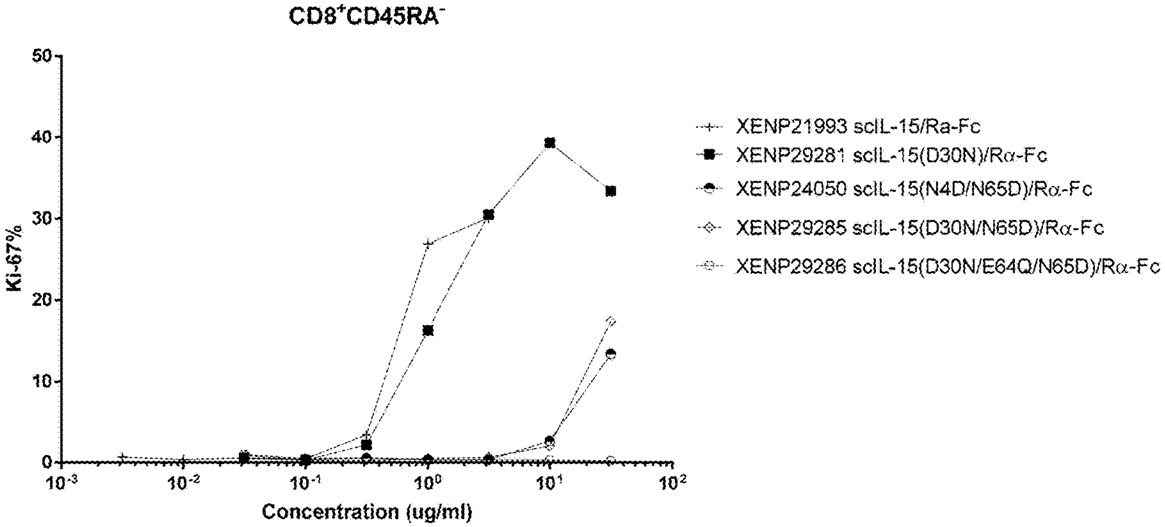
Figure 45D:
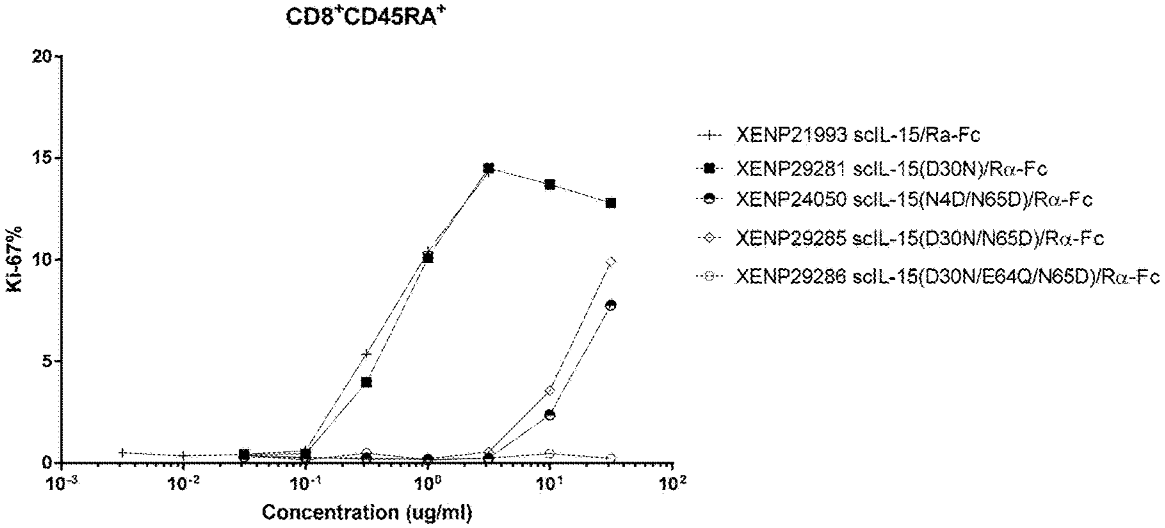
Figure 45E:
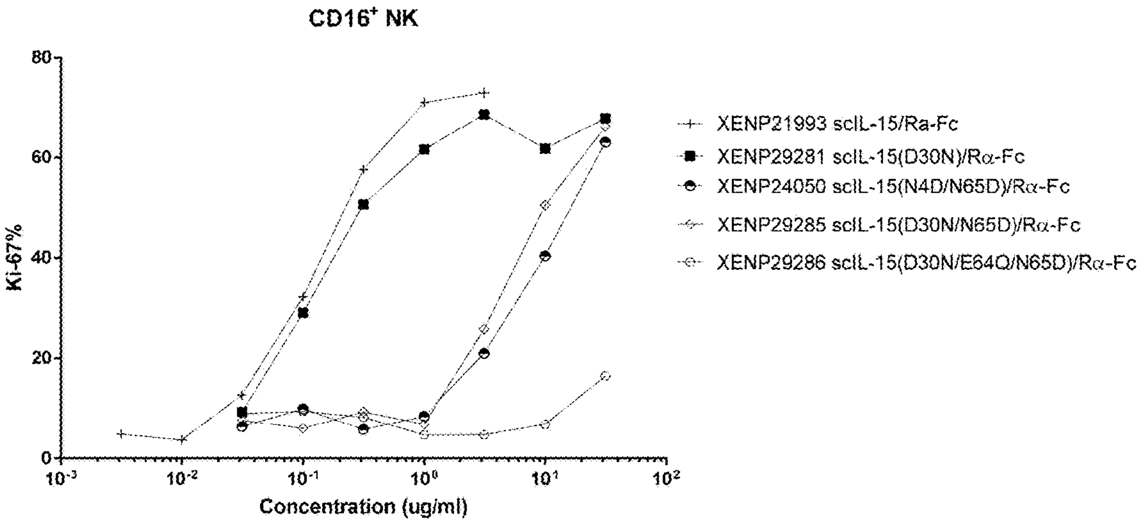
Figure 45F:
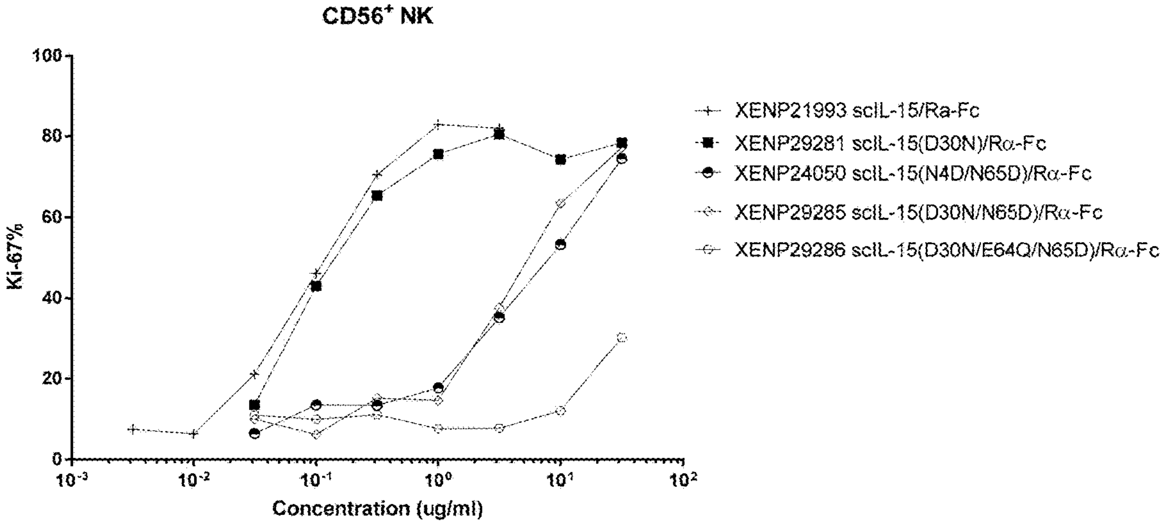
Figure 45G:
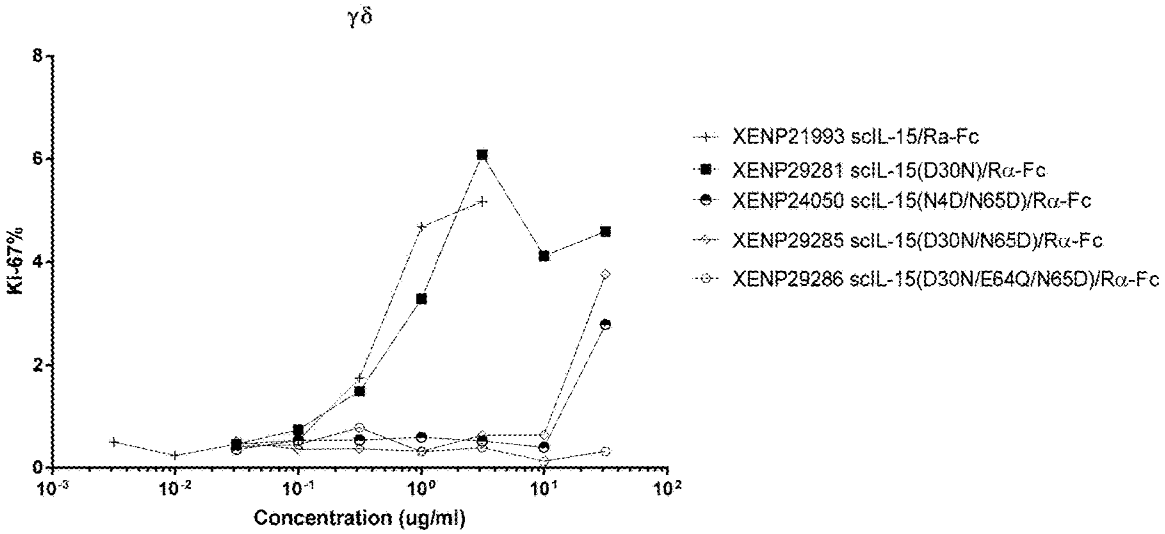

FIG. 43 depicts the serum concentration of the indicated test articles over time in cynomolgus monkeys following a first dose at the indicated relative concentrations.

FIGS. 44A-44C depict sequences of illustrative scIL-15/Rα-Fc fusions comprising additional IL-15 potency variants. IL-15 and IL-15Rα(sushi) are underlined, linkers are double underlined (although as will be appreciated by those in the art, the linkers can be replaced by other linkers, some of which are depicted in Figures some of which are depicted in FIGS. 9 and 10), and slashes (/) indicate the border(s) between IL-15, IL-15Rα, linkers, variable regions, and constant/Fc regions.

FIGS. 45A-45G depicts percentage of A) $CD4^+CD45RA^-$, B) $CD4^+CD45RA^+$, C) $CD8^+CD45RA^-$, D) $CD8^+CD45RA^+$, E) $CD16^+$ NK cells, F) $CD56^+$ NK cells, and G) γδ cells expression Ki67 following incubation of PBMCs with the indicated test articles for 3 days.

FIGS. 46A and 46B depict sequences of illustrative LAG-3-targeted IL-15/Rα-Fc fusions comprising IL-15(D30N/N65D) variant. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions.

FIGS. 47A and 47B depicts sequences of illustrative LAG-3-targeted IL-15/Rα-Fc fusions comprising IL-15 (D30N/E64Q/N65D) variant. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions.

FIGS. 48A-48D depict sequences of illustrative LAG-3-targeted IL-15/Rα-Fc fusions comprising Xtend (M428L/N434S) substitutions for enhancing serum half-life. The CDRs are in bold. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are underlined, linkers are double underlined (although as will be appreciated by those in the art, the linkers can be replaced by other linkers, some of which are depicted in FIGS. 9 and 10), and slashes (/) indicate the border(s) between IL-15, IL-15Rα, linkers, variable regions, and constant/Fc regions. It should be noted that any of the sequences depicted herein may include or exclude the M428L/N434S substitutions.

FIGS. 49A and 49B depict the sequences of XENP26007, XENP29481, and XENP30432, control RSV-targeted IL-15/Rα-Fc fusions. The CDRs are underlined. As noted herein and is true for every sequence herein containing CDRs, the exact identification of the CDR locations may be slightly different depending on the numbering used as is shown in Table 2, and thus included herein are not only the CDRs that are underlined but also CDRs included within the $V_H$ and $V_L$ domains using other numbering systems. IL-15 and IL-15Rα(sushi) are italicized, linkers are double underlined (although as will be appreciated by those in the art, the linkers can be replaced by other linkers, some of which are depicted in Figures some of which are depicted in FIGS. 9 and 10), and slashes (/) indicate the border(s) between IL-15, IL-15Rα, linkers, variable regions, and constant/Fc regions.

DETAILED DESCRIPTION

I. Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore™ assay. Of particular use in the ablation of FcγR binding are those shown in FIG. 6. However, unless otherwise noted, the Fc monomers of the invention retain binding to the FcRn receptor.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity. As is discussed herein, many embodiments of the invention ablate ADCC activity entirely.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antigen binding domain" or "ABD" herein is meant a set of six Complementary Determining Regions (CDRs) that, when present as part of a polypeptide sequence, specifically binds a target antigen as discussed herein. Thus, a "LAG-3 antigen binding domain" binds a human LAG-3 antigen as outlined herein. As is known in the art, these CDRs are generally present as a first set of variable heavy CDRs (vhCDRs or $V_H$CDRs) and a second set of variable light CDRs (vlCDRs or $V_L$CDRs), each comprising three CDRs:vhCDR1, vhCDR2, vhCDR3 for the heavy chain and vlCDR1, vlCDR2 and vlCDR3 for the light. The CDRs are present in the variable heavy and variable light domains, respectively, and together form an Fv region. Thus, in some cases, the six CDRs of the antigen binding domain are contributed by a variable heavy and variable light chain. In a "Fab" format, the set of 6 CDRs are contributed by two different polypeptide sequences, the variable heavy domain ($V_H$ or vh or $V_H$; containing the vhCDR1, vhCDR2 and vhCDR3) and the variable light domain ($V_L$ or vl or $V_L$; containing the vlCDR1, vlCDR2 and vlCDR3), with the C-terminus of the $V_H$ domain being attached to the N-terminus of the CH1 domain of the heavy chain and the C-terminus of the vl domain being attached to the N-terminus of the constant light domain (and thus forming the light chain). In a scFv format, the VH and VL domains are covalently attached, generally through the use of a linker as outlined herein, into a single polypeptide sequence, which can be either (starting from the N-terminus) VH-linker-VL or VL-linker-VH, with the former being generally preferred (including optional domain linkers on each side, depending on the format used (e.g., from FIG. 1 of U.S. 62/353,511).

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g., the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233− or E233 #, E233( ) or E233del designates a deletion of glutamic acid at position 233. Additionally, EDA233− or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4. The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it.

"Variant," as used herein can also refer to particular amino acid modifications (e.g., substitutions, deletions, insertions) in a variant protein (e.g., a variant Fc domain), for example, heterodimerization variants, ablation variants, FcKO variants, etc., as disclosed in Section II.C. below.

Accordingly, by "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S.

It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et at, 1969, Proc Natl Acad Sci USA 63:78-85, hereby entirely incorporated by reference). The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et at, (2002), Journal of the American Chemical Society 124:9026-9027; J. W. Chin, & P. G. Schultz, (2002), ChemBioChem 11:1135-1137; J. W. Chin, et at, (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full-length antibody, antibody fragment or Fab fusion protein.

By "Fv" or "Fv fragment" or "Fv region" as used herein is meant a polypeptide that comprises the VL and VH domains of a single antibody. As will be appreciated by those in the art, these generally are made up of two chains, or can be combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (VH-linker-VL or VL-linker-VH).

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes.

By "FcRn" or "neonatal Fc Receptor" as used herein is meant a protein that binds the IgG antibody Fc region and is encoded at least in part by an FcRn gene. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants can be used to increase binding to the FcRn receptor, and in some cases, to increase serum half-life. In general, unless otherwise noted, the Fc monomers of the invention retain binding to the FcRn receptor (and, as noted below, can include amino acid variants to increase binding to the FcRn receptor).

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it.

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Thus, in some cases, the Fc domain includes, from N- to C-terminal, CH2-CH3 and hinge-CH2-CH3. In some embodiments, the Fc domain is that from IgG1, IgG2, IgG3 or IgG4, with IgG1 hinge-CH2-CH3 and IgG4 hinge-CH2-CH3 finding particular use in many embodiments. Additionally, in certain embodiments, wherein the Fc domain is a human IgG1 Fc domain, the hinge includes a C220S amino acid substitution. Furthermore, in some embodiments where the Fc domain is a human IgG4 Fc domain, the hinge includes a S228P amino acid substitution. Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3).

As will be appreciated by those in the art, the exact numbering and placement of the heavy constant region domains can be different among different numbering systems. A useful comparison of heavy constant region numbering according to EU and Kabat is as below, see Edelman et al., 1969, Proc Natl Acad Sci USA 63:78-85 and Kabat et al., 1991, Sequences of Proteins of Immunological Interest, 5th Ed., United States Public Health Service, National Institutes of Health, Bethesda, entirely incorporated by reference.

TABLE 1

| | EU Numbering | Kabat Numbering |
|---|---|---|
| CH1 | 118-215 | 114-223 |
| Hinge | 216-230 | 226-243 |
| CH2 | 231-340 | 244-360 |
| CH3 | 341-447 | 361-478 |

In the embodiments herein, when a scFv or IL-15 complex is attached to an Fc domain, it is the C-terminus of the scFv, IL-15 or IL-15Rα construct that is attached to the Fc domain via a domain linker; for example, a hinge domain as depicted in FIG. 8. In some embodiments, as is more fully described below, amino acid modifications are made to the Fc region, for example to alter binding to one or more FcγR receptors or to the FcRn receptor, and to enable heterodimer formation and purification, as outlined herein.

By "heavy constant region" herein is meant the CH1-hinge-CH2-CH3 portion of an antibody.

By "Fc fusion protein" or "immunoadhesin" herein is meant a protein comprising an Fc region, generally linked (optionally through a linker moiety, as described herein) to a different protein, such as to IL-15 and/or IL-15R, as described herein. In some instances, two Fc fusion proteins can form a homodimeric Fc fusion protein or a heterodimeric fusion protein with the latter being preferred. In some cases, one monomer of the heterodimeric fusion protein comprises an Fc domain alone (e.g., an empty Fc domain) and the other monomer is a Fc fusion, comprising a variant Fc domain and a protein domain, such as a receptor, ligand or other binding partner.

By "position" as used herein is meant a location in the sequence of a protein. Positions may be numbered sequentially, or according to an established format, for example the EU index for antibody numbering.

By "strandedness" in the context of the monomers of the heterodimeric antibodies of the invention herein is meant that, similar to the two strands of DNA that "match", heterodimerization variants are incorporated into each monomer so as to preserve the ability to "match" to form heterodimers. For example, if some pI variants are engineered into monomer A (e.g., making the pI higher) then steric variants that are "charge pairs" that can be utilized as well do not interfere with the pI variants, e.g., the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer that incorporates one set of the pair will go, such that pI separation is maximized using the pI of the skews as well.

By "target cell" as used herein is meant a cell that expresses the target antigen, in this case, LAG-3.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The subject LAG-3 targeted heterodimeric proteins are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated protein," refers to a protein which is substantially free of other proteins having different binding specificities. "Recombinant" means the proteins are generated using recombinant nucleic acid techniques in exogeneous host cells.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

"Specific binding" or "specifically binds to" or is "specific for" a particular antigen or an epitope (in this case, human LAG-3) means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000-or more times greater for the epitope relative to a control, where KA or Ka refers to an association rate of a particular antibody-antigen interaction. Binding affinity is generally measured using a Biacore™ assay.

II. Introduction

The invention provides heterodimeric fusion proteins that contain an IL-15 complex on one side and an anti-human LAG-3 antigen binding domain on the other. Thus, the heterodimeric fusion proteins of the invention can bind to the checkpoint LAG-3 antigen and can complex with the common gamma chain (γc; CD132) and/or the IL-2 receptor β-chain (IL-2Rβ; CD122). In general, the heterodimeric fusion proteins of the invention have three functional components: an IL-15/IL-15Rα(sushi) component, generally referred to herein as an "IL-15 complex", an anti-LAG-3 ABD component which serves as a "targeting" moiety by bringing the fusion protein to a cell expressing LAG-3, and an Fc component, each of which can take different forms and each of which can be combined with the other components in any configuration.

In general, as is more fully described herein, the fusion proteins of the invention are heterodimeric proteins that are based on the association of antibody Fc domains. That is, by using two different variant Fc domains that have been engineered to favor the formation of heterodimers over homodimers, the heterodimeric proteins are formed. In this case, one of the variant Fc domains is fused to an IL-15/RA complex and the other has a LAG-3 ABD as more fully outlined herein. By including optional pI variants, the heterodimers can be more easily purified away from the homodimers. Additionally, the inclusion of ablation variants eliminates the effector functions of the Fc domains.

A. IL-15/IL-15Rα(Sushi) Domains

As shown in the figures, the IL-15 complex can take several forms. As stated above, the IL-15 protein on its own is less stable than when complexed with the IL-15Rα protein. As is known in the art, the IL-15Rα protein contains a "sushi domain", which is the shortest region of the receptor that retains IL-15 binding activity. Thus, while heterodimeric fusion proteins comprising the entire IL-15Rα protein can be made, preferred embodiments herein include complexes that just use the sushi domain, the sequence of which is shown in the figures.

Accordingly, the IL-15 complex generally comprises the IL-15 protein and the sushi domain of IL IL-15Rα (unless otherwise noted that the full length sequence is used, "IL-15Rα", "IL-15Rα(sushi)", "IL-15RA" and "sushi" are used interchangeably throughout).

Importantly, the IL-15 component is generally engineered to reduce its potency. In many embodiments, the wild-type IL-15 is too potent and can cause undesirable toxicity. Accordingly, the IL-15 component of the IL-15 complex can have one or more amino acid substitutions that result in decreased activity. Various amino acid substitutions were made (see FIG. 19) and tested (see FIG. 20). Of particular interest in some embodiments are a double variant, N4D/N65D or D30N/N65D, or a triple variant, D30N/E64Q/N65D.

The targeted IL-15/IL-15Rα heterodimeric fusion proteins of the present invention include an IL-15/IL-15 receptor alpha (IL-15Rα)-Fc fusion monomer; reference is made to US2018/0118828, filed 16, October 2017, U.S. Ser. No. 62/408,655, filed on Oct. 14, 2016, U.S. Ser. No. 62/416,087, filed on October Nov. 1, 2016, U.S. Ser. No. 62/443,465, filed on Jan. 6, 2017, U.S. Ser. No. 62/477,926, filed on Mar. 28, 2017, and U.S. Ser. No. 62/659,571, filed on Apr. 18, 2018, hereby incorporated by reference in their entirety and in particular for the sequences outlined therein. In some cases, the IL-15 and IL-15 receptor alpha (IL-15Rα) protein domains are in different orientations. Exemplary embodiments of IL-15/IL-15Rα-Fc fusion monomers are provided in XENP21480 (chain 1; FIG. 64A), XENP22022 (chain 1, FIG. 64D), XENP22112, (chains 1 and 3; FIG. 64E), XENP22641 (chains 2 and 4; FIG. 64F), XENP22642, (chains 1 and 4; FIG. 64H) and XENP22644 (chains 1 and 4; FIG. 64I) as described, for example, in US 2018/0118828.

1. IL-15 Variants

In some embodiments, the human IL-15 protein has the amino acid sequence set forth in NCBI Ref. Seq. No. NP_000576.1 as shown in FIG. 2. In some cases, the coding sequence of human IL-15 is set forth in NCBI Ref. Seq. No. NM_000585. An exemplary IL-15 protein of the Fc fusion heterodimeric protein outlined herein can have the amino acid sequence of SEQ ID NO:2 or amino acids 49-162 of SEQ ID NO:1. In some embodiments, the IL-15 protein has at least 90%, e.g., 90%, 91%, 92%, 93%, 94%, 95%, 96%, 97%, 98%, 99%, or more sequence identity to SEQ ID NO:2. In some embodiments, the IL-15 protein has the amino acid sequence set forth in SEQ ID NO:2 except with the amino acid substitution N72D. In other embodiments, the IL-15 protein has the amino acid sequence of SEQ ID NO:2 except with one or more amino acid substitutions selected from the group consisting of C42S, L45C, Q48C, V49C, L52C, E53C, E87C, and E89C. In some aspects, the IL-15 protein has one or more amino acid substitutions selected from the group consisting of N1D, N4D, D8N, D30N, D61N, E64Q, N65D, and Q108E. In other embodiments, the amino acid substitutions are N4D/N65D. In certain embodiments, the amino acid substitutions are D30N/N65D. In some embodiments, the amino acid substitution is Q108E. In certain embodiments, the amino acid substitution is N65D. In other embodiments, the amino acid substitutions are D30N/E64Q/N65D. In certain embodiments, the amino acid substitution is N65D. In some instances, the amino acid substitutions are N1D/N65D. In some instances, the amino acid substitutions are D30N/N65D. Optionally, the IL-15 protein also has an N72D substitution. The IL-15 protein of the Fc fusion protein can have 1, 2, 3, 4, 5, 6, 7, 8 or 9 amino acid substitutions. In some embodiments, the IL-15 protein of the Fc fusion protein comprises a D30N substitution. In some embodiments, the IL-15 protein of the Fc fusion protein comprises a N65D substitution. In some embodiments, the IL-15 protein of the Fc fusion contains one or more amino acid substitutions at the IL-15:CD132 interface. In certain embodiments, the Fc fusion protein described herein induces proliferation of NK cells and CD8+ T cells. Additionally, IL-15 variants that can be used with the subject targeted IL-15/IL-15Rα heterodimer proteins are included in FIGS. 19A-C.

In some embodiments, the human IL-15 receptor alpha (IL-15Rα) protein has the amino acid sequence set forth in NCBI Ref. Seq. No. NP_002180.1 or SEQ ID NO:3. In some cases, the coding sequence of human IL-15Rα is set forth in NCBI Ref. Seq. No. NM_002189.3. An exemplary the IL-15Rα protein of the Fc fusion heterodimeric protein outlined herein can comprise or consist of the sushi domain of SEQ ID NO:3 (e.g., amino acids 31-95 of SEQ ID NO:3), or in other words, the amino acid sequence of SEQ ID NO:4. In some embodiments, the IL-15Rα protein has the amino acid sequence of SEQ ID NO:4 and an amino acid insertion selected from the group consisting of D96, P97, A98, D96/P97, D96/C97, D96/P97/A98, D96/P97/C98, and D96/C97/A98, wherein the amino acid position is relative to full-length human IL-15Rα protein or SEQ ID NO:3. For instance, amino acid(s) such as D (e.g., Asp), P (e.g., Pro), A (e.g., Ala), DP (e.g., Asp-Pro), DC (e.g., Asp-Cys), DPA (e.g., Asp-Pro-Ala), DPC (e.g., Asp-Pro-Cys), or DCA (e.g., Asp-Cys-Ala) can be added to the C-terminus of the IL-15Rα protein of SEQ ID NO:4. In some embodiments, the IL-15Rα protein has the amino acid sequence of SEQ ID NO:4 and one or more amino acid substitutions selected from the group consisting of K34C, A37C, G38C, S40C, and L42C, wherein the amino acid position is relative to SEQ ID NO:4. The IL-15Rα protein can have 1, 2, 3, 4, 5, 6, 7, 8 or more amino acid mutations (e.g., substitutions, insertions and/or deletions).

2. IL-15/RA Complexes

As outlined herein, the IL-15 variants and the sushi domain can be complexed in at least three different ways to form an IL-15 complex.

Figure 21A:
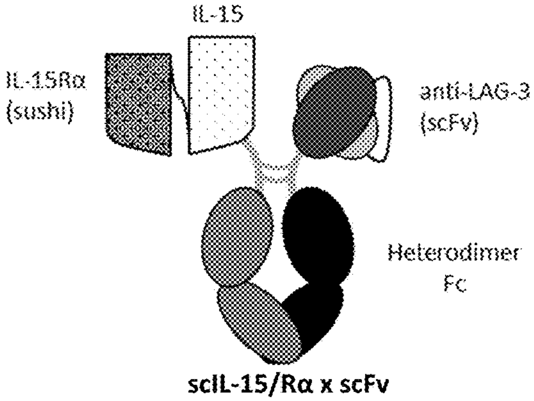
Figure 21B:
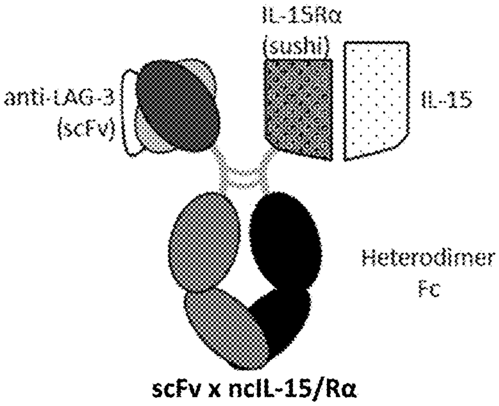

In some embodiments, as shown in FIGS. 21B, for example, the IL-15 protein and the IL-15Rα(sushi) are not covalently attached, but rather are self-assembled through regular ligand-ligand interactions. As is more fully described herein, it can be either the IL-15 domain or the sushi domain that is covalently linked to the Fc domain (generally using an optional domain linker). Again, of particular use in this embodiment are a double variant, N4D/N65D or D30N/N65D, or a triple variant, D30N/E64Q/N65D, used with a wild type sushi domain.

Figure 21C:
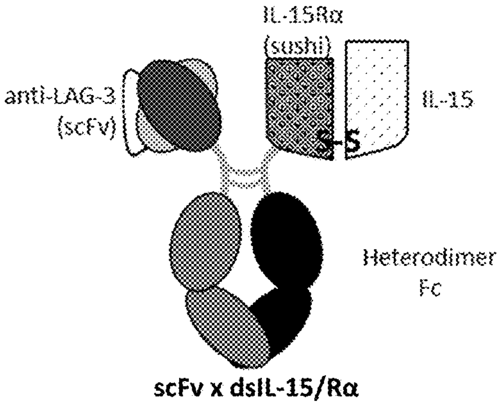
Figure 21D:
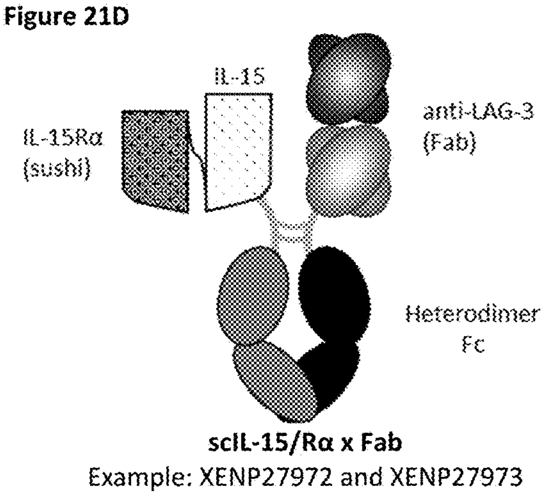

In alternative embodiments, the variant IL-15 can be complexed to the sushi domain using a domain linker, such that they are covalently attached as generally shown in FIG. 21D; this figure depicts the sushi domain as the N-terminal domain, although this can be reversed. Again, of particular use in this embodiment are a double variant, N4D/N65D or D30N/N65D, or a triple variant, D30N/E64Q/N65D, used with a wild type sushi domain. Exemplary domain linkers that can be used to attach the IL-15 variant to the sushi domain are depicted in FIG. 8.

Alternatively, each of the IL-15 and sushi domains can be engineered to contain a cysteine amino acid, that forms a disulfide bond to form the complex as is generally shown in FIGS. 21C, again, with either the IL-15 domain or the sushi domain being covalently attached (using an optional domain linker) to the Fc domain. Again, of particular use in this embodiment are a double variant, N4D/N65D or D30N/N65D, (additionally including an amino acid substitution to cysteine), or a triple variant, D30N/E64Q/N65D (additionally including an amino acid substitution to cysteine), used with a sushi domain also comprising an amino acid substitution to provide a cysteine.

Additional particular embodiments are outlined below.

B. Anti-LAG-3 Components

In some embodiments, the heterodimeric fusion proteins provided herein include some antibody components.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies or antibody fragments (antibody monomers) that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

In addition, many of the monomer sequences herein have at least one the cysteines at position 220 replaced by a serine, to reduce disulfide formation. Specifically included within the sequences herein are one or both of these cysteines replaced (C220S).

Thus, "isotype" as used herein is meant any of the subclasses of immunoglobulins defined by the chemical and antigenic characteristics of their constant regions.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g., residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g., vhCDR1, vhCDR2 and vhCDR3) and the disclosure of each variable light region is a disclosure of the vlCDRs (e.g., vlCDR1, vlCDR2 and vlCDR3).

A useful comparison of CDR numbering is as below, see Lafranc et al., Dev. Comp. Immunol. 27(1):55-77 (2003):

TABLE 2

| | Kabat + Chothia | IMGT | Kabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g., a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the invention not only includes the enumerated antigen binding domains and antibodies herein, but those that compete for binding with the epitopes bound by the enumerated antigen binding domains.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. As shown herein and described below, the pI variants can be in one or more of the CH regions, as well as the hinge region, discussed below.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. As noted herein, pI variants can be made in the hinge region as well.

The light chain generally comprises two domains, the variable light domain (containing the light chain CDRs and together with the variable heavy domains forming the Fv region), and a constant light chain region (often referred to as CL or Cκ).

Another region of interest for additional substitutions, outlined herein, is the Fc region.

Thus, the present heterodimeric fusion proteins provided herein include one or more antibody domains. As described herein and known in the art, the heterodimeric antibodies provided herein comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

As generally outlined herein, the heterodimeric proteins of the invention include one or more LAG-3 antigen binding domains (e.g., Fvs) that binds human LAG-3. “Lymphocyte-activation gene 3,” “LAG-3,” “LAG3,” “CD223,” and “cluster of differentiation 3,” (e.g., Genebank Accession Numbers NM_002286 and NP_002277 (human)) as used herein is meant a member of an immunoglobulin (Ig) superfamily, that is a type I transmembrane protein with four extracellular Ig-like domains. LAG-3 is a negative regulator of T cells and appears to work in concert with other checkpoint molecules, including CTLA-4 and PD-1. In 1990, Triebel et al. discovered LAG3 as a transmembrane protein expressed by activated human natural killer (NK) and T-cell lines, although it can also be expressed on B cells. The human LAG3 gene has 20% identity with the human CD4 gene, resulting in surface-expressed LAG-3 protein being able to bind major histocompatibility complex (MHC) class II molecules with high affinity. LAG-3 either exists as a cell surface dimer or as a soluble form released by interferon-gamma-producing CD4-positive T cells via proteolytic cleavage of a membrane-proximal connecting peptide. Exemplary LAG-3 sequences are depicted in FIG. 3.

This Fv, or anti-LAG-3 component (the anti-LAG-3 antigen binding domain or LAG-3 ABD) of the subject heterodimer fusion proteins is generally a set of 6 CDRs and/or a variable heavy domain and a variable light domain that form an Fv domain that can bind human LAG-3. As described herein, there are a number of different formats that can be used, generally either by using a scFv or a Fab as outlined herein.

In certain embodiments, the ABDs of the invention comprise a heavy chain variable region with frameworks from a particular germline heavy chain immunoglobulin gene and/or a light chain variable region from a particular germline light chain immunoglobulin gene. For example, such ABDs may comprise or consist of a human ABD comprising heavy or light chain variable regions that are “the product of” or “derived from” a particular germline sequence. An ABD that is “the product of” or “derived from” a human germline immunoglobulin sequence can be identified as such by comparing the amino acid sequence of the ABD to the amino acid sequences of human germline immunoglobulins and selecting the human germline immunoglobulin sequence that is closest in sequence (i.e., greatest % identity) to the sequence of the ABD. An ABD that is “the product of” or “derived from” a particular human germline immunoglobulin sequence may contain amino acid differences as compared to the germline sequence, due to, for example, CDRs, naturally-occurring somatic mutations or intentional introduction of site-directed mutation. However, a humanized ABD typically is at least 90% identical in amino acids sequence to an amino acid sequence encoded by a human germline immunoglobulin gene and contains amino acid residues that identify the ABD as being derived from human sequences when compared to the germline immunoglobulin amino acid sequences of other species (e.g., murine germline sequences). In certain cases, a humanized ABD may be at least 95, 96, 97, 98 or 99%, or even at least 96%, 97%, 98%, or 99% identical in amino acid sequence to the amino acid sequence encoded by the germline immunoglobulin gene. Typically, a humanized ABD derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants of the invention). In certain cases, the humanized ABD may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants of the invention). In one embodiment, the parent ABD has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

As shown herein, the anti-LAG-3 ABD can be in the form of either a Fab or an scFv.

In some embodiments, for example as depicted in FIGS. 21B and C, the anti-LAG-3 ABD is a scFv, wherein the VH and VL domains are joined using an scFv linker, which can be optionally a charged scFv linker. As will be appreciated by those in the art, the scFv can be assembled from N- to C-terminus, as N-VH-scFv linker-VL-C or as N-VL-scFv linker-VH-C, with the C terminus of the scFv domain generally being linked to the hinge-CH2-CH3 Fc domain, wherein the hinge in this case serving as a domain linker. Suitable Fvs (including CDR sets and variable heavy/variable light domains) can be used in scFv formats or Fab formats are shown in the Figures as well as disclosed in WO2017/218707, the contents are hereby incorporated in its entirety for all purposes, and in particular for the LAG-3 ABDs in FIG. 11, the data in FIG. 18, FIG. 55, FIG. 56, FIG. 63 and SEQ ID NO:s 36819-36962, SEQ ID NO:s 35417-35606, SEQ ID NO:s 25914-32793 and SEQ ID NO:s 32794-33002 sequences in the sequence listing.

As will further be appreciated by those in the art, all or part of the hinge (which can also be a wild type hinge from IgG1, IgG2 or IgG4 or a variant thereof, such as the IgG4 S241P or S228P hinge variant with the substitution proline at position 228 relative to the parent IgG4 hinge polypeptide (wherein the numbering S228P is according to the EU index and the S241P is the Kabat numbering)) can be used as the domain linker between the scFv and the CH2-CH3 domain, or a different domain linker such as depicted in the Figures can be used.

Alternatively, the LAG-3 ABD can be in the form of a Fab fragment. In this embodiment, the ABD is made up of a variable heavy domain, contributed by a heavy chain, and a variable light domain, contributed by a light chain. Suitable Fvs (including CDR sets and variable heavy/variable light domains) can be used in scFv formats or Fab formats are shown in the Figures as well as disclosed in in WO2017/218707, the contents are hereby incorporated in its entirety for all purposes, and in particular for the LAG-3 ABDs in FIG. 11, the data in FIG. 18, FIG. 55, FIG. 56, FIG. 63 and SEQ ID NO:s 36819-36962, SEQ ID NO:s 35417-35606, SEQ ID NO:s 25914-32793 and SEQ ID NO:s 32794-33002 sequences in the sequence listing.

As will be appreciated by those in the art, suitable LAG-3 binding domains can comprise a set of 6 CDRs as depicted in the sequence listing and figures (e.g., FIGS. 12 and 13), either as they are underlined/bolded or, in the case where a different numbering scheme is used as described herein and as shown in Table 2, as the CDRs that are identified using other alignments within the variable heavy (VH) domain and variable light domain (VL) sequences of those depicted in the figures (e.g., FIGS. 12 and 13A-C) and the sequence listing. Suitable LAG-3 ABDs that find use in the subject targeted IL-15/IL-15Rα heterodimeric fusion proteins can also include the entire VH and VL sequences as depicted in these sequences and figures, used as scFvs or as Fabs.

In one embodiment, the LAG-3 antigen binding domain includes the 6 CDRs (i.e., vhCDR1-3 and vlCDR1-3) of any of the LAG-3 binding domains described in FIGS. 12 and 13A-C or the sequence listing.

In addition to the parental CDR sets disclosed in the figures and sequence listing that form an ABD to LAG-3, provided herein are variant LAG-3 ABDS having CDRs that include at least one modification of the LAG-3 ABD CDRs disclosed herein (e.g., FIGS. 12 and 13A-C). In one embodiment, the heterodimeric fusion protein includes a LAG-3 ABD that includes a set of 6 CDRs with 1, 2, 3, 4, 5, 6, 7, 8, 9, 10 amino acid modifications as compared to the 6 CDRs of a LAG-3 ABD as depicted in FIGS. 112 and 3A-C or the sequence listing. In certain embodiments, the LAG-3 ABD is capable of binding LAG-3 antigen, as measured by at least one of a Biacore™, surface plasmon resonance (SPR) and/or BLI (biolayer interferometry, e.g., Octet® assay) assay, with the latter finding particular use in many embodiments.

In one embodiment, the LAG-3 ABD of the subject targeted IL-15/IL-15Rα heterodimeric fusion protein includes 6 CDRs that are at least 90, 95, 97, 98 or 99% identical to the 6 CDRs of a LAG-3 ABD as depicted in FIGS. 12 and 13A-C or the sequence listing. In certain embodiments, the LAG-3 ABD is capable of binding to the LAG-3, as measured by at least one of a Biacore™, surface plasmon resonance (SPR) and/or BLI (biolayer interferometry, e.g., Octet® assay) assay, with the latter finding particular use in many embodiments.

In one embodiment of the subject targeted IL-15/IL-15Rα heterodimeric fusion protein, the LAG-3 antigen binding domain includes the 6 CDRs (i.e., vhCDR1-3 and vlCDR1-3) of one of the following LAG-3 ABDs: 7G8[LAG-3]_H0_L0, 7G8[LAG-3]_H3_L1, 7G8[LAG-3]_H3.30_L1.34. 2A11[LAG-3]_H0_L0, 2A11[LAG-3]_H1_L2, 2A11[LAG-3]_H1.44_L2.142, BMS-986016[LAG-3], IMP731[LAG-3], 13E2[LAG-3], 34F4[LAG-3], IMP761[LAG-3], H5L7[LAG-3], hu22D2[LAG-3], H4sH15482P[LAG-3], L35D4[LAG-3], L35G6[LAG-3], L33H11[LAG-3], L32A9[LAG-3], L32D10[LAG-3], L32A4[LAG-3], L3A1[LAG-3], L3A10[LAG-3], L3C5[LAG-3], and L3E3[LAG-3] (see, e.g., FIGS. 12 and 13A-C). In an exemplary embodiment, the LAG-3 ABD is 7G8[LAG-3]_H3.30_L1.34 or 2A11[LAG-3]_H1.144_L2.142 LAG-3 ABD (see, e.g., FIG. 12).

In one embodiment, the LAG-3 antigen binding domain is a variant LAG-3 antigen binding domain that includes 6 CDRs (i.e., vhCDR1-3 and vlCDR1-3), where the 6 CDRs include 1, 2, 3, 4, 5, 6, 7, 8, 9, or 10 modifications as compared to the 6 CDRs of one of the following LAG-3 ABDs: 7G8[LAG-3]_H0_L0, 7G8[LAG-3]_H3_L1, 7G8[LAG-3]_H3.30_L1.34. 2A11[LAG-3]_H0_L0, 2A11[LAG-3]_H1_L2, 2A11[LAG-3]_H1.44_L2.142, BMS-986016[LAG-3], IMP731[LAG-3], 13E2[LAG-3], 34F4[LAG-3], IMP761[LAG-3], H5L7[LAG-3], hu22D2[LAG-3], H4sH15482P[LAG-3], L35D4[LAG-3], L35G6[LAG-3], L33H11[LAG-3], L32A9[LAG-3], L32D10[LAG-3], L32A4[LAG-3], L3A1[LAG-3], L3A10[LAG-3], L3C5[LAG-3], and L3E3[LAG-3] (see, e.g., FIGS. 12 and 13A-C). In an exemplary embodiment, the LAG-3 ABD is 7G8[LAG-3]_H3.30_L1.34 or 2A11[LAG-3]_H1.144_L2.142 LAG-3 ABD (see, e.g., FIG. 12).

In one embodiment, the LAG-3 antigen binding domain of the IL-15/IL-15Rα heterodimeric fusion protein is a variant LAG-3 antigen binding domain that includes 6 CDRs (i.e., vhCDR1-3 and vlCDR1-3), where the 6 CDRs are at least 90, 95, 97, 98 or 99% identical as compared to the 6 CDRs) of one of the following LAG-3 ABDs: 7G8[LAG-3]_H0_L0, 7G8[LAG-3]_H3_L1, 7G8[LAG-3]_H3.30_L1.34. 2A11[LAG-3]_H0_L0, 2A11[LAG-3]_H1_L2, 2A11[LAG-3]_H1.44_L2.142, BMS-986016[LAG-3], IMP731[LAG-3], 13E2[LAG-3], 34F4[LAG-3], IMP761[LAG-3], H5L7[LAG-3], hu22D2[LAG-3], H4sH15482P[LAG-3], L35D4[LAG-3], L35G6[LAG-3], L33H11[LAG-3], L32A9[LAG-3], L32D10[LAG-3], L32A4[LAG-3], L3A1[LAG-3], L3A10[LAG-3], L3C5[LAG-3], and L3E3[LAG-3] (see, e.g., FIGS. 12 and 13A-C). In an exemplary embodiment, the LAG-3 ABD is 7G8[LAG-3]_H3.30_L1.34 or 2A11[LAG-3]_H1.144_L2.142 LAG-3 ABD (see, e.g., FIG. 12).

In some embodiments, the LAG-3 ABD of the IL-15/IL-15Rα heterodimeric fusion protein includes the variable heavy domain (VH) and variable light domain (VL) of any of the LAG-ABDs disclosed herein, including, but not limited to those disclosed in FIGS. 12 and 13A-C. In addition to the parental LAG-3 variable heavy and variable light domains disclosed herein, provided herein are subject targeted IL-15/IL-15Rα heterodimeric fusion proteins having one or more LAG-3 ABDs that include a variable heavy domain and/or a variable light domain that are variants of a LAG-3 ABD VH and VL domain disclosed herein. In one embodiment, the variant VH domain and/or VL domain has from 1, 2, 3, 4, 5, 6, 7, 8, 9 or 10 amino acid changes from a VH and/or VL domain of a LAG-3 ABD depicted in FIGS. 12, 13A-C, 29A and B, or the sequence listing. In certain embodiments, the LAG-3 ABD is capable of binding to LAG-3, as measured at least one of a Biacore™, surface plasmon resonance (SPR) and/or BLI (biolayer interferometry, e.g., Octet® assay) assay, with the latter finding particular use in many embodiments.

In one embodiment, the variant VH and/or VL domain of the IL-15/IL-15Rα heterodimeric fusion protein is at least 90, 95, 97, 98 or 99% identical to the VH and/or VL of a LAG-3 ABD as depicted in FIGS. 12 and 13A-C or the sequence listing. In certain embodiments, the LAG-3 ABD is capable of binding to LAG-3, as measured by at least one of a Biacore™, surface plasmon resonance (SPR) and/or BLI (biolayer interferometry, e.g., Octet® assay) assay, with the latter finding particular use in many embodiments.

In some embodiments, the LAG-3 ABD includes the VH and VL of one of the following LAG-3 ABDs: 7G8[LAG-3]_H0_L0, 7G8[LAG-3]_H3_L1, 7G8[LAG-3]_H3.30_L1.34. 2A11[LAG-3]_H0_L0, 2A11[LAG-3]_H1_L2, 2A11[LAG-3]_H1.44_L2.142, BMS-986016[LAG-3], IMP731[LAG-3], 13E2[LAG-3], 34F4[LAG-3], IMP761[LAG-3], H5L7[LAG-3], hu22D2[LAG-3], H4sH15482P[LAG-3], L35D4[LAG-3], L35G6[LAG-3], L33H11[LAG-3], L32A9[LAG-3], L32D10[LAG-3], L32A4[LAG-3], L3A1[LAG-3], L3A10[LAG-3], L3C5

[LAG-3], and L3E3[LAG-3] (see, e.g., FIGS. 12 and 13A-C). In an exemplary embodiment, the LAG-3 ABD is 7G8[LAG-3]_H3.30_L1.34 or 2A11[LAG-3]_H1.144_L2.142 LAG-3 ABD (see, e.g., FIG. 12).

In some embodiments, the LAG-3 ABD includes a VH and VL, where the VH and/or VL includes 1, 2, 3, 4, 5, 6, 7, 8, 9 or 10 amino acid modifications as compared to a VH and/or VL of a 7G8_H3.30_L1.34 or 2A11_H1.144_L2.142 LAG-3 ABD (see, e.g., FIG. 12).

In certain embodiments, the LAG-3 ABD includes a VH and VL, where the VH and VL are at least 90, 95, 97, 98 or 99% identical as compared to a VH and VL of one of the following LAG-3 ABDs: 7G8[LAG-3]_H0_L0, 7G8[LAG-3]_H3_L1, 7G8[LAG-3]_H3.30_L1.34. 2A11[LAG-3]_H0_L0, 2A11[LAG-3]_H1_L2, 2A11[LAG-3]_H1.44_L2.142, BMS-986016[LAG-3], IMP731[LAG-3], 13E2[LAG-3], 34F4[LAG-3], IMP761[LAG-3], H5L7[LAG-3], hu22D2[LAG-3], H4sH15482P[LAG-3], L35D4[LAG-3], L35G6[LAG-3], L33H11[LAG-3], L32A9[LAG-3], L32D10[LAG-3], L32A4[LAG-3], L3A1[LAG-3], L3A10[LAG-3], L3C5[LAG-3], and L3E3[LAG-3] (see, e.g., FIGS. 12 and 13A-C). In an exemplary embodiment, the LAG-3 ABD is 7G8[LAG-3]_H3.30_L1.34 or 2A11[LAG-3]_H1.144_L2.142 LAG-3 ABD (see, e.g., FIG. 12).

C. Fc Domains

The Fc domain component of the invention is as described herein, which generally contains skew variants and/or optional pI variants and/or ablation variants are outlined herein. See for example the disclosure of WO2017/218707 under the heading "IV Heterodimeric Antibodies", including sections IV.A, IV.B, IV.C, IV.D, IV.E, IV.F, IV.G, IV.H and IV.I, all of which are expressly incorporated by reference in their entirety. Of particular use in the heterodimeric proteins of the present invention are Fc domains containing "skew variants", "pI variants", "ablation variants" and FcRn variants as outlined therein. Particularly useful combinations of such variants are depicted, for example, FIGS. 7A-F.

The Fc domains can be derived from IgG Fc domains, e.g., IgG1, IgG2, IgG3 or IgG4 Fc domains. In an exemplary embodiment, the subject heterodimeric fusion protein provided herein includes an IgG1 Fc domain. The following describes Fc domains that are useful for IL-15/IL-15Rα Fc fusion monomers and anti-LAG-3 antibody fragments of the targeted IL-15/IL-15Rα heterodimeric fusion proteins.

Thus, the "Fc domain" includes the —CH2-CH3 domain, and optionally a hinge domain, and can be from human IgG1, IgG2, IgG3 or IgG4, with Fc domains derived from IgG1. In some of the embodiments herein, when a protein fragment, e.g., IL-15 or IL-15Rα is attached to an Fc domain, it is the C-terminus of the IL-15 or IL-15Rα construct that is attached to all or part of the hinge of the Fc domain. In other embodiments, when a protein fragment, e.g., IL-15 or IL-15Rα, is attached to an Fc domain, it is the C-terminus of the IL-15 or IL-15Rα construct that is attached to the CH1 domain of the Fc domain.

In some of the constructs and sequences outlined herein of an Fc domain protein, the C-terminus of the IL-15 or IL-15Rα protein fragment is attached to the N-terminus of a domain linker, the C-terminus of which is attached to the N-terminus of a constant Fc domain (N-IL-15 or IL-15Rα protein fragment-linker-Fc domain-C) although that can be switched (N-Fc domain-linker-IL-15 or IL-15Rα protein fragment-C). In other constructs and sequence outlined herein, C-terminus of a first protein fragment is attached to the N-terminus of a second protein fragment, optionally via a domain linker, the C-terminus of the second protein fragment is attached to the N-terminus of a constant Fc domain, optionally via a domain linker. In yet other constructs and sequences outlined herein, a constant Fc domain that is not attached to a first protein fragment or a second protein fragment is provided. A heterodimeric fusion protein can contain two or more of the exemplary monomeric Fc domain proteins described herein. Any domain linker can be used to attach a IL-15 or IL-15Rα protein fragment to an Fc domain of the heterodimeric fusion protein provided herein. In some embodiments, the linker is any one of the linkers in FIG. 8.

In some embodiments, the linker is a "domain linker", used to link any two domains (e.g., IL-15 or IL-15Rα protein fragment to Fc domain or scFv to Fc domain) as outlined herein together, some of which are depicted in FIG. 8. While any suitable linker can be used, many embodiments utilize a glycine-serine polymer, including for example (GS)n, (GSGGS)n (SEQ ID NO: 382), (GGGGS)n (SEQ ID NO: 14), and (GGGS)n (SEQ ID NO: 383), where n is an integer of at least one (and generally from 1 to 2 to 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers.

In one embodiment, the heterodimeric fusion proteins contain at least two constant domains which can be engineered to produce heterodimers, such as pI engineering. Other Fc domains that can be used include fragments that contain one or more of the CH1, CH2, CH3, and hinge domains of the invention that have been pI engineered. In particular, the formats depicted in FIG. 21 are heterodimeric fusion proteins, meaning that the protein has two associated Fc sequences self-assembled into a heterodimeric Fc domain and at least one fusion protein (e.g., 1, 2 or more fusion proteins) as more fully described below. In some cases, a first fusion protein is linked to a first Fc and a second fusion protein is linked to a second Fc. In other cases, a first fusion protein is linked to a first Fc, and the first fusion protein is non-covalently attached to a second fusion protein that is not linked to an Fc. In some cases, the heterodimeric fusion protein contains a first fusion protein linked to a second fusion protein which is linked a first Fc sequence, and a second Fc sequence that is not linked to either the first or second fusion proteins.

Accordingly, in some embodiments the present invention provides heterodimeric fusion proteins that rely on the use of two different heavy chain variant Fc sequences, that will self-assemble to form a heterodimeric Fc domain fusion polypeptide.

The present invention is directed to novel constructs to provide heterodimeric fusion proteins that allow binding to one or more binding partners, ligands or receptors. The heterodimeric fusion constructs are based on the self-assembling nature of the two Fc domains of the heavy chains of antibodies, e.g., two "monomers" that assemble into a "dimer". Heterodimeric Fc fusions are made by altering the amino acid sequence of each monomer as more fully discussed below. Thus, the present invention is generally directed to the creation of heterodimeric fusion proteins which can co-engage binding partner(s) or ligand(s) or receptor(s) in several ways, relying on amino acid variants in the constant regions that are different on each chain to promote heterodimeric formation and/or allow for ease of purification of heterodimers over the homodimers. Specific variants that are included in the Fc domains of specific embodiments of the subject heterodimeric fusion protein are described in greater detail below.

1. Heterodimerization Variants

The present invention provides heterodimeric proteins, including heterodimeric fusion proteins in a variety of formats. Such heterodimeric proteins include two different Fc domains (one on each of the first and second monomers) that include modifications that facilitate the heterodimerization of the first and second monomers and/or allow for ease of purification of heterodimers over homodimers, collectively referred to herein as "heterodimerization variants." As discussed below, heterodimerization variants can include skew variants (e.g., the "knobs and holes" and "charge pairs" variants described below) as well as "pI variants" that facilitates the separation of homodimers away from heterodimers. As is generally described in U.S. Pat. No. 9,605,084, hereby incorporated by reference in its entirety and specifically as below for the discussion of heterodimerization variants, useful mechanisms for heterodimerization include "knobs and holes" ("KIH") as described in U.S. Pat. No. 9,605,084, "electrostatic steering" or "charge pairs" as described in U.S. Pat. No. 9,605,084, pI variants as described in U.S. Pat. No. 9,605,084, and general additional Fc variants as outlined in U.S. Pat. No. 9,605,084 and below.

a. Skew Variants

In some embodiments, the subject heterodimeric protein includes skew variants, which are one or more amino acid modifications in a first Fc domain (A) and/or a second Fc domain (B) that favor the formation of Fc heterodimers (Fc dimers that include the first and the second Fc domain; A-B) over Fc homodimers (Fc dimers that include two of the first Fc domain or two of the second Fc domain; A-A or B-B). Suitable skew variants are included in the FIG. 29 of US Publ. App. No. 2016/0355608, hereby incorporated by reference in its entirety and specifically for its disclosure of skew variants, as well as in FIG. 4.

One mechanism for skew variants is generally referred to in the art as "knobs and holes," referring to amino acid engineering that creates steric influences to favor heterodimeric formation and disfavor homodimeric formation, as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety and specifically for the disclosure of "knobs and holes" mutations. This is sometime referred to herein as "steric variants." The figures identify a number of "monomer A-monomer B" pairs that rely on "knobs and holes". In addition, as described in Merchant et al., Nature Biotech. 16:677 (1998), these "knobs and holes" mutations can be combined with disulfide bonds to further favor formation of Fc heterodimers.

An additional mechanism for skew variants that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs." In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "skew variants." These include, but are not limited to, D221E/P228E/L368E paired with D221R/P228R/K409R (e.g., these are "monomer" corresponding sets) and C220E/P228E/368E paired with C220R/E224R/P228R/K409R.

In some embodiments, the skew variants advantageously and simultaneously favor heterodimerization based on both the "knobs and holes" mechanism as well as the "electrostatic steering" mechanisms described above. In some embodiments, the heterodimeric protein includes one or more sets of such heterodimerization skew variants. These variants come in "pairs" of "sets." That is, one set of the pair is incorporated into the first monomer and the other set of the pair is incorporated into the second monomer. Exemplary "skew variants' in this category include S364K/E357Q: L368D/K370S; L368D/K370S:S364K; L368E/K370S: S364K; T411T/E360E/Q362E:D401K; L368D/K370S: S364K/E357L; K370S:S364K/E357Q; or a T366S/L368A/Y407V:T366W (optionally including a bridging disulfide, T366S/L368A/Y407V/Y349C:T366W/S354C) "skew" variant amino acid substitution sets. In terms of nomenclature, the pair "S364K/E357Q:L368D/K370S" means that one of the monomers includes an Fc domain that includes the amino acid substitutions S364K and E357Q and the other monomer includes an Fc domain that includes the amino acid substitutions L368D and K370S; as above, the "strandedness" of these pairs depends on the starting pI. It should be noted that these sets do not necessarily behave as "knobs in holes" variants, with a one-to-one correspondence between a residue on one monomer and a residue on the other. That is, these pairs of sets may instead form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B: 25% homodimer B/B).

In exemplary embodiments, the heterodimeric fusion protein includes a S364K/E357Q:L368D/K370S; L368D/K370S:S364K; L368E/K370S:S364K; T411T/E360E/Q362E:D401K; L368D/K370S:S364K/E357L; K370S:S364K/E357Q; or a T366S/L368A/Y407V:T366W (optionally including a bridging disulfide, T366S/L368A/Y407V/Y349C:T366W/S354C) "skew" variant amino acid substitution set. In an exemplary embodiment, the heterodimeric fusion protein includes a "S364K/E357Q:L368D/K370S" amino acid substitution set.

In some embodiments, the skew variants provided herein are independently incorporated with other modifications, including, but not limited to, other skew variants (see, e.g., in FIG. 37 of US Publ. App. No. 2012/0149876, herein incorporated by reference, particularly for its disclosure of skew variants), pI variants, isotpypic variants, FcRn variants, ablation variants, etc. into one or both of the first and second Fc domains of the heterodimeric fusion protein. Further, individual modifications can also independently and optionally be included or excluded from the subject heterodimeric fusion proteins.

b. pI (Isoelectric Point) Variants for Heterodimers

In some embodiments, the heterodimeric fusion protein includes purification variants that advantageously allow for the separation of heterodimeric fusion proteins from homodimeric proteins ("pI variants").

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

There are several basic mechanisms that can lead to ease of purifying heterodimeric proteins. One such mechanism relies on the use of pI variants which include one or more modifications that affect the isoelectric point of one or both of the monomers of the fusion protein, such that each monomer, and subsequently each dimeric species, has a different pI, thus allowing the isoelectric purification of A-A, A-B and B-B dimeric proteins. Alternatively, some formats also allow separation on the basis of size. As is further outlined above, it is also possible to "skew" the formation of heterodimers over homodimers using skew variants. Thus, a combination of heterodimerization skew variants and pI variants find particular use in the subject heterodimeric fusion proteins provided herein.

Additionally, as more fully outlined below, depending on the format of the heterodimeric fusion protein, pI variants can be either contained within the constant region and/or Fc domains of a monomer, and/or domain linkers can be used. In some embodiments, the heterodimeric fusion protein includes additional modifications for alternative functionalities can also create pI changes, such as Fc, FcRn and KO variants.

In the embodiments that utilizes pI as a separation mechanism to allow the purification of heterodimeric fusion proteins, amino acid modifications can be introduced into one or both of the monomers of the heterodimeric fusion protein. That is, the pI of one of the monomers (referred to herein for simplicity as "monomer A") can be engineered away from monomer B, or both monomer A and B can be changed, with the pI of monomer A increasing and the pI of monomer B decreasing. As discussed, the pI changes of either or both monomers can be done by removing or adding a charged residue (e.g., a neutral amino acid is replaced by a positively or negatively charged amino acid residue, e.g., glutamine to glutamic acid), changing a charged residue from positive or negative to the opposite charge (e.g., aspartic acid to lysine) or changing a charged residue to a neutral residue (e.g., loss of a charge; lysine to serine). A number of these variants are shown in the figures, including, FIGS. 4 and 5.

Creating a sufficient change in pI in at least one of the monomers such that heterodimers can be separated from homodimers can be done by using a "wild type" heavy chain constant region and a variant region that has been engineered to either increase or decrease its pI (wt A:B+ or wt A:B−), or by increasing one region and decreasing the other region (A+:B− or A−:B+).

Thus, in general, a component of some embodiments of the present subject fusion proteins are amino acid variants in the Fc domains or constant domain regions that are directed to altering the isoelectric point (pI) of at least one, if not both, of the monomers of a dimeric protein by incorporating amino acid substitutions ("pI variants" or "pI substitutions") into one or both of the monomers. The separation of the heterodimers from the two homodimers can be accomplished if the pIs of the two monomers differ by as little as 0.1 pH unit, with 0.2, 0.3, 0.4 and 0.5 or greater all finding use in the present invention.

As will be appreciated by those in the art, the number of pI variants to be included on each or both monomer(s) of a heterodimeric fusion protein to achieve good separation will depend in part on the starting pI of the components. That is, to determine which monomer to engineer or in which "direction" (e.g., more positive or more negative), the sequences of the Fc domains and any IL-15, IL-15Rα or linker included in each monomer are calculated and a decision is made from there based on the pIs of the monomers. As is known in the art, different Fc domains, linkers IL-15, and IL-15Rα will have different starting pIs. In general, as outlined herein, the pIs are engineered to result in a total pI difference of each monomer of at least about 0.1 logs, with 0.2 to 0.5 being preferred as outlined herein.

In general, as will be appreciated by those in the art, there are two general categories of amino acid modifications that affect pI: those that increase the pI of the protein (basic changes) and those that decrease the pI of the protein (acidic changes). As described herein, all combinations of these variants can be used: one monomer may include a wild type Fc domain, or a variant Fc domain that does not display a significantly different pI from wild-type, and the other monomer includes a Fc domain that is either more basic or more acidic. Alternatively, each monomer may be changed, one to more basic and one to more acidic.

In the case where pI variants are used to achieve heterodimerization, a more modular approach to designing and purifying heterodimeric fusion proteins is provided. Thus, in some embodiments, heterodimerization variants (including skew and pI variants) must be engineered. In addition, in some embodiments, the possibility of immunogenicity resulting from the pI variants is significantly reduced by importing pI variants from different IgG isotypes such that pI is changed without introducing significant immunogenicity (see isotypic variants below). Thus, an additional problem to be solved is the elucidation of low pI constant domains with high human sequence content, e.g., the minimization or avoidance of non-human residues at any particular position. Alternatively or in addition to isotypic substitutions, the possibility of immunogenicity resulting from the pI variants is significantly reduced by utilizing isosteric substitutions (e.g., Asn to Asp; and Gln to Glu).

A side benefit that can occur with this pI engineering is also the extension of serum half-life and increased FcRn binding. That is, as described in US Publ. App. No. US 2012/0028304 (incorporated by reference in its entirety and specifically for the disclosure of pI variants that provide additional function), lowering the pI of antibody constant domains (including those found in Fc fusions) can lead to longer serum retention in vivo. These pI variants for increased serum half-life also facilitate pI changes for purification.

In addition, it should be noted that the pI variants of the heterodimerization variants give an additional benefit for the analytics and quality control process of Fc fusion proteins, as the ability to either eliminate, minimize and distinguish when homodimers are present is significant. Similarly, the ability to reliably test the reproducibility of the heterodimeric fusion protein production is important.

Exemplary combinations of pI variants are shown in FIGS. 4 and 5, and FIG. 30 of US Publ. App. No. 2016/0355608, all of which are herein incorporated by reference in its entirety and specifically for the disclosure of pI variants. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In some embodiments, modifications are made in the hinge of the Fc domain, including positions 208, 216, 217, 218, 219, 220, 221, 222, 223, 224, 225, 226, 227, 228, 229, and 230 based on EU numbering. Thus, pI mutations and particularly substitutions can be made in one or more of positions 216-230, with 1, 2, 3, 4 or 5 mutations finding use.

Again, all possible combinations are contemplated, alone or with other pI variants in other domains.

Specific substitutions that find use in lowering the pI of hinge domains include, but are not limited to, a deletion at position 221, a non-native valine or threonine at position 222, a deletion at position 223, a non-native glutamic acid at position 224, a deletion at position 225, a deletion at position 235 and a deletion or a non-native alanine at position 236. In some cases, only pI substitutions are done in the hinge domain, and in others, these substitution(s) are added to other pI variants in other domains in any combination.

In some embodiments, mutations can be made in the CH2 region, including positions 233, 234, 235, 236, 274, 296, 300, 309, 320, 322, 326, 327, 334 and 339, based on EU numbering. It should be noted that changes in 233-236 can be made to increase effector function (along with 327A) in the IgG2 backbone. Again, all possible combinations of these 14 positions can be made; e.g., a heterodimeric fusion protein may include a variant Fc domain with 1, 2, 3, 4, 5, 6, 7, 8, 9 or 10 CH2 pI substitutions.

Specific substitutions that find use in lowering the pI of CH2 domains include, but are not limited to, a non-native glutamine or glutamic acid at position 274, a non-native phenylalanine at position 296, a non-native phenylalanine at position 300, a non-native valine at position 309, a non-native glutamic acid at position 320, a non-native glutamic acid at position 322, a non-native glutamic acid at position 326, a non-native glycine at position 327, a non-native glutamic acid at position 334, a non-native threonine at position 339, and all possible combinations within CH2 and with other domains.

In this embodiment, the modifications can be independently and optionally selected from position 355, 359, 362, 384, 389,392, 397, 418, 419, 444 and 447 (EU numbering) of the CH3 region. Specific substitutions that find use in lowering the pI of CH3 domains include, but are not limited to, a non-native glutamine or glutamic acid at position 355, a non-native serine at position 384, a non-native asparagine or glutamic acid at position 392, a non-native methionine at position 397, a non-native glutamic acid at position 419, a non-native glutamic acid at position 359, a non-native glutamic acid at position 362, a non-native glutamic acid at position 389, a non-native glutamic acid at position 418, a non-native glutamic acid at position 444, and a deletion or non-native aspartic acid at position 447. Exemplary embodiments of pI variants are provided in FIG. 5.

In one embodiment, the heterodimeric fusion protein includes a monomer with a variant Fc domain having pI variant modifications 295E/384D/418E/421D (Q295E/N384D/Q418E/N421D when relative to human IgG1). In one embodiment, the heterodimeric fusion protein includes a monomer with a variant Fc domain having pI variant modifications 208D/295E/384D/418E/421D (N208D/Q295E/N384D/Q418E/N421D when relative to human IgG1). In some embodiments, the heterodimeric fusion protein includes a monomer with a variant Fc domain having pI variant modifications 295E/384D/418E/421D (Q295E/N384D/Q418E/N421D when relative to human IgG1). In one embodiment, the heterodimeric fusion protein includes a monomer with a variant Fc domain having pI variant modifications 196K/199T/217R/228R/276K (Q196K/I199T/P217R/P228R/N276K) when relative to human IgG1).

In one embodiment, the heterodimeric fusion protein includes a monomer with a variant Fc domain having pI variant modifications 217R/228R/276K (P217R/P228R/N276K when relative to human IgG1). Additional exemplary pI variant modification that can be incorporated into the Fc domain of a subject are depicted in FIG. 5.

c. Isotypic Variants

In addition, many embodiments of the invention rely on the "importation" of pI amino acids at particular positions from one IgG isotype into another, thus reducing or eliminating the possibility of unwanted immunogenicity being introduced into the variants. A number of these are shown in FIG. 21 of US Publ. App. No. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant Fc fusion protein. However, it should be noted as discussed below that even changes in IgG2 molecules allow for increased serum half-life.

In other embodiments, non-isotypic amino acid changes are made, either to reduce the overall charge state of the resulting protein (e.g., by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

d. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US2014/0370013. As discussed herein, which monomer to engineer is generally decided by the inherent pI of each monomer.

2. Additional Fc Variants for Additional Functionality

In addition to pI amino acid variants, there are a number of useful Fc amino acid modification that can be made for a variety of reasons, including, but not limited to, altering binding to one or more FcγR receptors, altered binding to FcRn receptors, etc.

Accordingly, the proteins of the invention can include amino acid modifications, including the heterodimerization variants outlined herein, which includes the pI variants and steric variants. Each set of variants can be independently and optionally included or excluded from any particular heterodimeric protein.

a. FcγR Variants

Accordingly, there are a number of useful Fc substitutions that can be made to alter binding to one or more of the FcγR receptors. Substitutions that result in increased binding as well as decreased binding can be useful. For example, it is known that increased binding to FcγRIIIa results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in Ser. No. 11/124,620 (particularly FIG. 41), Ser Nos. 11/174,287, 11/396,495, 11/538,406, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 243A, 243L, 264A, 264V and 299T.

In addition, amino acid substitutions that increase affinity for FcγRIIc can also be included in the Fc domain variants outlined herein. The substitutions described in, for example, Ser. Nos. 11/124,620 and 14/578,305 are useful.

In addition, there are additional Fc substitutions that find use in increased binding to the FcRn receptor and increased serum half-life, as specifically disclosed in U.S. Ser. No. 12/341,769, hereby incorporated by reference in its entirety, including, but not limited to, 434S, 434A, 428L, 308F, 2591, 428L/434S, 259I/308F, 436I/428L, 436I or V/434S, 436V/428L and 2591/308F/428L.

b. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g., FcγR1, FcγRIIa, FcγRIIb, FcγRIIIa, etc.) to avoid additional mechanisms of action. That is, for example, in many embodiments, particularly in the use of bispecific immunomodulatory antibodies desirable to ablate FcγRIIIa binding to eliminate or significantly reduce ADCC activity such that one of the Fc domains comprises one or more Fcγ receptor ablation variants. These ablation variants are depicted in FIG. 31 of U.S. Ser. No. 15/141,350, all of which are herein incorporated by reference in its entirety, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to the EU index. It should be noted that the ablation variants referenced herein ablate FcγR binding but generally not FcRn binding.

Exemplary ablation variants are provided in FIG. 5.

c. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein.

In addition, a monomeric Fc domain can comprise a set of amino acid substitutions that includes C220S/S267K/L368D/K370S or C220S/S267K/S364K/E357Q.

In addition, the heterodimeric fusion proteins can comprise skew variants (e.g., a set of amino acid substitutions as shown in FIGS. 1A-1C of U.S. Ser. No. 15/141,350, all of which are herein incorporated by reference in its entirety), with particularly useful skew variants being selected from the group consisting of S364K/E357Q:L368D/K370S; L368D/K370S:S364K; L368E/K370S:S364K; T411E/K360E/Q362E:D401K; L368D/K370S:S364K/E357L, K370S:S364K/E357Q, T366S/L368A/Y407V:T366W and T366S/L368A/Y407V/Y349C:T366W/S354C, optionally ablation variants, optionally charged domain linkers and the heavy chain comprises pI variants.

In some embodiments, the Fc domain comprising an amino acid substitution selected from the group consisting of: 236R, 239D, 239E, 243L, M252Y, V2591, 267D, 267E, 298A, V308F, 328F, 328R, 330L, 332D, 332E, M428L, N434A, N434S, 236R/328R, 239D/332E, M428L, 236R/328F, V2591/V308F, 267E/328F, M428L/N434S, Y436I/M428L, Y436V/M428L, Y436I/N434S, Y436V/N434S, 239D/332E/330L, M252Y/S254T/T256E, V2591/V308F/M428L, E233P/L234V/L235A/G236del/S267K, G236R/L328R and PVA/S267K. In some cases, the Fc domain comprises the amino acid substitution 239D/332E. In other cases, the Fc domain comprises the amino acid substitution G236R/L328R or PVA/S267K.

In one embodiment, a particular combination of skew and pI variants that finds use in the present invention is T366S/L368A/Y407V:T366W (optionally including a bridging disulfide, T366S/L368A/Y407V/Y349C:T366W/S354C) with one monomer comprises Q295E/N384D/Q418E/N481D and the other a positively charged domain linker. As will be appreciated in the art, the "knobs in holes" variants do not change pI, and thus can be used on either monomer. Useful combination of variants that can be used in particular formats of the invention are included in FIGS. 7A-7F.

III. IL-15/IL-15Rα Fc Fusion x LAG-3 ABD Heterodimeric Proteins

Provided herein are heterodimeric fusion proteins that can bind to the checkpoint inhibitor LAG-3 antigen and can complex with the common gamma chain (γc; CD132) and/or the 11-2 receptor β-chain (IL-2Rβ; CD122). The heterodimeric fusion proteins can contain an IL-15/IL-15Rα-Fc fusion protein and an antibody fusion protein. The IL-15/IL-15Rα-Fc fusion protein can include as IL-15 protein (generally including amino acid substitutions) covalently attached to an IL-15Rα, and an Fc domain. Optionally, the IL-15 protein and IL-15Rα protein are noncovalently attached.

IV. Useful Formats of the Invention

As shown in FIGS. 21, there are a number of useful formats of the subject targeted IL-15/IL-15Rα heterodimeric fusion proteins. In general, the heterodimeric fusion proteins provided herein have three functional components: an IL-15/IL-15Rα(sushi) component, an anti-LAG-3 component (also referred to as a "LAG-3 binding domain" or "LAG-3 antigen binding domain"), and an Fc component that includes a first Fc domain and second Fc domain, each of which can take different forms as outlined herein and each of which can be combined with the other components in any configuration.

The first and the second Fc domains can have a set of amino acid skew substitutions selected from the following skew variants: a) S267K/L368D/K370S:S267K/S364K/

E357Q; b) S364K/E357Q:L368D/K370S; c) L368D/K370S:S364K; d) L368E/K370S:S364K; e) T411E/K360E/Q362E:D401K; f) L368D/K370S:S364K/E357L and g) K370S:S364K/E357Q, according to EU numbering. In an exemplary embodiment, the skew variants are S364K/E357Q:L368D/K370S.

In some embodiments, the first and/or the second Fc domains have an additional set of pI amino acid substitutions selected from the following pI variants: Q295E/N384D/Q418E/N421D, N208/Q295E/N384D/Q418E/N421D or Q196K/I199T/P217R/P228R/N276K, according to EU numbering.

Optionally, the first and/or the second Fc domains have an additional set of ablation ("FcKO") variants selected from the following FcKO variants: G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

Optionally, the first and/or second Fc domains have 428L/434S variants for half-life extension.

In embodiments wherein a hinge or partial hinge is used to link an Fc domain to a scFv, IL-15 or IL-15Rα domain, the hinge may optional include a C220S substitution to prevent the hinge from forming undesirable disulfide bonds with any light chains.

Exemplary formats of the subject heterodimeric fusion proteins are provided below.

A. scIL-15/Rα X Scfv

One embodiment is shown in FIGS. 21A, and comprises two monomers. The first monomer comprises, from N- to C-terminus, the IL-15Rα(sushi) domain-(domain linker)-IL-15 variant-(domain linker)-CH2-CH3 (with the second domain linker frequently being a hinge domain), and the second monomer comprises VH-scFv linker-VL-hinge-CH2-CH3 or VL-scFv linker-VH-hinge-CH2-CH3, although in either orientation a domain linker can be substituted for the hinge. This is generally referred to as "scIL-15/Rα X scFv", with the "sc" standing for "single chain" referring to the attachment of the IL-15 variant and IL-15Rα(sushi) domain using a covalent linker. Preferred combinations of variants for this embodiment are found in FIGS. 21A and B.

In one embodiment, the targeted IL-15/IL-15Rα heterodimeric protein is an "scIL-15/Rα X scFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; and b) a second monomer that includes, from N- to C-terminus, an anti-LAG-3 scFv-(domain linker)-CH2-CH3, where CH2-CH3 is a second Fc domain. Any useful domain linker can be used to attach the various components of the heterodimeric protein including, but not limited to those in FIGS. 8 and 9A-C. In an exemplary embodiment, the domain linkers that attach the IL-15 variant to the first Fc domain and the anti-LAG-3 scFv to the second Fc domain are each antibody hinge domains.

In some embodiments, the anti-LAG-3 scFv includes a variable heavy domain (VH) covalently attached to a variable light domain (VL) by an scFv linker (e.g., FIGS. 9A-C). In one embodiment, the anti-LAG-3 scFv is from N- to C-terminus VH-scFv linker-VL. In another embodiment, the anti-LAG-3 scFv is from N- to C-terminus VL-scFv linker-VH. The C-terminus of the anti-LAG-3 scFv is attached to the N terminus of the first Fc domain by a domain linker (e.g., an antibody hinge domain).

In the scIL-15/Rα X scFv format, one preferred embodiment utilizes an anti-LAG-3 ABD having any of the variable heavy and light domain pairs as shown in FIGS. 12 and 13A-C.

In the scIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, an anti-LAG-3 scFv-(hinge)-CH2-CH3, where CH2-CH3 is a second Fc domain, and where the anti-LAG-3 scFv includes the variable heavy domain and variable light domain of 7G8_H3.30_L1.34. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, an anti-LAG-3 scFv-(hinge)-CH2-CH3, where CH2-CH3 is a second Fc domain, and where the anti-LAG-3 scFv includes the variable heavy domain and variable light domain of 2A11_H1.144_L2.142.

In the scIL-15/Rα X scFv format, one preferred embodiment utilizes an IL-15 variant that includes amino acid substitutions N4D/N65D, D30N/N65D, or D30N/E64Q/N65D. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, anti-LAG-3 scFv-(hinge)-CH2-CH3, where CH2-CH3 is a second Fc domain, and where the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the scIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, anti-LAG-3 scFv-(hinge)-CH2-CH3, where CH2-CH3 is a second Fc domain, where the anti-LAG-3 scFv includes the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and the scFv includes the variable heavy and light domain pair of 7G8_H3.30_L1.34. In another embodiment of the scIL-15/Rα X scFv format heterodimeric protein, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant is the IL-15 D30N/E64Q/N65D variant and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the scIL-15/Rα X scFv format, one preferred embodiment utilizes the skew variant pair S364K/E357Q:L368D/K370S. In one embodiment, the targeted IL-15/IL-15Rα heterodimeric protein is an "scIL-15/Rα X scFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-LAG-3 scFv-(domain linker)-CH2-CH3, where CH2-CH3 is a second variant Fc domain, and where the first and second variant Fc domains include the skew variant pair S364K/E357Q:L368D/K370S. In an exemplary embodiment, the first variant Fc domain includes skew variants L368D/K370S, and the second variant Fc domain includes skew variants L368D/K370S.

In one embodiment, the targeted IL-15/IL-15Rα heterodimeric protein is an "scIL-15/Rα X scFv" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-LAG-3 scFv-(domain linker)-CH2-CH3, where CH2-CH3 is a second variant Fc domain, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants L368D/K370S. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the scIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first variant Fc domain; and b) a second monomer that includes, from N- to C-terminus, anti-LAG-3 scFv-(hinge)-CH2-CH3, where CH2-CH3 is a second variant Fc domain, where the anti-LAG-3 scFv includes the variable heavy domain and variable light domain of 7G8_H3.30_L1.34, and where the first and second variant Fc domains include the skew variant pair S364K/E357Q:L368D/K370S. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first Fc domain; and b) a second monomer that includes, from N- to C-terminus, anti-LAG-3 scFv-(hinge)-CH2-CH3, where CH2-CH3 is a second Fc domain, and where the anti-LAG-3 scFv includes the variable heavy domain and variable light domain of 2A11_H1.144_L2.142, and where the first and second variant Fc domains include the skew variant pair S364K/E357Q:L368D/K370S. In an exemplary embodiment, the first variant Fc domain includes skew variants L368D/K370S, and the second variant Fc domain includes skew variants L368D/K370S.

In the scIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the "scIL-15/Rα X scFv" format heterodimeric protein includes: a) a first monomer that includes, from N- to C-terminus, an IL-15Rα(sushi) domain-(domain linker)-IL-15 variant-(hinge)-CH2-CH3, where CH2-CH3 is a first variant Fc domain; and b) a second monomer that includes, from N- to C-terminus, anti-LAG-3 scFv-(hinge)-CH2-CH3, where CH2-CH3 is a second variant Fc domain, where the anti-LAG-3 scFv includes the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants L368D/K370S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant is the IL-15 D30N/E64Q/N65D variant and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the scIL-15/Rα X scFv format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the "scIL-15/Rα X scFv" format heterodimeric protein includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-LAG-3 scFv-(hinge)-CH2-CH3, where CH2-CH3 is a second variant Fc domain; where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the scIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21A format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the "scIL-15/Rα X scFv" format heterodimeric protein includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; and b) a second monomer that includes, from N- to C-terminus, anti-LAG-3 scFv-(hinge)-CH2-CH3, where CH2-CH3 is a second variant Fc domain; where the anti-LAG-3 scFv includes the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

B. scFv X ncIL-15/Rα

This embodiment is shown in FIGS. 21B, and comprises three monomers. The first monomer comprises, from N- to C-terminus, the IL-15Rα(sushi) domain-domain linker-CH2-CH3, and the second monomer comprises VH-scFv linker-VL-hinge-CH2-CH3 or VL-scFv linker-VH-hinge-CH2-CH3, although in either orientation a domain linker can be substituted for the hinge. The third monomer is the variant IL-15 domain. This is generally referred to as "ncIL-15/Rα X scFv" or "scFv X ncIL-15/Rα" with the "nc" standing for "non-covalent" referring to the self-assembling non-covalent attachment of the IL-15 variant and IL-15Rα(sushi) domain.

In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the anti-LAG-3 scFv to the first Fc domain and the IL-15Rα(sushi) domain to the second Fc domain are each antibody hinge domains.

In some embodiments, the anti-LAG-3 scFv includes a variable heavy domain (VH) covalently attached to a variable light domain (VL) by an scFv linker (e.g., FIGS. 9A-C). In one embodiment, the anti-LAG-3 scFv is, from N- to C-terminus, VH-scFv linker-VL. In another embodiment, the anti-LAG-3 scFv is from, N- to C-terminus, VL-scFv linker-VH. The C-terminus of the anti-LAG-3 scFv is attached to the N terminus of the first Fc domain by a domain linker (e.g., an antibody hinge domain).

In the ncIL-15/Rα X scFv format, one preferred embodiment utilizes an anti-LAG-3 ABD having any of the variable heavy and light domain pairs as shown in FIGS. 12 and 13A-C.

In the ncIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα(sushi) domain form an IL-15 complex, and where the anti-LAG-3 scFv includes the variable heavy domain and variable light domain of 7G8_H3.30_L1.34. In another embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα(sushi) domain form an IL-15 complex, and where the anti-LAG-3 scFv includes the variable heavy domain and variable light domain of 2A11_H1.144_L2.142.

In the ncIL-15/Rα X scFv format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα (sushi) domain form an IL-15 complex, and where the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the ncIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain; and c) an IL-15 variant, where the IL-15 variant and the IL-15Rα (sushi) domain form an IL-15 complex, where the anti-LAG-3 scFv includes the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the ncIL-15/Rα X scFv format, one preferred embodiment utilizes the skew variant pair S364K/E357Q:L368D/K370S. In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the ncIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q: L368D/K370S. In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-LAG-3 scFv includes the variable heavy domain and variable light domain of 7G8_H3.30_L1.34, and where the first and second variant Fc domains include the skew variant pair S364K/E357Q:L368D/K370S. In another embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-LAG-3 scFv includes the variable heavy domain and variable light domain of 2A11_H1.144_L2.142, and where the first and second variant Fc domains include the skew variant pair S364K/E357Q:L368D/K370S.

In the ncIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q: L368D/K370S with either the IL-15 N4D/N65D variant or the IL-15 D30N/N65D variant or the IL-15 D30N/E64Q/N65D variant. In an exemplary embodiment, the first variant Fc domain includes skew variants L368D/K370S, and the second variant Fc domain includes skew variants L368D/K370S. In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-LAG-3 scFv includes the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q: L368D/K370S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the ncIL-15/Rα X scFv format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the ncIL-15/Rα X scFv format, one preferred embodiment utilizes an anti-LAG-3 ABD having the variable heavy and light domain pair of 7G8_H3.30_L1. or the variable heavy and light domain pair 2A11_H1.144_L2.142 as shown in FIG. 12 with the FIG. 21B format, the skew variant set S364K/E357Q:L368D/K370S, the pI variants Q295E/N384D/Q418E/N421D, the ablation variants E233P/L234V/

L235A/G236JS267K on both first and second monomers, and optionally the 428L/434S variants on both first and second monomers.

In one embodiment, the targeted IL-15/IL-15Rα heterodimeric protein is an "scFv X ncIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; and c) an IL-15 variant, where the IL-15 variant and the IL-15Rα(sushi) domain form an IL-15 complex, where the anti-LAG-3 scFv includes the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first and second monomers also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

C. scFv X dsIL-15/Rα

This embodiment is shown in FIGS. 21C, and comprises three monomers. The first monomer comprises, from N- to C-terminus, the IL-15Rα(sushi) domain-domain linker-CH2-CH3, wherein the IL-15Rα(sushi) domain has an engineered cysteine residue and the second monomer comprises VH-scFv linker-VL-hinge-CH2-CH3 or VL-scFv linker-VH-hinge-CH2-CH3, although in either orientation a domain linker can be substituted for the hinge. The third monomer is the variant IL-15 domain, also engineered to have a cysteine variant amino acid, thus allowing a disulfide bridge to form between the IL-15Rα(sushi) domain and the variant IL-15 domain. This is generally referred to as "scFv X dsIL-15/Rα" or "dsIL-15/Rα X scFv", with the "ds" standing for "disulfide".

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, and where the cysteine residue on the IL-15 variant and the cysteine residue on the IL-15Rα(sushi) domain form a disulfide bond. Any useful domain linker can be used to attach the various components of the heterodimeric protein including, but not limited to those in FIGS. 8 and 9A-C. In an exemplary embodiment, the domain linkers that attach the anti-LAG-3 scFv to the first Fc domain and the IL-15Rα(sushi) domain to the second Fc domain and are each antibody hinge domains.

Any useful domain linker can be used to attach the various components of the heterodimeric protein including, but not limited to those in FIGS. 8 and 9A-C. In an exemplary embodiment, the domain linkers that attach the anti-LAG-3 scFv to the first Fc domain and the IL-15Rα(sushi) domain to the second Fc domain and are each antibody hinge domains (e.g., an antibody hinge domain).

In some embodiments, the anti-LAG-3 scFv includes a variable heavy domain (VH) covalently attached to a variable light domain (VL) by an scFv linker (e.g., FIGS. 9A-C). In one embodiment, the anti-LAG-3 scFv is from N- to C-terminus VH-scFv linker-VL. In another embodiment, the anti-LAG-3 scFv is from N- to C-terminus VL-scFv linker-VH. The C-terminus of the anti-LAG-3 scFv is attached to the N terminus of the first Fc domain by a domain linker (e.g., an antibody hinge domain).

In the dsIL-15/Rα X scFv format, one preferred embodiment utilizes an anti-LAG-3 ABD having any of the variable heavy and light domain pairs as shown in FIGS. 12 and 13A-C.

In the dsIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, and where the anti-LAG-3 scFv includes the variable heavy domain and variable light domain of 7G8_H3.30_L1.34. In another embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα (sushi) domain form a disulfide bond, and where the anti- LAG-3 scFv includes the variable heavy domain and variable light domain of 2A11_H1.144_L2.142.

In the dsIL-15/Rα X scFv format, one preferred embodiment utilizes the IL-15 N4D/N65D variant or the IL-15 D30N/N65D variant or the IL-15 D30N/E64Q/N65D variant, as well as appropriate cysteine substitutions. In on embodiment, the targeted IL-15/IL-15Rα heterodimeric protein is an "scFv X dsIL-15/Rea" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα (sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα (sushi) domain form a disulfide bond, and where the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the dsIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant, as well as appropriate cysteine substitutions. In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-LAG-3 scFv includes the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the dsIL-15/Rα X scFv format, one preferred embodiment utilizes the skew variant pair S364K/E357Q:L368D/K370S. In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the dsIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "scFv X dsIL-15/Rα"

format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-LAG-3 scFv includes the variable heavy domain and variable light domain of 7G8_H3.30_L1.34, and where the first and second variant Fc domains include the skew variant pair S364K/E357Q: L368D/K370S. In another embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-LAG-3 scFv includes the variable heavy domain and variable light domain of 2A11_H1.144_L2.142, and where the first and second variant Fc domains include the skew variant pair S364K/E357Q: L368D/K370S.

In the dsIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q: L368D/K370S with either the IL-15 N4D/N65D variant or the IL-15 D30N/N65D variant or the IL-15 D30N/E64Q/N65D variant with the appropriate cysteine substitutions.

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(domain linker)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-LAG-3 scFv includes the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

In the dsIL-15/Rα X scFv format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(hinge)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα (sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer and second monomer also each include amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the LAG-3 scFv includes the VH and VL of any of the LAG-3 ABDs in FIGS. 12 and 13A-C. In an exemplary embodiment, the LAG-3 scFv includes the VH and VL of any of the LAG-3 ABDs in FIGS. 12 and 13A-C and the IL-15 variant includes amino acid substitutions N4D/N65D. In another exemplary embodiment, the LAG-3 scFv includes the VH and VL of any of the LAG-3 ABDs in FIGS. 12 and 13A-C and the IL-15 variant includes amino acid substitutions D30N/N65D. In yet another exemplary embodiment, the LAG-3 scFv includes the VH and VL of any of the LAG-3 ABDs in FIGS. 12 and 13A-C and the IL-15 variant includes amino acid substitutions D30N/E64Q/N65D.

In the dsIL-15/Rα X scFv format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21C format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "scFv X dsIL-15/Rα" format heterodimeric protein that includes: a) a first monomer that includes, from N- to C-terminus, an anti-LAG-3 scFv-(hinge)-CH2-CH3, where CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα (sushi) domain includes an amino acid substitution for a cysteine residue; and c) an IL-15 variant that includes an amino acid substitution for a cysteine residue, where the cysteine residue on the IL-15 variant and the cysteine residue on the IL-15Rα(sushi) domain form a disulfide bond, where the anti-LAG-3 scFv includes the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer and second monomer also each include amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

D. scIL-15/Rα X Fab

This embodiment is shown in FIGS. 21D, and comprises three monomers. The first monomer comprises, from N- to C-terminus, the IL-15Rα(sushi) domain-(domain linker)-variant IL-15-domain linker-CH2-CH3 and the second monomer comprises a heavy chain, VH-CH1-hinge-CH2-CH3. The third monomer is a light chain, VL-CL. This is generally referred to as "scIL-15/Rα X Fab", with the "sc" standing for "single chain". The scIL-15/Rα x Fab format (see FIG. 21 FIG. 21D) comprises IL-15Rα(sushi) fused to a variant IL-15 by a variable length linker (termed "scIL-15/Rα") which is then fused to the N-terminus of a heterodimeric Fc-region (inclusive of the hinge). The second monomer is a heavy chain, VH-CH1-hinge-CH2-CH3, while a corresponding light chain (the third monomer) is transfected separately so as to form a Fab with the VH.

In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, where VH and VL form a LAG-3 binding domain. Any useful domain linker can be used to attach the various components of the heterodimeric protein including, but not limited to those in FIGS. 8 and 9A-C. In an exemplary embodiment, the domain linkers that attach the IL-15 variant to the first Fc domain is an antibody hinge domain (e.g., an antibody hinge domain).

In the scIL-15/Rα X Fab format, one preferred embodiment utilizes an anti-LAG-3 ABD having any of the variable heavy and light domain pairs as shown in FIGS. 12 and 13A-C.

In the scIL-15/Rα X Fab format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric fusion protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, and where VH and VL are the variable heavy domain and variable light domain of 7G8_H3.30_L1.34, respectively. In another embodiment, the targeted IL-15/IL-15Rα heterodimeric protein is an "scIL-15/Rα Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, and where VH and VL are the variable heavy domain and variable light domain of 2A11_H1.144_L2.142, respectively.

In the scIL-15/Rα X Fab format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, wherein the VH and VL form a LAG-3 binding domain, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the scIL-15/Rα X Fab format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first Fc domain; b) a second monomer that includes, from N- to C-terminus, a VH-CH1-hinge-CH2-CH3, where VH is a variable heavy domain and CH2-CH3 is a second Fc domain, and c) a light chain that includes from, N- to C-terminus, VL-VC, where VL is a variable light domain, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the scIL-15/Rα X Fab format, one preferred embodiment utilizes the skew variant pair S364K/E357Q:L368D/K370S. In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a LAG-3 binding domain, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL form a LAG-3 binding domain, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the scIL-15/Rα X Fab format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, 2A11_H1.144_L2.142 the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 7G8_H3.30_L1.34, respectively, and where the first and second variant Fc domains include the skew variant pair S364K/E357Q:L368D/K370S. In another embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, where VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 2A11_H1.144_L2.142, respectively, and where the first and second variant Fc domains include the skew variant pair S364K/E357Q:L368D/K370S.

In the scIL-15/Rα X Fab format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the scIL-15/Rα X Fab format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL form a LAG-3 binding domain, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the scIL-15/Rα X Fab format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21D format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL are the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 7G8_H3.30_L1.34. In another embodiment, the IL-15 variant includes amino acid substitutions N4D/N65D and the scFv includes the variable heavy and light domain pair of 2A11_H1.144_L2.142. In one embodiment, the IL-15 variant includes amino acid substitutions D30N/N65D and the scFv includes the variable heavy and light domain pair of 7G8_H3.30_L1.34. In another embodiment of the scIL-15/Rα X scFv format heterodimeric protein, the IL-15 variant includes amino acid substitutions D30N/N65D and the scFv includes the variable heavy and light domain pair of 2A11_H1.144_L2.142. In yet another of embodiment, the IL-15 variant includes amino acid substitutions D30N/E64Q/N65D and the scFv includes the variable heavy and light domain pair of 7G8_H3.30_L1.34. In another embodiment, the IL-15 variant includes amino acid substitutions D30N/E64Q/N65D and the scFv includes the variable heavy and light domain pair of 2A11_H1.144_L2.142.

E. Fab X ncIL-15/Rα

Figure 21E:
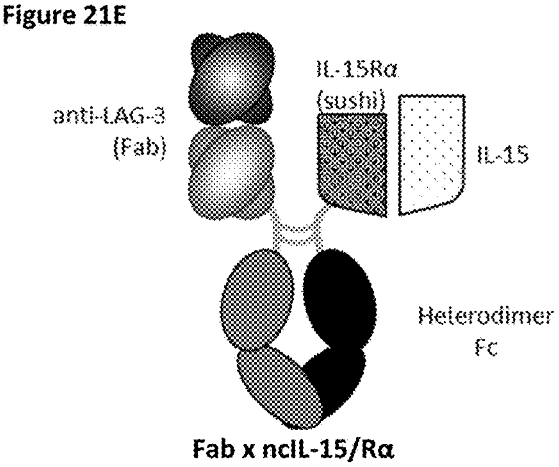

This embodiment is shown in FIGS. 21E, and comprises four monomers. The first monomer comprises, from N- to C-terminus, the IL-15Rα(sushi)domain-(domain linker)-CH2-CH3, and the second monomer comprises a heavy chain, VH-CH1-hinge-CH2-CH3. The third monomer is the light chain that includes, from N- to C-terminus, a variable light domain (VL) and a light constant domain (CL). The fourth monomer is a variant IL-15 domain. This is generally referred to as "Fab X ncIL-15/Rα", with the "nc" standing for "non-covalent" referring to the self-assembling non-covalent attachment of the IL-15 variant and IL-15Rα (sushi)domain.

In one embodiment, the targeted IL-15/IL-15Rα heterodimeric protein is an "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL form a LAG-3 binding domain, and where the IL-15 and IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the IL-15Rα (sushi) domain to the second Fc domain is an antibody hinge domain (e.g., an antibody hinge domain).

In the Fab X ncIL-15/Rα format, one preferred embodiment utilizes an anti-LAG-3 ABD having any of the variable heavy and light domain pairs as shown in FIG. 12.

In the Fab X ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 7G8_H3.30_L1.34, respectively, and where the IL-15 and IL-15Rα(sushi) domain form an IL-15 complex. In another embodiment, the targeted IL-15/IL-15Rα heterodimeric protein is an "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 2A11_H1.144_L2.142, respectively, and where the IL-15 and IL-15Rα(sushi) domain form an IL-15 complex.

In the Fab X ncIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the Fab X ncIL-15/Rα format, one preferred embodiment utilizes the skew variant pair S364K/E357Q:L368D/K370S. In one embodiment, the targeted IL-15/IL-15Rα heterodimeric protein is an "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 7G8_H3.30_L1.34, respectively, where the IL-15 and IL-15Rα(sushi) domain form an IL-15 complex and where the first and second variant Fc domains include the skew variant pair S364K/E357Q:L368D/K370S. In another embodiment, the targeted IL-15/IL-15Rα heterodimeric protein is an "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL are the variable heavy domain and variable light domain of 2A11_H1.144_L2.142, respectively, where the IL-15 and IL-15Rα(sushi) domain form an IL-15 complex, and where the first and second variant Fc domains include the skew variant pair S364K/E357Q:L368D/K370S.

In the Fab X ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant.

In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the Fab X ncIL-15/Rα format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21E format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is a "Fab X ncIL-15/Rα" format heterodimeric protein that includes: a) a first monomer that includes, from N- to C-terminus, a VH-CH1-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain; c) a third monomer that includes from, N- to C-terminus, VL-VC, where VL is a variable light domain, and d) a fourth monomer comprising an IL-15 variant, where the VH and the VL form a LAG-3 binding domain, where the IL-15 and IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In a particular embodiment, the IL-15 variant includes amino acid substitutions N4D/N65D and the scFv includes the variable heavy and light domain pair of 7G8_H3.30_L1.34. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

F. Fab X dsIL-15/Rα

Figure 21F:
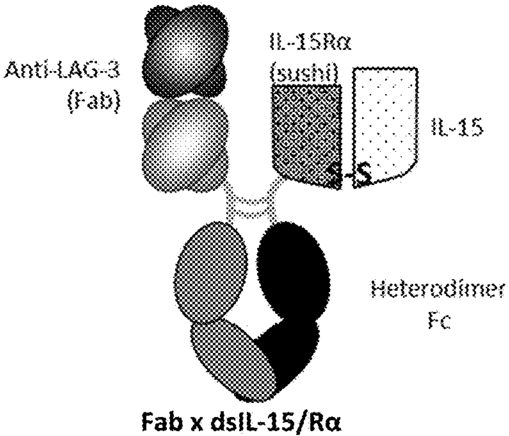

This embodiment is shown in FIGS. 21F, and comprises four monomers. The first monomer comprises, from N- to C-terminus, the IL-15Rα(sushi)domain-domain linker-CH2-CH3, wherein the IL-15Rα(sushi)domain has been engineered to contain a cysteine residue, and the second monomer comprises a heavy chain, VH-CH1-hinge-CH2-

CH3. The third monomer is a light chain that includes, from N- to C-terminus, a variable light domain (VL) and a constant light domain (CL). The fourth monomer is the variant IL-15 domain, also engineered to have a cysteine residue, such that a disulfide bridge is formed under native cellular conditions. This is generally referred to as "Fab X dsIL-15/Rα", with the "ds" standing for "disulfide".

In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, and where the cysteine residue on the IL-15 variant and the cysteine residue on the IL-15Rα(sushi) domain form a disulfide bond. Any useful domain linker can be used to attach the various components of the heterodimeric protein including, but not limited to those in FIGS. 8 and 9A-C. In an exemplary embodiment, the domain linkers that attach the IL-15Rα(sushi) domain to the second Fc domain is an antibody hinge domain (e.g., an antibody hinge domain).

In the Fab X dsIL-15/Rα format, one preferred embodiment utilizes an anti-LAG-3 ABD having any of the variable heavy and light domain pairs as shown in FIG. 12.

In the Fab X dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino add substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 7G8_H3.30_L1.34, respectively, and where the cysteine residue on the IL-15 variant and the cysteine residue on the IL-15Rα(sushi) domain form a disulfide bond. In another embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα (sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 2A11_H1.144_L2.142, respectively, and where the cysteine residue on the IL-15 variant and the cysteine residue on the IL-15Rα(sushi) domain form a disulfide bond.

In the Fab X dsIL-15/Rα format, one preferred embodiment utilizes an IL-15 variant that includes amino acid substitutions N4D/N65D, D30N/N65D, or D30N/E64Q/N65D, with the appropriate cysteine amino acid substitutions. In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant, with the appropriate cysteine amino acid substitutions. In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first Fc domain; b) a second monomer that includes, from N- to C-terminus, an IL-15Rα(sushi) domain-(domain linker)-CH2-CH3, where CH2-CH3 is a second Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the Fab X dsIL-15/Rα format, one preferred embodiment utilizes the skew variant pair S364K/E357Q:L368D/K370S. In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q.

In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a variant second Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 7G8_H3.30_L1.34, respectively, where the cysteine residue on the IL-15 variant and the cysteine residue on the IL-15Rα (sushi) domain form a disulfide bond, and where the first and second variant Fc domains include the skew variant pair S364K/E357Q:L368D/K370S. In another embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα (sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL are the variable heavy domain and variable light domain of 2A11_H1.144_L2.142, respectively, where the cysteine residue on the IL-15 variant and the cysteine residue on the IL-15Rα(sushi) domain form a disulfide bond, and where the first and second variant Fc domains include the skew variant pair S364K/E357Q:L368D/K370S.

In the Fab X dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant with appropriate cysteine substitutions. In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q: L368D/K370S. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the Fab X dsIL-15/Rα format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the Fab X dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21F format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "Fab X dsIL-15/Rα" format heterodimeric protein that includes: a) a first monomer that includes, from N- to C-terminus, a VH-hinge-CH2-CH3, where VH is a variable heavy domain and CH2-CH3 is a first variant Fc domain; b) a second monomer that includes, from N- to C-terminus, an IL-15Rα(sushi) domain-(domain linker)-CH2-CH3, where CH2-CH3 is a second variant Fc domain and the IL-15Rα(sushi) domain includes an amino acid substitution for a cysteine residue; c) a third monomer that includes, from N- to C-terminus, a VL-CL, where VL is a variable light domain; and d) an IL-15 variant that includes an amino acid substitution for a cysteine residue, where the VH and VL form a LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the hinge-first variant Fc domain of the first monomer includes pI variants N208D/Q295E/N384D/Q418E/N421D, and where numbering is according to EU numbering. In some embodiments, the hinge of the second monomer also includes amino acid substitution C220S. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

G. mAb-scIL-15/Rα

Figure 21G:
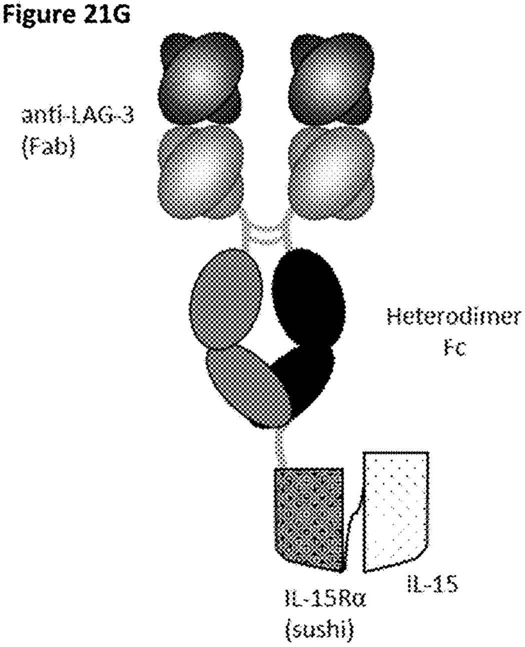

This embodiment is shown in FIGS. 21G, and comprises three monomers (although the fusion protein is a tetramer). The first monomer comprises a heavy chain, VH-CH1-hinge-CH2-CH3. The second monomer comprises a heavy chain with a scIL-15 complex, VH-CH1-hinge-CH2-CH3-domain linker-IL-15Rα(sushi)domain-domain linker-IL-15 variant. The third (and fourth) monomer are light chains, VL-CL. This is generally referred to as "mAb-scIL-15/Rα", with the "sc" standing for "single chain". This binds the LAG-3 molecule bivalently.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C.

In the mAb-scIL-15/Rα format, one preferred embodiment utilizes an anti-LAG-3 ABD having any of the variable heavy and light domain pairs as shown in FIG. 12.

In the mAb-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, and where the IL-15 variant and the IL-15Rα(sushi) domain form an IL-15 complex. In another embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, and where the IL-15 variant and the IL-15Rα(sushi) domain form an IL-15 complex.

In the mAb-scIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the mAb-scIL-15/Rα format, one preferred embodiment utilizes the skew variant pair S364K/E357Q:L368D/K370S. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, where the IL-15 variant and the IL-15Rα(sushi) domain form an IL-15 complex, where the IL-15 variant and the IL-15Rα(sushi) domain form an IL-15 complex, and where the first and second variant Fc domains include the skew variant pair S364K/E357Q:L368D/K370S. In another embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, where the IL-15 variant and the IL-15Rα(sushi) domain form an IL-15 complex, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S.

In the mAb-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q: L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142. In an exemplary embodiment, the first variant Fc domain includes skew variants L368D and K370S, and the second variant Fc domain includes skew variants S364K and E357Q. In an exemplary embodiment, the first variant Fc domain includes skew variants S364K and E357Q, and the second variant Fc domain includes skew variants L368D and K370S.

In the mAb-scIL-15/Rα format, one preferred embodiment utilizes the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants L368D/

K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21G format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-scIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker)-IL-15 variant, where CH2-CH3 is a second variant Fc domain; and c) a third and fourth monomer that each include, from N- to C-terminus, a VL-CL, where VL is a variable light domain, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another of embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

H. mAb-ncIL-15/Rα

Figure 21H:
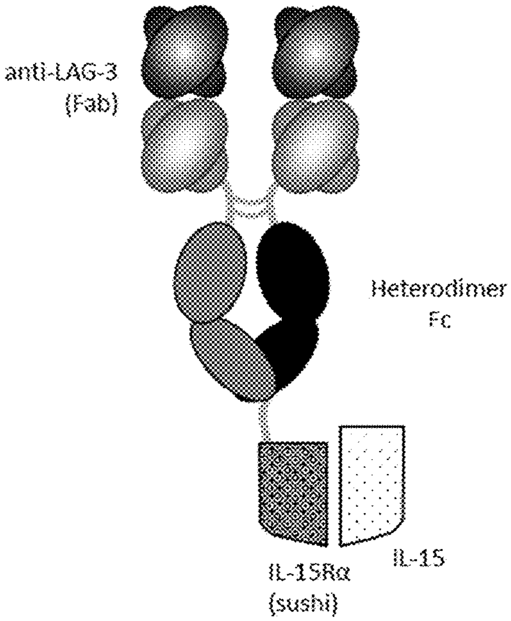

This embodiment is shown in FIGS. 21H, and comprises four monomers (although the heterodimeric fusion protein is a pentamer). The first monomer comprises a heavy chain, VH-CH1-hinge-CH2-CH3. The second monomer comprises a heavy chain with an IL-15Rα(sushi) domain: e.g., VH-CH1-hinge-CH2-CH3-domain linker-IL-15Rα(sushi) domain. The third monomer is a variant IL-15 domain. The fourth (and fifth) monomer are light chains, VL-CL. This is generally referred to as "mAb-ncIL-15/Rα", with the "nc" standing for "non-covalent". This also binds the LAG-3 bivalently.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C.

In the mAb-ncIL-15/Rα format, one preferred embodiment utilizes an anti-LAG-3 ABD having any of the variable heavy and light domain pairs as shown in FIG. 12.

In the mAb-ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer are the variable heavy domain and variable light domain of 7G8_H3.30_L1.34, respectively, where the VH of the second monomer and the VL of the fifth monomer are the variable heavy domain and variable light domain of 7G8_H3.30_L1.34, respectively, and where the IL-15 variant and the IL-15Rα(sushi) domain form an IL-15 complex. In another embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer are the variable heavy domain and variable light domain of 2A11_H1.144_L2.142, respectively, where the VH of the second monomer and the VL of the fifth monomer are the variable heavy domain and variable light domain of 2A11_H1.144_L2.142, respectively, and where the IL-15 variant and the IL-15Rα(sushi) domain form an IL-15 complex.

In the mAb-ncIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where CH2-CH3 is a second Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the mAb-ncIL-15/Rα format, one preferred embodiment utilizes the skew variant pair S364K/E357Q:L368D/K370S. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer are the variable heavy domain and variable light domain of 7G8_H3.30_L1.34, respectively, where the VH of the second monomer and the VL of the fifth monomer are the variable heavy domain and variable light domain of 7G8_H3.30_L1.34, respectively, where the IL-15 variant and the IL-15Rα(sushi) domain form an IL-15 complex, and where the first and second variant Fc domains include the skew variant pair S364K/E357Q:L368D/K370S. In another embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant;

and d) a fourth and fifth monomer that each include, from N- to C-terminus, a VL-CL, where VL is a variable light domain, where the VH of the first monomer and the VL of the fourth monomer are the variable heavy domain and variable light domain of 2A11_H1.144_L2.142, respectively, where the VH of the second monomer and the VL of the fifth monomer are the variable heavy domain and variable light domain of 2A11_H1.144_L2.142, respectively, where the IL-15 variant and the IL-15Rα(sushi) domain form an IL-15 complex, and where the first and second variant Fc domains include the skew variant pair S364K/E357Q:L368D/K370S.

In the mAb-ncIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the first variant Fc domain includes skew variants S364K/E357Q, and the second variant Fc domain includes skew variants L368D/K370S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the mAb-ncIL-15/Rα format, one preferred embodiment utilizes the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-ncIL-15/Rα format, one preferred embodiment utilizes an anti-LAG-3 ABD having the variable heavy and light domain pair of 7G8_H3.30_L1.34 or 2A11_H1.144_L2.142 as shown in FIG. 12 with the FIG. 21H format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers. In an exemplary embodiment, the IL-15 variant includes amino acid substitutions N4D/N65D, D30N/N65D, or D30N/E64Q/N65D.

In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-ncIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where CH2-CH3 is a second variant Fc domain; c) a third monomer that includes an IL-15 variant; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the IL-15 variant and the IL-15Rα(sushi) domain form an IL-15 complex, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

I. mAb-dsIL-15/Rα

Figure 21I:
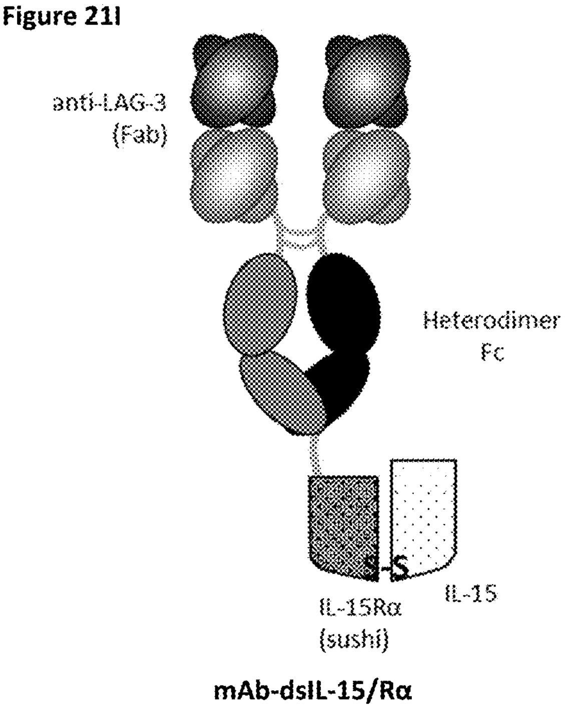

This embodiment is shown in FIGS. 21I, and comprises four monomers (although the heterodimeric fusion protein is a pentamer). The first monomer comprises a heavy chain, VH-CH1-hinge-CH2-CH3. The second monomer comprises a heavy chain with an IL-15Rα(sushi) domain: e.g., VH-CH1-hinge-CH2-CH3-domain linker-IL-15Rα(sushi) domain, where the IL-15Rα(sushi) domain has been engineered to contain a cysteine residue. The third monomer is a variant IL-15 domain, which has been engineered to contain a cysteine residue, such that the IL-15 complex is formed under physiological conditions. The fourth (and fifth) monomer are light chains, VL-CL. This is generally referred to as “mAb-dsIL-15/Rα”, with the “ds” standing for “disulfide”, and it binds LAG-3 bivalently.

In one embodiment, the targeted IL-15/IL-15Rα heterodimeric protein is an “mAb-dsIL-15/Rα” format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, and where the cysteine residue on the IL-15 variant and the cysteine residue on the IL-15Rα(sushi) domain form a disulfide bond. Any useful domain linker can be used to attach the various components of the heterodimeric protein including, but not limited to those in FIGS. 8 and 9A-C.

In the mAb-dsIL-15/Rα format, one preferred embodiment utilizes an anti-LAG-3 ABD having any of the variable heavy and light domain pairs as shown in FIG. 12.

In the mAb-dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an “mAb-dsIL-15/Rα” format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain of 7G8_H3.30_L1.34, respectively, where the VH of the second monomer and the VL of the fifth monomer are the variable heavy domain and variable light domain of 7G8_H3.30_L1.34, respectively, and where the cysteine residue on the IL-15 variant and the cysteine residue on the IL-15Rα(sushi) domain form a disulfide bond. In another embodiment, the targeted IL-15/IL-15Rα heterodimeric protein is an “mAb-dsIL-15/Rα” format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain of 2A11_H1.144_L2.142, respectively, where the VH of the second monomer and the VL of the fifth monomer are the variable heavy domain and variable light domain of 2A11_H1.144_L2.142, respectively, and where the cysteine residue on the IL-15 variant and the cysteine residue on the IL-15Rα(sushi) domain form a disulfide bond.

In the mAb-dsIL-15/Rα format, one preferred embodiment utilizes an IL-15 variant that includes amino acid substitutions N4D/N65D, D30N/N65D, or D30N/E64Q/N65D, with the appropriate cysteine amino acid substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-dsIL-15/Rα format, one preferred embodiment 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant, with the appropriate cysteine amino acid substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the mAb-dsIL-15/Rα format, one preferred embodiment utilizes the skew variant pair S364K/E357Q:L368D/K370S. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino add substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In another exemplary embodiment, the first variant Fc domain includes skew variants S364K/E357Q, and the second variant Fc domain includes skew variants L368D/K370S. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain of 7G8_H3.30_L1.34, respectively, where the VH of the second monomer and the VL of the fifth monomer are the variable heavy domain and variable light domain of 7G8_H3.30_L1.34, respectively, where the cysteine residue on the IL-15 variant and the cysteine residue on the IL-15Rα (sushi) domain form a disulfide bond, and where the first and second variant Fc domains include the skew variant pair S364K/E357Q:L368D/K370S. In another embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first variant Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second variant Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer are the variable heavy domain and variable light domain of 2A11_H1.144_L2.142, respectively, where the VH of the second monomer and the VL of the fifth monomer are the variable heavy domain and variable light domain of 2A11_H1.144_L2.142, respectively, where the cysteine residue on the IL-15 variant and the cysteine residue on the IL-15Rα(sushi) domain form a disulfide bond, and where the first and second variant Fc domains include the skew variant pair S364K/E357Q:L368D/K370S.

In the mAb-dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant with appropriate cysteine substitutions. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D/K370S, and the second variant Fc domain includes skew variants S364K/E357Q. In an exemplary embodiment, the first variant Fc domain includes skew variants S364K/E357Q, and the second variant Fc domain includes skew variants L368D/K370S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the mAb-dsIL-15/Rα format, one preferred embodiment utilizes the skew variant set S364K/E357Q:L368D/

K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα (sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the mAb-dsIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 with the FIG. 21I format, the skew variant set S364K/E357Q:L368D/K370S, the pI variants N208D/Q295E/N384D/Q418D/N421D and/or Q196K/I199T/P271R/P228R/N276K, the ablation variants E233P/L234V/L235A/G236JS267K on both first and second monomers, and optionally the 428L/434S variants on both first and second monomers. In an exemplary embodiment, the IL-15 variant includes amino acid substitutions N4D/N65D, D30N/N65D, or D30N/E64Q/N65D.

In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D and the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-first variant Fc domain of the first monomer includes pI substitutions N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the hinge-second variant Fc domain of the second monomer includes pI variants Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K and the hinge-second variant Fc domain of the second monomer includes pI variants N208D/Q295E/N384D/Q418D/N421D, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-first variant Fc domain of the first monomer includes pI substitutions Q196K/I199T/P271R/P228R/N276K, and where numbering is according to EU numbering. In one embodiment, the targeted IL-15/IL-15Rα heterodimeric protein is an "mAb-dsIL-15/Rα" format heterodimeric protein that includes: a) a first monomer that includes, from N- to C-terminus, a VH-hinge-CH2-CH3, where CH2-CH3 is a first Fc domain; b) a second monomer that includes, from N- to C-terminus, a VH-hinge-CH2-CH3-(domain linker)-IL-15Rα(sushi) domain-(domain linker), where the IL-15Rα(sushi) domain includes an amino acid substitution for a cysteine residue and CH2-CH3 is a second Fc domain; c) a third monomer that includes an IL-15 variant that includes an amino acid substitution for a cysteine residue; and d) a fourth and fifth monomer that each include, from N- to C-terminus, a VL-CL, where VL is a variable light domain, where the VH of the first monomer and the VL of the fourth monomer form a first LAG-3 binding domain, where the VH of the second monomer and the VL of the fifth monomer form a second LAG-3 binding domain, where the cysteine residue on the IL-15 variant and the cysteine residue on the IL-15Rα(sushi) domain form a disulfide bond, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the hinge-second variant Fc domain of the second monomer includes pI variants N208D/Q295E/N384D/Q418D/N421D, and where numbering is according to EU numbering. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

J. Central-IL-15/Rα

Figure 21J:
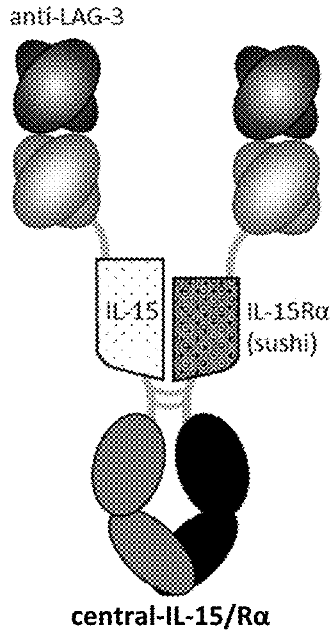

This embodiment is shown in FIGS. 21J, and comprises four monomers forming a tetramer. The first monomer comprises a VH-CH1-[optional domain linker]-IL-15 variant-[optional domain linker]-CH2-CH3, with the second optional domain linker sometimes being the hinge domain. The second monomer comprises a VH-CH1-[optional domain linker]-IL-15Rα(sushi) domain-[optional domain linker]-CH2-CH3, with the second optional domain linker sometimes being the hinge domain. The third (and fourth) monomers are light chains, VL-CL. This is generally referred to as "central-IL-15/Rα".

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linkers that attach the IL-15 variant to the first Fc domain and the IL-15Rα(sushi) domain to the second Fc domain are each antibody hinge domains.

In the central-IL-15/Rα format, one preferred embodiment utilizes an anti-LAG-3 ABD having any of the variable heavy and light domain pairs as shown in FIG. 12.

In the central-IL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, and where the IL-15 variant and the IL-15Rα(sushi) domain form an IL-15 complex. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, and where the IL-15 variant and the IL-15Rα(sushi) domain form an IL-15 complex.

In the "central-IL-15/Rα" format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the central-IL-15/Rα format, one preferred embodiment utilizes an anti-LAG-3 ABD having the variable heavy and light domain pair 7G8_H3.30_L1.34 or the variable heavy and light domain pair 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the central-IL-15/Rα format, one preferred embodiment utilizes the skew variant pair S364K/E357Q:L368D/K370S. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first Fc domain; b) a second monomer that includes, from N- to C-terminus, a VH-(domain linker)-IL-15Rα(sushi) domain-(domain linker)-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the central-IL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first variant Fc domain; b) a second monomer that includes, from N- to C-terminus, a VH-(domain linker)-IL-15Rα (sushi) domain-(domain linker)-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, where the IL-15 variant and the IL-15Rα(sushi) domain form an IL-15 complex, and where the first and second variant Fc domains include the skew variant pair S364K/E357Q:L368D/K370S. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first variant Fc domain; b) a second monomer that includes, from N- to C-terminus, a VH-(domain linker)-IL-15Rα(sushi) domain-(domain linker)-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, where the IL-15 variant and the IL-15Rα(sushi) domain form an IL-15 complex, and where the first and second variant Fc domains include the skew variant pair S364K/E357Q:L368D/K370S.

In the central-IL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/E64Q/N65D variant with appropriate cysteine substitutions. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(domain linker)-CH2-CH3, where CH2-CH3 is a first variant Fc domain; b) a second monomer that includes, from N- to C-terminus, a VH-(domain linker)-IL-15Rα(sushi) domain-(domain linker)-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants S364K and E357Q, and the second variant Fc domain includes skew variants L368D and K370S. In another exemplary embodiment, the first variant Fc domain includes skew variants L368D and K370S, and the second variant Fc domain includes skew variants S364K and E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the central-IL-15/Rα format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants L368D/K370S and the second variant Fc domain include the skew variant pair S364K/E357Q, where the first and second variant Fc domains each include FcKO variants E233P/L234V/L235A/G236del/S267K, where the first variant Fc domain includes pI substitutions Q295E/N384D/Q418D/N421D, and where numbering is according to EU numbering. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the second variant Fc domain of the second monomer includes pI substitutions Q295E/N384D/Q418D/N421D, and where numbering is according to EU numbering. In certain embodiments, the first and second variant Fc domains each further include half-life extension variants M428L/N434S. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

Figure 21K:
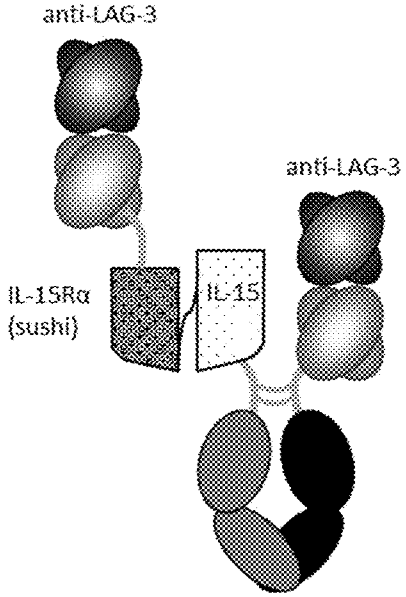

In the central-IL-15/Rα format, one preferred embodiment utilizes an anti-LAG-3 ABD having the variable heavy and light domain pair of 7G8_H3.30_L1.34 or 2A11_H1.144_L2.142 as shown in FIG. 12 with the FIGS. 21K, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers. In one embodiment, the targeted IL-15/IL-15Rα heterodimeric protein is an "central-IL-15/Rα" format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain include the skew variant pair S364K/E357Q, where the first and second variant Fc domains each include FcKO variants E233P/L234V/L235A/

G236del/S267K, where the first variant Fc domain includes pI substitutions Q295E/N384D/Q418D/N421D, and where numbering is according to EU numbering. In one embodiment, the targeted IL-15/IL-15Rα heterodimeric protein is an “central-IL-15/Rα” format heterodimeric protein that includes: a) a first monomer that includes, from N- to C-terminus, a VH-(domain linker)-IL-15 variant-(hinge)-CH2-CH3, where CH2-CH3 is a first variant Fc domain; b) a second monomer that includes, from N- to C-terminus, a VH-(domain linker)-IL-15Rα(sushi) domain-(hinge)-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants S364K/E357Q and the second variant Fc domain include the skew variant pair L368D/K370S, where the first and second variant Fc domains each include FcKO variants E233P/L234V/L235A/G236del/S267K, where the second variant Fc domain of the second monomer includes pI substitutions Q295E/N384D/Q418D/N421D, and where numbering is according to EU numbering.

In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

K. Central scIL-15/Rα

This embodiment is shown in FIGS. 21K, and comprises four monomers forming a tetramer. The first monomer comprises a VH-CH1-[optional domain linker]-IL-15Rα (sushi) domain-domain linker-IL-15 variant-[optional domain linker]-CH2-CH3, with the second optional domain linker sometimes being the hinge domain. The second monomer comprises a VH-CH1-hinge-CH2-CH3. The third (and fourth) monomers are light chains, VL-CL. This is generally referred to as “central-scIL-15/Rα”, with the “sc” standing for “single chain”.

In one embodiment, the targeted IL-15/IL-15Rα heterodimeric protein is an “central-scIL-15/Rα” format heterodimeric protein that includes: a) a first monomer that includes, from N- to C-terminus, a VH-(domain linker)-IL-15Rα (sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, and where the IL-15 variant and the IL-15Rα(sushi) domain form an IL-15 complex. Any useful domain linker can be used to attach the various components of the heterodimeric protein including, but not limited to those in FIGS. 8 and 9A-C. In an exemplary embodiment, the domain linker that attaches the IL-15 variant to the first Fc domain is an antibody hinge domain.

In the central-scIL-15/Rα format, one preferred embodiment utilizes an anti-LAG-3 ABD having any of the variable heavy and light domain pairs as shown in FIG. 12.

In the central-scIL-15/Rα format, one preferred embodiment utilizes an anti-LAG-3 ABD having the variable heavy and light domain pair 7G8_H3.30_L1.34 34 or the variable heavy and light domain pair 2A11_H1.144_L2.142 as shown in as shown in FIG. 12.

In one embodiment, the targeted IL-15/IL-15Rα heterodimeric protein is an “central-scIL-15/Rα” format heterodimeric protein that includes: a) a first monomer that includes, from N- to C-terminus, a VH-(domain linker)-IL-15Rα (sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, and where the IL-15 variant and the IL-15Rα(sushi) domain form an IL-15 complex. In another embodiment, the targeted IL-15/IL-15Rα heterodimeric protein is an “central-scIL-15/Rα” format heterodimeric protein that includes: a) a first monomer that includes, from N- to C-terminus, a VH-(domain linker)-IL-15Rα(sushi) domain-(domain linker)-(domain linker)-IL-15 variant —CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, and where the IL-15 variant and the IL-15Rα(sushi) domain form an IL-15 complex.

In the central-scIL-15/Rα format, one preferred embodiment utilizes an IL-15 variant that includes amino acid substitutions N4D/N65D, D30N/N65D, or D30N/E64Q/N65D. In one embodiment, the targeted IL-15/IL-15Rα heterodimeric protein is an “central-scIL-15/Rα” format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the central-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12, with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first Fc domain; b) a second monomer that includes, from N- to C-terminus, a VH-hinge-CH2-CH3, where CH2-CH3 is a second Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, and where the IL-15 variant includes amino acid substitutions N4D/N65D, D30N/N65D, or D30N/E64Q/N65D. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the central-scIL-15/Rα format, one preferred embodiment utilizes the skew variant pair S364K/E357Q:L368D/K370S. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα (sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the IL-15 variant includes amino acid substitutions N4D/N65D, D30N/N65D, or D30N/E64Q/N65D, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the central-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain of 7G8_H3.30_L1.34, respectively, where the VH of the second monomer and the VL of the fourth monomer are the variable heavy domain and variable light domain of 7G8_H3.30_L1.34, respectively, where the IL-15 variant and the IL-15Rα(sushi) domain form an IL-15 complex, and where the first and second variant Fc domains include the skew variant pair S364K/E357Q:L368D/K370S. In another embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer are the variable heavy domain and variable light domain of 2A11_H1.144_L2.142, respectively, where the VH of the second monomer and the VL of the fourth monomer are the variable heavy domain and variable light domain of 2A11_H1.144_L2.142, respectively, where the IL-15 variant and the IL-15Rα(sushi) domain form an IL-15 complex, and where the first and second variant Fc domains include the skew variant pair S364K/E357Q:L368D/K370S. In an exemplary embodiment, the first variant Fc domain includes skew variants L368D and K370S, and the second variant Fc domain includes skew variants S364K and E357Q.

In the central-scIL-15/Rα format, one preferred embodiment utilizes an anti-LAG-3 ABD having the variable heavy and light domain pair of 7G8_H3.30_L1.34 or the variable heavy and light domain pair of 2A11_H1.144_L2.142 as shown in FIG. 12 and the skew variant pair S364K/E357Q:L368D/K370S with either the IL-15 N4D/N65D variant or the IL-15 D30N/N65D variant or the IL-15 D30N/E64Q/N65D variant. In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the IL-15 variant includes amino acid substitutions N4D/N65D, D30N/N65D, or D30N/E64Q/N65D, and where the first and second variant Fc domains include the skew variant pair L368D/K370S:S364K/E357Q. In an exemplary embodiment, the first variant Fc domain includes skew variants L368D/K370S, and the second variant Fc domain includes skew variants S364K/E357Q. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

In the central-scIL-15/Rα format, one preferred embodiment utilizes the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα(sushi) domain-(domain linker)-IL-15 variant-(hinge)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

In the central-scIL-15/Rα format, one preferred embodiment utilizes an anti-LAG-3 ABD having the variable heavy and light domain pair of 7G8_H3.30_L1.34 or 2A11_H1.144_L2.142 as shown in FIG. 12 with the FIG. 21K format, the skew variant set S364K/E357Q:L368D/K370S, the pI variants Q295E/N384D/Q418E/N421D, the ablation variants E233P/L234V/L235A/G236JS267K on both first and second monomers, and optionally the 428L/434S variants on both first and second monomers.

In one embodiment, the targeted IL-15/IL-15Rα heterodimeric protein is an "central-scIL-15/Rα" format heterodimeric protein that includes: a) a first monomer that includes, from N- to C-terminus, a VH-(domain linker)-IL-15Rα (sushi) domain-(domain linker)-IL-15 variant-(hinge)-CH2-CH3, where CH2-CH3 is a first variant Fc domain; b) a second monomer that includes, from N- to C-terminus, a VH-hinge-CH2-CH3, where CH2-CH3 is a second variant Fc domain; and d) a third and fourth monomer that each include from N- to C-terminus, a VL-CL, where the VH of the first monomer and the VL of the third monomer form a first LAG-3 binding domain, where the VH of the second monomer and the VL of the fourth monomer form a second LAG-3 binding domain, where the IL-15 variant and the IL-15Rα(sushi) domain form an IL-15 complex, where VH and VL are the variable heavy domain and variable light domain of 7G8_H3.30_L1.34 or 2A11_H1.144_L2.142, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In certain embodiments, the hinge of the first monomer further includes variant C220S. In certain embodiments, the first and second variant Fc domains each further include half-life extension variants M428L/N434S. In a particular embodiment, the IL-15 variant includes amino acid substitutions N4D/N65D and VH and VL are the variable heavy domain and variable light domain of 7G8_H3.30_L1.34. In another embodiment, the IL-15 variant includes amino acid substitutions N4D/N65D and VH and VL are the variable heavy domain and variable light domain of 2A11_H1.144_L2.142. In one embodiment, the IL-15 variant includes amino acid substitutions D30N/N65D and VH and VL are the variable heavy domain and variable light domain of 7G8_H3.30_L1.34. In another embodiment, the IL-15 variant includes amino acid substitutions D30N/N65D and VH and VL are the variable heavy domain and variable light domain of 2A11_H1.144_L2.142. In yet another embodiment, the IL-15 variant includes amino acid substitutions D30N/E64Q/N65D and VH and VL are the variable heavy domain and variable light domain of 7G8_H3.30_L1.34. In another embodiment, the IL-15 variant includes amino acid substitutions D30N/E64Q/N65D and VH and VL are the variable heavy domain and variable light domain of 2A11_H1.144_L2.142.

V. Particularly Useful Embodiments of the Invention

The present invention provides a targeted IL-15/IL-15Rα heterodimeric protein comprising at least two monomers, one of which contains an anti-LAG-3 ABD and the other that contains an IL-15/RA complex, joined using heterodimeric Fc domains.

In some embodiments, the first and the second Fc domains have a set of amino acid substitutions selected from the group consisting of S267K/L368D/K370S:S267K/S364K/E357Q; S364K/E357Q:L368D/K370S; L368D/K370S:S364K; L368E/K370S:S364K; T411E/K360E/Q362E:D401K; L368D/K370S:S364K/E357L and K370S:S364K/E357Q, according to EU numbering.

In some instances, the first and/or the second Fc domains have an additional set of amino acid substitutions comprising Q295E/N384D/Q418E/N421D, according to EU numbering. In some cases, the first and/or the second Fc domains have an additional set of amino acid substitutions consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, according to EU numbering.

In some embodiments, the IL-15 protein has a polypeptide sequence selected from the group consisting of SEQ ID NO:1 (full-length human IL-15) and SEQ ID NO:2 (truncated human IL-15), and the IL-15Rα protein has a polypeptide sequence selected from the group consisting of SEQ ID NO:3 (full-length human IL-15Rα) and SEQ ID NO:4 (sushi domain of human IL-15Rα).

In embodiments the IL-15 protein and the IL-15Rα protein can have a set of amino acid substitutions selected from the group consisting of E87C:D96/P97/C98; E87C:D96/C97/A98; V49C:S40C; L52C:S40C; E89C:K34C; Q48C:G38C; E53C:L42C; C42S:A37C; and L45C:A37C, respectively.

In some embodiments, the IL-15 protein is a variant protein that has a sequence selected from FIG. 19 and FIG. 20 to reduce potency. In some embodiments, the IL-15 protein is a variant protein having one or more amino acid substitutions at the IL-15:CD132 interface.

In some embodiments, the LAG-3 antigen binding domain comprises an anti-LAG-3 scFv or an anti-LAG-3 Fab. In an exemplary embodiment, the LAG-3 ABD includes the VH and VL of any of the LAG-3 ABDs depicted in FIGS. 12 and 13A-C.

In an exemplary embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL form a LAG-3 binding domain, where the IL-15 variant is an IL-15 N4D/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S. In some embodiments, the VH and VL are the variable heavy domain and variable light domain of any of the LAG-3 ABDs in FIG. 12 or 13A-C. In some embodiments, the VH and VL are the variable heavy domain and variable light domain of 7G8_H3.30_L1.34 or 2A11_H1.144_L2.142 (FIG. 12).

In an exemplary embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b)

a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL form a LAG-3 binding domain, where the IL-15 variant is an IL-15 D30N/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S. In some embodiments, the VH and VL are the variable heavy domain and variable light domain of any of the LAG-3 ABDs in FIG. 12 or 13A-C. In some embodiments, the VH and VL are the variable heavy domain and variable light domain of 7G8_H3.30_L1.34 or 2A11_H1.144_L2.142 (FIG. 12).

In an exemplary embodiment, the targeted IL-15/IL-15Rα heterodimeric protein is an "scIL-15/Rα X Fab" format heterodimeric protein that includes: a) a first monomer that includes, from N- to C-terminus, an IL-15Rα(sushi) domain-(domain linker)-IL-15 variant-(domain linker)-CH2-CH3, where CH2-CH3 is a first variant Fc domain; b) a second monomer that includes, from N- to C-terminus, a VH-CH1-hinge-CH2-CH3, variant here VH is a variable heavy domain and CH2-CH3 is a second variant Fc domain, and c) a light chain that includes from, N- to C-terminus, VL-VC, where VL is a variable light domain, where VH and VL form a LAG-3 binding domain, where the IL-15 variant is an IL-15 D30N/E64Q/N65D variant, where the first variant Fc domain includes skew variants L368D/K370S and the second variant Fc domain includes skew variants S364K/E357Q, where the first and second variant Fc domains each include FcKO variants E233P/L234V/L235A/G236del/S267K, where the first variant Fc domain includes pI variants Q295E/N384D/Q418E/N421D, and where numbering is according to EU numbering. In some embodiments, the hinge of the first monomer also includes amino acid substitution C220S. In certain embodiments, the first and second variant Fc domains each further include half-life extension variants M428L/N434S. In certain embodiments, the hinge of the first monomer includes also includes amino acid substitution C220S and the first and second variant Fc domains each further include half-life extension variants M428L/N434S. In some embodiments, the VH and VL are the variable heavy domain and variable light domain of any of the LAG-3 ABDs in FIG. 12 or 13A-C. In some embodiments, the VH and VL are the variable heavy domain and variable light domain of 7G8_H3.30_L1.34 or 2A11_H1.144_L2.142 (FIG. 12).

Useful "backbone" sequences that can be included in the "scIL-15/Rα X Fab" format heterodimeric protein are depicted in FIG. 10. In some embodiments, the "scIL-15/Rα X Fab" format heterodimeric protein that includes: a) a first monomer that includes, from N- to C-terminus, an IL-15Rα (sushi) domain-(domain linker)-IL-15 variant-(hinge)-CH2-CH3, where hinge-CH2-CH3 has the amino acid sequence of Chain 2 of "Backbone 1" in FIG. 10 (SEQ ID NO: 58); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 1" in FIG. 10 (SEQ ID NO: 57), and c) a light chain that includes from, N- to C-terminus, VL-VC, where VL is a variable light domain and VC has the sequence of "Constant Light Chain—Kappa" in FIG. 11 (SEQ ID NO: 63). In certain embodiments, the "scIL-15/Rα X Fab" format heterodimeric protein that includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of Chain 2 of "Backbone 2" in FIG. 10 (SEQ ID NO: 60); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 2" in FIG. 10 (SEQ ID NO: 59), and c) a light chain that includes from, N- to C-terminus, VL-VC, where VL is a variable light domain and VC has the sequence of "Constant Light Chain—Kappa" in FIG. 11 (SEQ ID NO: 63). In some embodiments, the "scIL-15/Rα X Fab" format heterodimeric protein that includes: a) a first monomer that includes, from N- to C-terminus, an IL-15Rα(sushi) domain-(domain linker)-IL-15 variant-(hinge)-CH2-CH3, where hinge-CH2-CH3 has the amino acid sequence of Chain 2 of "Backbone 3" in FIG. 10 (SEQ ID NO: 62); b) a second monomer that includes, from N- to C-terminus, a VH-CH1-hinge-CH2-CH3, where VH is a variable heavy domain and CH1-hinge-CH2-CH3 has the amino acid sequence of Chain 1 of "Backbone 3" in FIG. 10 (SEQ ID NO: 61), and c) a light chain that includes from, N- to C-terminus, VL-VC, where VL is a variable light domain and VC has the sequence of "Constant Light Chain—Kappa" in FIG. 11 (SEQ ID NO: 63). In an exemplary embodiment, the IL-15 variant includes amino acid substitutions N4D/N65D, D30N/N65D, or D30N/E64Q/N65D. In an exemplary embodiment, the IL-15 variant includes amino acid substitutions N4D/N65D, D30N/N65D, or D30N/E64Q/N65D. In an exemplary embodiment, the VH and VL are the VH and VL of any of the LAG-3 ABDs in FIGS. 12 and 13A-C and the IL-15 variant includes amino acid substitutions N4D/N65D. In another exemplary embodiment, the VH and VL are the VH and VL of any of the LAG-3 ABDs in FIGS. 12 and 13A-C and the IL-15 variant includes amino acid substitutions D30N/N65D. In yet another exemplary embodiment, the VH and VL are the VH and VL of any of the LAG-3 ABDs in FIGS. 12 and 13A-C and the IL-15 variant includes amino acid substitutions D30N/E64Q/N65D.

Particular preferred LAG-3 targeted IL-15/IL-15Rα-Fc heterodimeric fusion proteins include XENP27972, XENP27973, XENP27977, XENP27978, XENP029486, XENP029487, XENC1000, XENC1001, XENC1002, XENC1003, XENC1004 and XENC1005 "scIL-15/Rα X Fab" format heterodimeric protein. Exemplary embodiments of the LAG-3 targeted IL-15/IL-15Rα-Fc heterodimeric fusion proteins are shown in FIGS. 22A and B, FIGS. 29A and B, FIGS. 46A and B, FIGS. 47A and B, and FIGS. 48A-D.

VI. Nucleic Acids of the Invention

In another aspect, provided herein are nucleic acid compositions encoding the targeted heterodimeric fusion proteins (or, in the case of a monomer Fc domain protein, nucleic acids encoding those as well).

As will be appreciated by those in the art, the nucleic acid compositions will depend on the format of the targeted heterodimeric fusion protein. Thus, for example, when the format requires three amino acid sequences, three nucleic acid sequences can be incorporated into one or more expression vectors for expression. Similarly, some formats only two nucleic acids are needed; again, they can be put into one or two expression vectors, or four or 5. As noted herein, some constructs have two copies of a light chain, for example.

As is known in the art, the nucleic acids encoding the components of the invention can be incorporated into expression vectors as is known in the art, and depending on the host cells used to produce the targeted heterodimeric fusion proteins of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors provided herein are then transformed into any number of different types of host cells as is well known in the art, including mammalian, bacterial, yeast, insect and/or fungal cells, with mammalian cells (e.g., CHO cells), finding use in many embodiments.

In some embodiments, nucleic acids encoding each monomer, as applicable depending on the format, are each contained within a single expression vector, generally under different or the same promoter controls. In embodiments of particular use in the present invention, each of these two or three nucleic acids are contained on a different expression vector.

The targeted heterodimeric fusion protein of the invention are made by culturing host cells comprising the expression vector(s) as is well known in the art. Once produced, traditional fusion protein or antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the heterodimer (e.g., anionic exchange columns, cationic exchange columns). These substitutions also aid in the determination and monitoring of any contaminating homodimers post-purification (e.g., IEF gels, cIEF, and analytical IEX columns).

VII. Biological and Biochemical Functionality of Targeted LAG-3 Antibody x IL-15/IL-15Rα Heterodimeric Immunomodulatory Fusion Proteins Generally the targeted heterodimeric fusion proteins of the invention are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays. For example, evaluation of changes in immune status along with "old fashioned" measurements such as tumor burden, size, invasiveness, LN involvement, metastasis, etc. can be done. Thus, any or all of the following can be evaluated: the inhibitory effects of the heterodimeric proteins on $CD4^+$ T cell activation or proliferation, $CD8^+$ T (CTL) cell activation or proliferation, $CD8^+$ T cell-mediated cytotoxic activity and/or CTL mediated cell depletion, NK cell activity and NK mediated cell depletion, the potentiating effects of the heterodimeric protein on Treg cell differentiation and proliferation and Treg- or myeloid derived suppressor cell (MDSC)-mediated immunosuppression or immune tolerance, and/or the effects of heterodimeric protein on proinflammatory cytokine production by immune cells, e.g., IL-2, IFN-γ or TNF-α production by T or other immune cells.

In some embodiments, assessment of treatment is done by evaluating immune cell proliferation, using for example, CFSE dilution method, Ki67 intracellular staining of immune effector cells, and $^3$H-thymidine incorporation method.

In some embodiments, assessment of treatment is done by evaluating the increase in gene expression or increased protein levels of activation-associated markers, including one or more of: CD25, CD69, CD137, ICOS, PD1, GITR, OX40, and cell degranulation measured by surface expression of CD107A.

In general, gene expression assays are done as is known in the art.

In general, protein expression measurements are also similarly done as is known in the art.

In some embodiments, assessment of treatment is done by assessing cytotoxic activity measured by target cell viability detection via estimating numerous cell parameters such as enzyme activity (including protease activity), cell membrane permeability, cell adherence, ATP production, co-enzyme production, and nucleotide uptake activity. Specific examples of these assays include, but are not limited to, Trypan Blue or PI staining, $^{51}$Cr or $^{35}$S release method, LDH activity, MTT and/or WST assays, Calcein-AM assay, Luminescent based assay, and others.

In some embodiments, assessment of treatment is done by assessing T cell activity measured by cytokine production, measure either intracellularly in culture supernatant using cytokines including, but not limited to, IFNγ, TNFα, GM-CSF, IL2, IL6, IL4, IL5, IL10, IL13 using well known techniques.

Accordingly, assessment of treatment can be done using assays that evaluate one or more of the following: (i) increases in immune response, (ii) increases in activation of αβ and/or γδ T cells, (iii) increases in cytotoxic T cell activity, (iv) increases in NK and/or NKT cell activity, (v) alleviation of αβ and/or γδ T-cell suppression, (vi) increases in pro-inflammatory cytokine secretion, (vii) increases in IL-2 secretion; (viii) increases in interferon-γ production, (ix) increases in Th1 response, (x) decreases in Th2 response, (xi) decreases or eliminates cell number and/or activity of at least one of regulatory T cells (Tregs).

A. Assays to Measure Efficacy

In some embodiments, T cell activation is assessed using a Mixed Lymphocyte Reaction (MLR) assay as is known in the art. An increase in activity indicates immunostimulatory activity. Appropriate increases in activity are outlined below.

In one embodiment, the signaling pathway assay measures increases or decreases in immune response as measured for an example by phosphorylation or de-phosphorylation of different factors, or by measuring other post translational modifications. An increase in activity indicates immunostimulatory activity. Appropriate increases in activity are outlined below.

In one embodiment, the signaling pathway assay measures increases or decreases in activation of αβ and/or -γδ T cells as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in cytotoxic T cell activity as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in NK and/or NKT cell activity as measured for an example by direct killing of target cells like for an example cancer cells or by cytokine secretion or by changes in expression of activation markers like for an example CD107a, etc. An increase in activity indicates immunostimulatory activity. Appropriate increases in activity are outlined below.

In one embodiment, the signaling pathway assay measures increases or decreases in αβ and/or γδ T-cell suppression, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in pro-inflammatory cytokine secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in IL-2 secretion as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in interferon-γ production as measured for example by ELISA or by Luminex or by Multiplex bead based methods or by intracellular staining and FACS analysis or by Alispot etc. An increase in activity indicates immunostimulatory activity. Appropriate increases in activity are outlined below.

In one embodiment, the signaling pathway assay measures increases or decreases in Th1 response as measured for an example by cytokine secretion or by changes in expression of activation markers. An increase in activity indicates immunostimulatory activity. Appropriate increases in activity are outlined below.

In one embodiment, the signaling pathway assay measures increases or decreases in Th2 response as measured for an example by cytokine secretion or by changes in expression of activation markers. An increase in activity indicates immunostimulatory activity. Appropriate increases in activity are outlined below.

In one embodiment, the signaling pathway assay measures increases or decreases cell number and/or activity of at least one of regulatory T cells (Tregs), as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophages cell numbers, as measured for example by flow cytometry or by IHC. A decrease in response indicates immunostimulatory activity. Appropriate decreases are the same as for increases, outlined below.

In one embodiment, the signaling pathway assay measures increases or decreases in M2 macrophage pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in N2 neutrophils increase, as measured for example by flow cytometry or by IHC. A decrease in response indicates immunostimulatory activity. Appropriate decreases are the same as for increases, outlined below.

In one embodiment, the signaling pathway assay measures increases or decreases in N2 neutrophils pro-tumorigenic activity, as measured for an example by cytokine secretion or by changes in expression of activation markers. A decrease in response indicates immunostimulatory activity. Appropriate decreases are the same as for increases, outlined below.

In one embodiment, the signaling pathway assay measures increases or decreases in inhibition of T cell activation, as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in inhibition of CTL activation as measured for an example by direct killing of target cells like for an example cancer cells or by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in αβ and/or γδ T cell exhaustion as measured for an example by changes in expression of activation markers. A decrease in response indicates immunostimulatory activity. Appropriate decreases are the same as for increases, outlined below.

In one embodiment, the signaling pathway assay measures increases or decreases αβ and/or -γδ T cell response as measured for an example by cytokine secretion or by proliferation or by changes in expression of activation markers like for an example CD137, CD107a, PD1, etc. An increase in activity indicates immunostimulatory activity. Appropriate increases in activity are outlined below.

In one embodiment, the signaling pathway assay measures increases or decreases in stimulation of antigen-specific memory responses as measured for an example by cytokine secretion or by proliferation or by changes in expression of activation markers like for an example CD45RA, CCR7 etc. An increase in activity indicates immunostimulatory activity. Appropriate increases in activity are outlined below.

In one embodiment, the signaling pathway assay measures increases or decreases in apoptosis or lysis of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases in stimulation of cytotoxic or cytostatic effect on cancer cells. as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases direct killing of cancer cells as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, the signaling pathway assay measures increases or decreases Th17 activity as measured for an example by cytokine secretion or by proliferation or by changes in expression of activation markers. An increase in activity indicates immunostimulatory activity. Appropriate increases in activity are outlined below.

In one embodiment, the signaling pathway assay measures increases or decreases in induction of complement dependent cytotoxicity and/or antibody dependent cell-mediated cytotoxicity, as measured for an example by cytotoxicity assays such as for an example MTT, Cr release, Calcine AM, or by flow cytometry based assays like for an example CFSE dilution or propidium iodide staining etc. An increase in activity indicates immunostimulatory activity. Appropriate increases in activity are outlined below.

In one embodiment, T cell activation is measured for an example by direct killing of target cells like for an example cancer cells or by cytokine secretion or by proliferation or by changes in expression of activation markers like for an example CD137, CD107a, PD1, etc. For T-cells, increases in proliferation, cell surface markers of activation (e.g., CD25, CD69, CD137, PD1), cytotoxicity (ability to kill target cells), and cytokine production (e.g., IL-2, IL-4, IL-6, IFNγ, TNF-a, IL-10, IL-17A) would be indicative of immune modulation that would be consistent with enhanced killing of cancer cells.

In one embodiment, NK cell activation is measured for example by direct killing of target cells like for an example cancer cells or by cytokine secretion or by changes in expression of activation markers like for an example CD107a, etc. For NK cells, increases in proliferation, cytotoxicity (ability to kill target cells and increases CD107a, granzyme, and perforin expression), cytokine production (e.g., IFNγ and TNF), and cell surface receptor expression (e.g., CD25) would be indicative of immune modulation that would be consistent with enhanced killing of cancer cells.

In one embodiment, γδ T cell activation is measured for example by cytokine secretion or by proliferation or by changes in expression of activation markers.

In one embodiment, Th1 cell activation is measured for example by cytokine secretion or by changes in expression of activation markers.

Appropriate increases in activity or response (or decreases, as appropriate as outlined above), are increases of 10%, 20%, 30%, 40%, 50%, 60%, 70%, 80%, 90%, 95% or 98 to 99% percent over the signal in either a reference sample or in control samples, for example test samples that do not contain a heterodimeric protein of the invention. Similarly, increases of at least one-, two-, three-, four- or five-fold as compared to reference or control samples show efficacy.

VIII. Treatments

Once made, the compositions of the invention find use in a number of oncology applications, by treating cancer, generally by promoting T cell activation (e.g., T cells are no longer suppressed) with the binding of the heterodimeric fusion proteins of the invention.

Accordingly, the targeted heterodimeric compositions of the invention find use in the treatment of these cancers.

A. Targeted Heterodimeric Protein Compositions for In Vivo Administration

Formulations of the antibodies used in accordance with the present invention are prepared for storage by mixing an antibody having the desired degree of purity with optional pharmaceutically acceptable carriers, excipients or stabilizers (as generally outlined in Remington's Pharmaceutical Sciences 16th edition, Osol, A. Ed. [1980]), in the form of lyophilized formulations or aqueous solutions. Acceptable carriers, buffers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

B. Combination Therapies

In some embodiments, the heterodimeric proteins of the invention can be used in combination therapies with antibodies that bind to different checkpoint proteins, e.g., not LAG-3 antibodies. In this way, the antigen binding domains of the additional antibody do not compete for binding with the targeted heterodimeric protein. In this way, a sort of "triple combination" therapy is achieved, as three receptors are engaged (two from the targeted heterodimeric protein and one from the additional antibody). As discussed herein, the heterodimeric protein can have different valencies and specifities as outlined herein.

Surprisingly, as shown herein, these combinations can result in synergistic effects when co-administered. In this context, "co-administration" means that the two moieties can be administered simultaneously or sequentially. That is, in some cases, the drugs may be administered simultaneously, although generally this is through the use of two separate IV infusions; that is, the drugs are generally not combined into a single dosage unit. Alternatively, co-administration includes the sequential administration of the two separate drugs, either in a single day or separate days (including separate days over time).

1. Anti-PD-1 Antibodies for Use in Co-Administration Therapies

As is known in the art, there are two currently approved anti-PD-1 antibodies and many more in clinical testing. Thus, suitable anti-PD-1 antibodies for use in combination therapies as outlined herein include, but are not limited to, the two currently FDA approved antibodies, pembrolizumab and nivolizumab, as well as those in clinical testing currently, including, but not limited to, tislelizumab, Sym021, REGN2810 (developed by Rengeneron), JNJ-63723283 (developed by J and J), SHR-1210, pidilizumab, AMP-224, MEDIo680, PDR001 and CT-001, as well as others outlined in Liu et al., J. Hemat. & Oncol. (2017)10:136, the antibodies therein expressly incorporated by reference. As above, anti-PD-1 antibodies are used in combination when the targeted heterodimeric proteins of the invention do not have an antigen binding domain that binds PD-1.

2. Anti-PD-L1 Antibodies for Use in Co-Administration Therapies

In some embodiments, anti-PD-L1 antibodies are used in combination. As is known in the art, there are three currently approved anti-PD-L1 antibodies and many more in clinical testing. Thus, suitable anti-PD-L1 antibodies for use in combination therapies as outlined herein include, but are not limited to, the three currently FDA approved antibodies, atezolizumab, avelumab, durvalumab, as well as those in clinical testing currently, including, but not limited to, LY33000054 and CS1001, as well as others outlined in Liu et al., J. Hemat. & Oncol. (2017)10:136, the antibodies therein expressly incorporated by reference. As above, anti-PD-L1 antibodies are used in combination when the targeted heterodimeric proteins of the invention do not have an antigen binding domain that binds PD-L1.

3. Anti-TIM-3 Antibodies for Use in Co-Administration Therapies

In some embodiments, anti-TIM-3 antibodies can be used in combination with the targeted heterodimeric proteins of the invention. There are several TIM-3 antibodies in clinical development, including MBG453 and TSR-022. As above, anti-TIM-3 antibodies are used in combination when the targeted heterodimeric proteins of the invention do not have an antigen binding domain that binds TIM-3.

4. Anti-TIGIT Antibodies for Use in Co-Administration Therapies

In some embodiments, anti-TIGIT antibodies can be used in combination with the targeted heterodimeric proteins of the invention. There are several TIGIT antibodies in clinical development, BMS-986207, OMP-313M32 and MTIG7192A. As above, anti-TIGIT antibodies are used in combination when the targeted heterodimeric proteins of the invention do not have an antigen binding domain that binds TIGIT.

5. Anti-CTLA-4 Antibodies for Use in Co-Administration Therapies

In some embodiments, anti-CTLA-4 antibodies can be used in combination with the targeted heterodimeric proteins of the invention. Ipilimumab has been approved, and there are several more in development, including CP-675,206 and AGEN-1884. As above, anti-CTLA-4 antibodies are used in combination when the targeted heterodimeric proteins of the invention do not have an antigen binding domain that binds CTLA-4.

C. Administrative Modalities

The targeted heterodimeric proteins and chemotherapeutic agents of the invention are administered to a subject, in accord with known methods, such as intravenous administration as a bolus or by continuous infusion over a period of time.

D. Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the targeted heterodimeric protein used in the present invention depend on the disease or condition to be treated and may be determined by the persons skilled in the art.

An exemplary, non-limiting range for a therapeutically effective amount of a targeted heterodimeric protein used in the present invention is about 0.1-100 mg/kg.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

IX. EXAMPLES

Examples are provided below to illustrate the present invention. These examples are not meant to constrain the present invention to any particular application or theory of operation. For all constant region positions discussed in the present invention, numbering is according to the EU index as in Kabat (Kabat et at, 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Patent Publications 2015/0307629, 2014/0288275 and WO2014/145806, all of which are expressly incorporated by reference in their entirety and particularly for the techniques outlined therein. Examples 1 and 2 from U.S. Ser. No. 62,416,087, filed on Nov. 1, 2016 are expressly incorporated by reference in their entirety, including the corresponding figures. Additionally, USSNs 62/408,655, 62/443,465, 62/477,926, 15/785,401, 62/416,087 and Ser. No. 15/785,393 are expressly incorporated by reference in their entirety, and specifically for all the sequences, Figures and Legends therein.

A. Example 1: Anti-LAG-3 ABDs

Examples of antigen-binding domains which bind LAG-3 were described in in WO2017/218707, the contents are hereby incorporated in its entirety for all purposes, and in particular for the LAG-3 ABDs in FIG. 11, the data in FIG. 18, FIG. 55, FIG. 56, FIG. 63 and SEQ ID NO:s 36819-36962, SEQ ID NO:s 35417-35606, SEQ ID NO:s 25914-32793 and SEQ ID NO:s 32794-33002 sequences in the sequence listing.

B. Example 2: LAG-3-Targeted IL-15/Rα-Fc Fusions

Reference is made to WO2018/071919 which describes IL-15/RA-Fc fusions that do not contain ABDs as are generally depicted in FIGS. 9A-9G and FIGS. 39A-39D. WO2018/071919 is expressly incorporated by reference herein, and specifically for all of the sequences, formats, Figures and Legends therein.

2A: Generation of LAG-3-Targeted IL-15/Rα-Fc Fusions

Plasmids coding for IL-15, IL-15Rα sushi domain, or the anti-LAG-3 variable regions were constructed by standard gene synthesis, followed by subcloning into a pTT5 expression vector containing Fc fusion partners (e.g., constant regions as depicted in Figure). Cartoon schematics of illustrative LAG-3-targeted IL-15/Rα-Fc fusions are depicted in FIG. 21.

The "scIL-15/Rα x scFv" format (FIG. 21A) comprises IL-15Rα(sushi) fused to IL-15 by a variable length linker (termed "scIL-15/Rα") which is then fused to the N-terminus of a heterodimeric Fc-region, with an scFv fused to the other side of the heterodimeric Fc.

The "scFv x ncIL-15/Rα" format (FIG. 21B) comprises an scFv fused to the N-terminus of a heterodimeric Fc-region, with IL-15Rα(sushi) fused to the other side of the heterodimeric Fc, while IL-15 is transfected separately so that a non-covalent IL-15/Rα complex is formed.

The "scFv x dsIL-15/Rα" format (FIG. 21C) is the same as the "scFv x ncIL-15/Rα" format, but wherein IL-15Rα (sushi) and IL-15 are covalently linked as a result of engineered cysteines.

The "scIL-15/Rα x Fab" format (FIG. 21D) comprises IL-15Rα(sushi) fused to IL-15 by a variable length linker (termed "scIL-15/Rα") which is then fused to the N-terminus of a heterodimeric Fc-region, with a variable heavy chain (VH) fused to the other side of the heterodimeric Fc, while a corresponding light chain is transfected separately so as to form a Fab with the VH. Sequences for illustrative LAG-3-targeted IL-15/Rα-Fc fusion proteins of this format are depicted in Figure.

The "ncIL-15/Rα x Fab" format (FIG. 21E) comprises a VH fused to the N-terminus of a heterodimeric Fc-region, with IL-15Rα(sushi) fused to the other side of the heterodimeric Fc, while a corresponding light chain is transfected separately so as to form a Fab with the VH, and while IL-15 is transfected separately so that a non-covalent IL-15/Rα complex is formed.

The "dsIL-15/Rα x Fab" format (FIG. 21F) is the same as the "ncIL-15/Rα Fab" format, but wherein IL-15Rα(sushi) and IL-15 are covalently linked as a result of engineered cysteines.

The "mAb-scIL-15/Rα" format (FIG. 21G) comprises VH fused to the N-terminus of a first and a second heterodimeric Fc, with IL-15 is fused to IL-15Rα(sushi) which is then further fused to the C-terminus of one of the heterodimeric Fc-region, while corresponding light chains are transfected separately so as to form a Fabs with the VHs.

The "mAb-ncIL-15/Rα" format (FIG. 21H) comprises VH fused to the N-terminus of a first and a second heterodimeric Fc, with IL-15Rα(sushi) fused to the C-terminus of one of the heterodimeric Fc-region, while corresponding light chains are transfected separately so as to form a Fabs with the VHs, and while and while IL-15 is transfected separately so that a non-covalent IL-15/Rα complex is formed.

The "mAb-dsIL-15/Rα" format (FIG. 21I) is the same as the "mAb-ncIL-15/Rα" format, but wherein IL-15Rα(sushi) and IL-15 are covalently linked as a result of engineered cysteines.

The "central-IL-15/Rα" format (FIG. 21J) comprises a VH recombinantly fused to the N-terminus of IL-15 which is then further fused to one side of a heterodimeric Fc and a VH recombinantly fused to the N-terminus of IL-15Rα (sushi) which is then further fused to the other side of the heterodimeric Fc, while corresponding light chains are transfected separately so as to form a Fabs with the VHs.

The "central-scIL-15/Rα" format (FIG. 21K) comprises a VH fused to the N-terminus of IL-15Rα(sushi) which is fused to IL-15 which is then further fused to one side of a heterodimeric Fc and a VH fused to the other side of the heterodimeric Fc, while corresponding light chains are transfected separately so as to form a Fabs with the VHs.

2B: LAG-3-Targeted IL-15/Rα-Fc Fusions Enhance GVHD, and Combines Synergistically with Anti-PD-1 Antibody Illustrative LAG-3-targeted IL-15/Rα-Fc fusion proteins, XENP27972 and XENP27973 alone or in combination with (a bivalent anti-PD-1 mAb based on nivolumab with ablated effector function; sequences for which is depicted in FIG. 23), were evaluated in a Graft-versus-Host Disease (GVHD) model conducted in NSG (NOD-SCID-gamma) immunodeficient mice. When the NSG mice are injected with human PBMCs, the human PBMCs develop an autoimmune response against mouse cells. Dosing of NSG mice injected with human PBMCs followed with LAG-3-targeted IL-15/Rα-Fc fusion proteins proliferate the engrafted T cells and enhances engraftment.

10 million human PBMCs were engrafted into NSG mice via IV-OSP on Day −1 followed by dosing with the indicated test articles at the indicated concentrations on Days 0, 7, 14, and 21. Counts of various lymphocyte populations were performed on Days 6 and 10, data for which are depicted in Figures-. Body weights of mice were measured over time and depicted in Figure as percentage of initial body weight. The data show that dosing with either XENP27972 or XENP27973 following engraftment with human PBMCs enhanced GVHD as indicated by increased T cell (CD8+ and CD4+), NK cell, and CD45+ cell counts as well as decreased body weight in comparison to engraftment with PBMC alone. Notably, both XENP27972 and XENP27973 enhanced GVHD to a greater extent than dosing with XENP16432 alone. Additionally, the data show that XENP27972 and XENP27973 combine synergistically with XENP16432 in enhancing GVHD as indicated by the death of all mice by Day 19 following dosing with a combination of XENP27972 and XENP16432, and death of all but one mice by Day 19 following dosing with a combination of XENP27973 and XENP16432. This suggests that, in an immuno-oncology setting, treatment with LAG-3-targeted IL-15/Rα-Fc fusion proteins alone or in combination with checkpoint blockade antibodies will proliferate tumor-infiltrating lymphocytes and enhance anti-tumor activity.

2C: In Vitro Characterization of LAG-3-Targeted IL-15/Rα-Fc Fusions

The LAG-3-targeted IL-15/Rα-Fc fusions were further characterized in a cell proliferation assay. Human PBMCs were stimulated for 48 hours with 500 ng/ml plate-bound anti-CD3 (OKT3) and then labeled with CFSE and incubated with the following test articles for 4 days at 37° C.: XENP27972 (LAG-3-targeted IL-15/Rα-Fc fusion based on anti-LAG-3 clone 7G8); XENP27973 (LAG-3-targeted IL-15/Rα-Fc fusion based on anti-LAG-3 clone 2A11); XENP24306 (control untargeted IL-15(D30N/E64Q/N65D)/Rα-Fc fusion having D30N/E64Q/N65D IL-15 variant); and XENP26007 (control RSV-targeted IL-15/Rα-Fc fusion having N4D/N65D IL-15 variant). Cells were stained with the following antibodies: anti-CD8-PerCP-Cy5.5 (SK1), anti-CD3-PE-Cy7 (OKT3), anti-CD45RO-APC-Fire750 (UCHL1), anti-HLA-DR-Alexa700 (L243), anti-CD16-BV605 (3G6), anti-CD56-BV605 (HCD56), anti-CD25-BV711 (M-A251), anti-CD45RA-BV785 (HI100), anti-CD4-BUV395 (SK3), and Zombie Aqua-BV510 and analyzed by flow for various cell populations.

The proliferation of various T cell and NK cell populations based on CFSE dilution (Zombie Aqua to exclude dead cells) was investigated, data for which are depicted in FIGS. 30-35. The data show that the LAG-3-targeted IL-15/Rα-Fc fusions, in particular XENP27972, are more potent in inducing proliferation of both $CD8^+$ and $CD4^+$ T cells in comparison to untargeted IL-15(D30N/E64Q/N65D)/Rα-Fc fusion (as well as control RSV-targeted IL-15/Rα-Fc fusion), with a preference for $CD8^+$ T cells. Notably, the LAG-3-targeted IL-15/Rα-Fc fusions preferentially targets memory T cells, suggesting that in a clinical setting, the LAG-3-targeted IL-15/Rα-Fc fusions will be selective for activated tumor-infiltrating lymphocytes in the tumor environment.

The activation of various T cell populations based on expression of CD25 (a late stage T cell activation marker) and HLA-DR (another activation marker) were also investigated, data for which are depicted in FIGS. 36-38. The data show that LAG-3-targeted IL-15/Rα-Fc fusions generally appear more potent in inducing activation of CD8 memory T cell populations in comparison to untargeted IL-15(D30N/E64Q/N65D)/Rα-Fc fusion (as well as control RSV-targeted IL-15/Rα-Fc fusion).

C. Example 3: LAG-3-Targeted IL-15/Rα-Fc Fusions with Tuned IL-15 Potency 3A: IL-15(D30N/N65D) Variant In a study investigating the pharmacokinetics of IL-15-Fc potency variants with Xtend, cynomolgus monkeys were administered a first single intravenous (i.v.) dose of XENP22853 (WT IL-15/Rα-heteroFc with Xtend; sequences depicted in FIG. 39), XENP24306 (IL-15(D30N/E64Q/N65D)/Rα-heteroFc with Xtend; sequences depicted in FIG. 42), XENP24113 (IL-15(N4D/N65D)/Rα-heteroFc with Xtend; sequences depicted in FIG. 40), and XENP24294 (scIL-15(N4D/N65D)/Rα-Fc with Xtend; sequences depicted in FIG. 41) at varying concentrations.

FIG. 43 depicts the serum concentration of the test articles over time following the first dose. As expected, incorporating potency variants in addition to Xtend substitution (as in XENP24306 and XENP24113) greatly improves the pharmacokinetics of IL-15-Fc fusions (in comparison to XENP22583). Unexpectedly, however, IL-15/Rα-heteroFc fusion XENP24113 and scIL-15/Rα-Fc fusion XENP24294 (which have the same IL-15(N4D/N65D) potency variant) demonstrated reduced pharmacokinetics in comparison to XENP24306. This suggests that the reduced pharmacokinetics was due to the particular IL-15 potency variant rather than the format of the IL-15-Fc fusion. While a decrease in pharmacokinetics for XENP24113 and XENP24294 was expected on the basis of previous findings which demonstrated that the IL-15-Fc fusions having IL-15(N4D/N65D) variant had greater in vitro potency than IL-15-Fc fusions having the IL-15(D30N/E64Q/N65D) variant, the decrease in pharmacokinetics was unexpectedly disproportionate to the increase in potency. Accordingly, identification of alternative IL-15 potency variants for use in the LAG-3-targeted IL-15-Fc fusions of the invention was carried out.

It is noted that IL-15(N4D/N65D) has both its substitutions at the IL-15 interface responsible for binding to CD122, while IL-15(D30N/E64Q/N65D) has two substitutions (E64Q and N65D) at IL-15:CD122 interface; and one substitution (D30N) at the IL-15 interface responsible for binding to CD132. Accordingly, it is believed that the modification at the IL-15:CD132 interface may contribute to the superior pharmacokinetics observed for XENP24306. Notably, it was determined that scIL-15/Rα-Fc fusions comprising IL-15(N4D/N65D) variant and IL-15(D30N/N65D) variant demonstrated very similar potency in vitro, as depicted in FIG. 45. In view of the above, illustrative LAG-3-targeted IL-15-Fc fusion comprising the IL-15 (D30N/N65D) variants were conceived, sequences for which are depicted in FIG. 46. A control RSV-targeted IL-15/Rα-Fc fusion protein XENP29481 with IL-15(D30N/N65D) variant was also generated, sequences for which are depicted in FIG. 49.

3B: IL-15(D30N/E64Q/N65D) Variant

Although the LAG-3-targeted IL-15/Rα-Fc fusions were designed with the aim to be targeted to the tumor environment via the LAG-3-targeting arm, the cytokine moiety is still capable of signaling before reaching the tumor site and may contribute to systemic toxicity. Accordingly, LAG-3-targeted IL-15/Rα-Fc fusions with IL-15(D30N/E64Q/N65D) variant were constructed to further reduce the IL-15 potency, which as illustrated in Example 2C has drastically reduced activity and in FIG. 45. Sequences for illustrative LAG-3-targeted IL-15/Rα-Fc fusions comprising IL-15 (D30N/E64Q/N65D) variant are depicted in FIG. 47. Additionally, XENP30432, a RSV-targeted IL-15/Rα-Fc fusion comprising IL-15(D30N/E64Q/N65D) variant (sequences for which are depicted in FIG. 49) was constructed, to act as a surrogate for investigating the behavior of LAG-3-targeted IL-15/Rα-Fc fusions comprising IL-15(D30N/E64Q/N65D) variant outside of the tumor environment.

SEQUENCE LISTING

```
Sequence total quantity: 383
SEQ ID NO: 1          moltype = AA  length = 162
FEATURE               Location/Qualifiers
source                1..162
                      mol_type = protein
                      organism = Homo sapiens
SEQUENCE: 1
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                     162

SEQ ID NO: 2          moltype = AA  length = 114
FEATURE               Location/Qualifiers
source                1..114
                      mol_type = protein
                      organism = Homo sapiens
SEQUENCE: 2
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 3          moltype = AA  length = 267
FEATURE               Location/Qualifiers
source                1..267
                      mol_type = protein
                      organism = Homo sapiens
SEQUENCE: 3
MAPRRARGCR TLGLPALLLL LLLRPPATRG ITCPPPMSVE HADIWVKSYS LYSRERYICN  60
SGFKRKAGTS SLTECVLNKA TNVAHWTTPS LKCIRDPALV HQRPAPPSTV TTAGVTPQPE  120
SLSPSGKEPA ASSPSSNNTA ATTAAIVPGS QLMPSKSPST GTTEISSHES SHGTPSQTTA  180
KNWELTASAS HQPPGVYPQG HSDTTVAIST STVLLCGLSA VSLLACYLKS RQTPPLASVE  240
MEAMEALPVT WGTSSRDEDL ENCSHHL                                      267

SEQ ID NO: 4          moltype = AA  length = 65
FEATURE               Location/Qualifiers
source                1..65
                      mol_type = protein
                      organism = Homo sapiens
SEQUENCE: 4
ITCPPPMSVE HADIWVKSYS LYSRERYICN SGFKRKAGTS SLTECVLNKA TNVAHWTTPS  60
LKCIR                                                              65

SEQ ID NO: 5          moltype = AA  length = 175
FEATURE               Location/Qualifiers
source                1..175
                      mol_type = protein
                      organism = Homo sapiens
SEQUENCE: 5
```

```
ITCPPPMSVE HADIWVKSYS LYSRERYICN SGFKRKAGTS SLTECVLNKA TNVAHWTTPS  60
LKCIRDPALV HQRPAPPSTV TTAGVTPQPE SLSPSGKEPA ASSPSSNNTA ATTAAIVPGS  120
QLMPSKSPST GTTEISSHES SHGTPSQTTA KNWELTASAS HQPPGVYPQG HSDTT       175

SEQ ID NO: 6            moltype = AA  length = 551
FEATURE                 Location/Qualifiers
source                  1..551
                        mol_type = protein
                        organism = Homo sapiens
SEQUENCE: 6
MAAPALSWRL PLLILLLPLA TSWASAAVNG TSQFTCFYNS RANISCVWSQ DGALQDTSCQ  60
VHAWPDRRRW NQTCELLPVS QASWACNLIL GAPDSQKLTT VDIVTLRVLC REGVRWRVMA  120
IQDFKPFENL RLMAPISLQV VHVETHRCNI SWEISQASHY FERHLEFEAR TLSPGHTWEE  180
APLLTLKQKQ EWICLETLTP DTQYEFQVRV KPLQGEFTTW SPWSQPLAFR TKPAALGKDT  240
IPWLGHLLVG LSGAFGFIIL VYLLINCRNT GPWLKKVLKC NTPDPSKFFS QLSSEHGGDV  300
QKWLSSPFPS SSFSPGGLAP EISPLEVLER DKVTQLLLQQ DKVPEPASLS SNHSLTSCFT  360
NQGYFFFHLP DALEIEACQV YFTYDPYSEE DPDEGVAGAP TGSSPQPLQP LSGEDDAYCT  420
FPSRDDLLLF SPSLLGGPSP PSTAPGGSGA GEERMPPSLQ ERVPRDWDPQ PLGPPTPGVP  480
DLVDFQPPPE LVLREAGEEV PDAGPREGVS FPWSRPPGQG EFRALNARLP LNTDAYLSLQ  540
ELQGQDPTHL V                                                       551

SEQ ID NO: 7            moltype = AA  length = 214
FEATURE                 Location/Qualifiers
source                  1..214
                        mol_type = protein
                        organism = Homo sapiens
SEQUENCE: 7
AVNGTSQFTC FYNSRANISC VWSQDGALQD TSCQVHAWPD RRRWNQTCEL LPVSQASWAC  60
NLILGAPDSQ KLTTVDIVTL RVLCREGVRW RVMAIQDFKP FENLRLMAPI SLQVVHVETH  120
RCNISWEISQ ASHYFERHLE FEARTLSPGH TWEEAPLLTL KQKQEWICLE TLTPDTQYEF  180
QVRVKPLQGE FTTWSPWSQP LAFRTKPAAL GKDT                              214

SEQ ID NO: 8            moltype = AA  length = 369
FEATURE                 Location/Qualifiers
source                  1..369
                        mol_type = protein
                        organism = Homo sapiens
SEQUENCE: 8
MLKPSLPFTS LLFLQLPLLG VGLNTTILTP NGNEDTTADF FLTTMPTDSL SVSTLPLPEV  60
QCFVFNVEYM NCTWNSSSEP QPTNLTLHYW YKNSDNDKVQ KCSHYLFSEE ITSGCQLQKK  120
EIHLYQTFVV QLQDPREPRR QATQMLKLQN LVIPWAPENL TLHKLSESQL ELNWNNRFLN  180
HCLEHLVQYR TDWDHSWTEQ SVDYRHKFSL PSVDGQKRYT FRVRSRFNPL CGSAQHWSEW  240
SHPIHWGSNT SKENPFLFAL EAVVISVGSM GLIISLLCVY FWLERTMPRI PTLKNLEDLV  300
TEYHGNFSAW SGVSKGLAES LQPDYSERLC LVSEIPPKGG ALGEGPGASP CNQHSPYWAP  360
PCYTLKPET                                                          369

SEQ ID NO: 9            moltype = AA  length = 240
FEATURE                 Location/Qualifiers
source                  1..240
                        mol_type = protein
                        organism = Homo sapiens
SEQUENCE: 9
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240

SEQ ID NO: 10           moltype = AA  length = 525
FEATURE                 Location/Qualifiers
source                  1..525
                        mol_type = protein
                        organism = Homo sapiens
SEQUENCE: 10
MWEAQFLGLL FLQPLWVAPV KPLQPGAEVP VVWAQEGAPA QLPCSPTIPL QDLSLLRRAG  60
VTWQHQPDSG PPAAAPGHPL APGPHPAAPS SWGPRPRRYT VLSVGPGGLR SGRLPLQPRV  120
QLDERGRQRG DFSLWLRPAR RADAGEYRAA VHLRDRALSC RLRLRLGQAS MTASPPGSLR  180
ASDWVILNCS FSRPDRPASV HWFRNRGQGR VPVRESPHHH LAESFLFLPQ VSPMDSGPWG  240
CILTYRDGFN VSIMYNLTVL GLEPPTPLTV YAGAGSRVGL PCRLPAGVGT RSFLTAKWTP  300
PGGGPDLLVT GDNGDFTLRL EDVSQAQAGT YTCHIHLQEQ QLNATVTLAI ITVTPKSFGS  360
PGSLGKLLCE VTPVSGQERF VWSSLDTPSQ RSFSGPWLEA QEAQLLSQPW QCQLYQGERL  420
LGAAVYFTEL SSPGAQRSGR APGALPAGHL LLFLILGVLS LLLLVTGAFG FHLWRRQWRP  480
RRFSALEQGI HPPQAQSKIE ELEQEPEPEP EPEPEPEPEP EPEQL                  525

SEQ ID NO: 11           moltype = AA  length = 422
FEATURE                 Location/Qualifiers
source                  1..422
                        mol_type = protein
                        organism = Homo sapiens
SEQUENCE: 11
```

```
VPVVWAQEGA PAQLPCSPTI PLQDLSLLRR AGVTWQHQPD SGPPAAAPGH PLAPGPHPAA  60
PSSWGPRPRR YTVLSVGPGG LRSGRLPLQP RVQLDERGRQ RGDFSLWLRP ARRADAGEYR  120
AAVHLRDRAL SCRLRLRLGQ ASMTASPPGS LRASDWVILN CSFSRPDRPA SVHWFRNRGQ  180
GRVPVRESPH HHLAESFLFL PQVSPMDSGP WGCILTYRDG FNVSIMYNLT VLGLEPPTPL  240
TVYAGAGSRV GLPCRLPAGV GTRSFLTAKW TPPGGGPDLL VTGDNGDFTL RLEDVSQAQA  300
GTYTCHIHLQ EQQLNATVTL AIITVTPKSF GSPGSLGKLL CEVTPVSGQE RFVWSSLDTP  360
SQRSFSGPWL EAQEAQLLSQ PWQCQLYQGE RLLGAAVYFT ELSSPGAQRS GRAPGALPAG  420
HL                                                                422

SEQ ID NO: 12          moltype = AA  length = 533
FEATURE                Location/Qualifiers
VARIANT                74
                       note = Any amino acid
source                 1..533
                       mol_type = protein
                       organism = Macaca fascicularis
SEQUENCE: 12
MWEAQFLGLL FLQPLWVAPV KPPQPGAEIS VVWAQEGAPA QLPCSPTIPL QDLSLLRRAG  60
VTWQHQPDSG PPAXAPGHPP VPGHRPAAPY SWGPRPRRYT VLSVGPGGLR SGRLPLQPRV  120
QLDERGRQRG DFSLWLRPAR RADAGEYRAT VHLRDRALSC RLRLRVGQAS MTASPPGSLR  180
TSDWVILNCS FSRPDRPASV HWFRSRGQGR VPVQGSPHHH LAESFLFLPH VGPMDSGLWG  240
CILTYRDGFN VSIMYNLTVL GLEPATPLTV YAGAGSRVEL PCRLPPAVGT QSFLTAKWAP  300
PGGGPDLLVA GDNGDFTLRL EDVSQAQAGT YICHIRLQGQ QLNATVTLAI ITVTPKSFGS  360
PGSLGKLLCE VTPASGQEHF VWSPLNTPSQ RSFSGPWLEA QEAQLLSQPW QCQLHQGERL  420
LGAAVYFTEL SSPGAQRSGR APGALRAGHL PLFLILGVLF LLLLVTGAFG FHLWRRQWRP  480
RRFSALEQGI HPPQAQSKIE ELEQEPELEP EPELERELGP EPEPGPEPEP EQL         533

SEQ ID NO: 13          moltype = AA  length = 422
FEATURE                Location/Qualifiers
VARIANT                46
                       note = Any amino acid
source                 1..422
                       mol_type = protein
                       organism = Macaca fascicularis
SEQUENCE: 13
ISVVWAQEGA PAQLPCSPTI PLQDLSLLRR AGVTWQHQPD SGPPAXAPGH PPVPGHRPAA  60
PYSWGPRPRR YTVLSVGPGG LRSGRLPLQP RVQLDERGRQ RGDFSLWLRP ARRADAGEYR  120
ATVHLRDRAL SCRLRLRVGQ ASMTASPPGS LRTSDWVILN CSFSRPDRPA SVHWFRSRGQ  180
GRVPVQGSPH HHLAESFLFL PHVGPMDSGL WGCILTYRDG FNVSIMYNLT VLGLEPATPL  240
TVYAGAGSRV ELPCRLPPAV GTQSFLTAKW APPGGGPDLL VAGDNGDFTL RLEDVSQAQA  300
GTYICHIRLQ GQQLNATVTL AIITVTPKSF GSPGSLGKLL CEVTPASGQE HFVWSPLNTP  360
SQRSFSGPWL EAQEAQLLSQ PWQCQLHQGE RLLGAAVYFT ELSSPGAQRS GRAPGALRAG  420
HL                                                                422

SEQ ID NO: 14          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 14
GGGGS                                                             5

SEQ ID NO: 15          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 15
GGGGSGGGGS                                                        10

SEQ ID NO: 16          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 16
GGGGSGGGGS GGGGS                                                  15

SEQ ID NO: 17          moltype = AA  length = 20
FEATURE                Location/Qualifiers
REGION                 1..20
                       note = Description of Artificial Sequence: Synthetic peptide
source                 1..20
```

```
                        mol_type = protein
                        organism = synthetic construct
SEQUENCE: 17
GGGGSGGGGS GGGGSGGGGS                                            20

SEQ ID NO: 18           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 18
GGGGSGGGGS GGGGSGGGGS GGGGS                                      25

SEQ ID NO: 19           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 19
GGGGSGGGGS GGGGSGGGGS GGGGSGGGGS                                 30

SEQ ID NO: 20           moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 20
GGGGSGGGGS GGGGSGGGGS GGGGSGGGGS GGGGS                           35

SEQ ID NO: 21           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 21
DPALVHQRPA PPGGGGSGGG GSGGGGSGGG                                 30

SEQ ID NO: 22           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 22
GKPGS                                                            5

SEQ ID NO: 23           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 23
GKPGSGKPGS GKPGSGKPGS GKPGS                                      25

SEQ ID NO: 24           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 24
GKPGSGKPGS GKPGSGKPGS GKPGSGKPGS                                 30
```

```
SEQ ID NO: 25           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 25
GGGES                                                                   5

SEQ ID NO: 26           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 26
KTHTCPPCP                                                               9

SEQ ID NO: 27           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 27
EPKSSDKTHT CPPCP                                                        15

SEQ ID NO: 28           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 28
GGGGSGGGGS KTHTCPPCP                                                    19

SEQ ID NO: 29           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 29
GKPGSGKPGS KTHTCPPCP                                                    19

SEQ ID NO: 30           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 30
GKPGSKTHTC PPCP                                                         14

SEQ ID NO: 31           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 31
GGGGSGGGGS GGGGS                                                        15

SEQ ID NO: 32           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 32
GSTSGSGKPG SGEGSTKG                                                     18
```

```
SEQ ID NO: 33           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 33
IRPRAIGGSK PRVA                                                      14

SEQ ID NO: 34           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 34
GKGGSGKGGS GKGGS                                                     15

SEQ ID NO: 35           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 35
GGKGSGGKGS GGKGS                                                     15

SEQ ID NO: 36           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 36
GGGKSGGGKS GGGKS                                                     15

SEQ ID NO: 37           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 37
GKGKSGKGKS GKGKS                                                     15

SEQ ID NO: 38           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 38
GGGKSGGKGS GKGGS                                                     15

SEQ ID NO: 39           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 39
GKPGSGKPGS GKPGS                                                     15

SEQ ID NO: 40           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 40
```

```
GKPGSGKPGS GKPGSGKPGS                                              20

SEQ ID NO: 41          moltype = AA  length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 41
GKGKSGKGKS GKGKSGKGKS                                              20

SEQ ID NO: 42          moltype = AA  length = 20
FEATURE                Location/Qualifiers
REGION                 1..20
                       note = Description of Artificial Sequence: Synthetic peptide
source                 1..20
                       mol_type = protein
                       organism = synthetic construct
SEQUENCE: 42
GGGGSGGGGS GGGGSGGGGS                                              20

SEQ ID NO: 43          moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 43
STAGDTHLGG EDFD                                                    14

SEQ ID NO: 44          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 44
GEGGSGEGGS GEGGS                                                   15

SEQ ID NO: 45          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 45
GGEGSGGEGS GGEGS                                                   15

SEQ ID NO: 46          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 46
GGGESGGGES GGGES                                                   15

SEQ ID NO: 47          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 47
GEGESGEGES GEGES                                                   15

SEQ ID NO: 48          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
```

```
SEQUENCE: 48
GGGESGGEGS GEGGS                                                  15

SEQ ID NO: 49           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 49
GEGESGEGES GEGESGEGES                                             20

SEQ ID NO: 50           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 50
GGGGSGGGGS GGGGS                                                  15

SEQ ID NO: 51           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 51
GGGGSGGGGS GGGGSGGGGS                                             20

SEQ ID NO: 52           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 52
GSTSGSGKPG SGEGSTKG                                               18

SEQ ID NO: 53           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 53
PRGASKSGSA SQTGSAPGS                                              19

SEQ ID NO: 54           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 54
GTAAAGAGAA GGAAAGAAG                                              19

SEQ ID NO: 55           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 55
GTSGSSGSGS GGSGSGGGG                                              19

SEQ ID NO: 56           moltype = AA  length = 20
FEATURE                 Location/Qualifiers
REGION                  1..20
                        note = Description of Artificial Sequence: Synthetic peptide
source                  1..20
                        mol_type = protein
```

```
                        organism = synthetic construct
SEQUENCE: 56
GKPGSGKPGS GKPGSGKPGS                                          20

SEQ ID NO: 57           moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 57
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVKH EDPEVKFNWY VDGVEVHNAK TKPREEQYNS  180
TYRVVSVLTV LHQDWLNGKE YKCKVSNKAL PAPIEKTISK AKGQPREPQV YTLPPSREQM  240
TKNQVKLTCL VKGFYPSDIA VEWESNGQPE NNYKTTPPVL DSDGSFFLYS KLTVDKSRWQ  300
QGNVFSCSVM HEALHNHYTQ KSLSLSPGK                                329

SEQ ID NO: 58           moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 58
EPKSSDKTHT CPPCPAPPVA GPSVFLFPPK PKDTLMISRT PEVTCVVVDV KHEDPEVKFN  60
WYVDGVEVHN AKTKPREEEY NSTYRVVSVL TVLHQDWLNG KEYKCKVSNK ALPAPIEKTI  120
SKAKGQPREP QVYTLPPSRE EMTKNQVSLT CDVSGFYPSD IAVEWESDGQ PENNYKTTPP  180
VLDSDGSFFL YSKLTVDKSR WEQGDVFSCS VMHEALHNHY TQKSLSLSPG K           231

SEQ ID NO: 59           moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 59
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                329

SEQ ID NO: 60           moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 60
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 61           moltype = AA  length = 329
FEATURE                 Location/Qualifiers
REGION                  1..329
                        note = Description of Artificial Sequence: Synthetic
                         polypeptide
source                  1..329
                        mol_type = protein
                        organism = synthetic construct
SEQUENCE: 61
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                329
```

```
SEQ ID NO: 62          moltype = AA  length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 62
ASTKGPSVFP LAPSSKSTSG GTAALGCLVK DYFPEPVTVS WNSGALTSGV HTFPAVLQSS  60
GLYSLSSVVT VPSSSLGTKT YTCNVNHKPS NTKVDKKVER KSCDKTHTCP RCPAPPVAGP  120
SVFLFPPKPK DTLMISRTPE VTCVVVDVKH EDPEVKFKWY VDGVEVHNAK TKPREEQYNS  180
TYRVVSVLTV LHQDWLNGKE YKCKVSNKAL PAPIEKTISK AKGQPREPQV YTLPPSREQM  240
TKNQVKLTCL VKGFYPSDIA VEWESNGQPE NNYKTTPPVL DSDGSFFLYS KLTVDKSRWQ  300
QGNVFSCSVM HEALHNHYTQ KSLSLSPGK                                   329

SEQ ID NO: 63          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 63
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 64          moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 64
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                106

SEQ ID NO: 65          moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 65
EVKLEESGGG LVQPGGSMKL SCAASGFTFS DAWMDWVRQS PEKGLEWVAE IRTKANNHAT  60
YYAESVKGRF TISRDDSKSS VYLQMNSLRA EDTGIYYCTR LANWDWYFDV WGAGTTVTVS  120
S                                                                 121

SEQ ID NO: 66          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 66
DAWMD                                                             5

SEQ ID NO: 67          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 67
EIRTKANNHA TYYAESVKG                                              19

SEQ ID NO: 68          moltype = AA  length = 10
FEATURE                Location/Qualifiers
REGION                 1..10
                       note = Description of Artificial Sequence: Synthetic peptide
source                 1..10
```

```
                        mol_type = protein
                        organism = synthetic construct
SEQUENCE: 68
LANWDWYFDV                                                      10

SEQ ID NO: 69           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 69
DTVLTQSPAS LAVSLGQRAT ISCKASQSVD YDGDSYMNWY QQKPGQPPKL LIYAASNLES  60
GIPARLSGSG SGTDFTLNIH PVEEEDAATY YCQQSNEDPF TFGSGTKLEV K           111

SEQ ID NO: 70           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 70
KASQSVDYDG DSYMN                                                15

SEQ ID NO: 71           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 71
AASNLES                                                         7

SEQ ID NO: 72           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 72
QQSNEDPFT                                                       9

SEQ ID NO: 73           moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 73
EVQLVESGGG LVQPGGSLRL SCAASGFTFS DAWMDWVRQA PGKGLEWVAE IRTKANNHAT  60
YYAESVKGRF TISRDDSKSS VYLQMNSLRA EDTAVYYCTR LANWDWYFDV WGQGTTVTVS  120
S                                                               121

SEQ ID NO: 74           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 74
DAWMD                                                           5

SEQ ID NO: 75           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 75
EIRTKANNHA TYYAESVKG                                            19
```

```
SEQ ID NO: 76           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 76
LANWDWYFDV                                                            10

SEQ ID NO: 77           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 77
DTVLTQSPSS LSASVGDRVT ITCRASQSVD YDGDSYMNWY QQKPGKPPKL LIYAASNLES  60
GIPARLSGSG SGTDFTLTIS SLQPEDFATY YCQQSNEDPF TFGSGTKLEI K           111

SEQ ID NO: 78           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 78
RASQSVDYDG DSYMN                                                      15

SEQ ID NO: 79           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 79
AASNLES                                                               7

SEQ ID NO: 80           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 80
QQSNEDPFT                                                             9

SEQ ID NO: 81           moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 81
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
S                                                                     121

SEQ ID NO: 82           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 82
DAWMS                                                                 5

SEQ ID NO: 83           moltype = AA  length = 19
FEATURE                 Location/Qualifiers
REGION                  1..19
```

```
                        note = Description of Artificial Sequence: Synthetic peptide
source                  1..19
                        mol_type = protein
                        organism = synthetic construct
SEQUENCE: 83
EISTKANNHA TYYAESVKG                                               19

SEQ ID NO: 84           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 84
LATWDWYFDV                                                         10

SEQ ID NO: 85           moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 85
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI K           111

SEQ ID NO: 86           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 86
RASQSVDYDG DSYMN                                                   15

SEQ ID NO: 87           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 87
AASELES                                                            7

SEQ ID NO: 88           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 88
QQSNEDPFT                                                          9

SEQ ID NO: 89           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 89
EVQLQQSGAE LVRSGASVKL SCTASGFNIK DYYMHWVKQR PEQGLEWIGW IDPENGDTEY  60
APKFQGKATM TADTSSNTAY LQLSSLTSED TAVYYCYARG VRQALDYWGQ GTSVTVSS    118

SEQ ID NO: 90           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 90
```

```
DYYMH                                                             5

SEQ ID NO: 91          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 91
WIDPENGDTE YAPKFQG                                                17

SEQ ID NO: 92          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 92
RGVRQALDY                                                         9

SEQ ID NO: 93          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 93
DIQMTQTTSS LSASLGDRVT ISCRASQDIG NYLNWFQQKP DGTVKLLIYY TSRLHSGVPS  60
RFSGSGSGTD YSLTISNLEQ EDIATYFCQQ GNTLPYTFGG GTKLEIK                107

SEQ ID NO: 94          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 94
RASQDIGNYL N                                                      11

SEQ ID NO: 95          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 95
YTSRLHS                                                           7

SEQ ID NO: 96          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 96
QQGNTLPYT                                                         9

SEQ ID NO: 97          moltype = AA  length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 97
EVQLVQSGAE VKKPGATVKI SCKASGFNIK DYYMHWVQQA PGKGLEWMGW IDPENGDTEY  60
APKFQGRVTI TADTSTNTAY MELSSLRSED TAVYYCYARG VRQALDYWGQ GTLVTVSS    118

SEQ ID NO: 98          moltype = AA  length = 5
FEATURE                Location/Qualifiers
REGION                 1..5
```

```
                        note = Description of Artificial Sequence: Synthetic peptide
source                  1..5
                        mol_type = protein
                        organism = synthetic construct
SEQUENCE: 98
DYYMH                                                                   5

SEQ ID NO: 99           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 99
WIDPENGDTE YAPKFQG                                                      17

SEQ ID NO: 100          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 100
RGVRQALDY                                                               9

SEQ ID NO: 101          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 101
DIQMTQSPAF LSVTPGEKVT ITCQASQDIG NYLNWFQQKP DQTVKLLIYY TSRLHSGVPS  60
RFSGSGSGTD YTFTISSLEA EDAATYFCQQ GNTLPYTFGG GTKVEIK                107

SEQ ID NO: 102          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 102
QASQDIGNYL N                                                            11

SEQ ID NO: 103          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 103
YTSRLHS                                                                 7

SEQ ID NO: 104          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 104
QQGNTLPYT                                                               9

SEQ ID NO: 105          moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 105
EVQLVQSGAE VKKPGATVKI SCKASGFNIK DYFMHWVQQA PGKGLEWMGW IDPELGDTEY  60
```

```
APKFQGRVTI TADTSTNTAY MELSSLRSED TAVYYCYARG VYQALDYWGQ GTLVTVSS    118

SEQ ID NO: 106         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 106
DYFMH                                                               5

SEQ ID NO: 107         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 107
WIDPELGDTE YAPKFQG                                                  17

SEQ ID NO: 108         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 108
RGVYQALDY                                                           9

SEQ ID NO: 109         moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 109
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIK                107

SEQ ID NO: 110         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 110
QASQDIGNYL N                                                        11

SEQ ID NO: 111         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 111
FTSYLHS                                                             7

SEQ ID NO: 112         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 112
QQGNTLPYT                                                           9

SEQ ID NO: 113         moltype = AA  length = 120
FEATURE                Location/Qualifiers
REGION                 1..120
                       note = Description of Artificial Sequence: Synthetic
                        polypeptide
```

```
source                1..120
                      mol_type = protein
                      organism = synthetic construct
SEQUENCE: 113
QVQLQQWGAG LLKPSETLSL TCAVYGGSFS DYYWNWIRQP PGKGLEWIGE INHRGSTNSN  60
PSLKSRVTLS LDTSKNQFSL KLRSVTAADT AVYYCAFGYS DYEYNWFDPW GQGTLVTVSS  120

SEQ ID NO: 114        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 114
DYYWN                                                              5

SEQ ID NO: 115        moltype = AA  length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 115
EINHRGSTNS NPSLKS                                                  16

SEQ ID NO: 116        moltype = AA  length = 12
FEATURE               Location/Qualifiers
REGION                1..12
                      note = Description of Artificial Sequence: Synthetic peptide
source                1..12
                      mol_type = protein
                      organism = synthetic construct
SEQUENCE: 116
GYSDYEYNWF DP                                                      12

SEQ ID NO: 117        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 117
EIVLTQSPAT LSLSPGERAT LSCRASQSIS SYLAWYQQKP GQAPRLLIYD ASNRATGIPA  60
RFSGSGSGTD FTLTISSLEP EDFAVYYCQQ RSNWPLTFGQ GTNLEIK                107

SEQ ID NO: 118        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 118
RASQSISSYL A                                                       11

SEQ ID NO: 119        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 119
DASNRAT                                                            7

SEQ ID NO: 120        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 120
QQRSNWPLT                                                          9
```

```
SEQ ID NO: 121         moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 121
QVQLKESGPG LVAPSQSLSI TCTVSGFSLT AYGVNWVRQP PGKGLEWLGM IWDDGSTDYN  60
SALKSRLSIS KDNSKSQVFL KMNSLQTDDT ARYYCAREGD VAFDYWGQGT TLTVSS      116

SEQ ID NO: 122         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 122
AYGVN                                                              5

SEQ ID NO: 123         moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 123
MIWDDGSTDY NSALKS                                                  16

SEQ ID NO: 124         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 124
EGDVAFDY                                                           8

SEQ ID NO: 125         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 125
DIVMTQSPSS LAVSVGQKVT MSCKSSQSLL NGSNQKNYLA WYQQKPGQSP KLLVYFASTR  60
DSGVPDRFIG SGSGTDFTLT ISSVQAEDLA DYFCLQHFGT PPTFGGGTKL EIKR        114

SEQ ID NO: 126         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 126
KSSQSLLNGS NQKNYLA                                                 17

SEQ ID NO: 127         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 127
FASTRDS                                                            7

SEQ ID NO: 128         moltype = AA  length = 9
FEATURE                Location/Qualifiers
REGION                 1..9
                       note = Description of Artificial Sequence: Synthetic peptide
source                 1..9
```

```
                        mol_type = protein
                        organism = synthetic construct
SEQUENCE: 128
LQHFGTPPT                                                              9

SEQ ID NO: 129          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 129
QVTLKESGPG ILQPSQTLSL TCSFSGFSLS TSGMGLGWIR QPSGKGLEWL THIWWDDIKR  60
YNPDLRSRLT ISKDTSSSQI FLKIASVDTA DTATYYCARI VEGSYSSSYF DVWGAGTTVT  120
VSS                                                                123

SEQ ID NO: 130          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 130
TSGMGLG                                                                7

SEQ ID NO: 131          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 131
HIWWDDIKRY NPDLRS                                                      16

SEQ ID NO: 132          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 132
IVEGSYSSSY FDV                                                         13

SEQ ID NO: 133          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 133
DIVMTQPHKF MSTSVEDRVT ITCKASQDVI FDVAWYQQKP GQSPKLLIYS ASSRVSGVPD  60
RFTGSGSGTD FTFTISSVQA EDLAVYYCQQ HYSTPYTFGG GTTLEIK                107

SEQ ID NO: 134          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 134
KASQDVIFDV A                                                           11

SEQ ID NO: 135          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 135
SASSRVS                                                                7
```

```
SEQ ID NO: 136          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 136
QQHYSTPYT                                                      9

SEQ ID NO: 137          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 137
QVTLKESGPG ILQPSQTLSL TCSFSGFSLN TSGMGVGWIR QPSGKGLEWL THIWWDDVKR  60
YNPALKSRLT ISKDTSSSQV FLKIASVDTA DTATYYCARI EGDTYYDYYF DYWGQGVTLT  120
VSS                                                            123

SEQ ID NO: 138          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 138
TSGMGVG                                                        7

SEQ ID NO: 139          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 139
HIWWDDVKRY NPALKS                                              16

SEQ ID NO: 140          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 140
IEGDTYYDYY FDY                                                 13

SEQ ID NO: 141          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 141
DIVMTQSHKL MSTSVGDGLS ITCKASQDVS IAVVWYQQKP GQSPKLLIYS ASFRYTGVPD  60
RFTGSGSGTD FTFTISSVQA EDLAVYYCQQ HYSIPWTFGG GTKLEIK            107

SEQ ID NO: 142          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 142
KASQDVSIAV V                                                   11

SEQ ID NO: 143          moltype = AA  length = 7
FEATURE                 Location/Qualifiers
REGION                  1..7
```

```
                        note = Description of Artificial Sequence: Synthetic peptide
source                  1..7
                        mol_type = protein
                        organism = synthetic construct
SEQUENCE: 143
SASFRYT                                                         7

SEQ ID NO: 144          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 144
QQHYSIPWT                                                       9

SEQ ID NO: 145          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 145
QITLKESGPT LVKPTQTLTL TCTFSGFSLS TSGMGLGWIR QPPGKTLEWL THIWWDDIKR  60
YNPDLRSRLS ITKDTSKNQV VLTMTNMDPL DTGTYYCARI VEGSYSSSYF DVWGQGTLVT  120
VSS                                                             123

SEQ ID NO: 146          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 146
TSGMGLG                                                         7

SEQ ID NO: 147          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 147
HIWWDDIKRY NPDLRS                                               16

SEQ ID NO: 148          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 148
IVEGSYSSSY FDV                                                  13

SEQ ID NO: 149          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 149
DIVMTQTPSS LSASVGDRVT ITCKASQDVI FDVAWYQQRP GQAPKLLIYS ASSRVSGVPS  60
RFSGSGSGTD FTLTISSLQP EDFATYYCQQ HYSTPYTFGQ GTRLDIK             107

SEQ ID NO: 150          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
```

```
SEQUENCE: 150
KASQDVIFDV A                                                       11

SEQ ID NO: 151          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 151
SASSRVS                                                            7

SEQ ID NO: 152          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 152
QQHYSTPYT                                                          9

SEQ ID NO: 153          moltype = AA  length = 116
FEATURE                 Location/Qualifiers
REGION                  1..116
                        note = Description of Artificial Sequence: Synthetic
                         polypeptide
source                  1..116
                        mol_type = protein
                        organism = synthetic construct
SEQUENCE: 153
QVQLQESGPG LVKPSETLSL TCTVSGFSLT AYGVNWIRQP PGKGLEWIGM IWDDGSTDYD  60
SALKSRVTIS VDTSKNQFSL KLSSVTAADT AVYYCAREGD VAFDYWGQGT LVTVSS      116

SEQ ID NO: 154          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 154
AYGVN                                                              5

SEQ ID NO: 155          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 155
MIWDDGSTDY DSALKS                                                  16

SEQ ID NO: 156          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 156
EGDVAFDY                                                           8

SEQ ID NO: 157          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 157
DIQMTQSPSS LSASVGDRVT ITCKSSQSLL NPSNQKNYLA WYQQKPGKAP KLLVYFASTR  60
DSGVPSRFSG SGSGTDFTLT ISSLQPEDFA TYYCLQHFGT PPTFGQGTKL EIKR        114

SEQ ID NO: 158          moltype = AA  length = 17
FEATURE                 Location/Qualifiers
```

```
REGION                1..17
                      note = Description of Artificial Sequence: Synthetic peptide
source                1..17
                      mol_type = protein
                      organism = synthetic construct
SEQUENCE: 158
KSSQSLLNPS NQKNYLA                                            17

SEQ ID NO: 159        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 159
FASTRDS                                                       7

SEQ ID NO: 160        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 160
LQHFGTPPT                                                     9

SEQ ID NO: 161        moltype = AA  length = 119
FEATURE               Location/Qualifiers
REGION                1..119
                      note = Description of Artificial Sequence: Synthetic
                       polypeptide
source                1..119
                      mol_type = protein
                      organism = synthetic construct
SEQUENCE: 161
QMQLVQSGPE VKKPGTSVKV SCKASGYTFT DYNVDWVRQA RGQRLEWIGD INPNNGGTIY  60
AQKFQERVTI TVDKSTSTAY MELSSLRSED TAVYYCARNY RWFGAMDHWG QGTTVTVSS   119

SEQ ID NO: 162        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 162
DYNVD                                                         5

SEQ ID NO: 163        moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 163
DINPNNGGTI YAQKFQE                                            17

SEQ ID NO: 164        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 164
NYRWFGAMDH                                                    10

SEQ ID NO: 165        moltype = AA  length = 111
FEATURE               Location/Qualifiers
REGION                1..111
                      note = Description of Artificial Sequence: Synthetic
                       polypeptide
source                1..111
                      mol_type = protein
                      organism = synthetic construct
SEQUENCE: 165
```

```
DIVMTQTPLS LSVTPGQPAS ISCKASQSLD YEGDSDMNWY LQKPGQPPQL LIYGASNLES  60
GVPDRFSGSG SGTDFTLKIS RVEAEDVGVY YCQQSTEDPR TFGGGTKVEI K           111

SEQ ID NO: 166          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 166
KASQSLDYEG DSDMN                                                   15

SEQ ID NO: 167          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 167
GASNLES                                                            7

SEQ ID NO: 168          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 168
QQSTEDPRT                                                          9

SEQ ID NO: 169          moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 169
QVQLVESGGG VVQPGRSLRL SCVASGFTFS SYGMHWVRQA PGKGLEWVAI IWYDGSNKYY  60
ADSVKGRFTI SRDNSKNTQY LQMNSLRAED TAVYYCASVA TSGDFDYYGM DVWGQGTTVT  120
VSS                                                                123

SEQ ID NO: 170          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 170
SYGMH                                                              5

SEQ ID NO: 171          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 171
IIWYDGSNKY YADSVKG                                                 17

SEQ ID NO: 172          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 172
VATSGDFDYY GMDV                                                    14

SEQ ID NO: 173          moltype = AA  length = 107
FEATURE                 Location/Qualifiers
REGION                  1..107
```

```
                         note = Description of Artificial Sequence: Synthetic
                          polypeptide
source                   1..107
                         mol_type = protein
                         organism = synthetic construct
SEQUENCE: 173
EIVLTQSPAT LSLSPGERTT LSCRASQRIS TYLAWYQQKP GQAPRLLIYD ASKRATGIPA  60
RFSGSGSGTG FTLTISSLEP EDFAVYYCQQ RSNWPLTFGG GTKVEIK                107

SEQ ID NO: 174           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 174
RASQRISTYL A                                                       11

SEQ ID NO: 175           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 175
DASKRAT                                                            7

SEQ ID NO: 176           moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 176
QQRSNWPLT                                                          9

SEQ ID NO: 177           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 177
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 178           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 178
SYYMH                                                              5

SEQ ID NO: 179           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 179
IINPSAGSTS YAQKFQG                                                 17

SEQ ID NO: 180           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 180
```

```
ELMATGGFDY                                                       10

SEQ ID NO: 181          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 181
QSVLTQPPSA SGSPGQSVTI SCTGTSSDVG GYNYVSWYQQ YPGKAPRLMI FEVTERASGV  60
PDRFSGSKSG NTASLTVSGL QTEDEAVYFC SSYSGSNNPG AMFGGGTKLT VL          112

SEQ ID NO: 182          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 182
TGTSSDVGGY NYVS                                                  14

SEQ ID NO: 183          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 183
EVTERAS                                                          7

SEQ ID NO: 184          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 184
SSYSGSNNPG AM                                                    12

SEQ ID NO: 185          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 185
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 186          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 186
SYYMH                                                            5

SEQ ID NO: 187          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 187
IINPSAGSTS YAQKFQG                                               17

SEQ ID NO: 188          moltype = AA  length = 10
FEATURE                 Location/Qualifiers
REGION                  1..10
```

```
                        note = Description of Artificial Sequence: Synthetic peptide
source                  1..10
                        mol_type = protein
                        organism = synthetic construct
SEQUENCE: 188
ELMATGGFDY                                                          10

SEQ ID NO: 189          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 189
QAGLTQPASV SGSPGQSITI SCTGSSSDVG GYSYVSWYQK HPGKAPKLMI YDVTNRPSGV  60
SNRFSGSKSG NTASLTISGL QAEDEADYYC STYTRSNTLV FGPGTKVTVL             110

SEQ ID NO: 190          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 190
TGSSSDVGGY SYVS                                                     14

SEQ ID NO: 191          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 191
DVTNRPS                                                             7

SEQ ID NO: 192          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 192
STYTRSNTLV                                                          10

SEQ ID NO: 193          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 193
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 194          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 194
SYYMH                                                               5

SEQ ID NO: 195          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 195
```

```
IIINPSAGSTS YAQKFQG                                                   17

SEQ ID NO: 196          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 196
ELMATGGFDY                                                            10

SEQ ID NO: 197          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 197
LPVLTQPASV SGSPGQSITI SCTGTSSDVG GYNYVSWYQQ HPGKAPKLMI YDVTNRPSGV  60
SNRFSGSKSG NTASLTISGL QAEDEADYYC SSYTSSNTLL FGGGTQLTVL             110

SEQ ID NO: 198          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 198
TGTSSDVGGY NYVS                                                       14

SEQ ID NO: 199          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 199
DVTNRPS                                                               7

SEQ ID NO: 200          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 200
SSYTSSNTLL                                                            10

SEQ ID NO: 201          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 201
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 202          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 202
SYYMH                                                                 5

SEQ ID NO: 203          moltype = AA  length = 17
FEATURE                 Location/Qualifiers
REGION                  1..17
```

```
                         note = Description of Artificial Sequence: Synthetic peptide
source                   1..17
                         mol_type = protein
                         organism = synthetic construct
SEQUENCE: 203
IINPSAGSTS YAQKFQG                                                   17

SEQ ID NO: 204           moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 204
ELMATGGFDY                                                           10

SEQ ID NO: 205           moltype = AA  length = 110
FEATURE                  Location/Qualifiers
REGION                   1..110
                         note = Description of Artificial Sequence: Synthetic
                          polypeptide
source                   1..110
                         mol_type = protein
                         organism = synthetic construct
SEQUENCE: 205
QSVVTQPPSV SAAPGQKVTI SCSGSSSNIG NNYVSWYQQL PGTAPKLLIY DNNKRHSGIP  60
DRFSGSTSDT SATLGITRLQ TGDEADYYCG TWDSSLSAYV FGTGTKVTVL             110

SEQ ID NO: 206           moltype = AA  length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 206
SGSSSNIGNN YVS                                                       13

SEQ ID NO: 207           moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 207
DNNKRHS                                                              7

SEQ ID NO: 208           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 208
GTWDSSLSAY V                                                         11

SEQ ID NO: 209           moltype = AA  length = 119
FEATURE                  Location/Qualifiers
REGION                   1..119
                         note = Description of Artificial Sequence: Synthetic
                          polypeptide
source                   1..119
                         mol_type = protein
                         organism = synthetic construct
SEQUENCE: 209
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 210           moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 210
```

```
SYYMH                                                                 5

SEQ ID NO: 211          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 211
IINPSAGSTS YAQKFQG                                                    17

SEQ ID NO: 212          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 212
ELMATGGFDY                                                            10

SEQ ID NO: 213          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 213
QSVLTQPPSA SGSPGQSVTI SCTGTSSDVG GYDYVSWYQQ HQGKAPKLMI YDVSNRPSGV  60
SNRFSGSKSG NTASLTISGL QAEDEADYYC SSYTSSTTLV FGGGTKLTVL             110

SEQ ID NO: 214          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 214
TGTSSDVGGY DYVS                                                       14

SEQ ID NO: 215          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 215
DVSNRPS                                                               7

SEQ ID NO: 216          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 216
SSYTSSTTLV                                                            10

SEQ ID NO: 217          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 217
QVQLVQSGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 218          moltype = AA  length = 5
FEATURE                 Location/Qualifiers
REGION                  1..5
```

```
                        note = Description of Artificial Sequence: Synthetic peptide
source                  1..5
                        mol_type = protein
                        organism = synthetic construct
SEQUENCE: 218
SYYMH                                                                    5

SEQ ID NO: 219          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 219
IINPSAGSTS YAQKFQG                                                       17

SEQ ID NO: 220          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 220
ELMATGGFDY                                                               10

SEQ ID NO: 221          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 221
QSVLTQPASV SGSPGQSITI SCTGTSSDIG AYNFVSWYQQ HPGKAPKLMI YGVSNRPSGV  60
SSRFSGSKSG STASLTISGL QAEDEADYYC SSYTTSGSAV FGTGTKLTVL             110

SEQ ID NO: 222          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 222
TGTSSDIGAY NFVS                                                          14

SEQ ID NO: 223          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 223
GVSNRPS                                                                  7

SEQ ID NO: 224          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 224
SSYTTSGSAV                                                               10

SEQ ID NO: 225          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 225
EVQLLESGAE VKKPGASVKV SCKASGYTFT SYYMHWVRQA PGQGLEWMGI INPSAGSTSY  60
```

```
AQKFQGRVTM TRDTSTSTVY MELSSLRSED TAVYYCAREL MATGGFDYWG QGTLVTVSS   119

SEQ ID NO: 226         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 226
SYYMH                                                             5

SEQ ID NO: 227         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 227
IINPSAGSTS YAQKFQG                                                17

SEQ ID NO: 228         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 228
ELMATGGFDY                                                        10

SEQ ID NO: 229         moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 229
QSVLTQPASV SGSPGQSITI SCTGTSSDIG AYNFVSWYQQ HPGKAPKLMI YGVSNRPSGV  60
SSRFSGSKSG STASLTITGL QAEDEADYYC SSYTTSGSAV FGTGTKLTVL             110

SEQ ID NO: 230         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 230
TGTSSDIGAY NFVS                                                   14

SEQ ID NO: 231         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 231
GVSNRPS                                                           7

SEQ ID NO: 232         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 232
SSYTTSGSAV                                                        10

SEQ ID NO: 233         moltype = AA  length = 121
FEATURE                Location/Qualifiers
REGION                 1..121
                       note = Description of Artificial Sequence: Synthetic
                        polypeptide
```

```
source                  1..121
                        mol_type = protein
                        organism = synthetic construct
SEQUENCE: 233
EVQLLESGGG VVQPGRSLRV SCAASGFTFS NHAMHWVRQA PGKGLEWVAV ISYDGSKKFY  60
SDSVRGRFTI SRDNSKNTLY LQMNSLRPED TAVYYCAKGA HGYTSGWHDY WGQGTLVTVS  120
S                                                                  121

SEQ ID NO: 234          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 234
NHAMH                                                              5

SEQ ID NO: 235          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 235
VISYDGSKKF YSDSVRG                                                 17

SEQ ID NO: 236          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 236
GAHGYTSGWH DY                                                      12

SEQ ID NO: 237          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 237
DVVMTQSPSS LSASVGDRVS ITCRASQNIG RYLNWYQQKP GKAPKLLVSA ASSLQGGVPS  60
RFSGSGSGTD FTLTISRLQP EDFATYFCQQ TYSSPQCTFG QGTKVDIK               108

SEQ ID NO: 238          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 238
RASQNIGRYL N                                                       11

SEQ ID NO: 239          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 239
AASSLQG                                                            7

SEQ ID NO: 240          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 240
QQTYSSPQCT                                                         10
```

```
SEQ ID NO: 241          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 241
QVQLVQSGSE LKKPGASVKV SCKASGYTFT NYYMHWVRQA PGQGLEWMGI INPSGGATNY  60
AQKFQGRVTM TRDTSTSTVY MELSSLRSED TAVYYCARDS GYDLGYGMDV WGQGTLVTVS  120
S                                                                 121

SEQ ID NO: 242          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 242
NYYMH                                                             5

SEQ ID NO: 243          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 243
IINPSGGATN YAQKFQG                                                17

SEQ ID NO: 244          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 244
DSGYDLGYGM DV                                                     12

SEQ ID NO: 245          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 245
QSVLTQPASV SGSPGQSITI SCTGTSSDVG GYNYVSWYQQ HPGKAPKLMI YDVSNRPSGA  60
SNRFSGSKSG NTASLTISGL QAEDEADYYC SSYTNRNTLL FGGGTKLTVL            110

SEQ ID NO: 246          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 246
TGTSSDVGGY NYVS                                                   14

SEQ ID NO: 247          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 247
DVSNRPS                                                           7

SEQ ID NO: 248          moltype = AA  length = 10
FEATURE                 Location/Qualifiers
REGION                  1..10
```

```
                        note = Description of Artificial Sequence: Synthetic peptide
source                  1..10
                        mol_type = protein
                        organism = synthetic construct
SEQUENCE: 248
SSYTNRNTLL                                                          10

SEQ ID NO: 249          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 249
EVQLLESGAE VKKPGASVKV SCKASGYTFT SYYMHWVRQA PGQGLEWMGI INPSAGSTSY  60
AQKFQGRVTM TRDTSTSTVY MELSSLRSED TAVYYCAREL MATGGFDYWG QGTLVTVSS   119

SEQ ID NO: 250          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 250
SYYMH                                                               5

SEQ ID NO: 251          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 251
IINPSAGSTS YAQKFQG                                                  17

SEQ ID NO: 252          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 252
ELMATGGFDY                                                          10

SEQ ID NO: 253          moltype = AA  length = 110
FEATURE                 Location/Qualifiers
REGION                  1..110
                        note = Description of Artificial Sequence: Synthetic
                         polypeptide
source                  1..110
                        mol_type = protein
                        organism = synthetic construct
SEQUENCE: 253
QSVLTQPASA SGSPGQSITI SCTGTSSDVG GYNYVSWYQQ HPGKAPKLMI YDVSNRPSGV  60
SNRFSGSKSG NTASLTISGL QAEDEANYYC SSYTSSSTNV FGTGTKVTVL              110

SEQ ID NO: 254          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 254
TGTSSDVGGY NYVS                                                     14

SEQ ID NO: 255          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 255
```

```
DVSNRPS                                                          7

SEQ ID NO: 256          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 256
SSYTSSSTNV                                                       10

SEQ ID NO: 257          moltype = AA  length = 66
FEATURE                 Location/Qualifiers
REGION                  1..66
                        note = Description of Artificial Sequence: Synthetic
                         polypeptide
source                  1..66
                        mol_type = protein
                        organism = synthetic construct
SEQUENCE: 257
ITCPPPMSVE HADIWVKSYS LYSRERYICN SGFKRKAGTS SLTECVLNKA TNVAHWTTPS  60
LKCIRD                                                           66

SEQ ID NO: 258          moltype = AA  length = 67
FEATURE                 Location/Qualifiers
REGION                  1..67
                        note = Description of Artificial Sequence: Synthetic
                         polypeptide
source                  1..67
                        mol_type = protein
                        organism = synthetic construct
SEQUENCE: 258
ITCPPPMSVE HADIWVKSYS LYSRERYICN SGFKRKAGTS SLTECVLNKA TNVAHWTTPS  60
LKCIRDP                                                          67

SEQ ID NO: 259          moltype = AA  length = 68
FEATURE                 Location/Qualifiers
REGION                  1..68
                        note = Description of Artificial Sequence: Synthetic
                         polypeptide
source                  1..68
                        mol_type = protein
                        organism = synthetic construct
SEQUENCE: 259
ITCPPPMSVE HADIWVKSYS LYSRERYICN SGFKRKAGTS SLTECVLNKA TNVAHWTTPS  60
LKCIRDPA                                                         68

SEQ ID NO: 260          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 260
NWVNVISDLK KIEDLIQSMH IDATLYTESD VHPSCKVTAM KCFLLELQVI SLESGDASIH  60
DTVENLIILA NNSLSSNGNV TESGCKCCEE LEEKNIKEFL QSFVHIVQMF INTS        114

SEQ ID NO: 261          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 261
NWVNVISDLK KIEDLIQSMH IDATLYTESD VHPSCKVTAM KCFLLELQCI SLESGDASIH  60
DTVENLIILA NNSLSSNGNV TESGCKECEE LEEKNIKEFL QSFVHIVQMF INTS        114

SEQ ID NO: 262          moltype = AA  length = 114
FEATURE                 Location/Qualifiers
REGION                  1..114
                        note = Description of Artificial Sequence: Synthetic
                         polypeptide
source                  1..114
                        mol_type = protein
```

```
                         organism = synthetic construct
SEQUENCE: 262
NWVNVISDLK KIEDLIQSMH IDATLYTESD VHPSCKVTAM KCFLLELQVI SCESGDASIH  60
DTVENLIILA NNSLSSNGNV TESGCKECEE LEEKNIKEFL QSFVHIVQMF INTS        114

SEQ ID NO: 263           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 263
NWVNVISDLK KIEDLIQSMH IDATLYTESD VHPSCKVTAM KCFLLELQVI SLESGDASIH  60
DTVENLIILA NNSLSSNGNV TESGCKECCE LEEKNIKEFL QSFVHIVQMF INTS        114

SEQ ID NO: 264           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 264
NWVNVISDLK KIEDLIQSMH IDATLYTESD VHPSCKVTAM KCFLLELCVI SLESGDASIH  60
DTVENLIILA NNSLSSNGNV TESGCKECEE LEEKNIKEFL QSFVHIVQMF INTS        114

SEQ ID NO: 265           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 265
NWVNVISDLK KIEDLIQSMH IDATLYTESD VHPSCKVTAM KCFLLELQVI SLCSGDASIH  60
DTVENLIILA NNSLSSNGNV TESGCKECEE LEEKNIKEFL QSFVHIVQMF INTS        114

SEQ ID NO: 266           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 266
NWVNVISDLK KIEDLIQSMH IDATLYTESD VHPSCKVTAM KSFLLELQVI SLESGDASIH  60
DTVENLIILA NNSLSSNGNV TESGCKECEE LEEKNIKEFL QSFVHIVQMF INTS        114

SEQ ID NO: 267           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 267
NWVNVISDLK KIEDLIQSMH IDATLYTESD VHPSCKVTAM KCFLCELQVI SLESGDASIH  60
DTVENLIILA NNSLSSNGNV TESGCKECEE LEEKNIKEFL QSFVHIVQMF INTS        114

SEQ ID NO: 268           moltype = AA  length = 67
FEATURE                  Location/Qualifiers
REGION                   1..67
                         note = Description of Artificial Sequence: Synthetic
                          polypeptide
source                   1..67
                         mol_type = protein
                         organism = synthetic construct
SEQUENCE: 268
ITCPPPMSVE HADIWVKSYS LYSRERYICN SGFKRKAGTS SLTECVLNKA TNVAHWTTPS  60
LKCIRDC                                                            67

SEQ ID NO: 269           moltype = AA  length = 68
FEATURE                  Location/Qualifiers
```

```
REGION                  1..68
                        note = Description of Artificial Sequence: Synthetic
                         polypeptide
source                  1..68
                        mol_type = protein
                        organism = synthetic construct
SEQUENCE: 269
ITCPPPMSVE HADIWVKSYS LYSRERYICN SGFKRKAGTS SLTECVLNKA TNVAHWTTPS  60
LKCIRDPC                                                           68

SEQ ID NO: 270          moltype = AA  length = 68
FEATURE                 Location/Qualifiers
REGION                  1..68
                        note = Description of Artificial Sequence: Synthetic
                         polypeptide
source                  1..68
                        mol_type = protein
                        organism = synthetic construct
SEQUENCE: 270
ITCPPPMSVE HADIWVKSYS LYSRERYICN SGFKRKAGTS SLTECVLNKA TNVAHWTTPS  60
LKCIRDCA                                                           68

SEQ ID NO: 271          moltype = AA  length = 65
FEATURE                 Location/Qualifiers
REGION                  1..65
                        note = Description of Artificial Sequence: Synthetic
                         polypeptide
source                  1..65
                        mol_type = protein
                        organism = synthetic construct
SEQUENCE: 271
ITCPPPMSVE HADIWVKSYS LYSRERYICN SGFKRKAGTC SLTECVLNKA TNVAHWTTPS  60
LKCIR                                                              65

SEQ ID NO: 272          moltype = AA  length = 65
FEATURE                 Location/Qualifiers
REGION                  1..65
                        note = Description of Artificial Sequence: Synthetic
                         polypeptide
source                  1..65
                        mol_type = protein
                        organism = synthetic construct
SEQUENCE: 272
ITCPPPMSVE HADIWVKSYS LYSRERYICN SGFCRKAGTS SLTECVLNKA TNVAHWTTPS  60
LKCIR                                                              65

SEQ ID NO: 273          moltype = AA  length = 65
FEATURE                 Location/Qualifiers
REGION                  1..65
                        note = Description of Artificial Sequence: Synthetic
                         polypeptide
source                  1..65
                        mol_type = protein
                        organism = synthetic construct
SEQUENCE: 273
ITCPPPMSVE HADIWVKSYS LYSRERYICN SGFKRKACTS SLTECVLNKA TNVAHWTTPS  60
LKCIR                                                              65

SEQ ID NO: 274          moltype = AA  length = 65
FEATURE                 Location/Qualifiers
REGION                  1..65
                        note = Description of Artificial Sequence: Synthetic
                         polypeptide
source                  1..65
                        mol_type = protein
                        organism = synthetic construct
SEQUENCE: 274
ITCPPPMSVE HADIWVKSYS LYSRERYICN SGFKRKAGTS SCTECVLNKA TNVAHWTTPS  60
LKCIR                                                              65

SEQ ID NO: 275          moltype = AA  length = 65
FEATURE                 Location/Qualifiers
REGION                  1..65
                        note = Description of Artificial Sequence: Synthetic
                         polypeptide
source                  1..65
                        mol_type = protein
                        organism = synthetic construct
SEQUENCE: 275
```

```
ITCPPPMSVE HADIWVKSYS LYSRERYICN SGFKRKCGTS SLTECVLNKA TNVAHWTTPS  60
LKCIR                                                              65

SEQ ID NO: 276          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 276
DWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 277          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 277
NWVDVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 278          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 278
NWVNVISNLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 279          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 279
NWVNVISDLK KIEDLIQSMH IDATLYTESN VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 280          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 280
NWVNVISDLK KIEDLIQSMH IDATLYTESD VHPSCKVTAM KCFLLELQVI SLESGDASIH  60
NTVENLIILA NNSLSSNGNV TESGCKECEE LEEKNIKEFL QSFVHIVQMF INTS        114

SEQ ID NO: 281          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 281
NWVNVISDLK KIEDLIQSMH IDATLYTESD VHPSCKVTAM KCFLLELQVI SLESGDASIH  60
DTVQNLIILA NNSLSSNGNV TESGCKECEE LEEKNIKEFL QSFVHIVQMF INTS        114

SEQ ID NO: 282          moltype = AA  length = 114
FEATURE                 Location/Qualifiers
REGION                  1..114
                        note = Description of Artificial Sequence: Synthetic
```

```
                          polypeptide
source                   1..114
                         mol_type = protein
                         organism = synthetic construct
SEQUENCE: 282
NWVNVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 283           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 283
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVEMF INTS        114

SEQ ID NO: 284           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 284
DWVNVISDLK KIEDLIQSMH IDATLYTESD VHPSCKVTAM KCFLLELQVI SLESGDASIH  60
NTVENLIILA NNSLSSNGNV TESGCKECEE LEEKNIKEFL QSFVHIVQMF INTS        114

SEQ ID NO: 285           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 285
DWVNVISDLK KIEDLIQSMH IDATLYTESD VHPSCKVTAM KCFLLELQVI SLESGDASIH  60
DTVQNLIILA NNSLSSNGNV TESGCKECEE LEEKNIKEFL QSFVHIVQMF INTS        114

SEQ ID NO: 286           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 286
NWVDVISDLK KIEDLIQSMH IDATLYTESD VHPSCKVTAM KCFLLELQVI SLESGDASIH  60
NTVENLIILA NNSLSSNGNV TESGCKECEE LEEKNIKEFL QSFVHIVQMF INTS        114

SEQ ID NO: 287           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 287
NWVDVISDLK KIEDLIQSMH IDATLYTESD VHPSCKVTAM KCFLLELQVI SLESGDASIH  60
DTVQNLIILA NNSLSSNGNV TESGCKECEE LEEKNIKEFL QSFVHIVQMF INTS        114

SEQ ID NO: 288           moltype = AA  length = 114
FEATURE                  Location/Qualifiers
REGION                   1..114
                         note = Description of Artificial Sequence: Synthetic
                          polypeptide
source                   1..114
                         mol_type = protein
                         organism = synthetic construct
SEQUENCE: 288
NWVNVISNLK KIEDLIQSMH IDATLYTESD VHPSCKVTAM KCFLLELQVI SLESGDASIH  60
NTVENLIILA NNSLSSNGNV TESGCKECEE LEEKNIKEFL QSFVHIVQMF INTS        114
```

```
SEQ ID NO: 289          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 289
NWVNVISNLK KIEDLIQSMH IDATLYTESD VHPSCKVTAM KCFLLELQVI SLESGDASIH  60
DTVQNLIILA NNSLSSNGNV TESGCKECEE LEEKNIKEFL QSFVHIVQMF INTS        114

SEQ ID NO: 290          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 290
NWVNVISDLK KIEDLIQSMH IDATLYTESD VHPSCKVTAM KCFLLELQVI SLESGDASIH  60
NTVQNLIILA NNSLSSNGNV TESGCKECEE LEEKNIKEFL QSFVHIVQMF INTS        114

SEQ ID NO: 291          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 291
NWVNVISDLK KIEDLIQSMH IDATLYTESD VHPSCKVTAM KCFLLELQVI SLESGDASIH  60
DTVQNLIILA NNSLSSNGNV TESGCKECEE LEEKNIKEFL QSFVHIVEMF INTS        114

SEQ ID NO: 292          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 292
DWVDVISNLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 293          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 293
NWVNVISDLK KIEDLIQSMH IDATLYTESD VHPSCKVTAM KCFLLELQVI SLESGDASIH  60
NTVQDLIILA NNSLSSNGNV TESGCKECEE LEEKNIKEFL QSFVHIVQMF INTS        114

SEQ ID NO: 294          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 294
DWVNVISDLK KIEDLIQSMH IDATLYTESD VHPSCKVTAM KCFLLELQVI SLESGDASIH  60
NTVQNLIILA NNSLSSNGNV TESGCKECEE LEEKNIKEFL QSFVHIVEMF INTS        114

SEQ ID NO: 295          moltype = AA  length = 114
FEATURE                 Location/Qualifiers
REGION                  1..114
                        note = Description of Artificial Sequence: Synthetic
                         polypeptide
source                  1..114
```

```
                        mol_type = protein
                        organism = synthetic construct
SEQUENCE: 295
NWVDVISDLK KIEDLIQSMH IDATLYTESD VHPSCKVTAM KCFLLELQVI SLESGDASIH  60
NTVQNLIILA NNSLSSNGNV TESGCKECEE LEEKNIKEFL QSFVHIVEMF INTS        114

SEQ ID NO: 296          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 296
DWVNVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 297          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 297
DWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVEMF INTS        114

SEQ ID NO: 298          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 298
NWVDVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 299          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 299
NWVNVISDLK KIEDLIQSMH IDATLYTESN VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 300          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 300
NWVNVISDLK KIEDLIQSMH IDATLYTESN VHPSCKVTAM KCFLLELQVI SLESGDASIH  60
DTVENLIILA NNSLSSNGNV TESGCKECEE LEEKNIKEFL QSFVHIVEMF INTS        114

SEQ ID NO: 301          moltype = AA  length = 114
FEATURE                 Location/Qualifiers
REGION                  1..114
                        note = Description of Artificial Sequence: Synthetic
                         polypeptide
source                  1..114
                        mol_type = protein
                        organism = synthetic construct
SEQUENCE: 301
NWVNVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVEMF INTS        114

SEQ ID NO: 302          moltype = AA  length = 114
```

```
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 302
NWVNVISDLK KIEDLIQSMH IDATLYTESD VHPSCKVTAM KCFLLELQVI SLESGDASIH  60
DTVQDLIILA NNSLSSNGNV TESGCKECEE LEEKNIKEFL QSFVHIVQMF INTS        114

SEQ ID NO: 303         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 303
DWVDVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 304         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 304
NWVNVISDLK KIEDLIQSMH IDATLYTESN VHPSCKVTAM KCFLLELQVI SLESGDASIH  60
DTVQDLIILA NNSLSSNGNV TESGCKECEE LEEKNIKEFL QSFVHIVQMF INTS        114

SEQ ID NO: 305         moltype = AA  length = 114
FEATURE                Location/Qualifiers
REGION                 1..114
                       note = Description of Artificial Sequence: Synthetic
                        polypeptide
source                 1..114
                       mol_type = protein
                       organism = synthetic construct
SEQUENCE: 305
NWVDVISDLK KIEDLIQSMH IDATLYTESD VHPSCKVTAM KCFLLELQVI SLESGDASIH  60
NTVEDLIILA NNSLSSNGNV TESGCKECEE LEEKNIKEFL QSFVHIVQMF INTS        114

SEQ ID NO: 306         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 306
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                   435

SEQ ID NO: 307         moltype = AA  length = 65
FEATURE                Location/Qualifiers
REGION                 1..65
                       note = Description of Artificial Sequence: Synthetic
                        polypeptide
source                 1..65
                       mol_type = protein
                       organism = synthetic construct
SEQUENCE: 307
ITCPPPMSVE HADIWVKSYS LYSRERYICN SGFKRKAGTS SLTECVLNKA TNVAHWTTPS  60
LKCIR                                                              65

SEQ ID NO: 308         moltype = AA  length = 114
FEATURE                Location/Qualifiers
```

```
REGION                  1..114
                        note = Description of Artificial Sequence: Synthetic
                         polypeptide
source                  1..114
                        mol_type = protein
                        organism = synthetic construct
SEQUENCE: 308
NWVDVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTS        114

SEQ ID NO: 309          moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 309
EPKSSDKTHT CPPCPAPPVA GPSVFLFPPK PKDTLMISRT PEVTCVVVDV KHEDPEVKFN  60
WYVDGVEVHN AKTKPREEEY NSTYRVVSVL TVLHQDWLNG KEYKCKVSNK ALPAPIEKTI  120
SKAKGQPREP QVYTLPPSRE EMTKNQVSLT CDVSGFYPSD IAVEWESDGQ PENNYKTTPP  180
VLDSDGSFFL YSKLTVDKSR WEQGDVFSCS VMHEALHNHY TQKSLSLSPG K           231

SEQ ID NO: 310          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 310
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 311          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 311
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
S                                                                  121

SEQ ID NO: 312          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 312
DAWMS                                                              5

SEQ ID NO: 313          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 313
EISTKANNHA TYYAESVKG                                               19

SEQ ID NO: 314          moltype = AA  length = 10
FEATURE                 Location/Qualifiers
REGION                  1..10
                        note = Description of Artificial Sequence: Synthetic peptide
```

```
source                  1..10
                        mol_type = protein
                        organism = synthetic construct
SEQUENCE: 314
LATWDWYFDV                                                  10

SEQ ID NO: 315          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 315
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                    218

SEQ ID NO: 316          moltype = AA  length = 111
FEATURE                 Location/Qualifiers
REGION                  1..111
                        note = Description of Artificial Sequence: Synthetic
                         polypeptide
source                  1..111
                        mol_type = protein
                        organism = synthetic construct
SEQUENCE: 316
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI K           111

SEQ ID NO: 317          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 317
RASQSVDYDG DSYMN                                            15

SEQ ID NO: 318          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 318
AASELES                                                     7

SEQ ID NO: 319          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 319
QQSNEDPFT                                                   9

SEQ ID NO: 320          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 320
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                            435
```

```
SEQ ID NO: 321          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 321
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVMHE ALHNHYTQKS LSLSPGK                                    447

SEQ ID NO: 322          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 322
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 323          moltype = AA  length = 442
FEATURE                 Location/Qualifiers
REGION                  1..442
                        note = Description of Artificial Sequence: Synthetic
                         polypeptide
source                  1..442
                        mol_type = protein
                        organism = synthetic construct
SEQUENCE: 323
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKK VEPKSCDKTH TCPPCPAPPV AGPSVFLFPP  240
KPKDTLMISR TPEVTCVVVD VKHEDPEVKF NWYVDGVEVH NAKTKPREEQ YNSTYRVVSV  300
LTVLHQDWLN GKEYKCKVSN KALPAPIEKT ISKAKGQPRE PQVYTLPPSR EEMTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP GK                                         442

SEQ ID NO: 324          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 324
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 325          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 325
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
```

```
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                   435

SEQ ID NO: 326          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 326
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV LHEALHSHYT QKSLSLSPGK                                   450

SEQ ID NO: 327          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 327
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 328          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 328
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                   435

SEQ ID NO: 329          moltype = AA  length = 447
FEATURE                 Location/Qualifiers
REGION                  1..447
                        note = Description of Artificial Sequence: Synthetic
                         polypeptide
source                  1..447
                        mol_type = protein
                        organism = synthetic construct
SEQUENCE: 329
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVLHE ALHSHYTQKS LSLSPGK                                      447

SEQ ID NO: 330          moltype = AA  length = 214
FEATURE                 Location/Qualifiers
REGION                  1..214
                        note = Description of Artificial Sequence: Synthetic
                         polypeptide
source                  1..214
                        mol_type = protein
```

```
                         organism = synthetic construct
SEQUENCE: 330
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 331           moltype = AA  length = 350
FEATURE                  Location/Qualifiers
REGION                   1..350
                         note = Description of Artificial Sequence: Synthetic
                          polypeptide
source                   1..350
                         mol_type = protein
                         organism = synthetic construct
SEQUENCE: 331
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTSGGGGSE  120
PKSSDKTHTC PPCPAPPVAG PSVFLFPPKP KDTLMISRTP EVTCVVVDVK HEDPEVKFNW  180
YVDGVEVHNA KTKPREEEYN STYRVVSVLT VLHQDWLNGK EYKCKVSNKA LPAPIEKTIS  240
KAKGQPREPQ VYTLPPSREE MTKNQVSLTC DVSGFYPSDI AVEWESDGQP ENNYKTTPPV  300
LDSDGSFFLY SKLTVDKSRW EQGDVFSCSV LHEALHSHYT QKSLSLSPGK              350

SEQ ID NO: 332           moltype = AA  length = 301
FEATURE                  Location/Qualifiers
REGION                   1..301
                         note = Description of Artificial Sequence: Synthetic
                          polypeptide
source                   1..301
                         mol_type = protein
                         organism = synthetic construct
SEQUENCE: 332
ITCPPPMSVE HADIWVKSYS LYSRERYICN SGFKRKAGTS SLTECVLNKA TNVAHWTTPS  60
LKCIRGGGGS EPKSSDKTHT CPPCPAPPVA GPSVFLFPPK PKDTLMISRT PEVTCVVVDV  120
KHEDPEVKFN WYVDGVEVHN AKTKPREEQY NSTYRVVSVL TVLHQDWLNG KEYKCKVSNK  180
ALPAPIEKTI SKAKGQPREP QVYTLPPSRE QMTKNQVKLT CLVKGFYPSD IAVEWESNGQ  240
PENNYKTTPP VLDSDGSFFL YSKLTVDKSR WQQGNVFSCS VLHEALHSHY TQKSLSLSPG  300
K                                                                  301

SEQ ID NO: 333           moltype = AA  length = 350
FEATURE                  Location/Qualifiers
REGION                   1..350
                         note = Description of Artificial Sequence: Synthetic
                          polypeptide
source                   1..350
                         mol_type = protein
                         organism = synthetic construct
SEQUENCE: 333
NWVDVISDLK KIEDLIQSMH IDATLYTESD VHPSCKVTAM KCFLLELQVI SLESGDASIH  60
DTVEDLIILA NNSLSSNGNV TESGCKECEE LEEKNIKEFL QSFVHIVQMF INTSGGGGSE  120
PKSSDKTHTC PPCPAPPVAG PSVFLFPPKP KDTLMISRTP EVTCVVVDVK HEDPEVKFNW  180
YVDGVEVHNA KTKPREEEYN STYRVVSVLT VLHQDWLNGK EYKCKVSNKA LPAPIEKTIS  240
KAKGQPREPQ VYTLPPSREE MTKNQVSLTC DVSGFYPSDI AVEWESDGQP ENNYKTTPPV  300
LDSDGSFFLY SKLTVDKSRW EQGDVFSCSV LHEALHSHYT QKSLSLSPGK              350

SEQ ID NO: 334           moltype = AA  length = 301
FEATURE                  Location/Qualifiers
REGION                   1..301
                         note = Description of Artificial Sequence: Synthetic
                          polypeptide
source                   1..301
                         mol_type = protein
                         organism = synthetic construct
SEQUENCE: 334
ITCPPPMSVE HADIWVKSYS LYSRERYICN SGFKRKAGTS SLTECVLNKA TNVAHWTTPS  60
LKCIRGGGGS EPKSSDKTHT CPPCPAPPVA GPSVFLFPPK PKDTLMISRT PEVTCVVVDV  120
KHEDPEVKFN WYVDGVEVHN AKTKPREEQY NSTYRVVSVL TVLHQDWLNG KEYKCKVSNK  180
ALPAPIEKTI SKAKGQPREP QVYTLPPSRE QMTKNQVKLT CLVKGFYPSD IAVEWESNGQ  240
PENNYKTTPP VLDSDGSFFL YSKLTVDKSR WQQGNVFSCS VLHEALHSHY TQKSLSLSPG  300
K                                                                  301

SEQ ID NO: 335           moltype = AA  length = 435
FEATURE                  Location/Qualifiers
REGION                   1..435
                         note = Description of Artificial Sequence: Synthetic
                          polypeptide
source                   1..435
                         mol_type = protein
                         organism = synthetic construct
```

SEQUENCE: 335
ITCPPPMSVE HADIWVKSYS LYSRERYICN SGFKRKAGTS SLTECVLNKA TNVAHWTTPS 60
LKCIRGGGGS GGGGSGGGGS GGGGSGGGGS NWVDVISDLK KIEDLIQSMH IDATLYTESD 120
VHPSCKVTAM KCFLLELQVI SLESGDASIH DTVEDLIILA NNSLSSNGNV TESGCKECEE 180
LEEKNIKEFL QSFVHIVQMF INTSEPKSSD KTHTCPPCPA PPVAGPSVFL FPPKPKDTLM 240
ISRTPEVTCV VVDVKHEDPE VKFNWYVDGV EVHNAKTKPR EEEYNSTYRV VSVLTVLHQD 300
WLNGKEYKCK VSNKALPAPI EKTISKAKGQ PREPQVYTLP PSREEMTKNQ VSLTCDVSGF 360
YPSDIAVEWE SDGQPENNYK TTPPVLDSDG SFFLYSKLTV DKSRWEQGDV FSCSVLHEAL 420
HSHYTQKSLS LSPGK 435

SEQ ID NO: 336 moltype = AA length = 231
FEATURE Location/Qualifiers
REGION 1..231
note = Description of Artificial Sequence: Synthetic polypeptide
source 1..231
mol_type = protein
organism = synthetic construct
SEQUENCE: 336
EPKSSDKTHT CPPCPAPPVA GPSVFLFPPK PKDTLMISRT PEVTCVVVDV KHEDPEVKFN 60
WYVDGVEVHN AKTKPREEQY NSTYRVVSVL TVLHQDWLNG KEYKCKVSNK ALPAPIEKTI 120
SKAKGQPREP QVYTLPPSRE QMTKNQVKLT CLVKGFYPSD IAVEWESNGQ PENNYKTTPP 180
VLDSDGSFFL YSKLTVDKSR WQQGNVFSCS VLHEALHSHY TQKSLSLSPG K 231

SEQ ID NO: 337 moltype = AA length = 350
FEATURE Location/Qualifiers
REGION 1..350
note = Description of Artificial Sequence: Synthetic polypeptide
source 1..350
mol_type = protein
organism = synthetic construct
SEQUENCE: 337
NWVNVISDLK KIEDLIQSMH IDATLYTESN VHPSCKVTAM KCFLLELQVI SLESGDASIH 60
DTVQDLIILA NNSLSSNGNV TESGCKECEE LEEKNIKEFL QSFVHIVQMF INTSGGGGSE 120
PKSSDKTHTC PPCPAPPVAG PSVFLFPPKP KDTLMISRTP EVTCVVVDVK HEDPEVKFNW 180
YVDGVEVHNA KTKPREEEYN STYRVVSVLT VLHQDWLNGK EYKCKVSNKA LPAPIEKTIS 240
KAKGQPREPQ VYTLPPSREE MTKNQVSLTC DVSGFYPSDI AVEWESDGQP ENNYKTTPPV 300
LDSDGSFFLY SKLTVDKSRW EQGDVFSCSV LHEALHSHYT QKSLSLSPGK 350

SEQ ID NO: 338 moltype = AA length = 301
FEATURE Location/Qualifiers
REGION 1..301
note = Description of Artificial Sequence: Synthetic polypeptide
source 1..301
mol_type = protein
organism = synthetic construct
SEQUENCE: 338
ITCPPPMSVE HADIWVKSYS LYSRERYICN SGFKRKAGTS SLTECVLNKA TNVAHWTTPS 60
LKCIRGGGGS EPKSSDKTHT CPPCPAPPVA GPSVFLFPPK PKDTLMISRT PEVTCVVVDV 120
KHEDPEVKFN WYVDGVEVHN AKTKPREEQY NSTYRVVSVL TVLHQDWLNG KEYKCKVSNK 180
ALPAPIEKTI SKAKGQPREP QVYTLPPSRE QMTKNQVKLT CLVKGFYPSD IAVEWESNGQ 240
PENNYKTTPP VLDSDGSFFL YSKLTVDKSR WQQGNVFSCS VLHEALHSHY TQKSLSLSPG 300
K 301

SEQ ID NO: 339 moltype = AA length = 435
FEATURE Location/Qualifiers
REGION 1..435
note = Description of Artificial Sequence: Synthetic polypeptide
source 1..435
mol_type = protein
organism = synthetic construct
SEQUENCE: 339
ITCPPPMSVE HADIWVKSYS LYSRERYICN SGFKRKAGTS SLTECVLNKA TNVAHWTTPS 60
LKCIRGGGGS GGGGSGGGGS GGGGSGGGGS NWVNVISDLK KIEDLIQSMH IDATLYTESD 120
VHPSCKVTAM KCFLLELQVI SLESGDASIH DTVENLIILA NNSLSSNGNV TESGCKECEE 180
LEEKNIKEFL QSFVHIVQMF INTSEPKSSD KTHTCPPCPA PPVAGPSVFL FPPKPKDTLM 240
ISRTPEVTCV VVDVKHEDPE VKFNWYVDGV EVHNAKTKPR EEEYNSTYRV VSVLTVLHQD 300
WLNGKEYKCK VSNKALPAPI EKTISKAKGQ PREPQVYTLP PSREEMTKNQ VSLTCDVSGF 360
YPSDIAVEWE SDGQPENNYK TTPPVLDSDG SFFLYSKLTV DKSRWEQGDV FSCSVMHEAL 420
HNHYTQKSLS LSPGK 435

SEQ ID NO: 340 moltype = AA length = 231
FEATURE Location/Qualifiers
REGION 1..231
note = Description of Artificial Sequence: Synthetic polypeptide

```
source                  1..231
                        mol_type = protein
                        organism = synthetic construct
SEQUENCE: 340
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 341          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 341
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                  435

SEQ ID NO: 342          moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 342
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 343          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 343
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVENLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                  435

SEQ ID NO: 344          moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 344
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 345          moltype = AA  length = 435
FEATURE                 Location/Qualifiers
REGION                  1..435
                        note = Description of Artificial Sequence: Synthetic
                         polypeptide
source                  1..435
```

```
                        mol_type = protein
                        organism = synthetic construct
SEQUENCE: 345
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                   435

SEQ ID NO: 346          moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 346
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 347          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 347
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                   435

SEQ ID NO: 348          moltype = AA  length = 231
FEATURE                 Location/Qualifiers
REGION                  1..231
                        note = Description of Artificial Sequence: Synthetic
                         polypeptide
source                  1..231
                        mol_type = protein
                        organism = synthetic construct
SEQUENCE: 348
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 349          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 349
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                   435

SEQ ID NO: 350          moltype = AA  length = 450
FEATURE                 Location/Qualifiers
REGION                  1..450
```

```
                         note = Description of Artificial Sequence: Synthetic
                          polypeptide
source                   1..450
                         mol_type = protein
                         organism = synthetic construct
SEQUENCE: 350
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 351           moltype = AA  length = 218
FEATURE                  Location/Qualifiers
REGION                   1..218
                         note = Description of Artificial Sequence: Synthetic
                          polypeptide
source                   1..218
                         mol_type = protein
                         organism = synthetic construct
SEQUENCE: 351
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 352           moltype = AA  length = 435
FEATURE                  Location/Qualifiers
REGION                   1..435
                         note = Description of Artificial Sequence: Synthetic
                          polypeptide
source                   1..435
                         mol_type = protein
                         organism = synthetic construct
SEQUENCE: 352
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                  435

SEQ ID NO: 353           moltype = AA  length = 447
FEATURE                  Location/Qualifiers
REGION                   1..447
                         note = Description of Artificial Sequence: Synthetic
                          polypeptide
source                   1..447
                         mol_type = protein
                         organism = synthetic construct
SEQUENCE: 353
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 354           moltype = AA  length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 354
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 355         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 355
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                  435

SEQ ID NO: 356         moltype = AA  length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 356
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 357         moltype = AA  length = 218
FEATURE                Location/Qualifiers
REGION                 1..218
                       note = Description of Artificial Sequence: Synthetic
                        polypeptide
source                 1..218
                       mol_type = protein
                       organism = synthetic construct
SEQUENCE: 357
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 358         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 358
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                  435

SEQ ID NO: 359         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 359
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
```

```
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 360         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 360
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 361         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 361
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                  435

SEQ ID NO: 362         moltype = AA  length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 362
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV LHEALHSHYT QKSLSLSPGK                                  450

SEQ ID NO: 363         moltype = AA  length = 218
FEATURE                Location/Qualifiers
REGION                 1..218
                       note = Description of Artificial Sequence: Synthetic
                        polypeptide
source                 1..218
                       mol_type = protein
                       organism = synthetic construct
SEQUENCE: 363
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 364         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
```

```
SEQUENCE: 364
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                   435

SEQ ID NO: 365         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 365
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVLHE ALHSHYTQKS LSLSPGK                                      447

SEQ ID NO: 366         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 366
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 367         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 367
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                   435

SEQ ID NO: 368         moltype = AA  length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 368
EVQLVESGGG LVQPGGSLRL SCAASGFTFD DAWMSWVRQA PGKGLEWVAE ISTKANNHAT  60
YYAESVKGRF TISRDDSKSS VYLQMNSLRA EDTAVYYCTR LATWDWYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPPVAG  240
PSVFLFPPKP KDTLMISRTP EVTCVVVDVK HEDPEVKFNW YVDGVEVHNA KTKPREEQYN  300
STYRVVSVLT VLHQDWLNGK EYKCKVSNKA LPAPIEKTIS KAKGQPREPQ VYTLPPSREQ  360
MTKNQVKLTC LVKGFYPSDI AVEWESNGQP ENNYKTTPPV LDSDGSFFLY SKLTVDKSRW  420
QQGNVFSCSV LHEALHSHYT QKSLSLSPGK                                   450

SEQ ID NO: 369         moltype = AA  length = 218
```

```
FEATURE                Location/Qualifiers
REGION                 1..218
                       note = Description of Artificial Sequence: Synthetic
                        polypeptide
source                 1..218
                       mol_type = protein
                       organism = synthetic construct
SEQUENCE: 369
DIVLTQSPSS LSASVGDRVT ITCRASQSVD YDGDSYMNWY QQKPGKPPKL LIYAASELES  60
GIPARFSGSG SGTDFTLTIS SLQPEDFATY YCQQSNEDPF TFGSGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 370         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 370
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVLHEAL  420
HSHYTQKSLS LSPGK                                                   435

SEQ ID NO: 371         moltype = AA  length = 447
FEATURE                Location/Qualifiers
REGION                 1..447
                       note = Description of Artificial Sequence: Synthetic
                        polypeptide
source                 1..447
                       mol_type = protein
                       organism = synthetic construct
SEQUENCE: 371
EVQLVQSGAE VKKPGATVKI SCKASGFNIK DYFMHWVQQA PGKGLEWMGW IDPELGDTEY  60
APKFQGRVTI TADTSTNTAY MELSSLRSED TAVYYCYARG VYQALDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPPVAGPSV  240
FLFPPKPKDT LMISRTPEVT CVVVDVKHED PEVKFNWYVD GVEVHNAKTK PREEQYNSTY  300
RVVSVLTVLH QDWLNGKEYK CKVSNKALPA PIEKTISKAK GQPREPQVYT LPPSREQMTK  360
NQVKLTCLVK GFYPSDIAVE WESNGQPENN YKTTPPVLDS DGSFFLYSKL TVDKSRWQQG  420
NVFSCSVLHE ALHSHYTQKS LSLSPGK                                      447

SEQ ID NO: 372         moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 372
DIQMTQSPAF LSVTPGEKVT ITCQASQDIG NYLNWFQQKP GQTVKLLIYF TSYLHSGVPS  60
RFSGSGSGTD YTFTISSLEA EDAATYFCQQ GNTLPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 373         moltype = AA  length = 435
FEATURE                Location/Qualifiers
REGION                 1..435
                       note = Description of Artificial Sequence: Synthetic
                        polypeptide
source                 1..435
                       mol_type = protein
                       organism = synthetic construct
SEQUENCE: 373
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVDVISDLK KIEDLIQSMH IDATLYTESD  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
```

```
HNHYTQKSLS LSPGK                                                435

SEQ ID NO: 374          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 374
QVTLRESGPA LVKPTQTLTL TCTFSGFSLS TAGMSVGWIR QPPGKALEWL ADIWWDDKKH  60
YNPSLKDRLT ISKDTSKNQV VLKVTNMDPA DTATYYCARD MIFNFYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPPVAGP  240
SVFLFPPKPK DTLMISRTPE VTCVVVDVKH EDPEVKFNWY VDGVEVHNAK TKPREEQYNS  300
TYRVVSVLTV LHQDWLNGKE YKCKVSNKAL PAPIEKTISK AKGQPREPQV YTLPPSREQM  360
TKNQVKLTCL VKGFYPSDIA VEWESNGQPE NNYKTTPPVL DSDGSFFLYS KLTVDKSRWQ  420
QGNVFSCSVM HEALHNHYTQ KSLSLSPGK                                 449

SEQ ID NO: 375          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 375
DIQMTQSPST LSASVGDRVT ITCSASSRVG YMHWYQQKPG KAPKLLIYDT SKLASGVPSR  60
FSGSGSGTEF TLTISSLQPD DFATYYCFQG SGYPFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                            213

SEQ ID NO: 376          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 376
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVEDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                435

SEQ ID NO: 377          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 377
QVTLRESGPA LVKPTQTLTL TCTFSGFSLS TAGMSVGWIR QPPGKALEWL ADIWWDDKKH  60
YNPSLKDRLT ISKDTSKNQV VLKVTNMDPA DTATYYCARD MIFNFYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPPVAGP  240
SVFLFPPKPK DTLMISRTPE VTCVVVDVKH EDPEVKFNWY VDGVEVHNAK TKPREEQYNS  300
TYRVVSVLTV LHQDWLNGKE YKCKVSNKAL PAPIEKTISK AKGQPREPQV YTLPPSREQM  360
TKNQVKLTCL VKGFYPSDIA VEWESNGQPE NNYKTTPPVL DSDGSFFLYS KLTVDKSRWQ  420
QGNVFSCSVM HEALHNHYTQ KSLSLSPGK                                 449

SEQ ID NO: 378          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 378
```

```
DIQMTQSPST LSASVGDRVT ITCSASSRVG YMHWYQQKPG KAPKLLIYDT SKLASGVPSR  60
FSGSGSGTEF TLTISSLQPD DFATYYCFQG SGYPFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 379          moltype = AA  length = 435
FEATURE                 Location/Qualifiers
REGION                  1..435
                        note = Description of Artificial Sequence: Synthetic
                         polypeptide
source                  1..435
                        mol_type = protein
                        organism = synthetic construct
SEQUENCE: 379
ITCPPPMSVE HADIWVKSYS LYSRERYICN SGFKRKAGTS SLTECVLNKA TNVAHWTTPS  60
LKCIRGGGGS GGGGSGGGGS GGGGSGGGGS NWVNVISDLK KIEDLIQSMH IDATLYTESN  120
VHPSCKVTAM KCFLLELQVI SLESGDASIH DTVQDLIILA NNSLSSNGNV TESGCKECEE  180
LEEKNIKEFL QSFVHIVQMF INTSEPKSSD KTHTCPPCPA PPVAGPSVFL FPPKPKDTLM  240
ISRTPEVTCV VVDVKHEDPE VKFNWYVDGV EVHNAKTKPR EEEYNSTYRV VSVLTVLHQD  300
WLNGKEYKCK VSNKALPAPI EKTISKAKGQ PREPQVYTLP PSREEMTKNQ VSLTCDVSGF  360
YPSDIAVEWE SDGQPENNYK TTPPVLDSDG SFFLYSKLTV DKSRWEQGDV FSCSVMHEAL  420
HNHYTQKSLS LSPGK                                                   435

SEQ ID NO: 380          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 380
QVTLRESGPA LVKPTQTLTL TCTFSGFSLS TAGMSVGWIR QPPGKALEWL ADIWWDDKKH  60
YNPSLKDRLT ISKDTSKNQV VLKVTNMDPA DTATYYCARD MIFNFYFDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPPVAGP  240
SVFLFPPKPK DTLMISRTPE VTCVVVDVKH EDPEVKFNWY VDGVEVHNAK TKPREEQYNS  300
TYRVVSVLTV LHQDWLNGKE YKCKVSNKAL PAPIEKTISK AKGQPREPQV YTLPPSREQM  360
TKNQVKLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 381          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 381
DIQMTQSPST LSASVGDRVT ITCSASSRVG YMHWYQQKPG KAPKLLIYDT SKLASGVPSR  60
FSGSGSGTEF TLTISSLQPD DFATYYCFQG SGYPFTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 382          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 382
GSGGS                                                              5

SEQ ID NO: 383          moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 383
GGGS                                                               4
```

What is claimed is:

1. A protein comprising a first monomer, a second monomer, and a third monomer on separate polypeptide chains:

a) the first monomer comprising the amino acid sequence set forth in SEQ ID NO: 367;

b) the second monomer comprising the amino acid sequence set forth in SEQ ID NO: 368; and c) the third monomer comprising the amino acid sequence set forth in SEQ ID NO: 369.

2. A nucleic acid composition comprising:

a) a first nucleic acid encoding said first monomer of claim 1;

b) a second nucleic acid encoding said second monomer of claim 1; and c) a third nucleic acid encoding said third monomer of claim 1.

3. An expression vector composition comprising:

a) a first expression vector comprising said first nucleic acid of claim 2;

b) a second expression vector comprising said second nucleic acid of claim 2; and c) a third expression vector comprising said third nucleic acid of claim 2.

4. A host cell comprising said expression vector composition of claim 3.

5. A method of making a protein according to claim 1 comprising culturing said host cell of claim 4 under conditions wherein said protein of claim 1 is expressed, and recovering said protein.

* * * * *